United States Patent
Nonogawa et al.

(10) Patent No.: US 10,214,555 B2
(45) Date of Patent: Feb. 26, 2019

(54) METHOD FOR LIQUID-PHASE SYNTHESIS OF NUCLEIC ACID

(71) Applicant: TAKEDA PHARMACEUTICAL COMPANY LIMITED, Osaka-shi, Osaka (JP)

(72) Inventors: Mitsuru Nonogawa, Osaka (JP); Toshiaki Nagata, Osaka (JP); Hideki Saito, Osaka (JP); Tsuneo Yasuma, Osaka (JP)

(73) Assignee: TAKEDA PHARMACEUTICAL COMPANY LIMITJED, Osaka (JP)

( * ) Notice: Subject to any disclaimer, the term of this patent is extended or adjusted under 35 U.S.C. 154(b) by 160 days.

(21) Appl. No.: 14/442,601

(22) PCT Filed: Nov. 13, 2013

(86) PCT No.: PCT/JP2013/080724
§ 371 (c)(1),
(2) Date: May 13, 2015

(87) PCT Pub. No.: WO2014/077292
PCT Pub. Date: May 22, 2014

(65) Prior Publication Data
US 2015/0315229 A1    Nov. 5, 2015

(30) Foreign Application Priority Data

Nov. 14, 2012  (JP) .................. 2012-250581

(51) Int. Cl.
| | | |
|---|---|---|
| C07H 1/00 | (2006.01) | |
| C07H 21/00 | (2006.01) | |
| C07H 21/04 | (2006.01) | |
| C07H 19/06 | (2006.01) | |
| C07H 19/16 | (2006.01) | |
| C07H 19/067 | (2006.01) | |
| C07H 19/073 | (2006.01) | |
| C07H 19/167 | (2006.01) | |
| C07H 19/207 | (2006.01) | |

(52) U.S. Cl.
CPC ............ *C07H 19/207* (2013.01); *C07H 1/00* (2013.01); *C07H 19/06* (2013.01); *C07H 19/067* (2013.01); *C07H 19/073* (2013.01); *C07H 19/16* (2013.01); *C07H 19/167* (2013.01); *C07H 21/00* (2013.01); *C07H 21/04* (2013.01)

(58) Field of Classification Search
CPC .... C07H 19/067; C07H 19/16; C07H 19/207; C07H 1/00; C07H 21/04
See application file for complete search history.

(56) References Cited

U.S. PATENT DOCUMENTS

| | | | | |
|---|---|---|---|---|
| 8,846,885 B2 * | 9/2014 | Hirai | ................... | C07H 19/073 536/22.1 |
| 9,029,528 B2 * | 5/2015 | Hirai | ..................... | C07H 21/00 536/25.34 |
| 2012/0296074 A1 | 11/2012 | Hirai | | |
| 2013/0267697 A1 | 10/2013 | Hirai | | |

FOREIGN PATENT DOCUMENTS

| | | |
|---|---|---|
| JP | 2000-327694 | 11/2000 |
| JP | 2009-185063 | 8/2009 |
| JP | 2010-275254 | 12/2010 |
| WO | WO 2005/070859 | 8/2005 |
| WO | WO 2012/157723 | 11/2012 |
| WO | WO 2013/122236 | 8/2013 |

OTHER PUBLICATIONS

Chen et al.; "Convergent Solution Phase Synthesis of Chimeric Oligonucleotides by a 2+2 and 3+3 Phosphoramidite Strategy", Aust. J. Chem., vol. 63, pp. 227-235, (2010).
Reese et al.; "Preparation of an Octadeoxyribonucleoside Heptaphosphorothioate by the Phosphotriester Approach in Solution", Nucleosides & Nucleotides, vol. 17, No. 1-3, pp. 451-470, (1998).
Kurata et al.; "Characterization of High Molecular Weight Impurities in Synthetic Phosphorothioate Oligonucleotides", Bioorganic & Medicinal Chemistry Letters, vol. 16, No. 3, pp. 607-614, (2006).
Puri et al.; "Synthesis of 5'-Polyarene-Tethered Oligo-DNAS and the Thermal Stability and Spectroscopic Properties of Their Duplexes and Triplexes", Tetrahedron, vol. 53, No. 30, pp. 10409-10432, (1997).

(Continued)

*Primary Examiner* — Lawrence E Crane
(74) *Attorney, Agent, or Firm* — Finnegan, Henderson, Farabow, Garrett & Dunner LLP

(57) ABSTRACT

In this method, an oligonucleotide is prepared by using, as a synthesis unit, a novel nucleoside monomer compound represented by formula (I) [wherein X, $R^1$, Y, Base, Z, Ar, $R^2$, $R^3$ and n are each as defined in Claim 1]. The novel nucleoside monomer compound is a nucleoside, the base moiety of which is substituted with an aromatic-hydrocarbon-ring-carbonyl or -thiocarbonyl group having at least one hydrophobic group. The method cars dispense with column-chromatographic purification in every reaction, and enables base elongation not only in the 3'-direction but also in the 5'-direction, thus attaining efficient liquid-phase mass synthesis of an oligonucleotide.

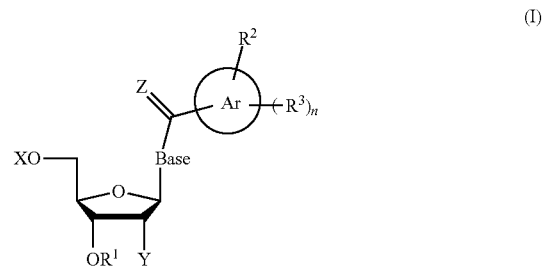

(I)

2 Claims, No Drawings

(56) References Cited

OTHER PUBLICATIONS

English-language International Search Report from the Japanese Patent Office for International Application No. PCT/JP2013/080724, dated Dec. 17, 2013.
CAS Registry No. 194786-29-3, Oct. 2, 1997 (1 page).
CAS Registry No. 194786-28-2, Oct. 2, 1997 (1 page).
CAS Registry No. 194786-20-4, Oct. 2, 1997 (1 page).
CAS Registry No. 194786-19-1, Oct. 2, 1997 (1 page).
Kim, Shokaku et al., "Liquid-Phase RNA Synthesis by Using Alkyl-Chain-Soluble Support," Chem. Eur. J., 19, pp. 8615-8620 (2013).

* cited by examiner

METHOD FOR LIQUID-PHASE SYNTHESIS OF NUCLEIC ACID

This Application is a U.S. National Stage of PCT/JP2013/080724, filed Nov. 13, 2013.

TECHNICAL FIELD

The present invention relates to a liquid-phase nucleic acid synthesis method. More specifically, the present invention relates to a novel nucleoside monomer compound in which the base moiety of a nucleoside is substituted by (i) an aromatic hydrocarbon ring carbonyl group having at least one hydrophobic group or (ii) an aromatic hydrocarbon ring thiocarbonyl group having at least one hydrophobic group, and a method for producing a nucleic acid oligomer using the nucleoside monomer compound as a synthetic unit. This production method can circumvent the need for column chromatography purification after every reaction and can achieve efficient large-scale synthesis. The present invention also relates to a method for producing the nucleic acid oligomer in a liquid phase.

BACKGROUND OF INVENTION

With rapid progress or development of leading-edge research on biotechnology including genomic drug discovery and genetic diagnosis or therapy, nucleic acid oligomers such as DNA probes, siRNA, antisense DNA, and antisense RNA have been actively utilized in recent years. Solid-phase synthesis methods using phosphoramidite are typically known as methods for synthesizing these nucleic acid oligomers.

Patent Literature 1 has proposed a method for synthesizing a nucleic acid oligomer in a liquid phase, wherein a nucleoside compound in which polyethylene glycol (PEG) as a hydrophilic polymer having a molecular weight distribution is introduced in the base moiety of a nucleoside is used as an end starting material or a building block to facilitate separating or purifying an intermediate product, thereby synthesizing a nucleic acid oligomer. Non Patent Literature 1 has proposed a method for producing a nucleic acid oligomer by: synthesizing nucleotide dimers or trimers in which adenine as the base moiety of a nucleoside is substituted by an unsubstituted benzoyl group by repeating reaction in a liquid phase and column chromatography purification; and binding these dimers or trimers by a phosphoramidite method, followed by column chromatography purification. Alternatively, Non Patent Literature 2 has proposed a method for producing a nucleic acid oligomer by: subjecting a nucleoside in which thymine as the base moiety of a nucleoside is substituted by a p-methoxybenzoyl group (p-toluyl group) to a phosphoric acid triester method in a liquid phase; and performing column chromatography purification after every reaction.

Meanwhile, Patent Literature 2 has proposed the easy step of separating by-products, etc. after reaction using, as an organic synthesis reagent, a compound having the property of shifting its liquid-phase state to a solid-phase state depending on change in solution composition or solution temperature after organic synthesis reaction. The literature has further described, as such an organic synthesis reagent, a compound having a group retaining hydrophobicity on an aromatic ring, for example, a benzylamine substituted by two docosyloxy groups as alkoxy groups each having 22 carbon atoms, and proposed use thereof for peptide synthesis.

CITATION LIST

Patent Literature

Patent Literature 1: JP 2000-327694 A
Patent Literature 2: JP 2009-185063 A

Non Patent Literature

Non Patent Literature 1: Chen et al., Aust. J. Chem. 2010, 63, 227-235
Non Patent Literature 2: Reese et al., NUCLEOSIDES & NUCLEOTIDES, 17 (1-3), 451-470 (1998)

SUMMARY OF INVENTION

Technical Problem

Solid-phase synthesis methods are currently used as typical methods for producing nucleic acid oligomers. Such solid-phase synthesis methods may achieve the easy production of nucleic acid oligomers. These methods, however, are limited by reactive sites for the convenience of reaction on resins, require dedicated synthesizers, and have the difficulty in expanding scales. Liquid-phase synthesis, which can employ general-purpose reactors, is effective for supplying nucleic acid oligomers in large amounts (e.g., exceeding several kg per batch), but is not appropriate for the large-scale production of oligo RNA on the ground that, for example, column chromatography purification is required for each of dozens of steps required for the synthesis of nucleic acid oligomers such as siRNA and antisense nucleic acids. Considering the risk of failure in the final step, for example, in the synthesis of siRNA of approximately 20 bases, it may be preferred to synthesis the siRNA using, for example, a building block of 2 to 11 bases. Such synthesis requires a method capable of elongating the bases both in a direction toward the 3' end and in a direction toward the 5' end. A method for producing a nucleic acid oligomer (e.g., oligo RNA) has not yet been known, which eliminates the need of performing column chromatography purification after every step and is capable of elongating bases both in a direction toward the 3' end and in a direction toward the 5' end.

Thus, an object of the present invention is to provide: a novel nucleoside monomer compound that facilitates removing unreacted reagents, activators, and the like after every reaction, can circumvent the need for complicated steps such as column chromatography purification, and permits base elongation both in a direction toward the 3' end and in a direction toward the 5' end, and enables a nucleic acid oligomer to be synthesized using a building block; and a method for producing a nucleic acid oligomer using this compound; etc.

Solution to Problem

The present inventors have conducted diligent studies to attain such an object and consequently found that the need for column chromatography purification after every reaction for during coupling reactions with nucleic acid monomers or nucleic acid oligomers can be circumvented by using a hovel nucleoside monomer compound (of a dimer compound, a trimer compound, or the like containing the monomer compound) in which the base moiety of a nucleoside is substituted by (i) an aromatic hydrocarbon ring carbonyl group having at least one hydrophobic group or (ii) an aromatic hydrocarbon ring thiocarbonyl group having at least one hydrophobic group as a synthetic unit. The present inventors have also found that bases can be elongated both in a direction toward the 3' end and in a direction toward the 5' end by using the novel nucleoside monomer compound. The present inventors have further found that efficient large-scale synthesis can be achieved by the synthesis of a nucleic acid oligomer in a liquid phase. As a result of conducting further studies on the basis of these findings, the present inventors have completed the present invention.

Thus, the present invention relates to:

[1] a compound represented by the following formula (I):

[Formula 1]

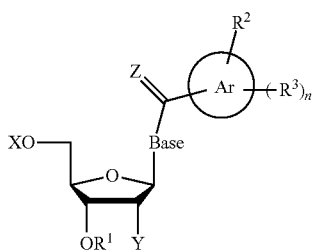

(I)

wherein

X and $R^1$ each independently represent a hydrogen atom or a protective group for a hydroxy group;

Y represents an optionally protected hydroxy group, a hydrogen atom, an optionally substituted $C_{1-6}$ alkoxy group, or a halogen atom;

Base represents thymine, adenine, guanine, cytosine, uracil, or a modified form thereof;

Z represents an oxygen atom or a sulfur atom;

ring Ar represents an aromatic hydrocarbon ring optionally substituted by a substituent selected from substituent group B described below;

$R^2$ represents a substituent selected from substituent group A described below;

$R^3$ independently represents a substituent selected from substituent group B described below;

n represents an integer of 1 to 4;

substituent group A:
(i) an optionally substituted $C_{10-30}$ alkoxy group,
(ii) an optionally substituted $C_{10-30}$ alkyl group,
(iii) an optionally substituted $C_{10-30}$ alkylsulfanyl group,
(iv) an optionally substituted $C_{10-30}$ alkylsulfinyl group,
(v) an optionally substituted $C_{10-30}$ alkylsulfonyl group,
(vi) an optionally substituted $C_{10-30}$ alkylsiloxy group, and
(vii) an optionally substituted $C_{10-30}$ alkylsilyl group; and substituent group B:
(i) an optionally substituted $C_{1-30}$ alkoxy group,
(ii) a halogen atom,
(iii) an optionally substituted $C_{1-30}$ alkyl group,
(iv) a nitro group,
(v) an optionally substituted $C_{1-30}$ alkylsulfanyl group,
(vi) an optionally substituted $C_{1-30}$ alkylsulfinyl group,
(vii) an optionally substituted $C_{1-30}$ alkylsulfonyl group,
(viii) an optionally substituted $C_{1-30}$ alkylsiloxy group,
(ix) an optionally substituted $C_{1-30}$ alkylsilyl group,
(x) a cyano group,
(xi) an optionally substituted amino group,
(xii) an optionally substituted $C_{1-32}$ alkoxy-carbonyl group, and
(xiii) an optionally substituted $C_{1-32}$ alkyl-carbonyl group, or a salt thereof;

[2] the compound according to [1], wherein ring Ar is a $C_{6-10}$ aromatic hydrocarbon ring optionally substituted by a substituent selected from substituent group B, or a salt thereof;

[3] the compound according to [1] or [2], wherein $R^2$ is an optionally substituted $C_{10-30}$ alkoxy group, or a salt thereof;

[4] the compound according to any of [1] to [3], wherein $R^3$ is an optionally substituted $C_{10-30}$ alkoxy group, or a salt thereof;

[5] the compound according to any of [1] to [4], wherein n is 1 or 2, or a salt thereof;

[6] a method for producing a compound represented by the following formula (II):

[Formula 2]

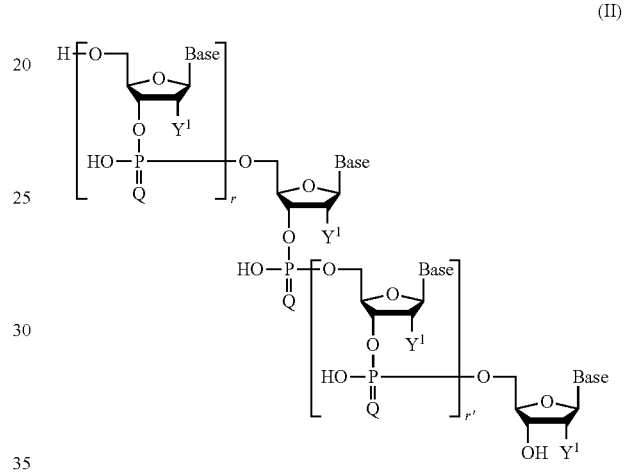

(II)

wherein

Base independently represents thymine, adenine, guanine, cytosine, uracil, or a modified form thereof;

$Y^1$ independently represents a hydroxy group, a hydrogen atom, an optionally substituted $C_{1-6}$ alkoxy group, or a halogen atom;

Q independently represents an oxygen atom or a sulfur atom; and r and r' each independently represent an integer of 0 to 100, or a salt thereof, the method comprising the following steps (a0) and (b0):

step (a0):
using a compound represented by the following formula (I):

[Formula 3]

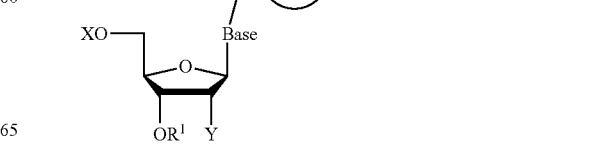

(I)

wherein

Base is as defined above;

X and $R^1$ each independently represent a hydrogen atom or a protective group for a hydroxy group;

Y represents an optionally protected hydroxy group, a hydrogen atom, an optionally substituted $C_{1-6}$ alkoxy group, or a halogen atom;

Z represents an oxygen atom or a sulfur atom;

ring Ar represents an aromatic hydrocarbon ring optionally substituted by a substituent selected from substituent group B described below;

$R^2$ represents a substituent selected from substituent group A described below;

$R^3$ independently represents a substituent selected from substituent group B described below;

n represents an integer of 1 to 4;

substituent group A:

(i) an optionally substituted $C_{10-30}$ alkoxy group,
(ii) an optionally substituted $C_{10-30}$ alkyl group,
(iii) an optionally substituted $C_{10-30}$ alkylsulfanyl group,
(iv) an optionally substituted $C_{10-30}$ alkylsulfinyl group,
(v) an optionally substituted $C_{10-30}$ alkylsulfonyl group,
(vi) an optionally substituted $C_{10-30}$ alkylsiloxy group, and
(vii) an optionally substituted $C_{10-30}$ alkylsilyl group; and substituent group B.

(i) an optionally substituted $C_{1-30}$ alkoxy group,
(ii) a halogen atom,
(iii) an optionally substituted $C_{1-30}$ alkyl group,
(iv) a nitro group,
(v) an optionally substituted $C_{1-30}$ alkylsulfanyl group,
(vi) an optionally substituted $C_{1-30}$ alkylsulfinyl group,
(vii) an optionally substituted $C_{1-30}$ alkylsulfonyl group,
(viii) an optionally substituted $C_{1-30}$ alkylsiloxy group,
(ix) an optionally substituted $C_{1-30}$ alkylsilyl group,
(x) a cyano group,
(xi) an optionally substituted amino group,
(xii) an optionally substituted $C_{1-32}$ alkoxy-carbonyl group, and
(xiii) an optionally substituted $C_{1-32}$ alkyl-carbonyl group, or a salt thereof to produce a compound represented by the following formula (IV'):

[Formula 4]

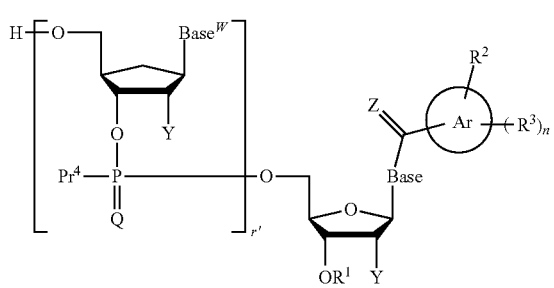

(IV')

wherein $R^1$, Base, Z, ring Ar, $R^2$, $R^3$, Q, r', and n are each as defined above;

Y is independently as defined above;

$Pr^4$ independently represents (i) a hydrogen atom, a protected hydroxy group, or a protected thiol group when Q is an oxygen atom and represents (ii) a protected hydroxy group when Q is a sulfur atom; and $Base^W$ independently represents thymine, adenine, guanine, cytosine, uracil, or a modified form thereof, or the following formula:

[Formula 5]

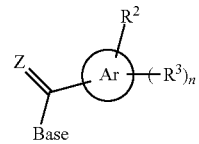

wherein Base, Z, ring Ar, $R^2$, $R^3$, and n are each independently as defined above, or a salt thereof; and step (b0):

using the compound represented by the formula (IV') or the salt thereof to produce the compound represented by the formula (II) or the salt thereof;

[7] a method for producing a compound represented by the following formula (II):

[Formula 6]

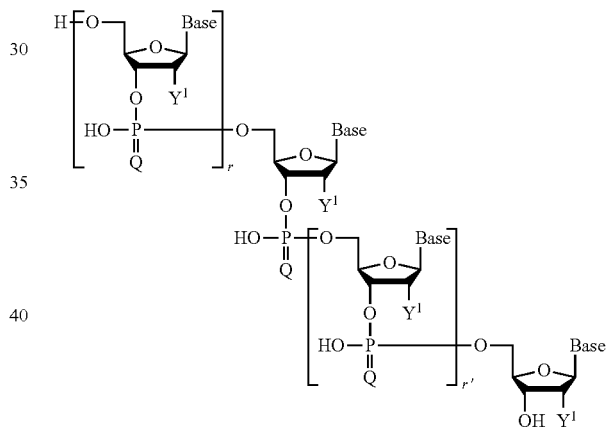

(II)

wherein

Base independently represents thymine, adenine, guanine, cytosine, uracil, or a modified form thereof;

$Y^1$ independently represents a hydroxy group, a hydrogen atom, an optionally substituted $C_{1-6}$ alkoxy group, or a halogen atom;

Q independently represents an oxygen atom or a sulfur atom; and r and r' each independently represent an integer of 0 to 100, or a salt thereof, the method comprising the following steps (a1), (b1), and (c1):

step (a1):

reacting a compound represented by the following formula (III):

[Formula 7]

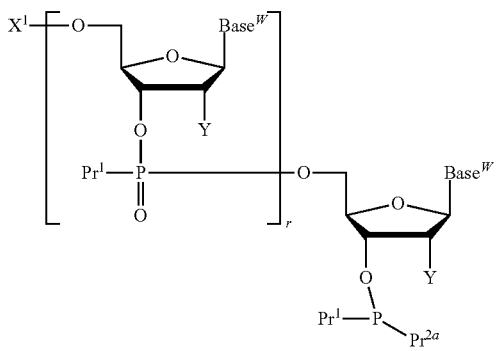

(III)

wherein $X^1$ represents a protective group for a hydroxy group;

$Pr^1$ independently represents a protected hydroxy group;

$Pr^{2a}$ represents a substituted amino, group;

$Base^W$ independently represents thymine, adenine, guanine, cytosine, uracil, or a modified form thereof, or the following formula:

[Formula 8]

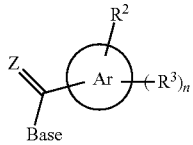

wherein

Z independently represents an oxygen atom or a sulfur atom;

ring Ar independently represents an aromatic hydrocarbon ring optionally substituted by a substituent selected from substituent group B described below;

$R^2$ independently a substituent selected from substituent group A described below;

$R^3$ independently represents a substituent selected from substituent group B described below;

n represents an integer of 1 to 4; and

Base is as defined above;

substituent group A:

(i) an optionally substituted $C_{10-30}$ alkoxy group, (ii) an optionally substituted $C_{10-30}$ alkyl group, (iii) an optionally substituted $C_{10-30}$ alkylsulfanyl group, (iv) an optionally substituted $C_{10-30}$ alkylsulfinyl group, (v) an optionally substituted $C_{10-30}$ alkylsulfonyl group, (vi) an optionally substituted $C_{10-30}$ alkylsiloxy group, and (vii) an optionally substituted $C_{10-30}$ alkylsilyl group; and substituent group B:

(i) an optionally substituted $C_{1-30}$ alkoxy group, (ii) a halogen atom, (iii) an optionally substituted $C_{1-30}$ alkyl group, (iv) a nitro group, (v) an optionally substituted $C_{1-30}$ alkylsulfanyl group, (vi) an optionally substituted $C_{1-30}$ alkylsulfinyl group, (vii) an optionally substituted $C_{1-30}$ alkylsulfonyl group, (viii) an optionally substituted $C_{1-30}$ alkylsiloxy group, (ix) an optionally substituted $C_{1-30}$ alkylsilyl group, (x) a cyano group, (xi) an optionally substituted amino group, (xii) an optionally substituted $C_{1-32}$ alkoxy-carbonyl group, and (xiii) an optionally substituted $C_{1-32}$ alkyl-carbonyl group;

Y represents an optionally protected hydroxy group, a hydrogen atom, an optionally substituted $C_{1-6}$ alkoxy group, or a halogen atom; and Q and r are as defined above, or a salt thereof with a compound represented by the following formula (IV):

[Formula 9]

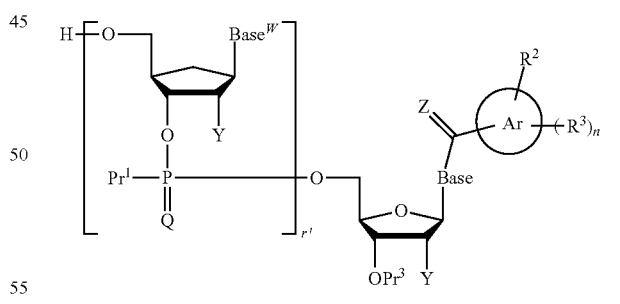

(IV)

wherein $Pr^3$ represents a protective group for a hydroxy group, and other symbols are as defined above, or a salt thereof in the presence of a coupling reagent for use in nucleic acid synthesis to produce a compound represented by the following formula (V):

[Formula 10]
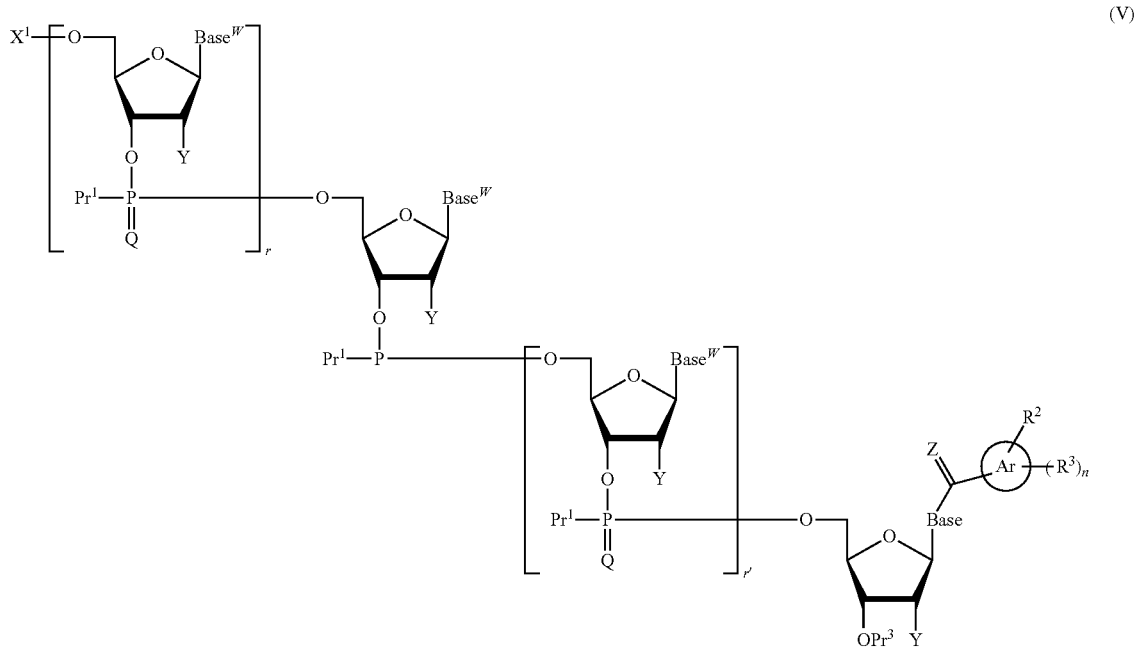
(V)
wherein each symbol is as defined above,
or a salt thereof;
step (b1):
subjecting the compound represented by the formula (V) or the salt thereof, which is produced in the step (a1), to oxidation reaction or sulfuration reaction to produce a compound represented by the following formula (VI):
[Formula 11]
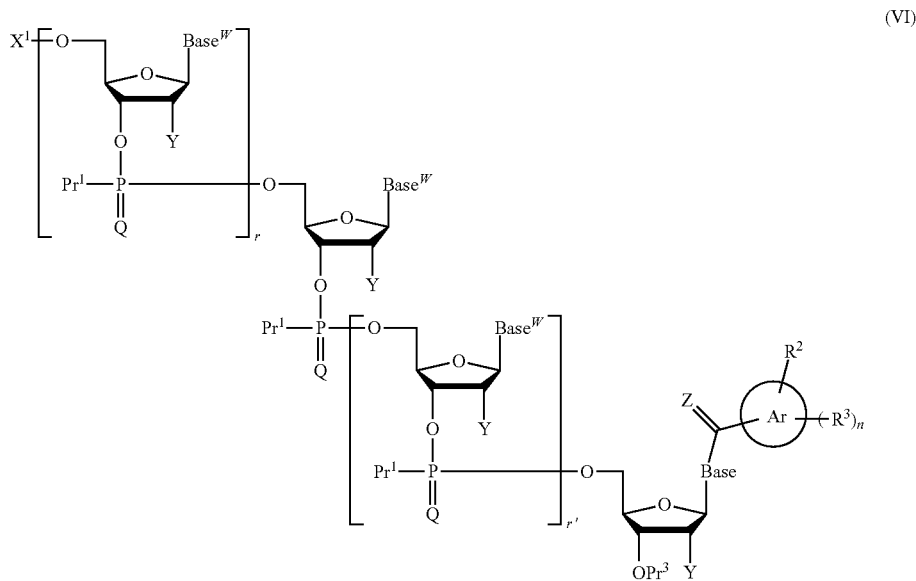
(VI)
wherein each symbol is as defined above,
or a salt thereof; and step (c1):
  subjecting the compound represented by the formula (VI) or the salt thereof, which is produced in the step (b1), to deprotection reaction;

[8] a method for producing a compound represented by the following formula (II):

[Formula 12]

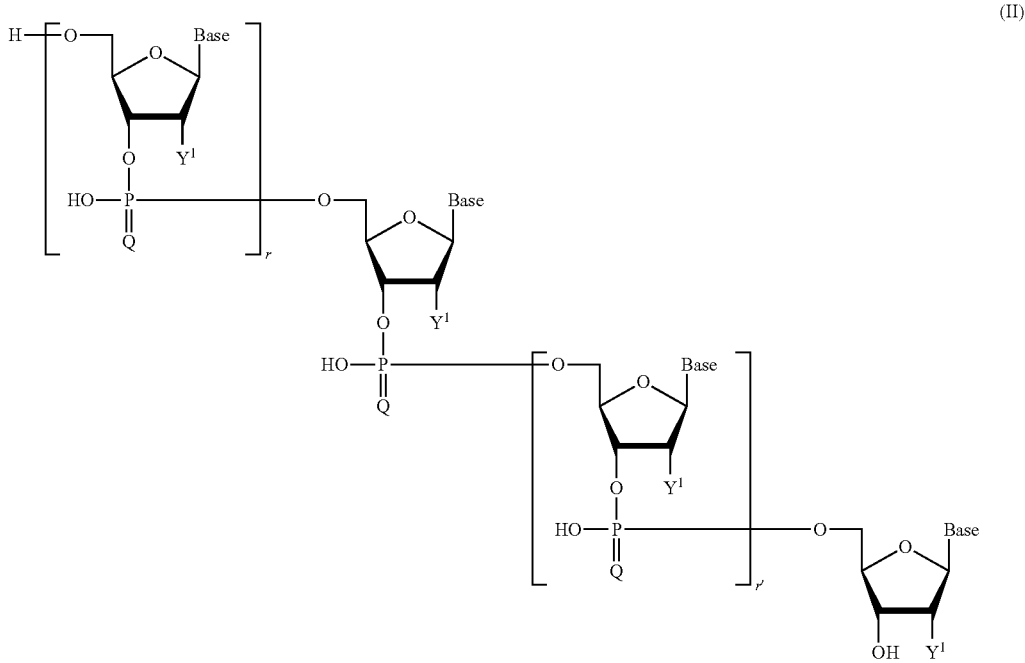

wherein
  Base independently represents thymine, adenine, guanine, cytosine, uracil, or a modified form thereof;
  $Y^1$ independently represents a hydroxy group, a hydrogen atom, an optionally substituted $C_{1-6}$ alkoxy group, or a halogen atom;
  Q independently represents an oxygen atom or a sulfur atom; and
  r and r' each independently represent an integer of 0 to 100,
or a salt thereof,
the method comprising the following steps (a2), (b2), and (c2):
step (a2):
  reacting a compound represented by the following formula (VII):

[Formula 13]

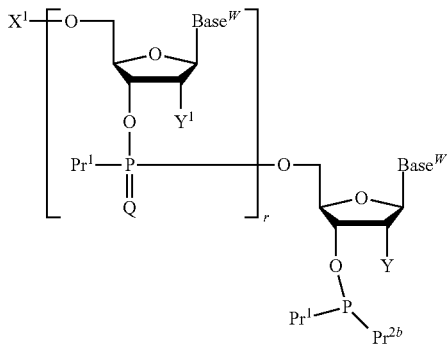

wherein
  $X^1$ represents a protective group for a hydroxy group;
  $Pr^1$ independently represents a protected hydroxy group;
  $Pr^{2b}$ represents a halogen atom;

$Base^W$ independently represents thymine, adenine, guanine, cytosine, uracil, or a modified form thereof, or the following formula:

[Formula 14]

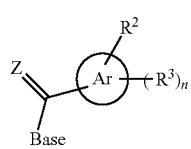

wherein
  Z independently represents an oxygen atom or a sulfur atom;
  ring Ar independently represents an aromatic hydrocarbon ring optionally substituted by a substituent selected from substituent group B described below;
  $R^2$ independently represents a substituent selected from substituent group A described below;
  $R^3$ independently represents a substituent selected from substituent group B described below;
  n represents an integer of 1 to 4;
  Base is as defined above;
  substituent group A:
  (i) an optionally substituted $C_{10-30}$ alkoxy group,
  (ii) an optionally substituted $C_{10-30}$ alkyl group,
  (iii) an optionally substituted $C_{10-30}$ alkylsulfanyl group,
  (iv) an optionally substituted $C_{10-30}$ alkylsulfinyl group,
  (v) an optionally substituted $C_{10-30}$ alkylsulfonyl group,
  (vi) an optionally substituted $C_{10-30}$ alkylsiloxy group, and (vii) an optionally substituted $C_{10-30}$ alkylsilyl group; and
substituent group B:
(i) an optionally substituted $C_{1-30}$ alkoxy group,
(ii) a halogen atom,
(iii) an optionally substituted $C_{1-30}$ alkyl group,
(iv) a nitro group,
(v) an optionally substituted $C_{1-30}$ alkylsulfanyl group,
(vi) an optionally substituted $C_{1-30}$ alkylsulfinyl group,
(vii) an optionally substituted $C_{1-30}$ alkylsulfonyl group,
(viii) an optionally substituted $C_{1-30}$ alkylsiloxy group,
(ix) an optionally substituted $C_{1-30}$ alkylsilyl group,
(x) a cyano group,
(xi) an optionally substituted amino group,
(xii) an optionally substituted $C_{1-32}$ alkoxy-carbonyl group, and
(xiii) an optionally substituted $C_{1-32}$ alkyl-carbonyl group; and Y represents an optionally protected hydroxy group, a hydrogen atom, an optionally substituted $C_{1-6}$ alkoxy group, or a halogen atom,
or a salt thereof with a compound represented by the following formula (IV):

[Formula 15]

$$\text{(IV)}$$

wherein $Pr^3$ represents a protective group for a hydroxy group, and other symbols are as defined above,
or a salt thereof to produce a compound represented by the following formula (V):

[Formula 16]

$$\text{(V)}$$

wherein each symbol is as defined above,
or a salt thereof;

step (b2):

subjecting the compound represented by the formula (V) or the salt thereof, which is produced in the step (a2), to oxidation reaction or sulfuration reaction to produce a compound represented by the following formula (VI):

[Formula 17]

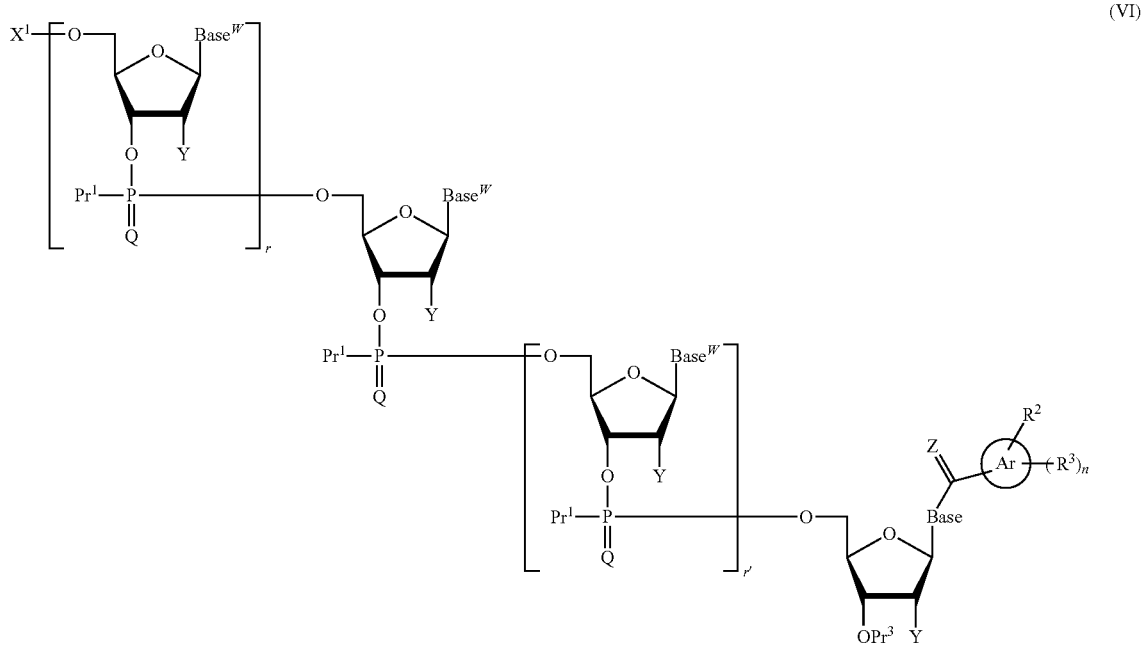

(VI)

wherein each symbol is as defined above, or a salt thereof; and step (c2):

subjecting the compound represented by the formula (VI) or the salt thereof, which is produced in the step (b2), to deprotection reaction; and

[9] a method for producing a compound represented by the following formula (II):

[Formula 18]

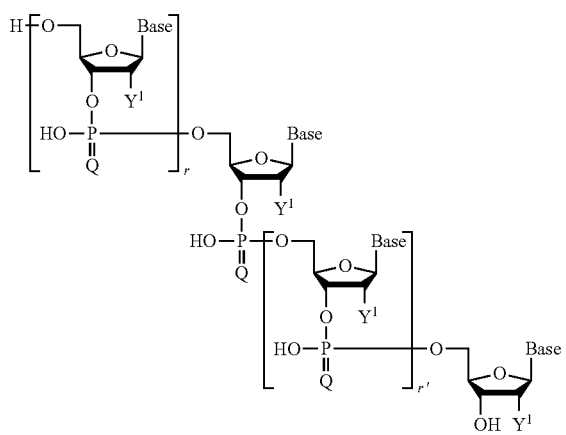

(II)

wherein

Base independently represents thymine, adenine, guanine, cytosine, uracil, or a modified form thereof;

$Y^1$ independently represents a hydroxy group, a hydrogen atom, an optionally substituted $C_{1-6}$ alkoxy group, or a halogen atom;

Q independently represents an oxygen atom or a sulfur atom; and r and r' each independently represent an integer of 0 to 100, or a salt thereof, the method comprising the following steps (a3), (b3), and (c3):

step (a3):

reacting a compound represented by the following formula (VIII):

[Formula 19]

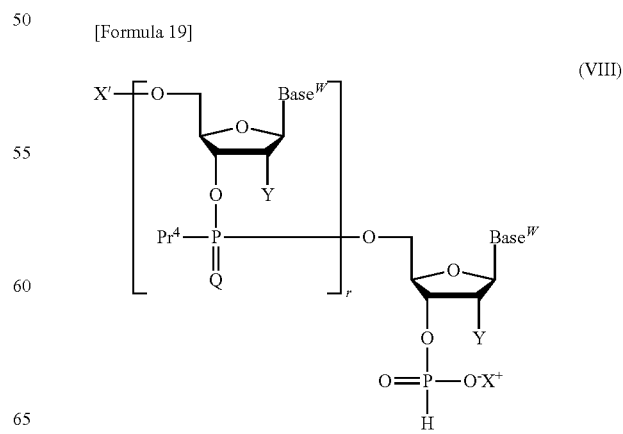

(VIII)

wherein

X$^+$ represents a cation;

X$^1$ represents a protective group for a hydroxy group;

Q independently represents an oxygen atom or a sulfur atom;

Pr$^4$ represents (i) a hydrogen atom, a protected hydroxy group, or a protected thiol group when Q is an oxygen atom and represents (ii) a protected hydroxy group when Q is a sulfur atom;

Base$^W$ independently represents thymine, adenine, guanine, cytosine, uracil, or a modified form thereof, or the following formula:

[Formula 20]

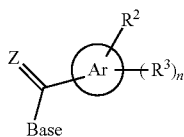

wherein

Z independently represents an oxygen atom or a sulfur atom;

ring Ar independently represents an aromatic hydrocarbon ring optionally substituted by a substituent selected from substituent group B described below;

R$^2$ independently represents a substituent selected from substituent group A described below;

R$^3$ independently represents a substituent selected from substituent group B described below;

n represents an integer of 1 to 4;

Base is as defined above;

substituent group A:
(i) an optionally substituted C$_{10-30}$ alkoxy group,
(ii) an optionally substituted C$_{10-30}$ alkyl group,
(iii) an optionally substituted C$_{10-30}$ alkylsulfanyl group,
(iv) an optionally substituted C$_{10-30}$ alkylsulfinyl group,
(v) an optionally substituted C$_{10-30}$ alkylsulfonyl group,
(vi) an optionally substituted C$_{10-30}$ alkylsiloxy group, and
(vii) an optionally substituted C$_{10-30}$ alkylsilyl group; and substituent group B:
(i) an optionally substituted C$_{1-30}$ alkoxy group,
(ii) a halogen atom,
(iii) an optionally substituted C$_{1-30}$ alkyl group,
(iv) a nitro group,
(v) an optionally substituted C$_{1-30}$ alkylsulfanyl group,
(vi) an optionally substituted C$_{1-30}$ alkylsulfinyl group,
(vii) an optionally substituted C$_{1-30}$ alkylsulfonyl group,
(viii) an optionally substituted C$_{1-30}$ alkylsiloxy group,
(ix) an optionally substituted C$_{1-30}$ alkylsilyl group,
(x) a cyano group,
(xi) an optionally substituted amino group,
(xii) an optionally substituted C$_{1-32}$ alkoxy-carbonyl group, and
(xiii) an optionally substituted C$_{1-32}$ alkyl-carbonyl group; and Y represents an optionally protected hydroxy group, a hydrogen atom, an optionally substituted C$_{1-6}$ alkoxy group, or a halogen atom, or a salt thereof with a compound represented by the following formula (IX):

[Formula 21]

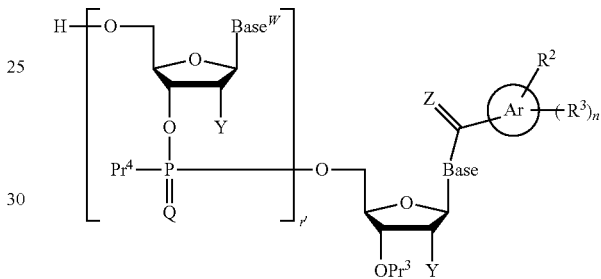

(IX)

wherein Pr$^3$ represents a protective group for a hydroxy group, and other symbols are as defined above, or a salt thereof in the presence of a coupling reagent for use in nucleic acid synthesis to produce a compound represented by the following formula (X):

[Formula 22]

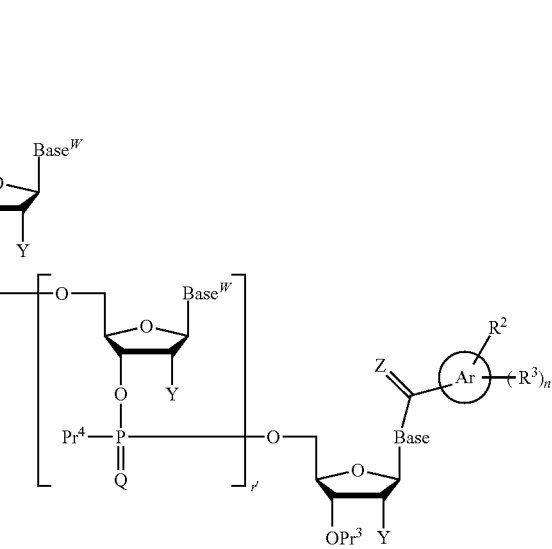

(X)

wherein each symbol is as defined above, or a salt thereof;

step (b3):

subjecting the compound represented by the formula (X) or the salt thereof, which is produced in the step (a3), to oxidation reaction or sulfuration reaction to produce a compound represented by the following formula (XI):

[Formula 23]

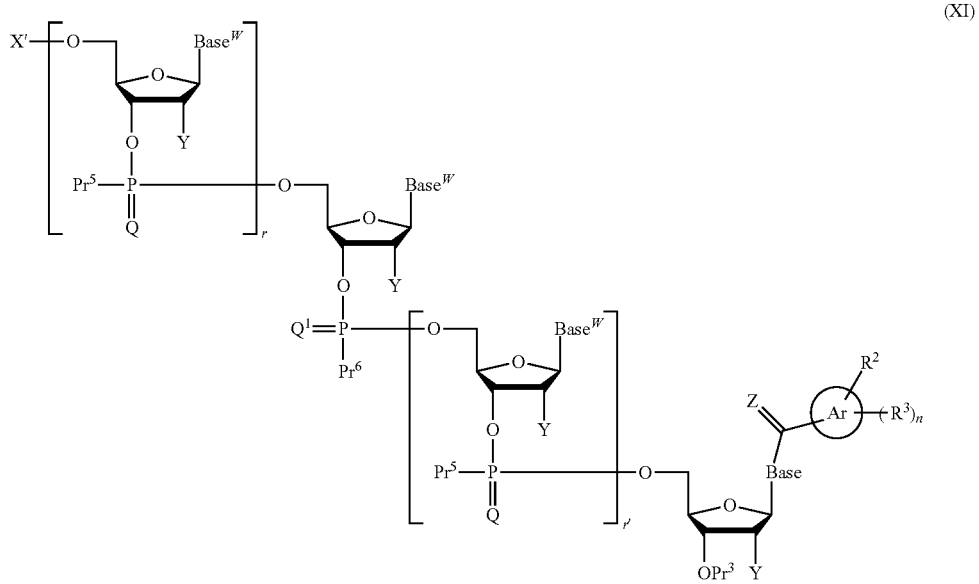

(XI)

wherein $Q^1$ represents an oxygen atom or a sulfur atom;

$Pr^5$ represents (i) an optionally protected hydroxy group or a protected thiol group when Q is an oxygen atom and represents (ii) a protected hydroxy group when Q is a sulfur atom;

$Pr^6$ represents (i) a hydroxy group or a protected thiol group when $Q^1$ is an oxygen atom and represents (ii) a hydroxy group when $Q^1$ is a sulfur atom; and other symbols are as defined above, or a salt thereof; and step (c3):

subjecting the compound represented by the formula (XI) or the salt thereof, which is produced in the step (b3), to deprotection reaction.

Advantageous Effects of Invention

According to the present invention, a novel nucleoside compound in which the base moiety of a nucleoside is substituted by (i) an aromatic hydrocarbon ring carbonyl group having at least one hydrophobic group or (ii) an aromatic hydrocarbon ring thiocarbonyl group having at least one hydrophobic group, etc. can be used as a synthetic unit to produce a nucleic acid oligomer. Use of the present invention can circumvent the need for column chromatography purification after every reaction. Also, use of the present invention can elongate bases both in a direction toward the 3' end and in a direction toward the 5' end. Use of the present invention can achieve the efficient large-scale synthesis of a nucleic acid oligomer by a liquid-phase synthesis method. The present invention is applicable to the production of nucleic acid oligomers such as siRNA, antisense nucleic acids, and vaccine adjuvants and is very useful in the fields of genomic drug discovery, genetic diagnosis or therapy, and the like.

DESCRIPTION OF EMBODIMENTS

Hereinafter, the novel nucleoside monomer compound of the present invention and a method for producing a nucleic acid oligomer using this compound will be described in detail.

The same symbols in the formulas used herein have the same meaning unless otherwise specified.

1. Novel Nucleoside Monomer Compound

The novel nucleoside monomer compound of the present invention is represented by the following formula (I):

[Formula 24]

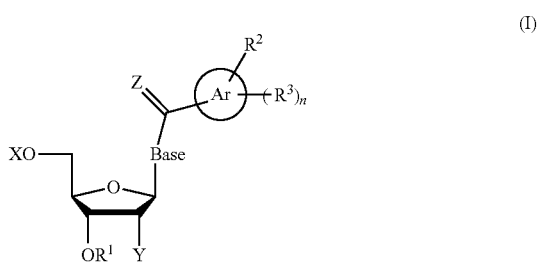

(I)

In the nucleoside monomer compound, the base moiety (Base) of a nucleoside is substituted by (i) an aromatic hydrocarbon ring (represented by Ar in the formula (I)) carbonyl group having at least one hydrophobic group or (ii) an aromatic hydrocarbon ring (represented by Ar in the formula (I)) thiocarbonyl group having at least one hydrophobic group.

X and $R^1$ each independently represent a hydrogen atom or a protective group for a hydroxy group.

The protective group for a hydroxy group can be any protective group usually used as a protective group for hydroxy groups in nucleic acids. Examples of such protective groups include: silyl-type protective groups such as trimethylsilyl (TMS), triethylsilyl, isopropyldimethylsilyl, t-butyldimethylsilyl (TBDMS), (triphenylmethyl)dimethylsilyl, t-butyldiphenylsilyl, methyldiisopropylsilyl, methyldi-t-butylsilyl, tribenzylsilyl, tri-p-xylylsilyl, triisopropylsilyl, and triphenylsilyl; trityl-type protective groups such as trityl, 4-methoxytrityl, and 4,4'-dimethoxytrityl (DMTr); heterocycle-type protective groups such as tetrahydropyranyl, 3-bromotetrahydropyranyl, tetrahydrothiopyranyl, 4-methoxytetrahydropyranyl, 4-methoxytetrahydrothiopyranyl, 4-methoxytetrahydrothiopyranyl S,S-dioxide, tetrahydrofuranyl, and tetrahydrothiofuranyl; benzyl-type protective groups such as benzyl, 4-methoxybenzyl, 2-nitrobenzyl, 4-nitrobenzyl, and 4-cyanobenzyl; aliphatic acyl-type protective groups such as acetyl, trichloroacetyl, trifluoroacetyl, butyryl, propionyl, pivaloyl, levulinyl, pentanoyl, valeryl, and octanoyl; aromatic acyl-type protective groups such as benzoyl, 2-fluorobenzoyl, 2,6-dichlorobenzoyl, 2-toluoyl, and 2,4,6-trimethylbenzoyl; and ether-type protective groups such as 2-(cyanoethoxy)ethyl (CEE) and cyanoethoxymethyl (CEM); and carbamoyl-type protective groups such as dimethyl carbamoyl and diphenylcarbamoyl.

For these protective groups for hydroxy groups, see, for example, Wuts et al., Protective Groups in Organic Synthesis, 4th Edition, 2006, John Wiley & Sons, Inc.

X is preferably a protective group for a hydroxy group, more preferably a trityl-type protective group, particularly preferably a DMTr group.

$R^1$ is preferably a hydrogen atom or an aliphatic acyl-type protective group, more preferably a hydrogen atom or a levulinyl group, particularly preferably a levulinyl group.

Y represents an optionally protected hydroxy group, a hydrogen atom, an optionally substituted $C_{1-6}$ alkoxy group, or a halogen atom.

The hydroxy group in the optionally protected hydroxy group represented by Y may be protected by the protective group for a hydroxy group.

Examples of the $C_{1-6}$ alkoxy group in the optionally substituted $C_{1-6}$ alkoxy group represented by Y include a methoxy group, an ethoxy group, and a propoxy group. The $C_{1-6}$ alkoxy group may be substituted by 1 to 3 substituents. Examples of such substituents include: halogen atoms such as fluorine, chlorine, bromine, and iodine; $C_{6-10}$ aryloxy groups (e.g., phenyloxy and naphthyloxy) each optionally substituted by 1 to 3 substituents selected from a halogen atom, a $C_{1-6}$ alkoxy group, and a cyano group; biphenyloxy; di-$C_{1-6}$ alkylamino groups (e.g., dimethylamino, diethylamino, and isobutylamino) each optionally substituted by 1 to 3 substitutents selected from a halogen atom, a $C_{1-6}$ alkoxy group, and a cyano group; and a cyano group.

Examples of the halogen atom represented by Y can include fluorine, chlorine, bromine, and iodine.

Y is preferably a protected hydroxy group (preferably, a hydroxy group protected with a trityl-type protective group or a hydroxy group protected with a silyl-type protective group), a hydrogen atom, or a $C_{1-6}$ alkoxy group (preferably, a methoxy group), more preferably a protected hydroxy group (preferably, a hydroxy group protected with a trityl-type protective group or a hydroxy group protected with a silyl-type protective group) or a hydrogen atom, particularly preferably a hydroxy group protected with TBDMS.

Base refers to the base moiety of a nucleoside and represents thymine, adenine, guanine, cytosine, uracil, or a modified form thereof. In this context, the modified form means a base moiety whose amino group is protected with a protective group for the amino group. In this context, the protective group for the amino group can be any protective group usually used as a protective group for amino groups in the base moieties of nucleic acids. Examples of such protective groups for amino groups include: aliphatic acyl groups (e.g., acetyl, propionyl, n-butyryl, and isobutyryl) each optionally substituted by 1 to 3 substituents selected from a halogen atom and a $C_{1-6}$ alkoxy group; aromatic acyl groups (e.g., benzoyl, 4-methylbenzoyl, and 4-methoxybenzoyl) each optionally substituted by 1 to 3 substituents selected from a halogen atom, a $C_{1-6}$ alkyl group, and a $C_{1-6}$ alkoxy group; $C_{7-12}$ aralkylacyl groups (e.g., phenylacetyl); $C_{6-10}$ aryloxy-acyl groups (e.g., phenoxyacetyl, 4-t-butyl-phenoxyacetyl, and 4-isopropylphenoxyacetyl) each optionally substituted by a $C_{1-6}$ alkyl group; ethyl groups having an electron-withdrawing group removable by P elimination (e.g., 2-cyanoethyl, 2-(p-nitrophenyl)ethyl, and 2-(benzenesulfonyl)ethyl); di-$C_{1-6}$ alkylaminomethylene groups (e.g., dimethylaminomethylene and dibutylaminomethylene); and $C_{1-6}$ alkoxy-carbonyl groups having an electron-withdrawing group removable by P elimination (e.g., 2-cyanoethoxycarbonyl, 2-(p-nitrophenyl)ethoxycarbonyl, and 2-(benzenesulfonyl)ethoxycarbonyl).

Base is preferably thymine, adenine, guanine, cytosine, or uracil, more preferably thymine, cytosine, or uracil, further preferably thymine or uracil.

Z represents an oxygen atom or a sulfur atom.

Z is preferably an oxygen atom.

Ring Ar represents an aromatic hydrocarbon ring optionally substituted by a substituent selected from substituent group B, in addition to $R^2$ and $R^3$. In this context, examples of the aromatic hydrocarbon ring can include rings corresponding to $C_{6-10}$ aryl groups such as phenyl and naphthyl (i.e., $C_{6-10}$ arene).

Substituent group B consists of:

(i) an optionally substituted $C_{1-30}$ alkoxy group, preferably a $C_{1-30}$ alkoxy group (e.g., methyloxy, ethyloxy, n- or iso-propyloxy, n-, iso-, sec-, or t-butyloxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, icosyloxy, henicosyloxy, docosyloxy, or triacontyloxy) optionally substituted by 1 to 3 substituents selected from a $C_{1-6}$ alkoxy group, a $C_{6-10}$ aryl group, a $C_{6-10}$ aryloxy group, a halogen atom, a di-Cu alkylamino group, a cyano group, and the like;

(ii) a halogen atom such as fluorine, chlorine, or bromine;

(iii) an optionally substituted $C_{1-30}$ alkyl group, preferably a $C_{1-30}$ alkyl group (e.g., methyl, ethyl, n- or iso-propyl, n-, iso-, sec-, or t-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, or triacontyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(iv) a nitro group;

(v) an optionally substituted $C_{1-30}$ alkylsulfanyl group, preferably a $C_{1-30}$ alkylsulfanyl group (e.g., methylsulfanyl, ethylsulfanyl, n- or iso-propylsulfanyl, n-, iso-, sec-, or t-butylsulfanyl, pentylsulfanyl, hexylsulfanyl, heptylsulfanyl, octylsulfanyl, nonylsulfanyl, decylsulfanyl, undecylsulfanyl, dodecylsulfanyl, tridecylsulfanyl, tetradecylsulfanyl, pentadecylsulfanyl, hexadecylsulfanyl, heptadecylsulfanyl, octadecylsulfanyl, nonadecylsulfanyl, icosylsulfanyl, henicosylsulfanyl, docosylsulfanyl, or triacontylsulfanyl)

optionally substituted by 1 to 3 substituents selected from a alkoxy group, a $C_{1-6}$ aryl group, a $C_{6-10}$ aryloxy group, a $C_{6-10}$ aryloxy group, a halogen atom, a di-$C_{1-6}$ alkylamino group, a cyano group, and the like;

(vi) an optionally substituted $C_{1-30}$ alkylsulfinyl group, preferably a $C_{1-30}$ alkylsulfinyl group (e.g., methylsulfinyl, ethylsulfinyl, n- or iso-propylsulfinyl, n-, iso-, sec-, or t-butylsulfinyl, pentylsulfinyl, hexylsulfinyl, heptylsulfinyl, octylsulfinyl, nonylsulfinyl, decylsulfinyl, undecylsulfinyl, dodecylsulfinyl, tridecylsulfinyl, tetradecylsulfinyl, pentadecylsulfinyl, hexadecylsulfinyl, heptadecylsulfinyl, octadecylsulfinyl, nonadecylsulfinyl, icosylsulfinyl, henicosylsulfinyl, docosylsulfinyl, or triacontylsulfinyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(vii) an optionally substituted $C_{1-30}$ alkylsulfonyl group, preferably a $C_{1-30}$ alkylsulfonyl group (e.g., methylsulfonyl, ethylsulfonyl, n- or iso-propylsulfonyl, n-, iso-, sec-, ort-butylsulfonyl, pentylsulfonyl, hexylsulfonyl, heptylsulfonyl, octylsulfonyl, nonylsulfonyl, decylsulfonyl, undecylsulfonyl, dodecylsulfonyl, tridecylsulfonyl, tetradecylsulfonyl, pentadecylsulfonyl, hexadecylsulfonyl, heptadecylsulfonyl, octadecylsulfonyl, nonadecylsulfonyl, icosylsulfonyl, henicosylsulfonyl, docosylsulfonyl, or triacontylsulfonyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(viii) an optionally substituted $C_{1-30}$ alkylsiloxy group, preferably a $C_{1-30}$ alkylsiloxy group (e.g., trimethylsiloxy, triethylsiloxy, tri n- or iso-propylsiloxy, dimethyl n-, iso-, sec-, or t-butylsiloxy, dimethylpentylsiloxy, dimethylhexylsiloxy, dimethylheptylsiloxy, dimethyloctylsiloxy, dimethylnonylsiloxy, dimethyldecylsiloxy, dimethylundecylsiloxy, dimethyldodecylsiloxy, dimethyltridecylsiloxy, dimethyltetradecylsiloxy, dimethylpentadecylsiloxy, dimethylhexadecylsiloxy, dimethylheptadecylsiloxy, dimethyloctadecylsiloxy, dimethylnonadecylsiloxy, dimethylicosylsiloxy, dimethylhenicosylsiloxy, dimethyldocosylsiloxy, dimethyltriacontylsiloxy, tridecylsiloxy, triundecylsiloxy, tridodecylsiloxy, tritridecylsiloxy, tritetradecylsiloxy, tripentadecylsiloxy, trihexadecylsiloxy, triheptadecylsiloxy, trioctadecylsiloxy, trinonadecylsiloxy, triicosylsiloxy, trihenicosylsiloxy, tridocosylsiloxy, or tritriacontylsiloxy) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(ix) an optionally substituted $C_{1-30}$ alkylsilyl group, preferably a $C_{1-30}$ alkylsilyl group (e.g., trimethylsilyl, triethylsilyl, tripropylsilyl, dimethyl-t-butylsilyl, dimethylpentylsilyl, dimethylhexylsilyl, dimethylheptylsilyl, dimethyloctylsilyl, dimethylnonylsilyl, dimethyldecylsilyl, dimethylundecylsilyl, dimethyldodecylsilyl, dimethyltridecylsilyl, dimethyltetradecylsilyl, dimethylpentadecylsilyl, dirnethylhexadecylsilyl, dimethylheptadecylsilyl, dimethyloctadecylsilyl, dimethylnonadecylsilyl, dimethylicosylsilyl, dimethylhenicosylsilyl, dimethyldocosylsilyl, dimethyltriacontylsilyl, tridecylsilyl, triundecylsilyl, tridodecylsilyl, tritridecylsilyl, tritetradecylsilyl, tripentadecylsilyl, trihexadecylsilyl, triheptadecylsilyl, trioctadecylsilyl, trinonadecylsilyl, triicosylsilyl, trihenicosylsilyl, tridocosylsilyl, or tritriacotitylsilyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(x) a cyano group;

(xi) an optionally substituted amino group, preferably an amino group optionally mono- or di-substituted by a $C_{1-30}$ alkyl group;

(xii) an optionally substituted $C_{1-32}$ alkoxy-carbonyl group, preferably a $C_{1-32}$ alkoxy-carbonyl group (e.g., methyloxycarbonyl, ethyloxycarbonyl, n- or iso-propyloxycarbonyl, n-, iso-, sec-, or t-butyloxycarbonyl, pentyloxycarbonyl, hexyloxycarbonyl, heptyloxycarbonyl, octyloxycarbonyl, nonyloxycarbonyl, decyloxycarbonyl, undecyloxycarbonyl, dodecyloxycarbonyl, tridecyloxycarbonyl, tetradecyloxycarbonyl, pentadecyloxycarbonyl, hexadecyloxycarbonyl, heptadecyloxycarbonyl, octadecyloxycarbonyl, nonadecyloxycarbonyl, icosyloxycarbonyl, henicosyloxycarbonyl, docosyloxycarbonyl, or triacontyloxycarbonyl) optionally substituted by 1 to 3 substituents selected from a alkoxy group, a $C_{6-10}$ aryl group, a $C_{6-10}$ aryloxy group, a halogen atom, a di-$C_{1-6}$ alkylamino group, a cyano group, and the like; and (xiii) an optionally substituted $C_{1-32}$ alkyl-carbonyl group, preferably a $C_{1-32}$ alkyl-carbonyl group (e.g., methylcarbonyl, ethylcarbonyl, n- or iso-propylcarbonyl, n-, iso-, sec-, or t-butylcarbonyl, pentylcarbonyl, hexylcarbonyl, hexylcarbonyl, octylcarbonyl, nonylcarbonyl, decylcarbonyl, undecylcarbonyl, dodecylcarbonyl, tridecylcarbonyl, tetradecylcarbonyl, pentadecylcarbonyl, hexadecylcarbonyl, heptadecylcarbonyl, octadecylcarbonyl, nonadecylcarbonyl, icosylcarbonyl, henicosylcarbonyl, docosylcarbonyl, or triacontylcarbonyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like.

Ring Ar is preferably a $C_{6-10}$ aromatic hydrocarbon ring (arene) optionally substituted by a substituent selected from substituent group B, more preferably $C_{6-10}$ arene, particularly preferably a benzene ring.

$R^2$ represents a substituent selected from substituent group A. In this context, substituent group A consists of:

(i) an optionally substituted $C_{10-30}$ alkoxy group, preferably a $C_{10-30}$ alkoxy group (e.g., decyloxy, undecyloxy, dodecyloxy, tridecyloxy, tetradecyloxy, pentadecyloxy, hexadecyloxy, heptadecyloxy, octadecyloxy, nonadecyloxy, icosyloxy, henicosyloxy, docosyloxy, or triacontyloxy) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(ii) an optionally substituted $C_{10-30}$ alkyl group, preferably a $C_{10-30}$ alkyl group (e.g., decyl, undecyl, dodecyl, tridecyl, tetradecyl, pentadecyl, hexadecyl, heptadecyl, octadecyl, nonadecyl, icosyl, henicosyl, docosyl, or triacontyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(iii) an optionally substituted $C_{10-30}$ alkylsulfanyl group, preferably a $C_{10-30}$ alkylsulfanyl group (e.g., decylsulfanyl, undecylsulfanyl, dodecylsulfanyl, tridecylsulfanyl, tetradecylsulfanyl, pentadecylsulfanyl, hexadecylsulfanyl, heptadecylsulfanyl, octadecylsulfanyl, nonadecylsulfanyl, icosylsulfanyl, henicosyl sulfanyl, docosylsulfanyl, or triacontylsulfanyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(iv) an optionally substituted $C_{10-30}$ alkylsulfinyl group, preferably a $C_{10-30}$ alkylsulfinyl group (e.g., decylsulfinyl, undecylsulfinyl, dodecylsulfinyl, tridecylsulfinyl, tetradecylsulfinyl, pentadecylsulfinyl, hexadecylsulfinyl, heptadecylsulfinyl, octadecylsulfinyl, nonadecylsulfinyl, icosylsulfinyl, henicosylsulfinyl, docosylsulfinyl, or triacontylsulfinyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(v) an optionally substituted $C_{10-30}$ alkylsulfonyl group, preferably a $C_{10-30}$ alkylsulfonyl group (e.g., decylsulfonyl, undecylsulfonyl, dodecylsulfonyl, tridecylsulfonyl, tetradecylsulfonyl, pentadecylsulfonyl, hexadecylsulfonyl, heptadecylsulfonyl, octadecylsulfonyl, nonadecylsulfonyl, icosylsulfonyl, henicosylsulfonyl, docosylsulfonyl, or triacontylsulfonyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like;

(vi) an optionally substituted $C_{10-30}$ alkylsiloxy group, preferably a $C_{10-30}$ alkylsiloxy group (e.g., dimethyldecylsiloxy, dimethylundecylsiloxy, dimethyldodecylsiloxy, dimethyltridecylsiloxy, dimethyltetradecylsiloxy, dimethylpentadecylsiloxy, dimethylhexadecylsiloxy, dimethylheptadecylsiloxy, dimethyloctadecylsiloxy, dimethylnonadecylsiloxy, dimethylicosylsiloxy, dimethylhenicosylsiloxy, dimethyldocosylsiloxy, dimethyltriacontylsiloxy, tridecylsiloxy, triundecylsiloxy, tridodecylsiloxy, tritridecylsiloxy, tritetradecylsiloxy, tripentadecylsiloxy, trihexadecylsiloxy, triheptadecylsiloxy, trioctadecylsiloxy, trinonadecylsiloxy, triicosylsiloxy, trihenicosylsiloxy, tridocosylsiloxy, or tritriacontylsiloxy) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like; and (vii) an optionally substituted $C_{10-30}$ alkylsilyl group preferably a $C_{10-30}$ alkylsilyl group (e.g., dimethyldecylsilyl, dimethylundecylsilyl, dimethyldodecylsilyl, dimethyltridecylsilyl, dimethyltetradecylsilyl, dimethylpentadecylsilyl, dimethylhexadecylsilyl, dimethylheptadecylsilyl, dimethyloctadecylsilyl, dimethylnonadecylsilyl, dimethylicosylsilyl, dimethylhenicosylsilyl, dimethyldocosylsilyl, dimethyltriacontylsilyl, tridecylsilyl, triundecylsilyl, tridodecylsilyl, tritridecylsilyl, tritetradecylsilyl, tripentadecylsilyl, trihexadecylsilyl, triheptadecylsilyl, trioctadecylsilyl, trinonadecylsilyl, triicosylsilyl, trihenicosylsilyl, tridocosylsilyl, or tritriacontylsilyl) optionally substituted by 1 to 3 substituents selected from a $C_{1-6}$ alkoxy group, a $C_{6-10}$ aryl group, a $C_{6-10}$ aryloxy group, a halogen atom, a di-$C_{1-6}$ alkylamino group, a cyano group, and the like.

$R^2$ is preferably an optionally substituted $C_{10-30}$ alkoxy group, more preferably a docosyloxy group, an icosyloxy group, an octadecyloxy group, a hexadecyloxy group, or a tetradecyloxy group, further preferably an octadecyloxy group or a tetradecyloxy group.

$R^3$ independently represents a substituent selected from substituent group B described above.

$R^3$ is preferably a halogen atom or an optionally substituted $C_{1-30}$ alkoxy group preferably a halogen atom, a docosyloxy group, an icosyloxy group, an octadecyloxy group, a hexadecyloxy group, or a tetradecyloxy group, further preferably a fluorine atom, an octadecyloxy group, or a tetradecyloxy group.

According to another preferred aspect, examples of $R^3$ include optionally substituted $C_{10-30}$ alkoxy groups (preferably, a docosyloxy group, an icosyloxy group, an octadecyloxy group, a hexadecyloxy group, and a tetradecyloxy group).

n represents an integer of 1 to 4.

n is preferably an integer of 1 to 3, more preferably 1 or 2.

Preferred specific examples of the novel nucleoside monomer of the present invention include the following:

a compound represented by the formula (I) wherein

X is a protective group for a hydroxy group (preferably, a trityl-type protective group (particularly, a DMTr group));

$R^1$ is a hydrogen atom or an aliphatic acyl-type protective group (preferably, a levulinyl group);

Y is an optionally protected hydroxy group (preferably, a hydroxy group protected with a trityl-type protective group or a hydroxy group protected with a silyl-type protective group (more preferably a hydroxy group protected with TBDMS)), a hydrogen atom, or an optionally substituted $C_{1-6}$ alkoxy group (preferably, methoxy);

Base is thymine, adenine, guanine, cytosine, or uracil (preferably, thymine, cytosine, or uracil);

Z is an oxygen atom;

ring Ar is $C_{6-10}$ arene (preferably, a benzene ring);

$R^2$ is an optionally substituted $C_{10-30}$ alkoxy group (preferably, a docosyloxy group, an icosyloxy group, an octadecyloxy group, a hexadecyloxy group, or a tetradecyloxy group);

$R^3$ is independently a halogen atom or an optionally substituted $C_{1-30}$ alkoxy group (e.g., a docosyloxy group, an icosyloxy group, an octadecyloxy group, a hexadecyloxy group, or a tetradecyloxy group); and n is 1 or 2, or a salt thereof.

The compound represented by the formula (I) of the present invention may be in the form of a salt thereof. Examples of such salts include, inorganic acid salts such as sulfate, nitrate, perchlorate, phosphate, carbonate, bicarbonate, hydrofluoride, hydrochloride, hydrobromide, and hydroiodide; organic carboxylic acid salts such as acetate, oxalate, maleate, tartrate, fumarate, and citrate; organic sulfonic acid salts such as methanesulfonate, trifluoromethanesulfonate, ethanesulfonate, benzenesulfonate, toluenesulfonate, and camphor sulfonate; amino acid salts such as aspartate and glutamate; quaternary amine salts; alkali metal salts such as sodium salt and potassium salt; and alkaline earth metal salts such as magnesium salt and calcium salt.

Hereinafter, methods for producing the compounds represented by the formulas (I) and (II) of the present invention will be described.

Starting materials or production intermediates for reactions given below may each be a salt. Examples of such salts include those exemplified above as the salt of the compound represented by the formula (I) of the present invention.

When a starting compound used in each reaction given below has an amino group, a carboxyl group, a hydroxy group, or a hydroxy group as a substituent, a protective group generally used may be introduced in these groups. In this case, the protective group can be removed, if necessary, after the reaction to obtain the compound of interest.

For example, a formyl group, or a $C_{1-6}$ alkyl-carbonyl group (e.g., acetyl or ethylcarbonyl), a phenylcarbonyl group, a $C_{1-6}$ alkyloxy-carbonyl group (e.g., methoxycarbonyl, ethoxycarbonyl, or tert-butoxycarbonyl (Boc)), an allyloxycarbonyl (Alloc) group, a phenyloxycarbonyl group, a fluorenylmethoxycarbonyl (Fmoc) group, a $C_{7-10}$ alkyl-carbonyl group (e.g., benzylcarbonyl), a $C_{7-10}$ aralkyl-oxycarbonyl group (e.g., benzyloxycarbonyl (Z)), a $C_{7-10}$ aralkyl group (e.g., benzyl), a 2-(trimethylsiiyl)ethoxymethyl (SEM) group, a trityl group, a phthaloyl group, or a N,N-dimethylaminomethylene group optionally having a substituent is used as a protective group for the amino group. A phenyl group, a halogen atom (e.g., a fluorine atom, a chlorine atom, a bromine atom, or an iodine atom), a $C_{1-6}$ alkyl-carbonyl group (e.g., methylcarbonyl, ethylcarbonyl, or butylcarbonyl), a nitro group, or the like is used as a substituent for these protective groups. The number of substituents is on the order of 1 to 3.

For example, a $C_{1-6}$ alkyl group (e.g., methyl, ethyl, n-propyl, isopropyl, n-butyl, or tert-butyl), an allyl group, a benzyl group, a phenyl group, a trityl group, or a trialkylsilyl group optionally having a substituent is used as a protective group for the carboxyl group. A halogen atom (e.g., a fluorine atom, a chlorine atom, a bromine atom, or an iodine atom), a formyl group, a $C_{1-6}$ alkyl-carbonyl group (e.g., acetyl, ethylcarbonyl, or butylcarbonyl), a nitro group, or the like is used as a substituent for these protective groups. The number of substituents is on the order of 1 to 3.

For example, a $C_{1-6}$ alkyl group (e.g., methyl, ethyl, n-propyl, isopropyl, n-butyl, or tert-butyl), a $C_{7-10}$ aralkyl group (e.g., benzyl), a formyl group, a $C_{1-6}$ alkyl-carbonyl group (e.g., acetyl or ethylcarbonyl), a benzoyl group, a $C_{7-10}$ aralkyl-carbonyl group (e.g., benzylcarbonyl), a tetrahydropyranyl group, a furanyl group, or a silyl group optionally having a substituent is used as a protective group for a hydroxy group. A halogen atom (e.g., a fluorine atom, a chlorine atom, a bromine atom, or an iodine atom), a $C_{1-6}$ alkyl group (e.g., methyl, ethyl, or n-propyl), a phenyl group, a $C_{7-10}$ aralkyl group (e.g., benzyl), a $C_{1-6}$ alkoxy group (e.g., methoxy, ethoxy, or n-propoxy), a nitro group, or the like is used as a substituent for these protective groups. The number of substituents is on the order of 1 to 4.

These protective groups can be introduced or removed according to a method known per se in the art, for example, a method described in "Protective Groups in Organic Synthesis, 4th Ed." (Wuts et al.) Wiley-Interscience (John Wiley & Sons, Inc.), 2006.

The novel nucleoside monomer compound of the present invention can be produced, for example, by reacting a compound represented by the following formula (a):

[Formula 25]

wherein each symbol is as defined above
with a compound represented by the following formula (b):

[Formula 26]

wherein G represents a leaving group, and other symbols are as defined above.

Examples of the leaving group represented by G in the formula (b) include: halogen atoms; $C_{1-6}$ acyloxy groups such as acetyloxy, propionyloxy, and butyryloxy; optionally halogenated $C_{1-6}$ alkylsulfonyloxy groups such as trifluoromethanesulfonyloxy; $C_{6-10}$ arylsulfonyloxy groups such as phenylsulfonyloxy; and an azolyl group. The compound of the formula (a) can be produced through a reaction known per se in the art from a nucleoside compound known in the art or a commercially available nucleoside compound. Also, the compound of the formula (b) can be produced by a method known per se in the art (e.g., a method of subjecting a compound of the formula (b) wherein G is OH to halogenation reaction).

The reaction of the compound of the formula (a) with the compound of the formula (b) can be carried out, for example, at 0° C. to 100° C. for 5 minutes to 72 hours in a solvent that does not inhibit the reaction, such as pyridine, N,N-dimethylformamide, 1,3-dimethyl-2-imidazolidinone, acetone, methylene chloride, chloroform, dioxane, acetonitrile, benzene, toluene, diethyl ether, tetrahydrofuran, or t-butyl methyl ether. This reaction may be carried out in the presence of, for example, an organic base such as triethylamine, tributylamine, N,N'-diisopropylethylamine, or 1,8-diazabicyclo[5.4.0]-7-undecene; an inorganic base such as sodium hydroxide, potassium hydroxide, sodium bicarbonate, sodium carbonate, cesium carbonate, or cesium fluoride; an organic metal compound such as n-butyllithium, lithium diisopropylamide, or (diethylamino)lithium; or a reaction accelerator such as chlorotrimethylsilane or chlorotriethylsilane.

The compound represented by the formula (I) or the salt thereof also encompasses a compound or a salt thereof labeled with a radioisotope (e.g., $^3H$, $^{14}C$, $^{35}S$, or $^{125}I$) or the like.

In addition, the compound represented by the formula (I) or the salt thereof also encompasses a deuterium conversion form in which $^1H$ is converted to $^2H(D)$.

The compound represented by the formula (I) or the salt thereof further encompasses solvates (e.g., hydrates) and non-solvates (e.g., non-hydrates).

The compound represented by the formula (I) or the salt thereof can be used in a coupling reaction with a nucleic acid monomer or a nucleic acid oligomer. Use of the compound represented by the formula (I) or the salt thereof can circumvent the need for column chromatography purification after every reaction and enables a product of the aforementioned reaction to be easily purified. By thus circumventing the need for column chromatography purification after every reaction, a purified product can be recovered at an excellent yield. In addition, use of the compound represented by the formula (I) or the salt thereof permits base elongation both in a direction toward the 3' end and in a direction toward the 5' end. Furthermore, a liquid-phase synthesis method using the compound represented by the formula (I) or the salt thereof can achieve the efficient large-scale synthesis of a nucleic acid oligomer. In the coupling reaction, at least one compound represented by the formula (I) or salt thereof can be used, though the number thereof is not limited.

A compound of the formula (I) wherein one of $R^2$ and $R^3$ is a sulfanyl group, a sulfinyl group, a sulfonyl group, a siloxy group, or a silyl group can be produced in the same way as in the compound represented by the formula (I) and also used in the coupling reaction with a nucleic acid monomer or a nucleic acid oligomer.

2. Production of Nucleic Acid Oligomer

The novel nucleoside monomer compound of the present invention can be used to produce a nucleic acid oligomer. Examples of such nucleic acid oligomers include a compound represented by the following formula (II):

[Formula 27]

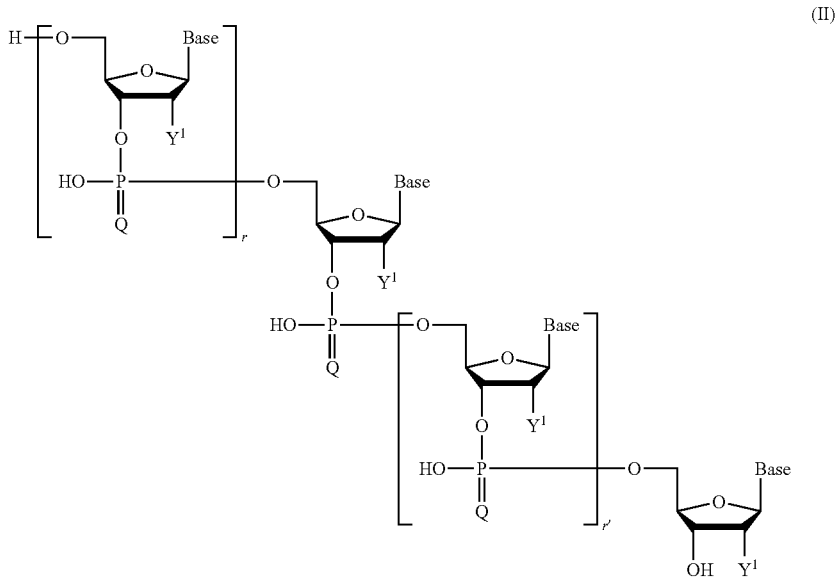

(II)

wherein each symbol is as defined above,
or a salt thereof. In the formula (II), $Y^1$ in each constituent unit independently represents a hydrogen atom, a hydroxy group, an optionally substituted $C_{1-6}$ alkoxy group, or a halogen atom. Examples of the $C_{1-6}$ alkoxy group in the optionally substituted $C_{1-6}$ alkoxy group represented by $Y^1$ include those exemplified above as Y.

$Y^1$ is preferably a hydrogen atom or a hydroxy group.

Q is preferably an oxygen atom or a sulfur atom.

Each of r and r' is an integer of 0 to 100, preferably an integer of 0 to 3.

The compound represented by the formula (II) or the salt thereof can be produced by the following steps (a0) and (b0):

1) Step (a0):

A compound represented by the following formula (I):

[Formula 28]

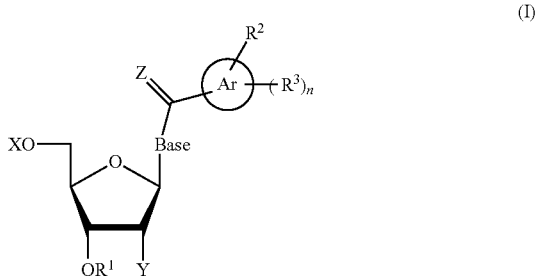

(I)

wherein each symbol is as defined above,
or a salt thereof is used to produce a compound represented by the following formula (IV'):

[Formula 29]

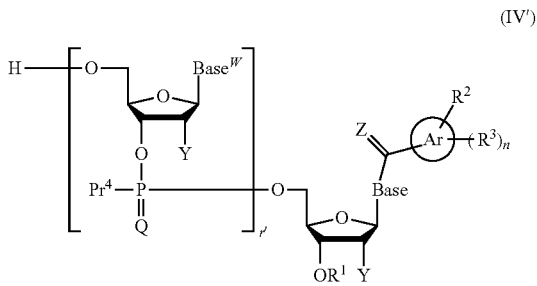

(IV')

wherein each symbol is as defined above,
or a salt thereof. In the formula (IV'), $Pr^4$ independently represents (i) a hydrogen atom, a protected hydroxy group, or a protected thiol group when Q is an oxygen atom and represents (ii) a protected hydroxy group when Q is a sulfur atom.

In this context, examples of the protective group in the protected hydroxy group or the protected thiol group represented by $Pr^4$ include: $C_{1-6}$ alkyl groups such as methyl, ethyl, n-propyl, isopropyl, n-butyl, isobutyl, s-butyl, t-butyl, pentyl, and isopentyl; cyanated $C_{1-6}$ alkyl groups such as 2-cyanoethyl and 2-cyano-1,1-dimethylethyl; an ethyl group substituted by a substituted silyl group (e.g., 2-methyldiphenylsilylethyl, 2-trimethylsilylethyl, and 2-triphenylsilylethyl); halogenated $C_{1-6}$ alkyl groups such as 2,2,2-trichloroethyl, 2,2,2-tribromoethyl, and 2,2,2-trifluoroethyl; $C_{2-6}$ alkenyl groups such as ethenyl, 1-propenyl, 2-propenyl, 1-methyl-2-propenyl, and 1-methyl-1-propenyl; $C_{3-6}$ cycloalkyl groups such as cyclopropyl, cyclobutyl, cyclopentyl, and cyclohexyl; cyanated $C_{1-6}$ alkenyl groups (e.g., 2-cyanobutenyl) each optionally substituted by 1 to 3 substituents selected from a $C_{1-6}$ alkyl group, a halogen atom, and a nitro group; $C_{7-11}$ aralkyl groups such as benzyl, α-naphthylmethyl, and β-naphthylmethyl; and $C_{6-10}$ aryl groups (e.g., phenyl, indenyl, and naphthyl) each optionally substituted by 1 to 3 substituents selected from a $C_{1-6}$ alkyl group, a halogen atom, and a nitro group.

Preferred examples of $Pr^4$ include a hydroxy group protected with a cyanated $C_{1-6}$ alkyl group (particularly preferably, 2-cyanoethyl).

In the formula (IV'), preferably, Q represents an oxygen atom, and $Pr^4$ represents a hydrogen atom, a protected hydroxy group, or a protected thiol group (particularly preferably, a hydroxy group protected with 2-cyanoethyl).

$Base^W$ independently represents thymine, adenine, guanine, cytosine, uracil, or a modified form thereof, or a compound represented by the following formula:

[Formula 30]

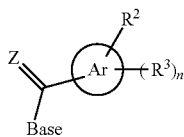

wherein each symbol is as defined above,
or a salt thereof.

In this context, examples of the modified form include those exemplified above as Base.

In the step (a0), the novel nucleoside monomer compound of the present invention is coupled with another one as starting materials by a phosphoramidite method, a method using a dihalophosphine derivative, an H-phosphonate method, or the like to form a dimer, which is then subjected, if necessary, to oxidation reaction or sulfuration reaction. Then, similar coupling is further repeated. Alternatively, oligomers (e.g., dimers or trimers) are coupled and subjected, if necessary, to oxidation reaction or sulfuration reaction. These coupling reactions are repeated in appropriate combination. Subsequently, the resulting coupling product is subjected to oxidation reaction or sulfuration reaction. Finally, the 5'-terminal nucleoside moiety can be converted to a 5-OH form through deprotection reaction to produce the compound represented by the formula (IV') or the salt thereof. These production methods will be described later in detail with reference to an exemplary method such as the phosphoramidite method, the method using a dihalophosphine derivative, or the H-phosphonate method.

2) Step (b0):

In the step (b0), the compound represented by the formula (IV') or the salt thereof, which has been produced in the step (a0), is further coupled with the novel nucleoside monomer compound of the present invention or an oligomer (e.g., a dimer or a trimer) thereof by the phosphoramidite method, the method using a dihalophosphine derivative, the H-phosphonate method, or the like. The coupling product is subjected, if necessary, to oxidation reaction or sulfuration reaction. Similar coupling and optional oxidation reaction or sulfuration reaction are performed. Finally, the substituent moiety represented by the following formula (c):

[Formula 31]

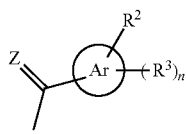

(c)

wherein each symbol is as defined above in the base moiety of each nucleoside in the obtained nucleic acid oligomer or the protective group of the base moiety is removed, and the protected hydroxy group of each nucleoside is converted, if necessary, to a free form through deprotection reaction. In this way, the compound represented by the formula (II) or the salt thereof can be produced. These production methods will be described later in detail with reference to an exemplary method such as the phosphoramidite method, the method using a dihalophosphine derivative, or the H-phosphonate method.

3. Production of Nucleic Acid Oligomer by Phosphoramidite Method

Steps (a1), (b1), and (c1) described below can be carried out by the phosphoramidite method using the novel nucleoside monomer compound of the present invention to produce the compound represented by the formula (II) or the salt thereof. For the production of a nucleic acid oligomer by the phosphoramidite method, see, for example, 5th Edition Jikken Kagaku Koza (Encyclopedia of Experimental Chemistry in English) 16, Organic Compound IV, The Chemical Society of Japan, ed., 2010, p. 377-381.

1) Step (a1):

In the step (a1), a compound represented by the following formula (III):

[Formula 32]

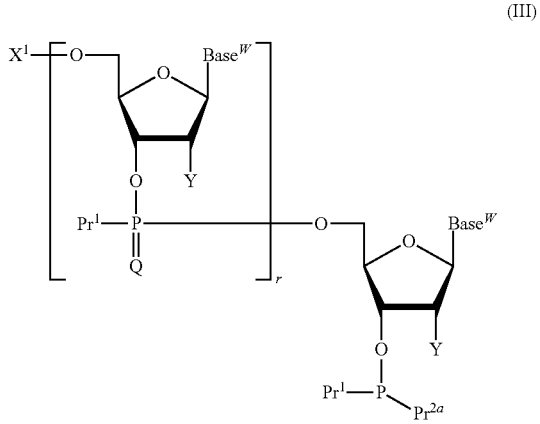

(III)

wherein each symbol is as defined above,
or a salt thereof is reacted with a compound represented by the following formula (IV):

[Formula 33]

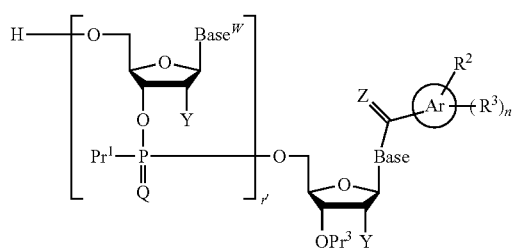

(IV)

wherein each symbol is as defined above,
or a salt thereof in the presence of a coupling reagent for use in nucleic acid synthesis to produce a compound represented by the following formula (V):

[Formula 34]

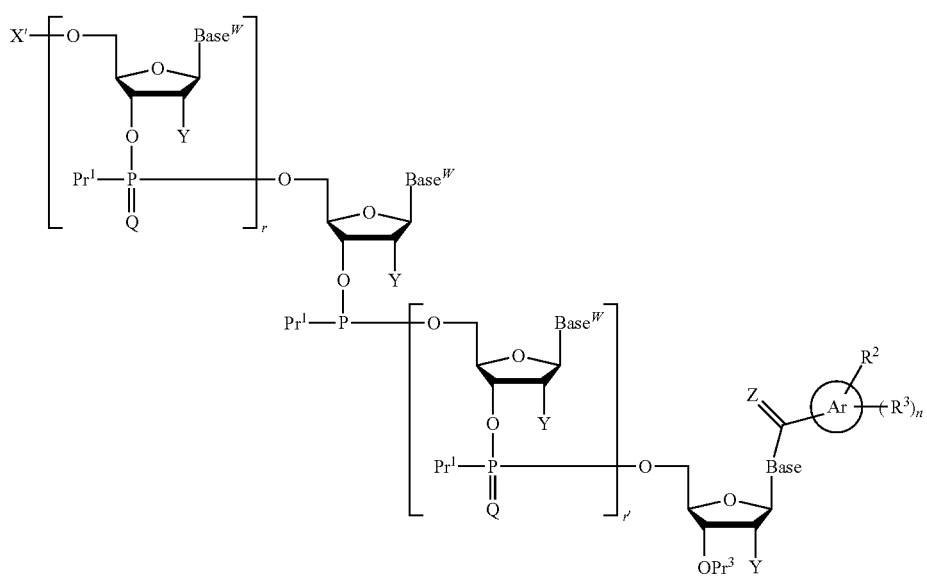

(V)

wherein each symbol is as defined above,
or a salt thereof.

In the formula (III), $X^1$ represents a protective group for a hydroxy group. Examples of this protective group for a hydroxy group include the same protective groups as those exemplified above as the protective group for a hydroxy group represented by X and $R^1$.
$X^1$ is preferably a trityl-type protective group, particularly preferably DMTr.

$Pr^1$ in each constituent unit independently represents a protected hydroxy group. Examples of this protective group for a hydroxy group include the same protective groups as those exemplified above as the protective group for a hydroxy group represented by $Pr^4$. $Pr^1$ is preferably a hydroxy group protected with a cyanated $C_{1-6}$ alkyl group, more preferably a hydroxy group protected with 2-cyanoethyl.

$Pr^{2a}$ represents a substituted amino group. The amino group may be mono- or di-substituted by a substituent. Examples of such substituents can include $C_{1-6}$ alkyl groups such as methyl, ethyl, n-propyl, isopropyl, n-butyl, t-butyl, pentyl, and hexyl. Preferred examples of $Pr^{2a}$ can include dimethylamino, diethylamino, dipropylamino, diisopropylamino, and dibutylamino (particularly preferably, diisopropylamino). Also, the substituted amino group represented by $Pr^{2a}$ includes cyclic amino groups such as morpholinyl and pyrrolidinyl.

$Pr^3$ represents a protective group for a hydroxy group. Examples of this protective group for a hydroxy group include the same protective groups as those exemplified above as the protective group for a hydroxy group represented by X and $R^1$. $Pr^3$ is preferably an aliphatic acyl-type protective group, particularly preferably a levulinyl group.

The compound represented by the formula (III) or the salt thereof is obtained by reacting a compound represented by the following formula (d):

[Formula 35]

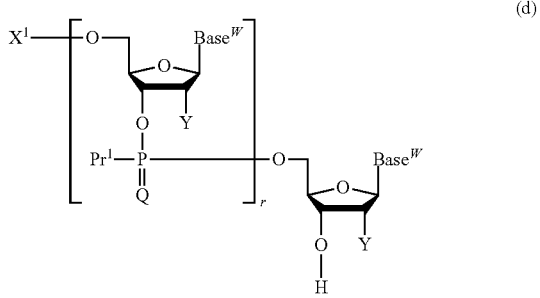

(d)

wherein $X^1$, $Pr^1$, Q, $Base^W$, Y, and r are each as defined above,
or a salt thereof with a compound represented by the following formula (e):

[Formula 36]

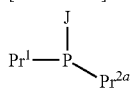
(e)

wherein J represents a leaving group, and $Pr^1$ and $Pr^{2a}$ are each as defined above,
or a salt thereof. Examples of the leaving group represented by J include the leaving groups exemplified above as G as well as an amino group optionally substituted by a $C_{1-6}$ alkyl group (e.g., diisopropylamino). The reaction of the compound represented by the formula (d) or the salt thereof with the compound represented by the formula (e) or the salt thereof can be carried out, for example, out at 0° C. to 100° C. for 5 minutes to 72 hours in a solvent that does not inhibit the reaction, such as N,N-dimethylformamide, acetone, methylene chloride, chloroform, dioxane, acetonitrile, benzene, toluene, tetrahydrofuran, or tert-butyl methyl ether. This reaction may be carried out in the presence of, for example, an organic base such as 2,6-lutidine, collidine, pyridine, triethylamine, tributylamine, or 1,8-diazabicyclo[5.4.0]-7-undecene; an inorganic base such as sodium hydroxide, potassium hydroxide, cesium carbonate, or cesium fluoride; an organic metal base such as n-butyllithium, lithium diisopropylamide, or (diethylamino)lithium; or a reaction accelerator such as 1-methylimidazole.

In the case of a compound of the formula (IV) wherein r' is 0 or a salt thereof, the novel nucleoside monomer compound of the present invention wherein X is a hydrogen atom can be used directly. A compound of the formula (IV) wherein r' is 1 or a salt thereof is obtained by subjecting the novel nucleoside monomer compound of the present invention wherein X is a hydrogen atom and a compound of the formula (III) wherein r is 0 or a salt thereof to the step (a1) described below. Likewise, a compound of the formula (IV) wherein r' is 2 or larger or a salt thereof can also be produced by repeating the step (a1).

Examples of the "coupling reagent for use in nucleic acid synthesis", which is used in the step (a1), can include coupling reagents usually used in the phosphoramidite method. For example, 1H-tetrazole, diisopropyl ammonium tetrazole, 5-(ethylthio)-1H-tetrazole, 5-benzylmercapto-1H-tetrazole, 4,5-dicyanoimidazole, 4,5-dichloroimidazole, hydroxybenzotriazole, 1-hydroxy-6-nitrobenzotriazole, or imidazolinium triflate can be used. The compound of the formula (III) or the salt thereof and the compound of the formula (IV) or the salt thereof can be coupled with each other through a reaction using this coupling reagent at −70° C. to 80° C., preferably −50° C. to 50° C., for 10 minutes to 24 hours in an appropriate organic solvent, for example, alkylnitrile such as acetonitrile, propionitrile, or butyronitrile; alkane halide such as methylene chloride, dichloromethane, 1,1-dichloroethane, 1,2-dichloroethane, or trichloroethane; ether such as tetrahydrofuran, dioxane, or dimethoxyethane; dimethylformamide; or toluene. In the present invention, this coupling reaction can be carried out in a liquid phase. By this coupling reaction, the phosphoramidite group introduced in 3'-OH of the 3'-terminal nucleoside moiety of the compound of the formula (III) or the salt thereof can be reacted with 5'-OH of the 5'-terminal nucleoside moiety of the compound of the formula (IV) or the salt thereof to obtain the compound of the formula (V) or the salt thereof.

The compound of the formula (V) or the salt thereof has, in its molecule, the hydrophobic group-containing structural moiety represented by the formula (c) and can therefore be separated after the reaction in a liquid phase, for example, by use of its solubility in a solvent, without column chromatography purification. For example, the compound of the formula (V) or the salt thereof can be separated by the concentration of the solvent after the reaction and suction filtration.

2) Step (b1):

In the step (b1), the compound of the formula (V) or the salt thereof obtained in the step (a1) is subjected to oxidation reaction or sulfuration reaction to produce a compound represented by the following formula (VI):

[Formula 37]

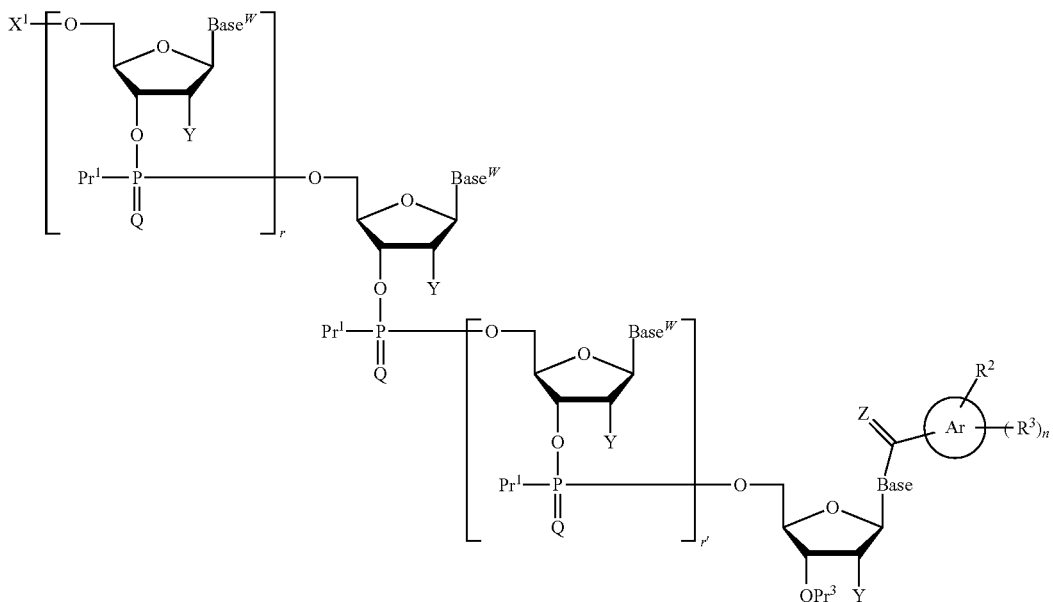
(VI)

wherein each symbol is as defined above, or a salt thereof.

For the oxidation reaction, oxidation reaction usually used in nucleic acid synthesis can be adopted. Examples of the oxidation reaction include oxidation reaction that is performed in a solution containing an oxidizing agent [e.g., a single halogen atom such as chlorine, bromine, or iodine (particularly preferably, iodine); peroxide such as t-butyl hydroperoxide, bis(trimethylsilyl) peroxide, 1,1-dihydroperoxycyclododecane (JP 2008-100976 A), or m-chloroperbenzoic acid; hydrogen peroxide water, 10-(camphor sulfonyl)oxaziridine (M. Manaoharan. Y. Lu et al., Org. Lett., 2, 243 (2000)), or dinitrogen tetraoxide] dissolved at a concentration of 0.01 M to 2 M in a single solvent such as pyridine, water, acetonitrile, or tetrahydrofuran or any mixed solvent thereof.

For the sulfuration reaction, sulfuration reaction usually used in the synthesis of modified nucleic acids having phosphorothioate bonds can be adopted. Examples of the sulfuration reaction include sulfuration reaction using a pyridine suspension of sulfur, a 2,6-lutidine suspension of sulfur, a collidine suspension of sulfur, a carbon disulfide solution of sulfur, tetraethylthiuram disulfide (TETD) (H. Vu et al., Tetrahedron Lett., 32, 3005-3008 (1991), a Beauge reagent (R. P. Lyer et al., J. Am. Chem. Soc, 112, 1253-1254 (1990), a Lawesson's reagent, or phenylacetyl disulfide. In such sulfuration reaction, a solvent that does not inhibit the reaction, for example, N,N-dimethylformamide, toluene, dichloromethane, chloroform, 2,4,6-trimethylpyridine, 2,6-lutidine, pyridine, N-methylpyrrolidone, acetone, tetrahydrofuran, or acetonitrile may be used. The sulfuration reaction can be carried out, for example, by stirring the reaction solution at −80° C. to 100° C., preferably −10° C. to 50° C., for a time on the order of 5 minutes to 24 hours.

By this oxidation reaction or sulfuration reaction, a compound of the formula (VI) having a pentavalent phosphoric acid triester bond or a salt thereof is obtained. When partially unreacted 5'-OH forms of the compound of the formula (IV) or the salt thereof in the step (a1) remain after the oxidation reaction or the sulfuration reaction, the obtained solution may be subjected, if necessary, to capping reaction. The capping reaction can be carried out by a usual method using an acetic anhydride/4-dimethylaminopyridine or acetic anhydride/lutidine/N-methylimidazole acylating agent as a capping agent.

3) Step (c1):

In the step (c1), the compound of the formula (VI) or the salt thereof obtained in the step (b1) is subjected to deprotection reaction to obtain the compound of the formula (II) of interest or the salt thereof. By this deprotection reaction, the protective groups for the hydroxy groups represented by $X^1$, $Pr^1$, and $Pr^3$ in the compound of the formula (VI) or the salt thereof are eliminated. Also, when Y is a protective group for a hydroxy group, the protective group for a hydroxy group represented by Y is eliminated. When $Base^W$ represents the following formula:

[Formula 38]

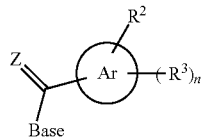

wherein each symbol is as defined above the aromatic hydrocarbon ring (Ar) carbonyl or thiocarbonyl group having at least one hydrophobic group (—$R^2$ and —$R^3$) bound with Base is eliminated. Likewise, the carbonyl or thiocarbonyl group bound with the 3'-terminal nucleoside moiety is eliminated. When Base is a modified form of thymine, adenine, guanine, cytosine, or uracil, i.e., thymine, adenine, guanine, cytosine, or uracil having a protected amino group, the protective group for this amino group is also eliminated.

For the deprotection reaction, deprotection reaction used in usual nucleic acid synthesis can be adopted. For example, a solution containing an alkaline aqueous solution such as concentrated ammonia water, an aqueous methylamine solution, an aqueous ethylamine solution, an aqueous dimethylamine solution, an aqueous diethylamine solution, an aqueous sodium hydroxide solution, or an aqueous potassium carbonate solution mixed with an organic solvent that does not inhibit the reaction, for example, ethanol, methanol, or isopropyl alcohol, at any ratio; for example, a solution containing an organic base such as methylamine, t-butylamine, triethylamine, N,N-diisopropylethylamine, or 1,8-diazabicyclo[5.4.0]undec-7-ene dissolved in a solvent that does not inhibit the reaction, for example, a single solvent such as ethanol, methanol, isopropyl alcohol, acetonitrile, dimethyl sulfoxide, or tetrahydrofuran or a mixed solvent thereof at any ratio; or a solution containing tetrabutylammonium fluoride, tetrabutylammonium fluoride-acetic acid, hydrogen fluoride-pyridine, triethylamine-hydrogen trifluoride, trifluoroacetic acid, dichloroacetic acid, trichloroacetic acid, or the like dissolved in an organic solvent that does not inhibit the reaction, for example, dichloromethane, chloroform, 1,2-dichlorbethane, acetonitrile, tetrahydrofuran, or dimethyl sulfoxide can be used as a deprotecting agent.

In this way, the compound of the formula (II) of interest or the salt thereof can be produced by the phosphoramidite method. In the present invention, as described above, since a synthetic intermediate used in each step has the structural moiety having a hydrophobic group, each synthesized compound can be separated after the reaction in a liquid phase, for example, by use of its solubility in a solvent, by extraction or filtration operation without column chromatography purification. For example, the synthesized compound can be separated by the concentration of the solvent after the reaction and suction filtration.

4 Production of Nucleic Acid Oligomer Using Dihalophosphine Derivative

Steps (a2), (b2), and (c2) described below can be carried out by the method using a dihalophosphine derivative and using the novel nucleoside monomer compound of the present invention to produce the compound of the formula (II) or the salt thereof. For the production of a nucleic acid oligomer using the dihalophosphine derivative, see, for example, 4th Edition Jikken Kagaku Koza (Encyclopedia of Experimental Chemistry in English) 22, Metal Complex/Transition Metal Cluster, The Chemical Society of Japan, ed., 1999, p. 426-431.

1) Step (a2):

In the step (a2), a compound represented by the following formula (VII):

[Formula 39]

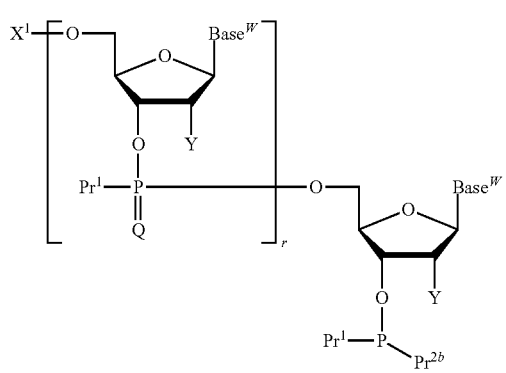

wherein Pr$^{2b}$ represents a halogen atom, and other symbols are as defined above, or a salt thereof is reacted with a compound represented by the following formula (IV):

[Formula 40]

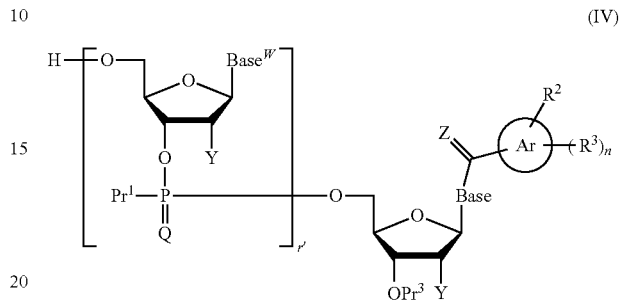

wherein each symbol is as defined above, or a salt thereof to produce a compound represented by the following formula (V):

[Formula 41]

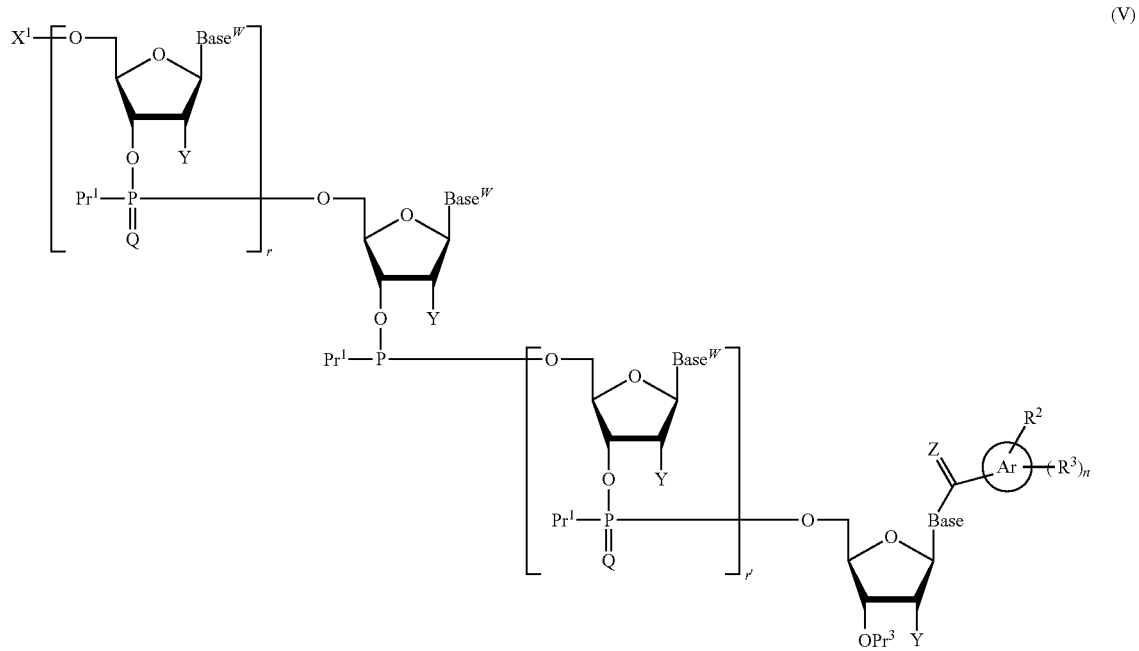

wherein each symbol is as defined above, or a salt thereof.

In the formula (VII), $Pr^{2b}$ represents a halogen atom such as fluorine, chlorine, bromine, or iodine.

The compound of the formula (VII) or the salt thereof is obtained by reacting a compound represented by the following formula (d):

[Formula 42]

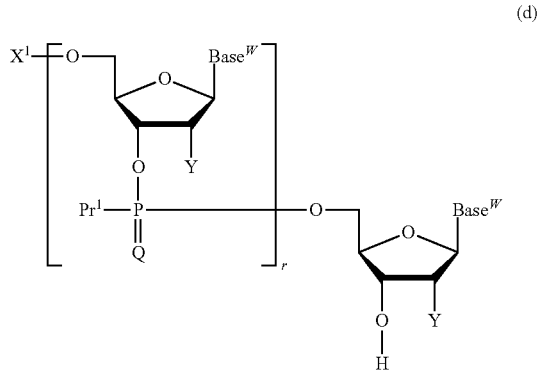

(d)

wherein $X^1$, $Pr^1$, Q, $Base^W$, Y, and r are each as defined above, or a salt thereof with a phosphitylating agent represented by the following formula (f):

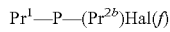

[Formula 43]

wherein Hal represents a halogen atom, and $Pr^1$ and $Pr^{2b}$ are each as defined above. Examples of the halogen atom represented by Hal in the formula (f) include chlorine. The halogen atom represented by $Pr^{2b}$ is preferably chlorine. Examples of the phosphitylating agent include 2-cyanoethyl=phosphorodichloridite, methyl=phosphorodichloridite, 2,2,2-trichloroethyl=phosphorodichloridite, 2,2,2-trichloro-1,1-dimethylethyl=phosphorodichloridite, allyl=phosphorodichloridite, and 2-chlorophenyl=phosphorodichloridite.

The reaction of the compound of the formula (d) or the salt thereof with the phosphitylating agent represented by the formula (f) may be carried out in the presence of a reaction accelerator such as collidine or 2,6-lutidine. The reaction of the compound of the formula (d) or the salt thereof with the phosphitylating agent represented by the formula (f) can be carried out, for example, at −78° C. to 50° C. for 5 minutes to 72 hours in the presence of collidine or 2,6-lutidine in a solvent that does not inhibit the reaction, such as tetrahydrofuran, N,N-dimethylformamide, acetone, chloroform, dichloromethane, dioxane, t-butyl methyl ether, acetonitrile, benzene, or toluene.

The reaction of the compound of the formula (VII) or the salt thereof thus obtained with the compound of the formula (IV) or the salt thereof can usually be carried out subsequently to the aforementioned reaction of the compound of the formula (d) or the salt thereof with the phosphitylating agent represented by the formula (f) and achieved by continuing the reaction by the addition of the compound of the formula (IV) or the salt thereof.

By this reaction of the compound of the formula (d) or the salt thereof with the phosphitylating agent of the formula (f) (e.g., a dihalophosphine derivative such as methyl=phosphorodichloridite or 2,2,2-trichloroethyl=phosphorodichloridite) and the subsequent reaction of the obtained compound of the formula (VET) or salt thereof with the compound of the formula (IV) or the salt thereof, the phosphite group introduced in 3'-OH of the 3'-terminal nucleoside moiety of the compound of the formula (VII) or the salt thereof can be bound to 5'-OH of the 5-terminal nucleoside moiety of the compound of the formula (IV) or the salt thereof to obtain the compound of the formula (V) or the salt thereof.

As described in the production of a nucleic acid oligomer by the phosphoramidite method, the compound of the formula (V) or the salt thereof has, in its molecule, the hydrophobic group-containing structural moiety represented by the formula (c) and can therefore be separated after the reaction in a liquid phase, for example, by use of its solubility in a solvent, without column chromatography purification. For example, the compound of the formula (V) or the salt thereof can be separated by the concentration of the solvent after the reaction and suction filtration. Also, the compound of the formula (V) or the salt thereof may be subjected to the next step (b2) without isolation.

2) Step (b2):

In the step (b2), the compound of the formula (V) or the salt thereof obtained in the step (a2) is subjected to oxidation reaction or sulfuration reaction in the same way as in the step (b1) of the phosphoramidite method to produce the compound of the formula (VI) or the salt thereof. The oxidation reaction, the sulfuration reaction, and subsequent optional capping reaction can be performed in the same way as the methods described above in the step (b1) of the phosphoramidite method.

3) Step (c2):

In the step (c2), the compound of the formula (VI) or the salt thereof obtained in the step (b2) is subjected to deprotection reaction in the same way as in the step (c1) of the phosphoramidite method to produce the compound of the formula (II) of interest or the salt thereof. The deprotection reaction can be performed in the same way as the method described above in the step (c1) of the phosphoramidite method.

In this way, the compound of the formula (II) of interest or the salt thereof can be produced by the method using a dihalophosphine derivative. Also in the method using a dihalophosphine derivative, as described above, since a synthetic intermediate used in each step has the structural moiety having a hydrophobic group, each synthesized compound can be separated after the reaction in a liquid phase without column chromatography purification. For example, the synthesized compound can be separated by the concentration of the solvent after the reaction and suction filtration.

5. Production of Nucleic Acid Oligomer Using H-Phosphonate Method

Steps (a3), (b3), and (c3) described below can be carried out by a method using the novel nucleoside monomer compound of the present invention and the H-phosphonate method to produce the compound of the formula (II) or the salt thereof.

First, the H-phosphonate method using the novel nucleoside monomer compound of the present invention will be summarized below with reference to a schematic reaction scheme.

As shown in reaction scheme 1 below, the H-phosphonate method involves coupling H-phosphonate of compound 1 with 5-OH of compound 2 in the presence of a coupling reagent such as pivaloyl chloride to bind the nucleic acid monomer or nucleic acid oligomer units through the H-phosphonate structure.

Reaction scheme 1

[Formula 44]

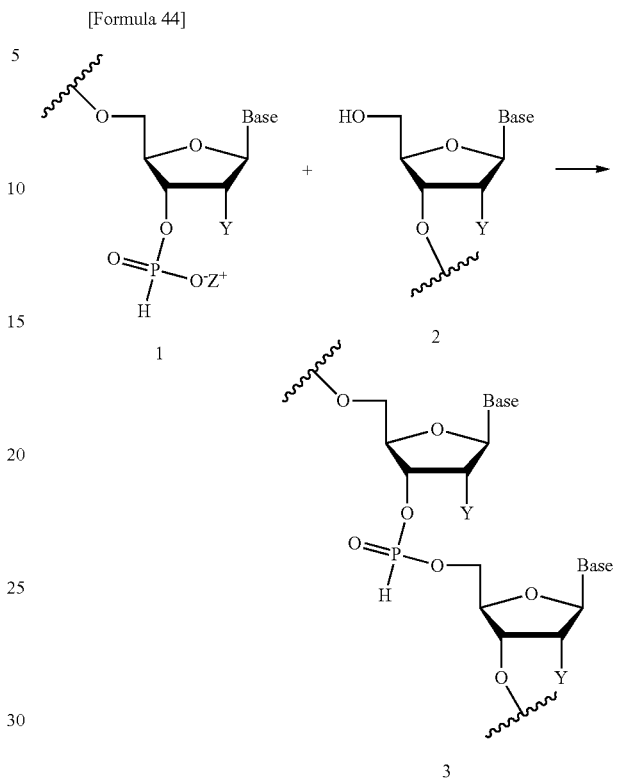

wherein each symbol is as defined above.

As shown in reaction scheme 2, compound 3 thus obtained is derivatized into phosphoric acid ester or thiophosphoric acid ester. Specifically, compound 3 can be derivatized into compound 4 by direct oxidation using an oxidizing agent such as iodine. Alternatively, compound 4 can be induced from sulfurated compound 5 (wherein RS represents a protected thiol group, and examples of the protective group for the thiol group include the same protective groups as those exemplified above as the protective group in the protected thiol group represented by $Pr^4$). Also, compound 3 may be derivatized into compound 6 by direct sulfuration (or oxidation), or compound 5 may be derivatized into compound 6 by deprotection.

[Formula 45]

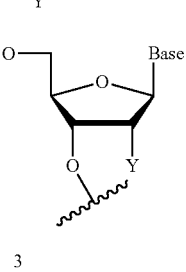

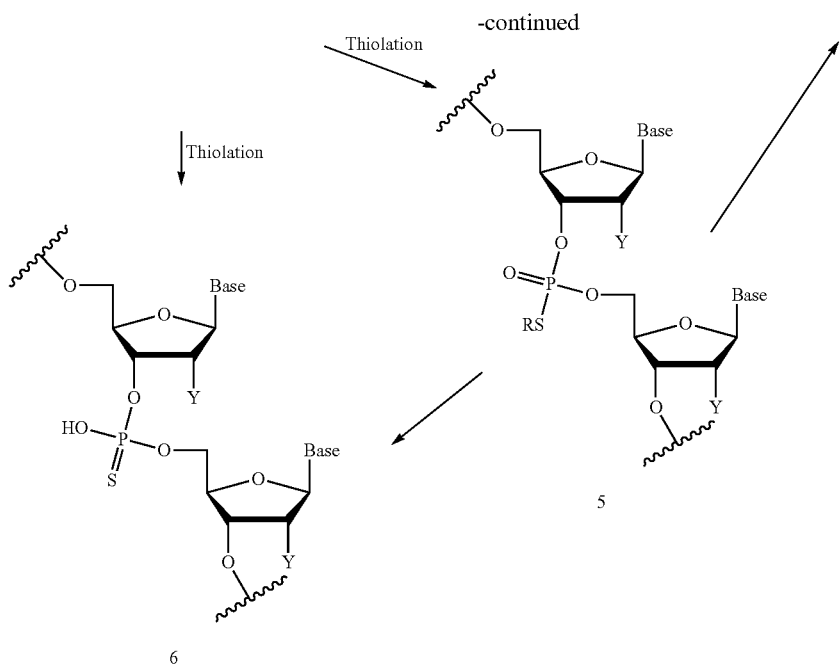

wherein each symbol is as defined above.

In light of this summarization, a method for producing a nucleic acid oligomer of the compound of the formula (II) or the salt thereof through the steps (a3), (b3), and (c3) will be described below. For such methods, see literatures such as Colin B. Reese et al., J. Chem. Soc, Perkin Trans. I, 1999, 1477-1468; and Colin B. Reese et al., J. Chem. Soc, Perkin Trans. I, 2002, 2619-2633. For the production of a nucleic acid oligomer by the H-phosphonate method, see, for example, 5th Edition Jikken Kagaku Koza (Encyclopedia of Experimental Chemistry in English) 16, Organic Compound IV, The Chemical Society of Japan, ed., 2010, p. 381-384.

1) Step (a3):

In the step (a3), a compound represented by the following formula (VIII):

[Formula 46]

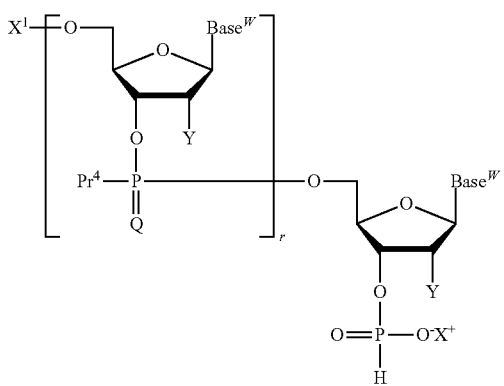

(VIII)

wherein

X$^+$ represents a cation;

Pr$^4$ represents a hydrogen atom, a protected hydroxy group, or a protected thiol group when Q is an oxygen atom and represents a protected hydroxy group when Q is a sulfur atom; and other symbols are as defined above, or a salt thereof is reacted with a compound represented by the following formula (IX):

[Formula 47]

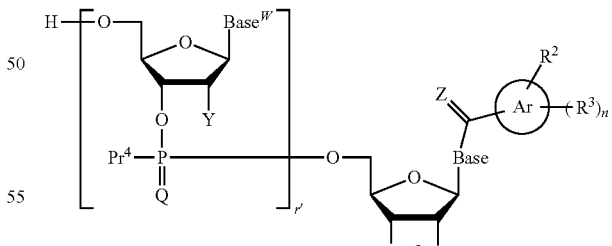

(IX)

wherein each symbol is as defined above, or a salt thereof in the presence of a coupling reagent for use in nucleic acid synthesis to produce a compound represented by the following formula (X):

[Formula 48]

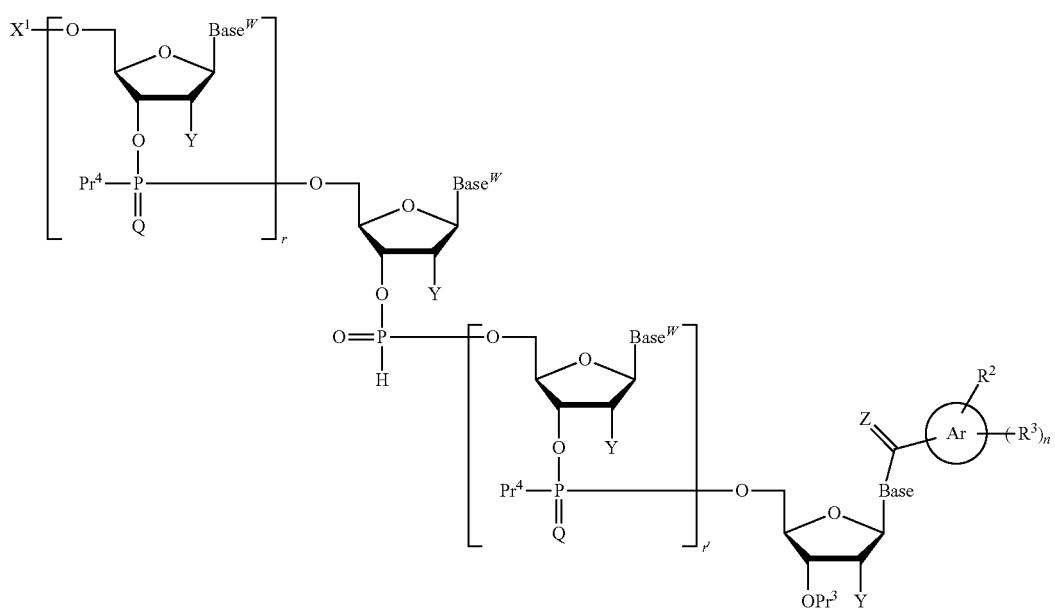

(X)

wherein each symbol is as defined above,
or a salt thereof. This step (a3) corresponds to the reaction of the reaction scheme 1.

In the formula (VIII), $X^+$ represents a cation. Examples of the cation can include optionally substituted ammonium ions and metal ions. In this context, examples of the substituted ammonium ions include: mono-$C_{1-6}$ alkylammonium ions such as methylammonium ions, ethylammonium ions, and isobutylammonium ions; di-$C_{1-6}$ alkylammonium ions such as dimethylammonium ions, diethylammonium ions, and diisobutylammonium ions; tri-$C_{1-6}$ alkylammonium ions such as trimethylammonium ions and triethylammonium ions; and N-ethyl-N-isopropylpropan-2-aminium and 3,4,5,6,7,8,9,10-octahydrido-2H-pyrimido[1,2-a]azepin-5-ium. Examples of the metal ions include sodium ions, potassium ions, and lithium ions.

In this context, the compound of the formula (VIII) wherein Q is an oxygen atom has, for example, the following structure:

[Formula 49]

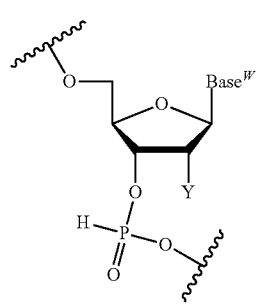

7

-continued

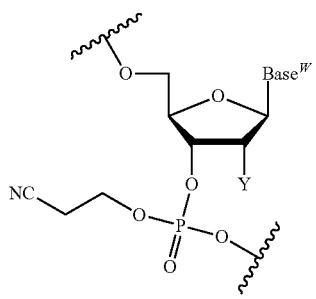

8

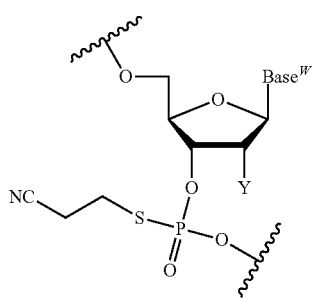

9 wherein each symbol is as defined above.

Compound 7 corresponds to a compound wherein $Pr^4$ is a hydrogen atom. Compound 8 corresponds to a compound wherein $Pr^4$ is a hydroxy group protected with a cyanoethyl group. Compound 9 corresponds to a compound wherein $Pr^4$ is a thiol group protected with a cyanoethyl group.

The compound of the formula (VIII) wherein Q is a sulfur atom has, for example, the following structure:

[Formula 50]

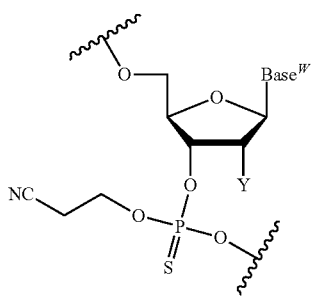

wherein each symbol is as defined above.

Compound 10 corresponds to a compound wherein $Pr^4$ is a hydroxy group protected with a cyanoethyl group.

The compound of the formula (VIII) or the salt thereof can be obtained, for example, by reacting a compound represented by the following formula (g):

[Formula 51]

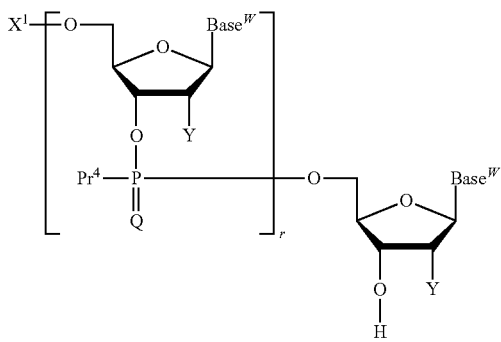

(g)

wherein $X^1$, $Pr^4$, Q, $Base^W$, and Y are each as defined above, or a salt thereof with a salt such as triethylammonium salt of p-toluyl H-phosphonate in the presence of an accelerator such as pivaloyl chloride in pyridine at −78° C. to 50° C., preferably −78° C. to 10° C. Alternatively, the compound of the formula (g) or the salt thereof can be phosphitylated by its reaction with a phosphitylating agent such as diphenyl phosphite, di(t-butyl) N,N-diethylphosphoramidite, di(tribenzylmethyl) N,N-diethylphosphoramidite, or di(2-trimethylsilyl-1,1-dimethylethyl) N,N-diethylphosphoramidite and subsequently treated with tertiary amine such as triethylamine or tributyiamine or alkali metal hydroxide such as potassium hydroxide or lithium hydroxide to obtain a 3'-H-phosphonate form.

In the case of a compound of the formula (IX) wherein r' is 0 or a salt thereof, the novel nucleoside monomer compound of the present invention wherein X is a hydrogen atom and $R^1$ is a protective group for a hydroxy group can be used directly. A compound of the formula (IX) wherein r' is 1 or a salt thereof can be produced by subjecting the novel nucleoside monomer compound of the present invention wherein X is a hydrogen atom and a compound of the formula (III) wherein r is 0 or a salt thereof to, for example, the aforementioned coupling reaction by the phosphoramidite method and subsequently to oxidation or sulfuration reaction, followed by, if necessary, the introduction of, for example, a protective group such as a cyanoethyl group to the hydroxy group or the thiol group. Likewise, a compound of the formula (IX) wherein r' is 2 or larger or a salt thereof can also be produced by repeating similar reaction.

Examples of the coupling reagent for use in nucleic acid synthesis, which is used in the step (a3), can include coupling reagents usually used in the H-phosphonate method. For example, pivaloyl chloride, 2-(benzoyltriazol-1-yloxy)-1,3-dimethyl-2-pyrrolidin-1-yl-1,3,2-diazaphospholidinium hexafluorate (BOMP), N,N-bis(2-oxazolidinyl) phosphonic chloride (BopCl), benzoyl chloride, or benzoic anhydride can be used.

The compound of the formula (VIII) or the salt thereof and the compound of the formula (IX) or the salt thereof can be coupled with each other through a reaction using this coupling reagent at −60° C. to 100° C., preferably −20° C. to 50° C., for 10 minutes to 24 hours in an appropriate organic solvent, for example, methylene chloride, chloroform, tetrahydrofuran, dioxane, dimethoxyethane, N,N-dimethylformamide, acetonitrile, toluene, or pyridine. In the present invention, this coupling reaction can be carried out in a liquid phase. By this coupling reaction, the phosphorous acid diester group introduced in 3'-OH of the 3'-terminal nucleoside moiety of the compound of the formula (VIII) or the salt thereof can be bound to 5'-OH in a free form of the 5'-terminal nucleoside moiety of the compound of the formula (IX) or the salt thereof to obtain the compound of the formula (X) or the salt thereof.

2) Step (b3):

In the step (b3), the compound of the formula (X) or the salt thereof obtained in the step (a3) is subjected to oxidation reaction or sulfuration reaction to produce a compound represented by the following formula (XI):

[Formula 52]

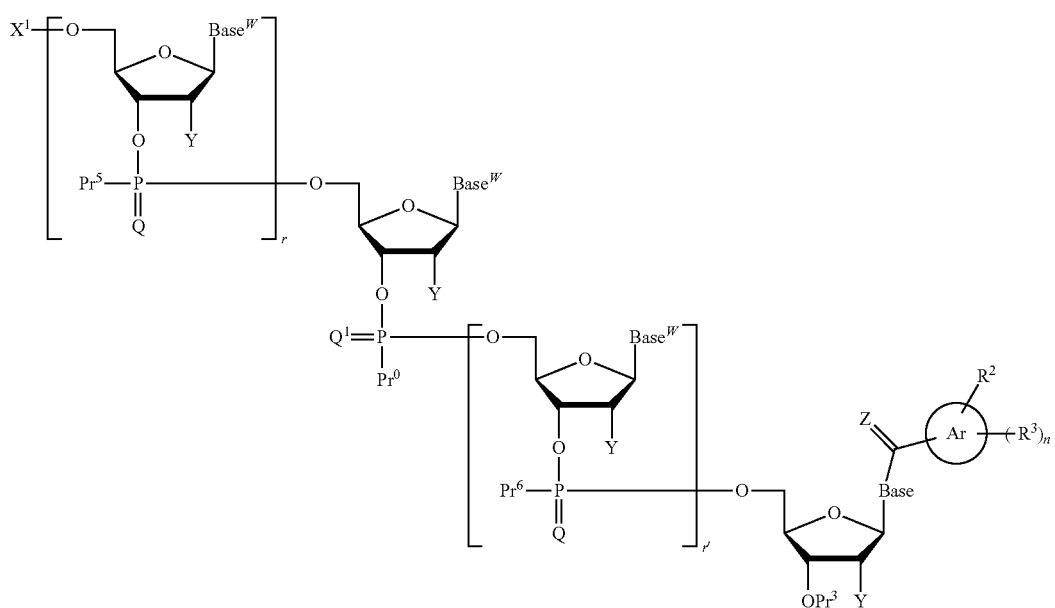

(XI)

wherein each symbol is as defined above, or a salt thereof.

In the formula (XI), $Pr^5$ represents (i) an optionally protected hydroxy group or a protected thiol group when Q is an oxygen atom and represents (ii) a protected hydroxy group when Q is a sulfur atom. $Pr^6$ represents (i) a hydroxy group or a protected thiol group when $Q^1$ is an oxygen atom and represents (ii) a hydroxy group when $Q^1$ is a sulfur atom. In this context, examples of the protective group in the optionally protected hydroxy group and the protected thiol group include the same protective groups as those exemplified above in $Pr^4$.

$Pr^5$ is preferably a protected hydroxy group, more preferably a hydroxy group protected with a cyanated $C_{1-6}$ alkyl group, particularly preferably a hydroxy group protected with 2-cyanoethyl.

$Pr^6$ is preferably a protected hydroxy group, more preferably a hydroxy group protected with a cyanated $C_{1-6}$ alkyl group, particularly preferably a hydroxy group protected with 2-cyanoethyl.

In the step (b3), the compound of the formula (X) or the salt thereof obtained in the step (a3) is subjected to oxidation reaction or sulfuration reaction in the same way as in the step (b1) of the phosphoramidite method to produce the compound of the formula (XI) or the salt thereof. The oxidation reaction, the sulfuration reaction, and subsequent optional capping reaction can be performed in the same way as the methods described above in the step (b1) of the phosphoramidite method.

In this context, $Pr^5$ in the compound of the formula (XI) corresponds to a substituent represented by $Pr^4$ excluding the H-phosphonate structure. The compound of the formula (XI) wherein $Q^1$ is an oxygen atom has, for example, the following structure (or the following structure to which a salt is added):

[Formula 53]

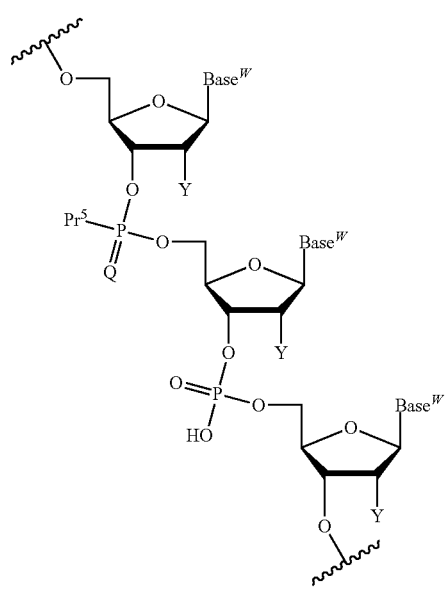

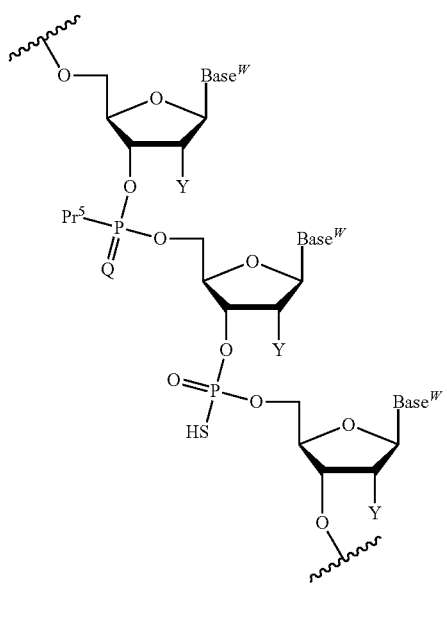

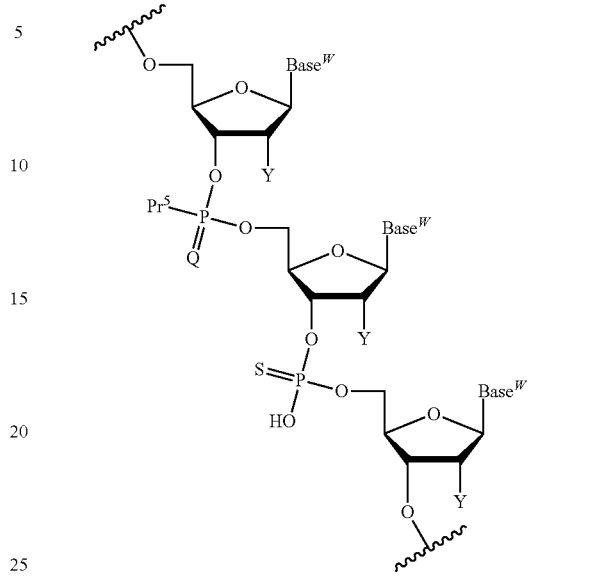

[Formula 54]

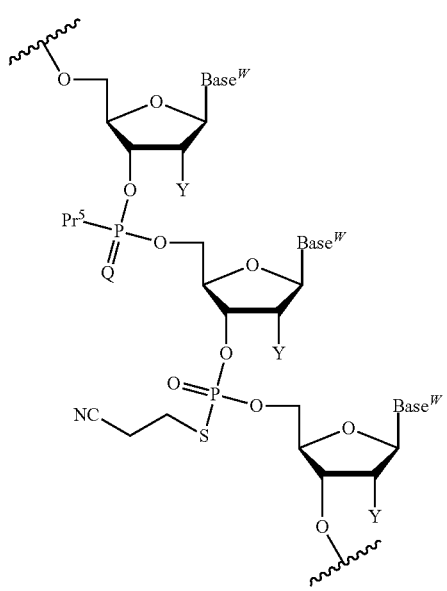

wherein each symbol is as defined above.

Compound 11 corresponds to a compound wherein $Pr^6$ is a hydroxy group. Compound 12 corresponds to a compound wherein $Pr^6$ is a thiol group. Compound 13 corresponds to a compound wherein $Pr^6$ is a thiol group protected with a cyanoethyl group.

The compound of the formula (XI) wherein $Q^1$ is a sulfur atom has, for example, the following structure (or the following structure to which a salt is added):

wherein each symbol is as defined above.

Compound 12' corresponds to a compound wherein $Pr^6$ is a hydroxy group.

3) Step (c3):

In the step (c3), the compound of the formula (XI) or the salt thereof obtained in the step (b3) is subjected to deprotection reaction in the same way as in the step (c1) of the phosphoramidite method to produce the compound of the formula (II) of interest or the salt thereof. The deprotection reaction can be performed in the same way as the method described above in the step (c1) of the phosphoramidite method.

In this way, the compound of the formula (II) of interest or the salt thereof can be produced by the H-phosphonate method. Also in the H-phosphonate method, as described above, since a synthetic intermediate used in each step has the structural moiety having a hydrophobic group, each synthesized compound can be separated after the reaction in a liquid phase without column chromatography purification. For example, the synthesized compound can be separated by the concentration of the solvent after the reaction and suction filtration.

In the above description of the method for producing a nucleic acid oligomer, the nucleic acid oligomer having an asymmetric point at the phosphoric acid site may be in an optically active form or may be a mixture of optically active forms, such as a racemate. The nucleic acid oligomer having a plurality of asymmetric points may be a mixture of diastereomers.

The nucleic acid oligomer thus produced is expected to be useful as a "medicament for treating a disease by inhibiting the functions of a gene", including antitumor agents and antiviral agents, when used as, for example, siRNA. The nucleic acid oligomer can be supplemented with, for example, routine aids such as a buffer and/or a stabilizer to prepare a preparation for parenteral administration. Alternatively, the nucleic acid oligomer may be supplemented with routine pharmaceutical carriers to prepare a preparation for local application such as an ointment, a cream, a solution, or a plaster.

Hereinafter, the present invention will be described in more detail with reference to Examples. However, the present invention is not intended to be limited by these Examples.

EXAMPLES

Example 1

Synthesis of a Deoxythymine (dT) Type Nucleoside Monomer Compound Having Three Octadecyloxy Groups (Compound (E5))

[Formula 55]

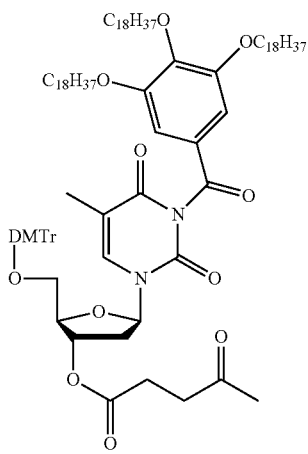

(E5)

(1) Methyl Benzoate Substituted with Three Octadecyloxy Groups (Compound (E1))

[Formula 56]

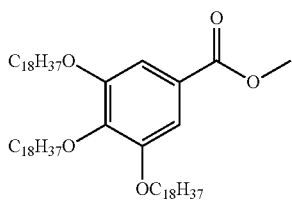

(E1)

To methyl gallate (9.2 g) and potassium carbonate (103.7 g), 1,3-dimethyl-2-imidazolidinone (170 mL) was added, and the mixture was stirred at 80° C. for 30 minutes. 1-Bromooctadecane (69.1 mL) was added thereto, and the mixture was stirred at 80° C. for 12 hours. 40° C. hot water was added to the reaction liquid for suspension, then the precipitate was collected by suction filtration, and then the obtained solid was washed with acetonitrile, acetone, and methanol to quantitatively obtain the compound represented by E1 (48.0 g).

$^1$H NMR (500 MHz, CDCl$_3$) δ 7.25 (s, 2H), 3.99-4.03 (m, 6H), 3.89 (s, 3H), 1.78-1.84 (m, 4H), 1.71-1.77 (m, 2H), 1.44-1.50 (m, 6H), 1.20-1.38 (m, 84H), 0.88 (t, J=7.0 Hz, 9H)

(2) Synthesis of Benzoic Acid Substituted with Three Octadecyloxy Groups (Compound (E2))

[Formula 57]

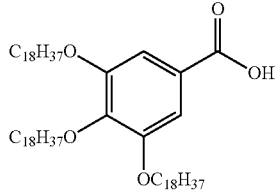

(E2)

The compound (E1) (22.5 g) and ethanol (225 mL) were measured into an eggplant type flask for suspension. Potassium hydroxide (13.4 g) was added thereto, and the mixture was stirred at 80° C. for 3 hours. The reaction liquid was concentrated under reduced pressure, 1 M hydrochloric acid (240 mL) was added thereto at room temperature, and the mixture was stirred for 30 minutes. The solid obtained by suction filtration was suspended in methanol at 50° C., then the suspended substance was collected by suction filtration to obtain the compound (E2) (21.4 g, percent yield: 96.7%).

$^1$H NMR (500 MHz, CDCl$_3$) δ 7.32 (s, 2H), 4.04 (t, J=6.5 Hz, 2H), 4.02 (t, J=6.5 Hz, 4H), 1.78-1.86 (m, 4H), 1.71-1.78 (m, 2H), 1.43-1.52 (m, 6H), 1.21-1.40 (m, 84H), 0.88 (t, J=7.0 Hz, 9H).

(3) Synthesis of Benzoyl Chloride Substituted with Three Octadecyloxy Groups (Compound (E3))

[Formula 58]

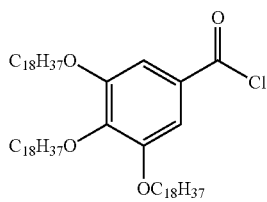

(E3)

The compound (E2) (15 g) was suspended in toluene (120 mL) in an eggplant type flask, thionyl chloride (3.5 mL) and N,N'-dimethylformamide (2.5 mL) were added thereto, and the mixture was stirred at 50° C. for 2 hours. The reaction liquid was concentrated under reduced pressure to obtain the compound (E3) (15.1 g, percent yield: 98.7%).

$^1$H NMR (500 MHz, CDCl$_3$) δ 7.33 (s, 2H), 4.08 (t, J=6.5 Hz, 2H), 4.02 (t, J=6.5 Hz, 4H), 1.78-1.86 (m, 4H), 1.70-1.78 (m, 2H), 1.40-1.52 (m, 6H), 1.21-1.40 (m, 84H), 0.88 (t, J=7.0 Hz, 9H).

(4) Synthesis of a dT-Type Nucleoside (Compound (E4))

[Formula 59]

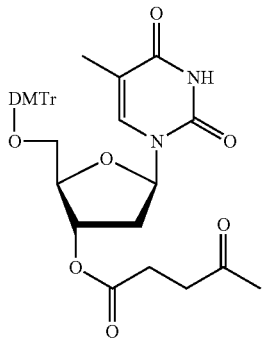

(E4)

1-((2R,4S,5R)-5-((bis(4-Methoxyphenyl)(phenyl) methoxy)methyl)-4-hydroxytetrahydrofaran-2-yl)-5-methylpyrimidine-2,4(1H,3H)-dione (100 g) was dissolved in tetrahydrofuran (500 mL), levulinic acid (33.0 g), 2.24 g N,N'-dimethylaminopyridine (18.4 mmol, 0.1 equivalent weight), and 1-ethyl-3-(3-dimethylaminopropyl)carbodiimide hydrochloride (53.8 g) were serially added, and the mixture was stirred at room temperature for 90 minutes. A 10% aqueous solution of acetic acid/triethylamine (500 mL) and ethyl acetate (500 mL) were added to the reaction liquid at room temperature for separatory extraction. The organic layer was concentrated under reduced pressure to obtain the compound (E4) (132.6 g, percent yield: 112.4%).

$^1$H NMR (500 MHz, CDCl$_3$) δ 9.93 (brs, 1H), 7.62 (s, 1H), 7.40 (d, J=7.3 Hz, 2H), 7.26-7.33 (m, 6H), 7.20-7.26 (m, 1H), 6.84 (d, J=8.8 Hz, 4H), 6.46 (dd, J=8.8, 5.7 Hz, 1H), 5.48 (d, J=5.7 Hz, 1H), 4.15 (d, J=1.6 Hz, 1H), 3.78 (s, 6H), 3.44-3.50 (m, 2H), 2.70-2.82 (m, 2H), 2.55-2.63 (m, 2H), 2.40-2.53 (m, 2H), 2.15-2.21 (m, 3H), 1.38 (s, 3H).

(5) Synthesis of a dT-Type Nucleoside Monomer Compound Having Three Octadecyloxy Groups (Compound (E5))

[Formula 60]

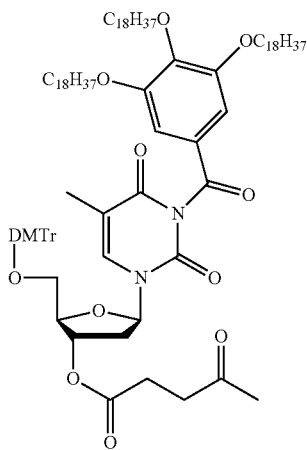

(E5)

To the compound (E4) (8.15 g), pyridine (100 mL), N,N'-diisopropylethylamine (6.83 g), and chlorotrimethylsilane (2.87 g) were serially added, and the mixture was stirred at room temperature for 30 minutes. To the mixture, 3,4,5-tris(octadecyloxy)benzoyl chloride (compound (E3)) (10 g) was added, and the mixture was stirred at 60° C. for 3 hours. Methanol was added to the reaction liquid at room temperature, and the mixture was ice-cooled. The precipitated solid was collected by suction filtration to obtain the compound (E5) (13.3 g, percent yield: 81.1%).

$^1$H NMR (500 MHz, CDCl$_3$) δ 7.71 (brs, 1H), 7.36-7.42 (d, J=7.3 Hz, 2H), 7.23-7.34 (m, 7H), 7.13 (s, 2H), 6.86 (d, J=8.8 Hz, 4H), 6.38-6.46 (m, 1H), 5.48 (d, J=5.4 Hz, 1H), 4.16 (d, J=1.3 Hz, 1H), 3.92-4.07 (m, 6H), 3.80 (s, 6H), 3.49 (br_s, 2H), 2.67-2.81 (m, 2H), 2.38-2.62 (m, 2H), 2.15-2.21 (m, 2H), 2.18 (s, 3H), 1.76-1.84 (m, 4H), 1.68-1.76 (m, 2H), 1.41-1.50 (m, 6H), 1.39 (s, 3H), 1.17-1.36 (m, 84H), 0.88 (t, J=7.0 Hz, 9H).

Example 2

Synthesis of a Uracil (U) Type Nucleoside Monomer Compound Having Three Octadecyloxy Groups (Compound (E7))

[Formula 61]

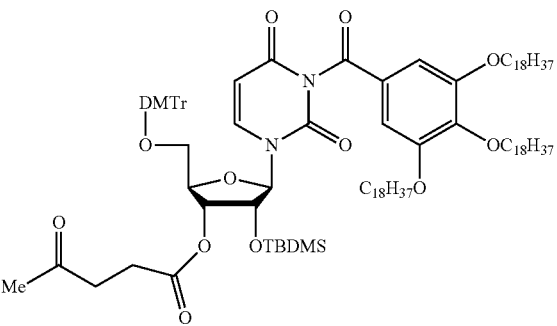

(E7)

(1) Synthesis of a U-Type Nucleoside (Compound (E6))

[Formula 62]

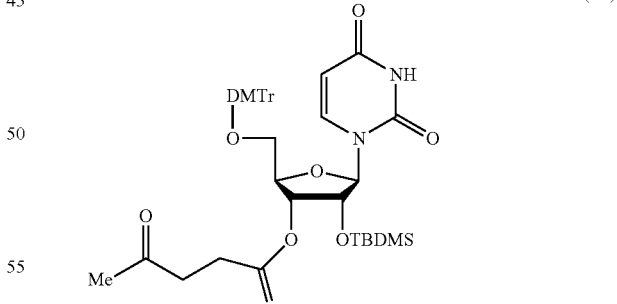

(E6)

1-((2R,3R,4R,5R)-5-((bis(4-Methoxyphenyl)(phenyl) methoxy)methyl)-3-((t-butyl dimethylsilyl)oxy)-4-hydroxytetrahydrofuran-2-yl)pyrimidine-2,4(1H,3H)-dione (1 g) was dissolved in tetrahydrofuran (5 mL). Levulinic acid (0.272 g), N,N'-dimethylaminopyridine (0.0185 g), and 1-ethyl-3-(3-dimethylaminopropyl)carbodiimide hydrochloride (0.444 g) were serially added thereto, and the mixture was stirred at room temperature for 18 hours. A 10% aqueous solution of acetic acid/triethylamine (10 mL) and ethyl acetate (10 mL) were added to the reaction liquid at room temperature for separatory extraction. The obtained organic layer was concentrated under reduced pressure to obtain the compound (E6) (1.21 g, percent yield: 105.7%).

$^1$H NMR (500 MHz, CDCl$_3$) δ 9.02 (brs, 1H), 7.89 (d, J=8.2 Hz, 1H), 7.33-7.38 (m, 2H), 7.31 (t, J=7.6 Hz, 2H), 7.22-7.28 (m, 5H), 6.85 (d, J=8.2 Hz, 4H), 5.98 (d, J=5.0 Hz, 1H), 5.34 (t, J=4.6 Hz, 1H), 5.29 (d, J=8.2 Hz, 1H), 4.50 (t, J=5.0 Hz, 1H), 4.21-4.27 (m, 1H), 3.80 (s, 6H), 3.53 (dd, J=11.1, 2.2 Hz, 1H), 3.44 (dd, J=11.0, 1.9 Hz, 1H), 2.75-2.84 (m, 1H), 2.64-2.75 (m, 2H), 2.56-2.63 (m, 1H), 2.20 (s, 3H), 0.86 (s, 9H), 0.09 (s, 3H), 0.08 (s, 3H).

(2) Synthesis of a U-Type Nucleoside Monomer Compound Having Three Octadecyloxy Groups (Compound (E7))

[Formula 63]

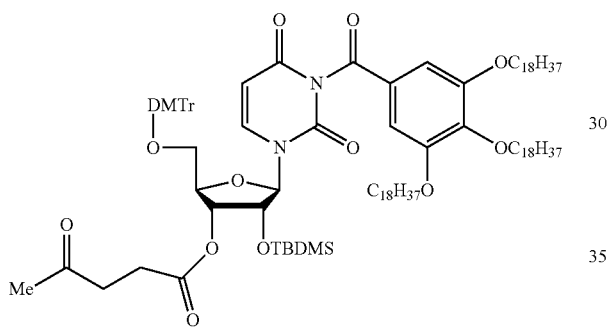

(E7)

To the compound (E6) (1.60 g), pyridine (15 mL), N,N'-diisopropylethylamine (1.02 g), and chlorotrimethylsilane (0.431 g) were serially added, and the mixture was stirred at room temperature for 30 minutes. To the mixture, 3,4,5-tris(octadecyloxy)benzoyl chloride (1.5 g) was added, and the mixture was stirred at 60° C. for 3 hours. Methanol was added to the reaction liquid at room temperature, and then the mixture was ice-cooled. The resultant was subjected to collection by suction filtration to obtain the compound (E7) (2.34 g, percent yield: 88.5%).

$^1$H NMR (500 MHz, CDCl$_3$) δ 7.98 (brd, J=7.6 Hz, 1H), 7.35-7.41 (m, 2H), 7.32 (t, J=7.6 Hz, 2H), 7.23-7.30 (m, 5H), 7.13 (s, 2H), 6.84-6.90 (m, 4H), 5.99 (d, J=4.7 Hz, 1H), 5.31-5.45 (m, 2H), 4.54 (t, J=4.9 Hz, 1H), 4.24 (brs, 1H), 4.04 (t, J=6.6 Hz, 2H), 3.91-4.01 (m, 4H), 3.80 (d, J=1.3 Hz, 6H), 3.56 (dd, J=11.1, 2.2 Hz, 1H), 3.47 (dd, J=11.1, 2.2 Hz, 1H), 2.74-2.83 (m, 1H), 2.64-2.73 (m, 2H), 2.53-2.61 (m, 1H), 2.19 (s, 3H), 1.75-1.83 (m, 4H), 1.69-1.75 (m, 2H), 1.45 (m, 6H), 1.17-1.36 (m, 84H), 0.88 (t, J=7.3 Hz, 9H), 0.86 (s, 9H), 0.09 (s, 3H), 0.08 (s, 3H).

Example 3

Synthesis of a Uracil (U) Type Nucleoside Monomer Compound Having Three Tetradecyloxy Groups (Compound (E8))

[Formula 64]

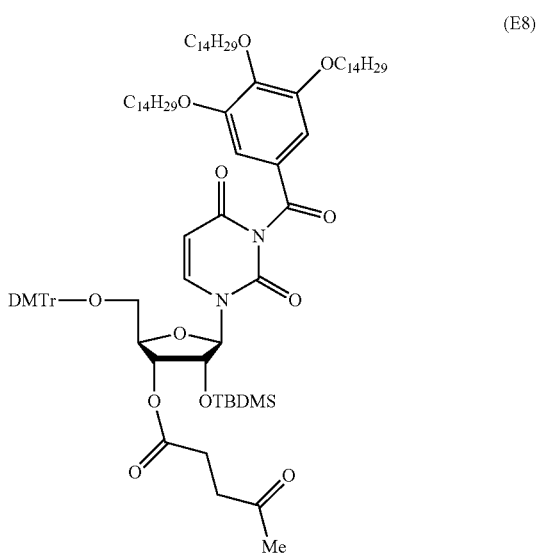

(E8)

(1) Methyl Benzoate Substituted with Three Tetradecyloxy Groups (Compound (E9))

[Formula 65]

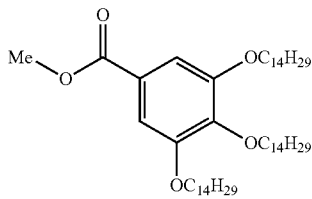

(E9)

To methyl gallate (5.5 g) and potassium carbonate (62.2 g), 1,3-dimethyl-2-imidazolidinone (100 mL) was added, and the mixture was stirred at 80° C. for 45 minutes. 1-Bromotetradecane (26.9 mL) was added thereto, and the mixture was stirred at 80° C. for 12 hours. Water was added to the reaction liquid for suspension, then the precipitate was collected by suction filtration, and the obtained solid was washed with a 50% aqueous solution of acetonitrile and acetonitrile to obtain the compound (E9) (22.6 g).

$^1$H NMR (500 MHz, CDCl$_3$) δ 7.25 (2H, s), 3.99-4.03 (6H, m), 3.89 (3H, s, COOMe), 1.71-1.84 (6H, m), 1.44-1.50 (6H, m), 1.23-1.38 (60H, br), 0.88 (9H, t J=7.0 Hz).

(2) Synthesis of Benzoic Acid Substituted with Three Tetradecyloxy Groups (Compound (E10))

[Formula 66]

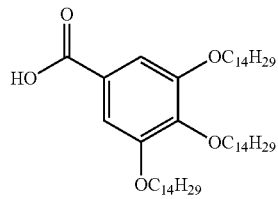

(E10)

Ethanol (100 mL) was added to the compound (E9) (7.7 g) and potassium hydroxide (6.7 g), and the mixture was stirred at 85° C. for 2 hours. The reaction liquid was concentrated under reduced pressure, 1 N hydrochloric acid (21 mL) was added thereto at room temperature, and the mixture was stirred for 30 minutes. The precipitate was collected by suction filtration, and the obtained solid was washed with water and acetonitrile to obtain the compound (E10) (8.2 g).
$^1$H NMR (500 MHz, CDCl$_3$) δ 7.19 (2H, s), 3.96 (2H, t J=6.5 Hz), 3.91 (4H, t J=6.5 Hz), 1.70-1.76 (6H, m), 1.37-1.49 (6H, m), 1.21-1.35 (60H, br), 0.88 (9H, t J=7.0 Hz).
(3) Synthesis of a U-Type Nucleoside Monomer Compound Having Three Tetradecyloxy Groups (Compound (E8))

[Formula 67]

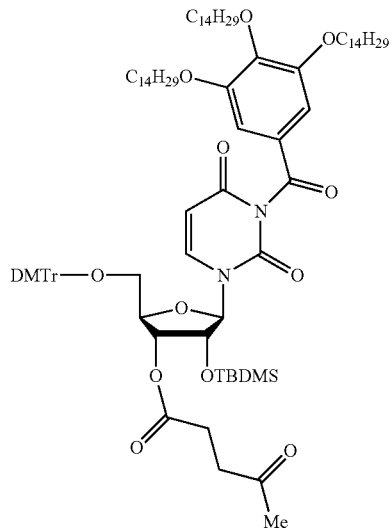

(E8)

To the compound (E10) (532 mg), thionyl chloride (5.2 mL) and N,N-dimethylformamide (110 μL) were added, then the mixture was stirred at 50° C. for 6.5 hours, then the solvent was distilled off under reduced pressure, N,N,-diisopropylethylamine (2 mL) and pyridine (2.6 mL) were added thereto, a solution of the compound (E6) (1.59 g) dissolved in pyridine (2 mL) was added thereto, and the mixture was stirred at room temperature for 2.5 hours, then methanol was added for concentration, the concentrate was cooled to 0° C., and then the precipitated solid was collected by suction filtration and washed with methanol to obtain the compound (E8) (595 mg).

$^1$H NMR (500 MHz, CDCl$_3$) δ 7.98 (1H, br d J=7.5 Hz), 7.25-7.38 (9H, m), 7.13 (2H, s), 6.85-6.88 (4H, m), 5.99 (1H, d J=4.8 Hz), 5.33-5.39 (2H, m), 4.53 (1H, m), 4.26 (1H, br), 3.94-4.08 (6H, m), 3.81 (6H, s), 3.43-3.57 (2H, m), 2.51-2.82 (4H, m), 2.19 (3H, s), 1.70-1.83 (6H, m), 1.42-1.50 (6H, m), 1.21-1.34 (60H, br), 0.85-0.89 (18H, m), 0.06-0.09 (6H, m).

Example 4

Synthesis of a Uracil (U) Type Nucleoside Monomer Compound Having Two Octadecyloxy Groups (Compound (E11))

[Formula 68]

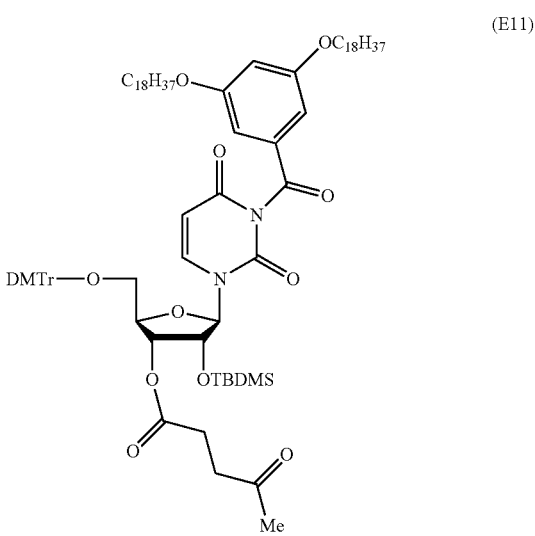

(E11)

(1) Synthesis of Methyl Benzoate Substituted with Two Octadecyloxy Groups (Compound (E12))

[Formula 69]

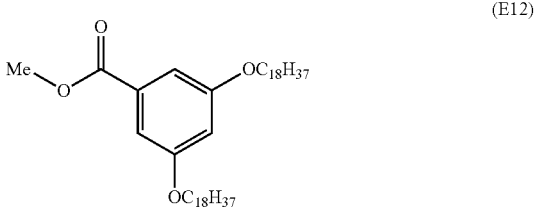

(E12)

To methyl 3,5-dihydroxybenzoate (5.0 g) and potassium carbonate (41.5 g), 1,3-dimethyl-2-imidazolidinone (100 mL) was added, and the mixture was stirred at 80° C. for 25 minutes. 1-Bromooctadecane (27.6 mL) was added thereto, and the mixture was stirred at 70° C. for 14 hours. Water was added to the reaction liquid, the solution was stirred, then the precipitate was collected by suction filtration, then the obtained solid was washed with water and acetonitrile to obtain the compound (E12) (6.5 g).

(2) Synthesis of Benzoic Acid Substituted with Two Octadecyloxy Groups (Compound (E13))

[Formula 70]

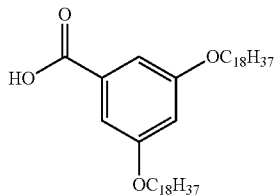

(E13)

Ethanol (100 mL) was added to the compound (E12) (6.8 g) and potassium hydroxide (6.7 g), and the mixture was stirred at 85° C. for 2 hours. The reaction liquid was concentrated under reduced pressure, 1 N hydrochloric acid (21 mL) was added thereto at room temperature, and the mixture was stirred for 30 minutes. The precipitate was collected by suction filtration, and the obtained solid was washed with water and acetonitrile to obtain the compound (E13) (6.5 g).

$^1$H NMR (500 MHz, CDCl$_3$) δ 7.20 (2H, d J=2.2 Hz), 6.68 (1H, t J 2.4 Hz), 3.97 (4H, t J=6.5 Hz), 1.75-1.81 (4H, m), 1.42-1.48 (4H, m), 1.21-1.36 (56H, br), 0.88 (6H; t J=7.0 Hz).

(3) Synthesis of a U-Type Nucleoside Monomer Compound Having Two Octadecyloxy Groups (Compound (E11))

[Formula 71]

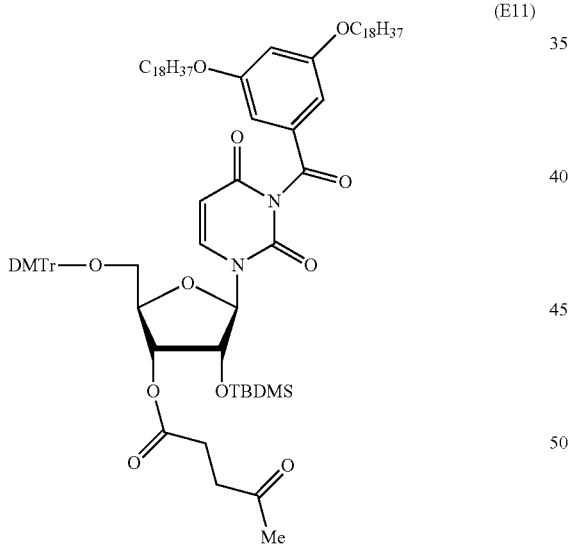

(E11)

To the compound (E13) (461 mg), thionyl chloride (5.2 mL) and N,N-dimethylformamide (110 µL) were added, the mixture was stirred at 50° C. for 4 hours, then the solvent was distilled off under reduced pressure, N,N-diisopropylethylamine (2 mL) and pyridine (2.6 mL) were added thereto, a solution of the compound (E6) (1.59 g) dissolved in pyridine (2 mL) was added thereto, the mixture was stirred at 50° C. for 3 hours, then methanol was added for concentration, the concentrate was cooled to −30° C., and then the precipitated solid was collected by suction filtration and washed with methanol to obtain the compound (E11) (658 mg).

$^1$H NMR (500 MHz, CDCl$_3$) δ 7.96 (1H, br d J=8.4 Hz), 7.25-7.38 (9H, m), 7.02 (2H, br d J=2.0 Hz), 6.85-6.88 (4H, m), 6.69 (1H, br s), 5.99 (1H, m), 5.40 (1H, t J=4.3 Hz), 5.34 (1H, m), 4.54 (1H, t J=4.8 Hz), 4.24 (1H, br), 3.95 (4H, t J=6.5 Hz), 3.81 (6H, br s), 3.43-3.56 (2H, m), 2.52-2.82 (4H, m), 2.19, 2.17 (3H, s), 1.74-1.79 (4H, m), 1.41-1.47 (4H, m), 1.22-1.33 (56H, br), 0.84-0.89 (15H, m), 0.06-0.11 (6H, m).

Example 5

Synthesis of a Uracil (U) Type Nucleoside Monomer Compound Having One Octadecyloxy Group (Compound (E14))

[Formula 72]

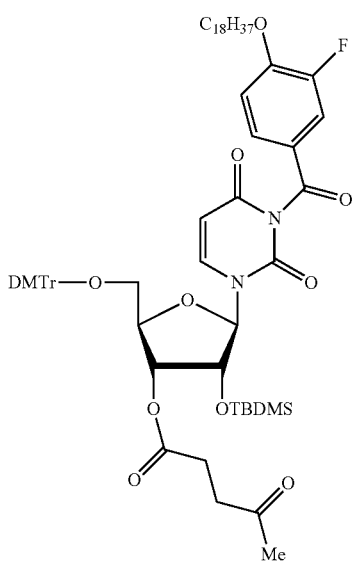

(E14)

(1) Synthesis of Methyl Benzoate Substituted with One Octadecyloxy Group (Compound (E15))

[Formula 73]

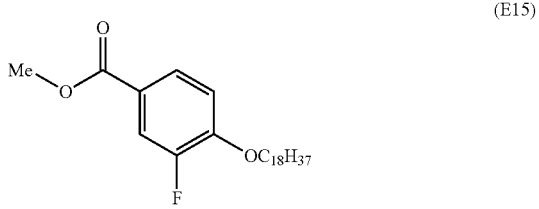

(E15)

To methyl 3-fluoro-4-hydroxybenzoate (851 mg) and potassium carbonate (3.5 g), 1,3-dimethyl-2-imidazolidinone (10 mL) was added, and the mixture was stirred at 70° C. for 15 minutes, then 1-bromooctadecane (2.3 mL) was added thereto, and the mixture was stirred at 70° C. for 10 hours. Water was added to the reaction liquid, the solution was stirred, and then the precipitate was collected by suction filtration, and the obtained solid was washed with water and acetonitrile to obtain the compound (E15) (2.0 g).

$^1$H NMR (500 MHz, CDCl$_3$) δ 7.78-7.80 (1H, m), 7.73 (1H, dd J=11.5, 2.3 Hz), 6.96 (1H, t J=8.0 Hz), 4.07 (2H, t J=6.3 Hz), 3.89 (3H, s), 1.81-1.87 (2H, m), 1.44-1.50 (2H, m), 1.22-1.38 (28H, br), 0.88 (3H, t J=7.0 Hz).

(2) Synthesis of Benzoic Acid Substituted with One Octadecyloxy Group (Compound (E16))

[Formula 74]

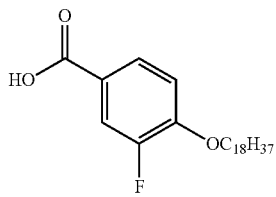

(E16)

Ethanol (20 mL) was added to the compound (E15) (1.1 g) and potassium hydroxide (1.7 g), and the mixture was stirred at 85° C. for 2 hours. The reaction liquid was concentrated under reduced pressure, 1 N hydrochloric acid (5 mL) was added thereto at room temperature, and the mixture was stirred for 30 minutes. The precipitate was collected by suction filtration, and the obtained solid was washed with water and acetonitrile to obtain the compound (E16) (1.1 g).

$^1$H NMR (500 MHz, CDCl$_3$) δ 7.84-7.86 (1H, m), 7.78 (1H, dd J=11.4; 1.9 Hz), 6.99 (1H, t J=8.5 Hz), 4.09 (2H, t J=6.6 Hz), 1.85 (2H, m), 1.48 (2H, m), 1.20-1.39 (28H, br), 0.88 (3H, t J=7.0 Hz).

(3) Synthesis of a U-Type Nucleoside Monomer Compound Having One Octadecyloxy Group (Compound (E14))

[Formula 75]

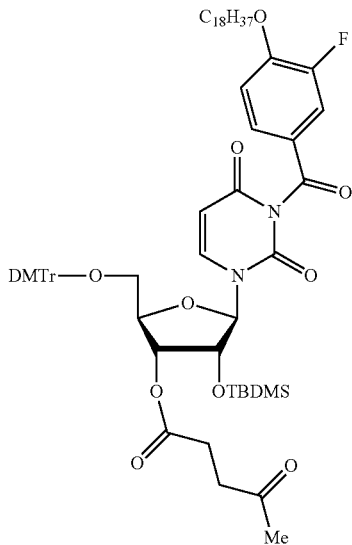

(E14)

To the compound (E16) (286 mg), thionyl chloride (5.2 mL) and N,N-dimethylformamide (110 μL) were added, the mixture was stirred at 50° C. for 5 hours, then the solvent was distilled off under reduced pressure, N,N-diisopropylethylamine (2 mL) and pyridine (2.6 mL) were added thereto, a solution of the compound (E6) (1.59 g) dissolved in pyridine (2.0 mL) was added thereto, the mixture was stirred at 50° C. for 1.5 hours, then methanol was added for concentration, the concentrate was cooled to −30° C., and then the precipitated solid was collected by suction filtration and washed with methanol to obtain the compound (E14) (309 mg).

$^1$H NMR (500 MHz, CDCl$_3$) δ 7.99 (1H, br d J=8.0), 7.61-7.85 (2H, m), 7.24-7.38 (9H, m), 6.94-7.01 (1H, m), 6.84-6.88 (4H, m), 5.96-5.98 (1H, m), 5.26-5.40 (2H, m), 4.55 (1H, br t J=4.9 Hz), 4.25 (1H, br), 4.08-4.11 (2H, m), 3.80-3.81 (6H, m), 3.43-3.57 (2H, m), 2.54-2.82 (4H, m), 2.17-2.20 (3H, m), 1.81-1.88 (2H, m), 1.43-1.49 (2H, m), 1.22-1.39 (28H, br), 0.86-0.89 (12H, m), 0.11 (3H, s), 0.08 (3H, s).

Example 6

Synthesis of a Uracil (U) Type Nucleoside Monomer Compound Having Three Hexadecyloxy Groups (Compound (E51))

[Formula 76]

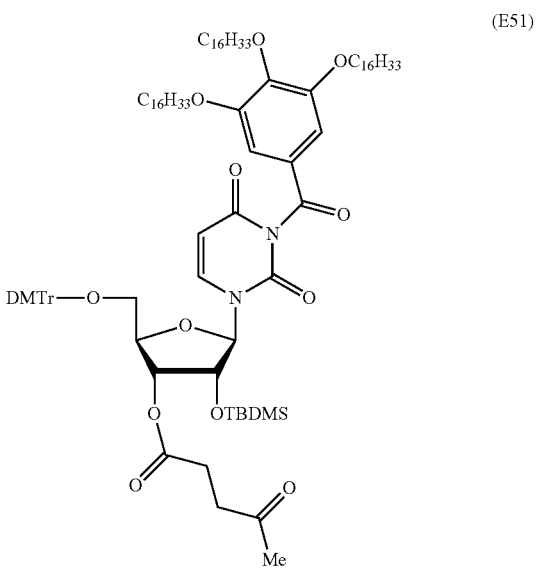

(E51)

(1) Synthesis of Methyl Benzoate Substituted with Three Hexadecyloxy Groups (Compound (E35))

[Formula 77]

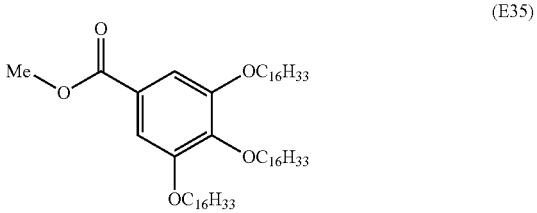

(E35)

To methyl gallate (5.5 g) and potassium carbonate (62.2 g), 1,3-dimethyl-2-imidazolidinone (100 mL) was added, and the mixture was stirred at 80° C. for 30 minutes. 1-Bromohexadecane (30.2 mL) was added thereto, and the mixture was stirred at 80° C. for 14 hours. Water (300 mL) was added to the reaction liquid for suspension, then the precipitate was collected by suction filtration, and the obtained solid was washed with an aqueous solution of acetone (1:1). The obtained white solid was dissolved in dichloromethane (500 mL), methanol was added thereto, and the precipitated solid was collected by suction filtration to obtain the compound represented by E35 (24.2 g, percent yield: 94%).

$^1$H NMR (500 MHz, CDCl$_3$) δ 7.25 (2H, s), 3.99-4.03 (6H, m), 3.89 (3H, s, COOMe), 1.71-1.84 (6H, m), 1.44-1.50 (6H, m), 1.23-1.38 (72H, br), 0.88 (9H, t J=7.0 Hz).

(2) Synthesis of Benzoic Acid Substituted with Three Hexadecyloxy Groups (Compound (E40))

[Formula 78]

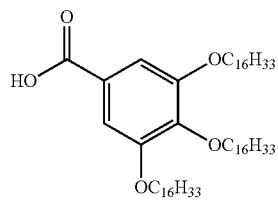

(E40)

Ethanol (100 mL) was added to the compound represented by E35 (8.6 g) and potassium hydroxide (6.7 g), and the mixture was stirred at 85° C. for 2.5 hours. The reaction liquid was cooled to room temperature, then water (200 mL) was added thereto, and the solution was stirred. 6 N Hydrochloric acid (21 mL) was added thereto. The precipitate was collected by suction filtration, and the obtained solid was washed with water (200 mL) and acetonitrile (200 mL) to quantitatively obtain the compound represented by E40 (8.6 g).

$^1$H NMR (500 MHz, CDCl$_3$) δ 7.25 (2H, s), 3.96-4.01 (6H, m), 1.71-1.81 (6H, m), 1.42-1.50 (6H, m), 1.21-1.36 (72H, br), 0.88 (9H, t J=6.9 Hz).

(3) Synthesis of a U-Type Nucleoside Monomer Compound Having Three Hexadecyloxy Groups (Compound (E51))

[Formula 79]

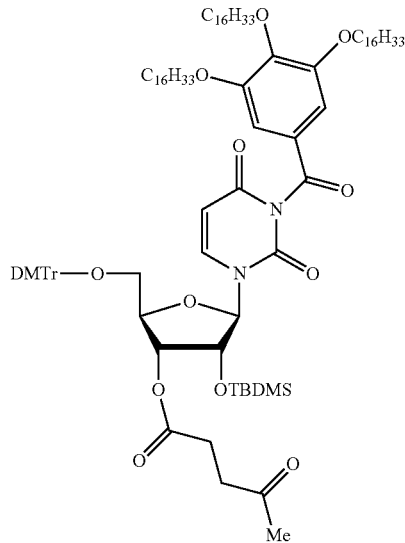

(E51)

To the compound (E40) (590 mg), thionyl chloride (5.2 mL) and N,N-dimethylformamide (110 μL) were added, the mixture was stirred at 50° C. for 3.5 hours, then the solvent was distilled off under reduced pressure, N,N-diisopropylethylamine (2.0 mL) and pyridine (4.0 mL) were added thereto, a solution of the compound (E6) (1.6 g) dissolved in pyridine (6 mL) and N,N-diisopropylethylamine (1.0 mL) was added thereto, chlorotrimethylsilane (500 μL) was added, the mixture was stirred at 60° C. for 5 hours, then methanol was added for concentration, and then the precipitated solid was collected by suction filtration and washed with methanol to obtain the compound (E51) (946 mg, percent yield: 85%).

$^1$H NMR (500 MHz, CDCl$_3$) δ 7.98 (1H, br d J=8.0 Hz), 7.26-7.38 (9H, m), 7.13 (2H, s), 6.85-6.88 (4H, m), 5.99 (1H, d J=4.9 Hz), 5.34-5.38 (2H, m), 4.53 (1H, t J=4.8 Hz), 4.26 (1H, br), 3.94-4.08 (6H, m), 3.81 (6H, s), 3.44-3.57 (2H, m), 2.54-2.82 (4H, m), 2.19 (3H, s), 1.70-1.82 (6H, m), 1.42-1.48 (6H, m), 1.21-1.35 (72H, s), 0.85-0.89 (18H, s), 0.09 (3H, s), 0.08 (3H, s).

Example 7

Synthesis of a Uracil (U) Type Nucleoside Monomer Compound Having Three Docosyloxy Groups (Compound (E52))

[Formula 80]

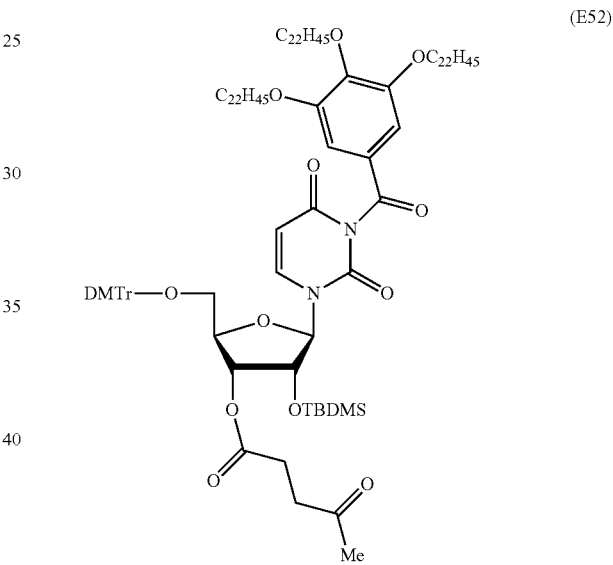

(E52)

(1) Synthesis of Methyl Benzoate Substituted with Three Docosyloxy Groups (Compound (E36))

[Formula 81]

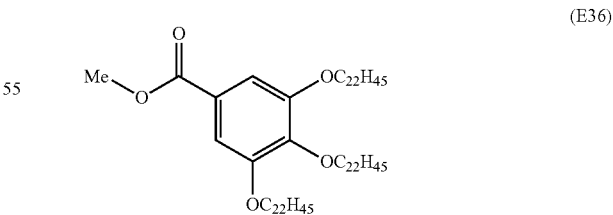

(E36)

To methyl gallate (5.5 g) and potassium carbonate (62.2 g), 1,3-dimethyl-2-imidazolidinone (140 mL) was added, then the mixture was stirred at 80° C. for 1 hour and then was cooled to 70° C. 1-Bromodocosane (38.6 g) was added thereto, and the mixture was stirred at 70° C. for 14 hours. Water (300 mL) was added to the reaction liquid, the solution was stirred, then the precipitate was collected by suction filtration and washed with water (300 mL), acetonitrile (200 mL), acetone (500 mL), and dichloromethane (200 mL) to obtain the compound represented by E36 (28.6 g, percent yield: 86%).

¹H NMR (500 MHz, CDCl₃) δ 7.25 (2H, s), 3.99-4.03 (6H, m), 3.89 (3H, s, COOMe), 1.71-1.84 (6H, m), 1.47 (6H, m), 1.22-1.38 (108H, br), 0.88 (9H, t J=9.0 Hz).

(2) Synthesis of Benzoic Acid Substituted with Three Docosyloxy Groups (Compound (E41))

[Formula 82]

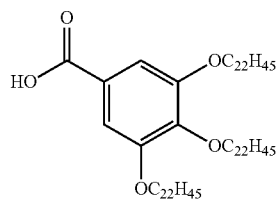

(E41)

Ethanol (100 mL) was added to the compound represented by E36 (11.1 g) and potassium hydroxide (6.7 g), and the mixture was stirred at 85° C. for 2.5 hours. The reaction liquid was cooled to room temperature, then water (200 mL) was added thereto, and the solution was stirred. 6 N Hydrochloric acid (21 mL) was added thereto. The precipitate was collected by suction filtration, and the obtained solid was washed with water (300 mL) and acetonitrile (200 mL) to obtain the compound represented by E41 (10.8 g, percent yield: 99%).

¹H NMR (500 MHz, CDCl₃) δ 7.28 (2H, s), 3.99-4.04 (6H, m), 1.71-1.85 (6H, m), 1.44-1.50 (6H, m), 1.22-1.36 (108H, br), 0.88 (9H, t J=7.0 Hz).

(3) Synthesis of Benzoyl Chloride Substituted with Three Docosyloxy Groups (Compound (E46))

[Formula 83]

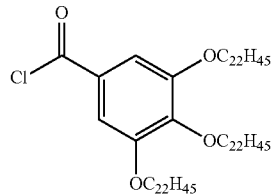

(E46)

The compound (E41) (24.1 g) was suspended in toluene (82 mL) in an eggplant type flask, and the solution was stirred at 65° C. for 30 minutes. Thionyl chloride (14.5 mL) and N,N'-dimethylformamide (3.4 mL) were added thereto, and the mixture was stirred at 65° C. for 3.5 hours. The reaction liquid was concentrated under reduced pressure to obtain the compound (E46) (24.2 g, percent yield: 99%).

¹H NMR (500 MHz, CDCl₃) δ 7.32 (2H, s), 4.08 (2H, t J=6.6 Hz), 4.02 (4H, t J=6.4 Hz), 1.79-1.85 (4H, m), 1.71-1.77 (2H, m), 1.43-1.50 (6H, m), 1.21-1.37 (108H, br), 0.88 (9H, t J=6.7 Hz).

(4) Synthesis of a U-Type Nucleoside Monomer Compound Having Three Docosyloxy Groups (Compound (E52))

[Formula 84]

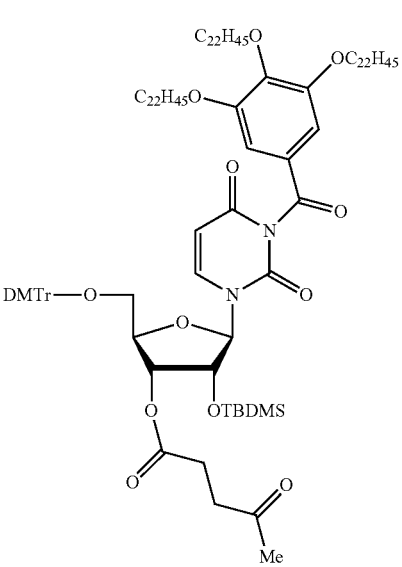

(E52)

To the compound (E6) (11.4 g), pyridine (111 mL), N,N-diisopropylethylamine (8.7 mL), and chlorotrimethylsilane (3.2 mL) were serially added. To the mixture, the compound (E46) (11.1 g) was added, and the mixture was stirred at 60° C. for 5.5 hours. Methanol (100 mL) was added to the reaction liquid at room temperature, and then the mixture was ice-cooled. The precipitated solid was collected by suction filtration and washed with methanol to obtain the compound (E52) (16.4 g, percent yield: 89%).

¹H NMR (500 MHz, CDCl₃) δ 7.99 (1H, br), 7.25-7.38 (9H, m), 7.13 (2H, s), 6.85-6.88 (4H, m), 5.99 (1H, d J=4.8 Hz), 5.33-5.39 (2H, m), 4.53 (1H, br t J=4.1 Hz), 4.26 (1H, m), 3.95-4.07 (6H, m), 3.81 (6H, s), 3.46-3.57 (2H, m), 2.52-2.82 (4H, m), 2.19 (3H, s), 1.69-1.82 (6H, m), 1.42-1.48 (6H, m), 1.14-1.34 (108H, s), 0.85-0.89 (18H, s), 0.09 (3H, s), 0.08 (3H, s).

Example 8

Synthesis of a Uracil (U) Type Nucleoside Monomer Compound Having Two Docosyloxy Groups (Compound (E53))

[Formula 85]

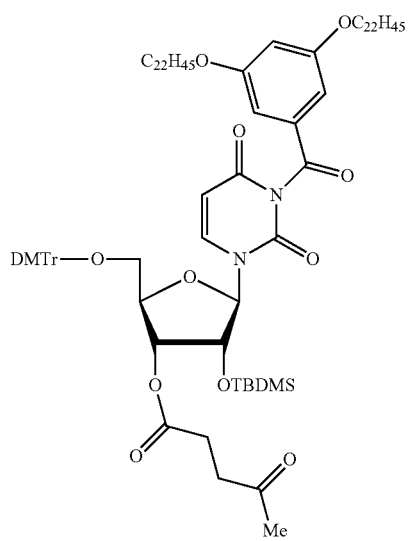

(E53)

(1) Synthesis of Methyl Benzoate Substituted with Two Docosyloxy Groups (Compound (E37))

[Formula 86]

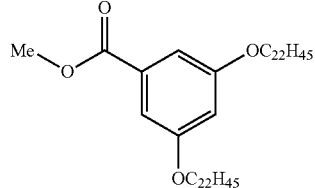

(E37)

To methyl 3,5-dihydroxybenzoate (5.0 g) and potassium carbonate (41.5 g), 1,3-dimethyl-2-imidazolidinone (100 mL) was added, and the mixture was stirred at 80° C. for 30 minutes. 1-Bromodocosane (25.7 g) was added thereto, and the mixture was stirred at 80° C. for 14 hours. Water (400 mL) was added to the reaction liquid, the solution was stirred, and then the precipitate was collected by suction filtration and washed with acetone (300 mL) and acetonitrile (300 mL) to quantitatively obtain the compound represented by E37 (23.8 g).

$^1$H NMR (500 MHz, CDCl$_3$) δ 7.15 (2H, br d J=2.1 Hz), 6.63 (1H, t J=6.4 Hz), 3.96 (4H, t J=6.3 Hz), 3.89 (3H, s, COOMe), 1.74-1.80 (4H, m), 1.41-1.47 (4H, m), 1.23-1.37 (72H, br), 0.88 (6H, t J=7.0 Hz).

(2) Synthesis of Benzoic Acid Substituted with Two Docosyloxy Groups (Compound (E42))

[Formula 87]

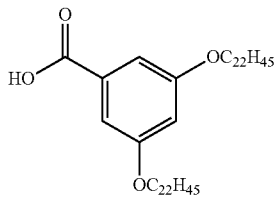

(E42)

Ethanol (100 mL) was added to the compound represented by E37 (7.9 g) and potassium hydroxide (6.7 g), and the mixture was stirred at 85° C. for 2.5 hours. The reaction liquid was cooled to room temperature, then water (200 mL) was added thereto, and the solution was stirred. 6 N Hydrochloric acid (21 mL) was added thereto. The precipitate was collected by suction filtration, the obtained solid was washed with water (200 mL) and acetonitrile (200 mL) to obtain the compound represented by E42 (7.4 g, percent yield: 96%).

$^1$H NMR (500 MHz, CDCl$_3$) δ 7.20 (2H, br), 6.67 (1H, br), 3.97 (4H, br), 1.77 (4H, br), 1.44 (4H, br), 1.25 (72H, br), 0.88 (6H, br).

(3) Synthesis of a U-Type Nucleoside Monomer Compound Having Two Docosyloxy Groups (Compound (E53))

[Formula 88]

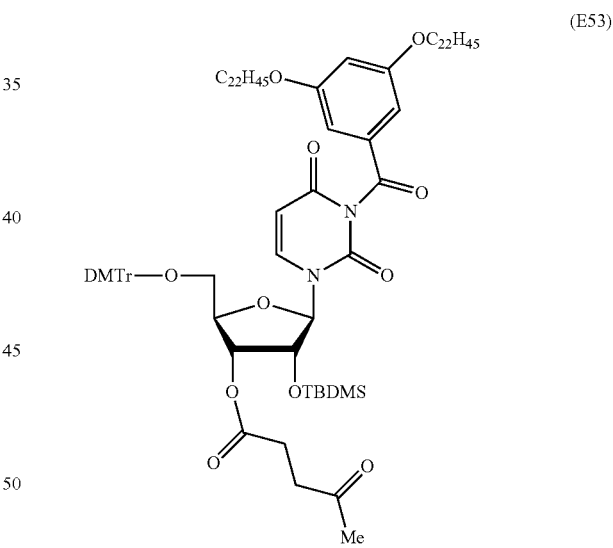

(E53)

To the compound (E42) (540 mg), thionyl chloride (5.2 mL) and N,N-dimethylformamide (110 µL) were added, the mixture was stirred at 50° C. for 3 hours, then the solvent was distilled off under reduced pressure, N,N-diisopropylethylamine (2.0 mL) and pyridine (4.0 mL) were added thereto, then a solution of the compound (E6) (1.6 g) dissolved in pyridine (6 mL) and N,N=diisopropylethylamine (1.0 mL) was added thereto, chlorotrimethylsilane (500 µL) was added and the mixture was stirred at 60° C. for 5 hours, then methanol was added for concentration, the resultant was ice-cooled, and the precipitated solid was collected by suction filtration and washed with methanol to obtain the compound (E53) (919 mg, percent yield: 87%).

$^1$H NMR (500 MHz, CDCl$_3$) δ 7.97 (1H, br d J=8.5 Hz), 7.25-7.38 (9H, m), 7.02 (2H, br), 6.85-6.88 (4H, m), 6.69 (1H, br s), 6.00 (1H, d J=4.7 Hz), 5.26-5.41 (2H, m), 4.54 (1H, t J=5.0 Hz), 4.24 (1H, br), 3.95 (4H, t J=6.3 Hz), 3.81 (6H, br s), 3.43-3.56 (2H, m), 2.52-2.82 (4H, m), 2.19 (3H, br s), 1.74-1.79 (4H, m), 1.41-1.47 (4H, m), 1.11-1.35 (72H, s), 0.84-0.89 (15H, s), 0.11 (3H s), 0.08 (3H, s).

Example 9

Synthesis of a Uracil (U) Type Nucleoside Monomer Compound Having One Docosyloxy Group (Compound (E54))

[Formula 89]

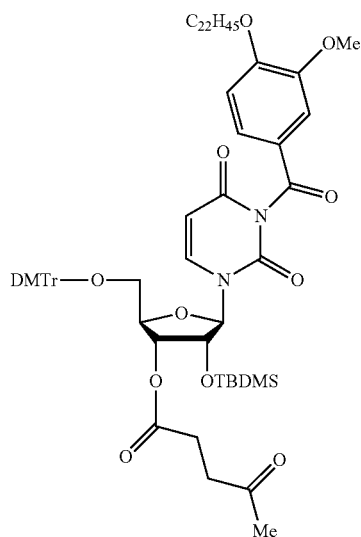

(E54)

(1) Synthesis of Methyl Benzoate Substituted with One Docosyloxy Group (Compound (E38))

[Formula 90]

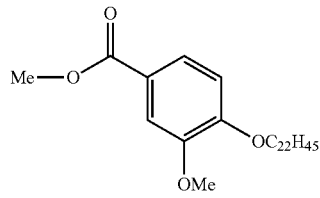

(E38)

To methyl vanillate (4.6 g) and potassium carbonate (17.3 g), 1,3-dimethyl-2-imidazolidinone (80 mL) was added, then the mixture was stirred at 80° C. for 30 minutes and then was cooled to 70° C. 1-Bromodocosane (10.7 g) was added thereto, and the mixture was stirred at 70° C. for 15 hours. Water (300 mL) was added to the reaction liquid, the solution was stirred, then the precipitate was collected by suction filtration and washed with water and acetonitrile to obtain the compound represented by E38 (12.1 g, percent yield: 99%).

$^1$H NMR (500 MHz, CDCl$_3$) δ 7.65 (1H, dd J=8.5, 1.9 Hz), 7.54 (1H, d J=1.9 Hz), 6.87 (1H, d J=8.5 Hz), 4.06 (2H, t J=6.9 Hz), 3.89 (3H, s), 3.9 (3H, s), 1.86 (2H, m), 1.46 (2H, m), 1.21-1.39 (36H, br), 0.88 (3H, t J=7.0 Hz).

(2) Synthesis of Benzoic Acid Substituted with One Docosyloxy Group (Compound (E43))

[Formula 91]

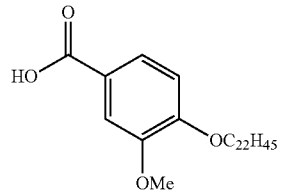

(E43)

Ethanol (100 mL) was added to the compound represented by E38 (4.9 g) and potassium hydroxide (6.7 g), and the mixture was stirred at 85° C. for 2.5 hours. The reaction liquid was cooled to room temperature, then water (200 mL) was added thereto, and the solution was stirred. 6 N Hydrochloric acid (21 mL) was added thereto. The precipitate was collected by suction filtration, and the obtained solid was washed with water (200 mL) and acetonitrile (200 mL) to quantitatively obtain the compound represented by E43 (4.8 g).

$^1$H NMR (500 MHz, CDCl$_3$) δ 7.72 (1H, dd J=8.5, 1.9 Hz), 7.58 (1H, d J=1.9 Hz), 6.89 (1H, d J=8.5 Hz), 4.08 (2H, t J=7.1 Hz), 3.92 (3H, s), 1.84-1.90 (2H, m), 1.42-1.50 (2H, m), 1.13-1.37 (36H, br), 0.88 (3H, t J=7.1 Hz).

(3) Synthesis of a U-Type Nucleoside Monomer Compound Having One Docosyloxy Group (Compound (E54))

[Formula 92]

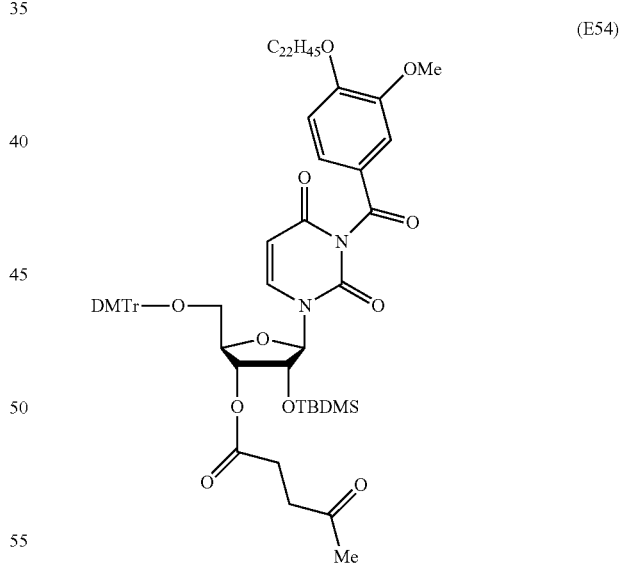

(E54)

To the compound (E43) (334 mg), thionyl chloride (5.2 mL) and N,N-dimethylformamide (110 μL) were added, and the mixture was stirred at 50° C. for 3 hours, then the solvent was distilled off under reduced pressure, N,N-diisopropylethylamine (2.0 mL) and pyridine (4.0 mL) were added thereto, a solution of the compound (E6) (1.6 g) dissolved in pyridine (6 mL) and N,N-diisopropylethylamine (1.0 mL) was added thereto, chlorotrimethylsilane (500 μL) was added and the mixture was stirred at 50° C. for 5 hours, then methanol was added for concentration, the solution was cooled to −30° C., and the precipitated solid was collected by suction filtration and washed with methanol to obtain the compound (E54) (684 mg, percent yield: 80%).

¹H NMR (500 MHz, CDCl₃) δ 7.98 (1H, br d J=6.9 Hz), 7.6 (1H, br d J=1.9 Hz), 7.24-7.38 (10H, m), 6.82-6.88 (5H, m), 5.98 (1H, d J=5.0 Hz), 5.33-5.40 (2H, m), 4.55 (1H, br), 4.25 (1H, br), 4.07 (2H, t J=6.8 Hz), 3.92 (3H, s), 3.81 (6H, br), 3.45-3.57 (2H, m), 2.54-2.82 (4H, m), 2.19 (3H, s), 1.83-1.88 (2H, m), 1.42-1.49 (2H, m), 1.21-1.37 (36H, br), 0.86-0.89 (12H, m), 0.11 (3H, s), 0.08 (3H, s).

Example 10

Synthesis of a Uracil (U) Type Nucleoside Monomer Compound Having One Docosyloxy Group (Compound (E55))

[Formula 93]

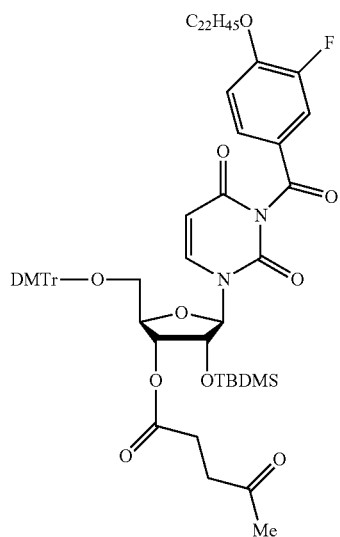

(E55)

(1) Synthesis of Methyl Benzoate Substituted with One Docosyloxy Group (Compound (E39))

[Formula 94]

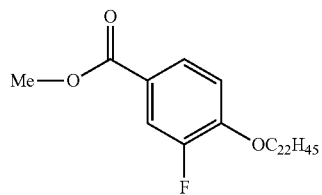

(E39)

To methyl 3-fluoro-4-hydroxybenzoate (850 mg) and potassium carbonate (3.5 g), 1,3-dimethyl-2-imidazolidinone (10 mL) was added, and the mixture was stirred at 70° C. for 15 minutes. 1-Bromodocosane (2.1 g) was added thereto, and the mixture was stirred at 70° C. for 13 hours. Water (200 mL) was added to the reaction liquid, the solution was stirred, then the precipitate was collected by suction filtration and washed with acetonitrile (100 mL) to obtain the compound represented by E39 (2.2 g, percent yield: 93%).

¹H NMR (500 MHz, CDCl₃) δ 7.79 (1H, br d J=8.6 Hz), 7.73 (1H, dd J=11.7, 2.0 Hz), 6.96 (1H, t J=8.3 Hz), 4.08 (2H, t J=6.6 Hz), 3.89 (3H, s), 1.84 (2H, m), 1.47 (2H, m), 1.19-1.37 (36H, br), 0.88 (3H, t J=7.0 Hz).

(2) Synthesis of Benzoic Acid Substituted with One Docosyloxy Group (Compound (E44))

[Formula 95]

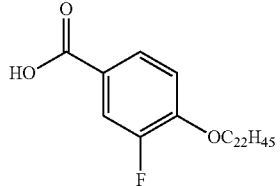

(E44)

Ethanol (20 mL) was added to the compound represented by E39 (1.2 g) and potassium hydroxide (1.7 g), and the mixture was stirred at 85° C. for 2.5 hours. The reaction liquid was cooled to room temperature, then water (80 mL) was added thereto, and the solution was stirred. 6 N Hydrochloric acid (5 mL) was added thereto. The precipitate was collected by suction filtration, and the obtained solid was washed with water (50 mL) and acetonitrile (50 mL) to quantitatively obtain the compound represented by E44 (1.2 g).

¹H NMR (500 MHz, THF-d8) δ 7.75-7.78 (1H, m), 7.68 (1H, dd J=11.7, 2.0 Hz), 7.10 (1H, t J=8.5 Hz), 4.10 (2H, t J=6.6 Hz), 1.78-1.84 (2H, m), 1.43-1.53 (2H, m), 1.23-1.42 (36H, br), 0.87-0.91 (3H, m).

(3) Synthesis of a U-Type Nucleoside Monomer Compound Having One Docosyloxy Group (Compound (E55))

[Formula 96]

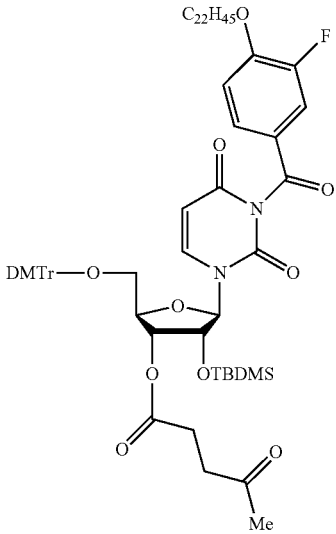

(E55)

To the compound (E44) (327 mg), thionyl chloride (5.2 mL) and N,N-dimethylformamide (110 µL) were added, and the mixture was stirred at 50° C. for 3 hours, then the solvent was distilled off under reduced pressure, N,N-diisopropylethylamine (2.0 mL) and pyridine (4.0 mL) were added thereto, a solution of the compound (E6) (1.6 g) dissolved in pyridine (6 mL) and N,N-diisopropylethylamine (1.0 mL) was added thereto, chlorotrimethylsilane (500 µL) was added, the mixture was stirred at 50° C. for 4 hours, then methanol was added thereto for concentration, the mixture was cooled to −30° C., and the precipitated solid was collected by suction filtration and washed with methanol to obtain the compound (E55) (425 mg, percent yield: 50%).

$^1$H NMR (500 MHz, CDCl$_3$) δ 7.99 (1H, br d J=7.7 Hz), 7.69 (1H, br d J=8.6 Hz), 7.63 (1H, dd J=11.2, 2.0 Hz), 7.24-7.38 (9H, m), 6.97 (1H, t J=8.1 Hz), 6.85-6.88 (4H, m), 5.98 (1H, d J=5.0 Hz), 5.40 (1H, t J=4.4 Hz), 5.34 (1H, d J=8.2 Hz), 4.55 (1H, br t J=5.0 Hz), 4.25 (1H, br), 4.09 (2H, t J=6.7 Hz), 3.81 (6H, br), 3.45-3.56 (2H, m), 2.54-2.82 (4H, m), 2.19 (3H, s), 1.81-1.87 (2H, m), 1.43-1.49 (2H, m), 1.21-1.39 (36H, br), 0.85-0.90 (12H, m), 0.11 (3H, s), 0.08 (3H, s).

Example 11

Synthesis of a Deoxythyme (dT) Type Nucleoside Monomer Compound Having Three Hexadecyloxy Groups (Compound (E56))

[Formula 97]

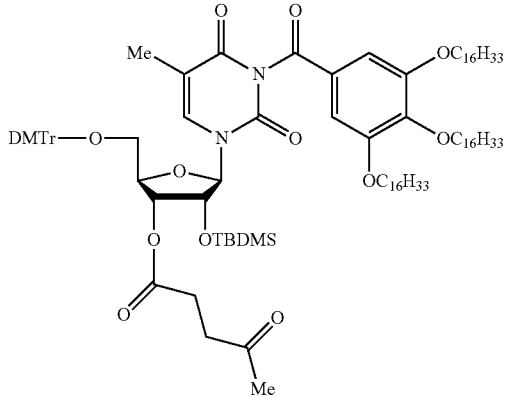

(E56)

(1) Synthesis Benzoyl Chloride Substituted with Three Hexadecyloxy Groups (Compound (E45))

[Formula 98]

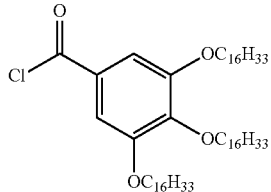

(E45)

The compound (E40) (2.5 g) was suspended in toluene (11.2 mL) in an eggplant type flask, and the solution was stirred at 65° C. for 30 minutes. Thionyl chloride (2.0 mL) and N,N'-dimethylformamide (464 μL) were added thereto, and the mixture was stirred at 65° C. for 3.5 hours. The reaction liquid was concentrated under reduced pressure to obtain the compound (E45) (2.5 g, percent yield: 97%).

$^1$H NMR (500 MHz, CDCl$_3$) δ 7.33 (2H, s), 4.08 (2H, t J=6.6 Hz), 4.02 (4H, t J=6.3 Hz), 1.79-1.85 (4H, m), 1.71-1.77 (2H, m), 1.44-1.51 (6H, m), 1.21-1.37 (72H, br), 0.88 (9H, t J=6.6 Hz).

(2) Synthesis of a dT-Type Nucleoside Monomer Compound Having Three Hexadecyloxy Groups (Compound (E56))

[Formula 99]

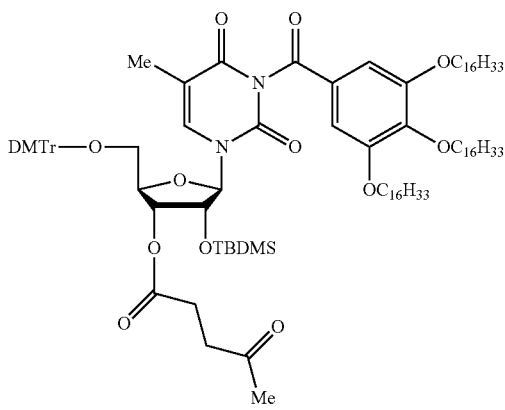

(E56)

To the compound (E4) (1.9 g), pyridine (22 mL), N,N'-diisopropylethylamine (1.7 mL), and chlorotrimethylsilane (640 μL) were serially added. To the mixture, the compound (E45) (1.7 g) was added, and the mixture was stirred at 60° C. for 5.5 hours. Methanol was added to the reaction liquid at room temperature, and the precipitated solid was collected by suction filtration and washed with methanol to obtain the compound (E56) (2.7 g, percent yield: 90%).

$^1$H NMR (500 MHz, CDCl$_3$) δ 7.71 (1H, br s), 7.38-7.41 (2H, m), 7.24-7.33 (7H, m), 7.13 (2H, s), 6.84-6.87 (4H, m), 6.42 (1H, dd J=6.5, 8.4 Hz); 5.74 (1H, br d J=5.7 Hz) 4.15 (1H, br), 3.95-4.05 (6H, m), 3.80 (6H, s), 3.49 (2H, br), 2.69-2.80 (2H, m), 2.42-2.61 (4H, m), 2.17 (3H, s), 1.70-1.82 (6H, m), 1.42-1.48 (6H, m), 1.40 (3H, s), 1.23-1.36 (72H, brs), 0.88 (9H, t J=7.0 Hz).

Example 12

Synthesis of a Uracil (U) Type Nucleoside Monomer Compound Having Three Octadecyloxy Groups (Compound (E57))

[Formula 100]

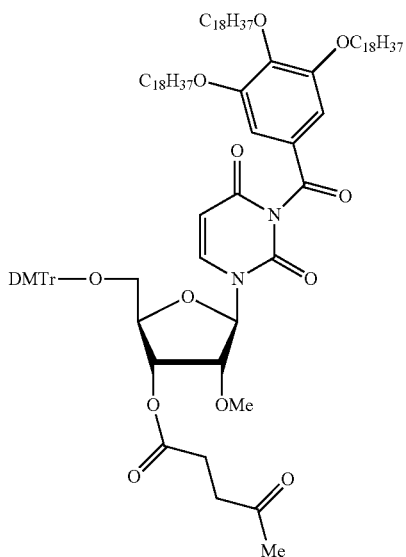

(E57)

(1) Synthesis of a U-Type Nucleoside (Compound (E47))

[Formula 101]

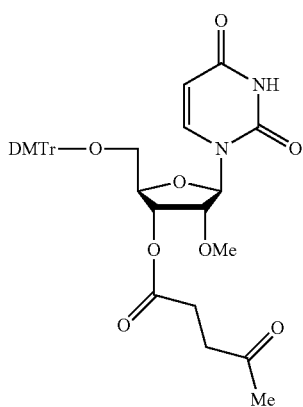

(E47)

3-OH rU (2'-OMe) (3.00 g, 5.35 mmol), N,N-dimethylaminopyridine (65 mg, 0.53 mmol), and THF (15 mL) were measured and dissolved in a 100-mL eggplant type flask, and then levulinic acid (0.93 g, 8.03 mmol) was added thereto. 1-Ethyl-3-(3-dimethylaminopropyl)carbodiimide hydrochloride (1.54 g, 8.03 mmol) was added thereto, and the mixture was stirred at the same temperature for 3.5 hours. THF was distilled off under reduced pressure, then EtOAc (40 mL) and a 0.2 M aqueous solution of AcOH.Et$_3$N (pH: 7.0) (20 mL) were added for separation. To the organic layer, a 0.2 M aqueous solution of AcOH.Et$_3$N (pH: 7.0) (20 mL) was added again for separation. The organic layer was dried over anhydrous sodium sulfate, and then the solvent was distilled off. The organic layer was concentrated and exsiccated under reduced pressure to obtain 3-OLev rU (2'-OMe) (3.61 g). The obtained product was purified by column chromatography [Silicagel 60 (20 g), 5% Et$_3$N contained EtOAc/n-hexane 0:95-95:0]. The effective fraction was concentrated and exsiccated under reduced pressure to obtain purified 3'-OLev rU (2'-OMe) (apparent yield: 3.85 g, residual EtOAc: 6.85%, Et$_3$N: 0.53%, n-hexane: 2.28%, moisture content: 3.75%, content-corrected yield: 3.34 g, content-corrected percent yield: 94.7%).

$^1$H NMR (500 MHz, CDCl$_3$) δ 2.19 (3H, s), 2.62 (2H, t, J=6.00 Hz), 2.72-2.79 (2H, m), 3.46 (1H, AB dd, J=11.00, 2.50 Hz), 3.48 (3H, s), 3.58 (1H, AB dd, J=11.00, 2.50 Hz), 3.80 (6H, s), 4.08 (1H, dd, J=5.00, 2.40 Hz), 4.24 (1H, dt, J=8.00, 2.00, 2.00 Hz), 5.28 (1H, brq, J=5.50 Hz), 5.32 (1H, d, J=5.10 Hz), 6.03 (1H, d, J=4.00 Hz), 6.85 (4H, dd, J=8.50, 2.00 Hz), 7.24-7.32 (7H, m), 7.37 (2H, dd, J=9.00, 1.50 Hz), 7.87 (1H, d, J=8.50 Hz), 8.2-9.0 (0.4H, brs, NH).

(2) Synthesis of a Uracil (U) Type Nucleoside Monomer Compound Having Three Octadecyloxy Groups (Compound (E57))

[Formula 102]

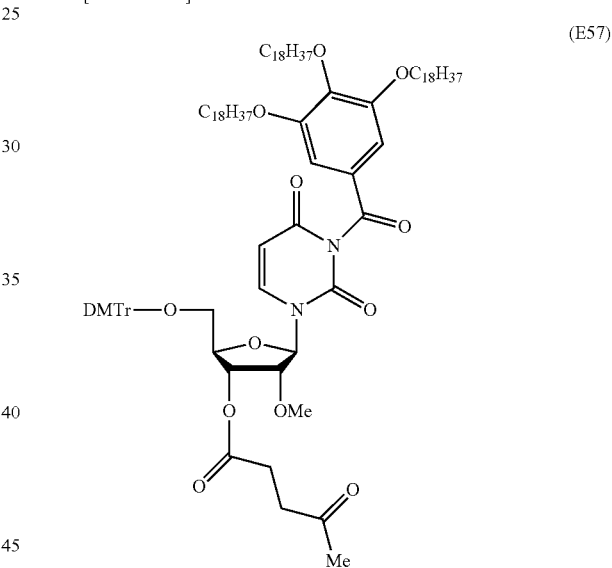

(E57)

3,4,5-tris(Octadecyloxy)benzoic acid (compound (E2)) (1.000 g) and toluene (3.5 mL) were measured and dissolved in a 100-mL eggplant type flask, and the solution was heated to an outside temperature of 70° C. DMF (0.17 mL) and SOCl$_2$ (0.71 mL) were serially added thereto, and the mixture was allowed to react at an outside temperature of 70° C. for 2.5 hours. The solvent was distilled off under reduced pressure. Toluene (10 mL) was added thereto, the solvent was distilled off again, and a concentration and exsiccation process was carried out twice to obtain a powder of 3,4,5-tris(octadecyloxy)benzoyl chloride (compound (E3)) containing the solvent (2.12 g).

The compound (E47) (901 mg-equivalent, 1.19 mmol), i-Pr$_2$NEt (1.29 mL), and pyridine (9 mL) were measured and dissolved in a separate 50-mL eggplant type flask. Chlorotrimethylsilane (0.48 mL) and 3,4,5-tris(octadecyloxy)benzoyl chloride (1.55 g-equivalent) were added thereto at room temperature. The mixture was washed with pyridine (5 mL). The mixture was allowed to react at an outside temperature of 60° C. for 3.5 hours. The reaction liquid was cooled to room temperature, and MeOH (15 mL) was added dropwise thereto. The suspension was stirred for 0.5 hours under ice cooling and then was subjected to collection by suction filtration. The powder was washed with MeOH (5 mLX7). The obtained powder was dried at room temperature for 18 hours under reduced pressure to obtain the compound (E57) (1.33 g, apparent percent yield: 81.9%).

$^1$H NMR (500 MHz, CDCl$_3$) δ 0.88 (9H, t, J=6.75 Hz), 1.22-1.39 (84H, m), 1.42-1.48 (6H m), 1.67-1.82 (6H, m), 2.19 (3H, s), 2.62 (2H, t, J=6.45 Hz), 2.73-2.81 (2H, m), 3.46 (3H, s), 3.48 (1H, AB dd, J=11.55, 1.90 Hz), 3.63 (1H, AB dd, J=11.30, 2.15 Hz), 3.808 (3H, s), 3.808 (3H, s), 3.99 (4H, t, J=6.60 Hz), 4.05 (2H, t, J=6.40 Hz), 4.10 (1H, dd, J=5.00, 3.00 Hz), 4.27 (1H, brd, J=6.80 Hz), 5.27 (1H, bit, J=5.75 Hz), 5.41 (1H, d, J=8.25 Hz), 6.00 (1H, d, J=2.90 Hz), 6.87 (4H, dd, J=11.85, 3.00 Hz), 7.13 (2H, s), 7.24-7.33 (7H, m), 7.38 (2H, dd, J=8.65, 1.40 Hz), 8.05 (1H, brd, J=7.85 Hz).

Example 13

Synthesis of an Adenine (A) Type Nucleoside Monomer Compound Having Three Docosyloxy Groups (Compound (E58))

[Formula 103]

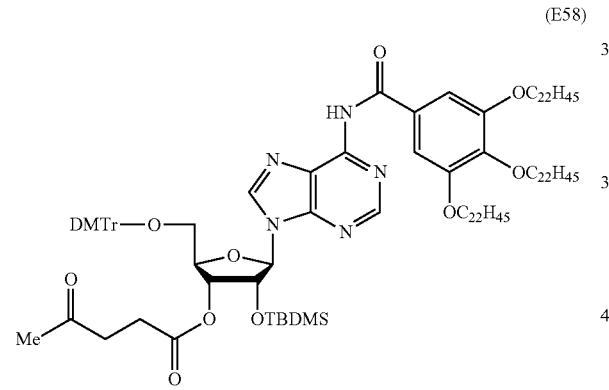

(E58)

(1) Synthesis of an A-Type Nucleoside (Compound (E48))

[Formula 104]

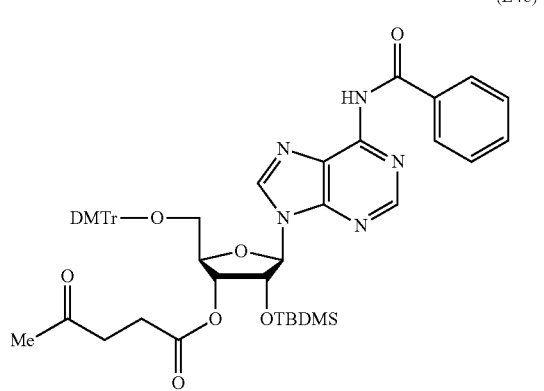

(E48)

5'-O-(1,1-bis(4-Methoxyphenyl)-1-phenylmethyl)-2'-O-tert-butyldimethylsilylade nosine (5.0 g) was dissolved in tetrahydrofuran (21 mL). N,N-Dimethylaminopyridine (77 mg), levulinic acid (973 μL), and 1-ethyl-3-(3-dimethylaminopropyl)carbodiimide hydrochloride (1.8 g) were serially added thereto, and the mixture was stirred at room temperature for 75 minutes, then N,N-dimethylaminopyridine (56 mg), levulinic acid (645 μL), and 1-ethyl-3-(3-dimethylaminopropyl)carbodiimide hydrochloride (1.2 g) were added thereto, and the mixture was further stirred at room temperature for 1 hour. To the reaction liquid, ethyl acetate (20 mL), a 10% aqueous solution of potassium hydrogensulfate (75 mL), and water (40 mL) were added for separatory extraction. The obtained organic layer was washed with a 10% aqueous solution of sodium hydrogen carbonate (75 mL) and then dried over anhydrous sodium sulfate, and then the solvent was distilled off. The residue was concentrated under reduced pressure to quantitatively obtain the compound (E48) (5.6 g).

$^1$H NMR (500 MHz, CDCl$_3$) δ 8.99 (1H, br s), 8.74 (1H, s), 8.23 (1H, s), 8.03 (2H, d J=7.6 Hz), 7.60-7.63 (1H, m), 7.52-7.55 (2H, m), 7.43-7.46 (2H, m), 7.21-7.34 (7H, m), 6.81-6.84 (4H, m), 6.12 (1H, d J=6.7 Hz), 5.48 (1H, dd J=5.2, 2.4 Hz), 5.13 (1H, dd J=5.1, 6.6 Hz), 4.32-4.34 (1H, m), 3.78 (6H, d J=1.0 Hz), 3.40-3.57 (2H, m), 2.60-2.84 (4H, m), 2.20 (3H, s), 0.73 (9H, s), −0.20 (3H, s), −0.27 (3H, s).

(2) Synthesis of an A-Type Nucleoside Monomer Compound Having Three Docosyloxy Groups (Compound (E58))

[Formula 105]

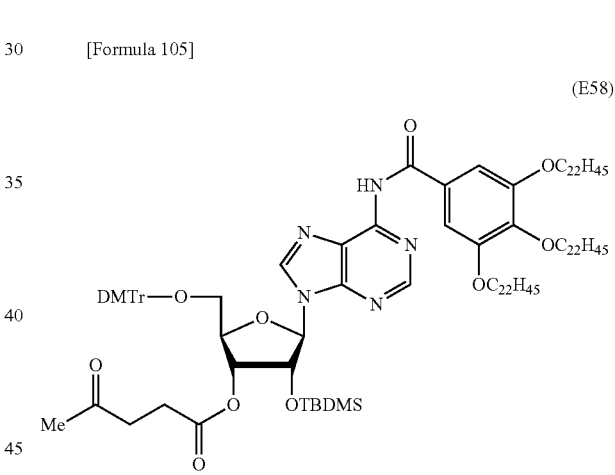

(E58)

The compound (E48) (75 mg) was dissolved in a mixed solution of pyridine (1.7 mL) and toluene (1.7 mL), then N,N'-diisopropylethylamine (325 μL) and chlorotrimethylsilane (162 μL) were serially added thereto, and the mixture was stirred at room temperature for 10 minutes. The compound (E46) (95 mg) was added thereto, and the mixture was stirred at 50° C. for 21 hours. The reaction liquid was cooled to room temperature, then morpholine (219 μL) was added, the mixture was stirred at room temperature for 2 hours, then methanol (100 mL) was added thereto, and the precipitated solid was collected by suction filtration and washed with methanol. The residue was dried and then purified by column chromatography by using toluene/acetonitrile/pyridine (48/1/1) as the mobile phase to obtain the compound (E58) (98 mg, percent yield: 62%).

$^1$H NMR (500 MHz, CDCl$_3$) δ 8.91 (1H, br), 8.70 (1H, s), 8.22, (1H, s), 7.10-7.46 (11H, m), 6.81-6.84 (4H, m), 6.11 (1H, d J=6.6 Hz), 5.47 (1H, dd J=4.9, 2.8 Hz), 5.12-5.15 (1H, m), 4.31-4.33 (1H, m), 3.93-4.07 (6H, m), 3.78 (6H, d J=1.5 Hz), 3.53-3.57 (1H, m), 3.38-3.41 (1H, m), 2.59-2.83

(4H, m), 2.20 (3H, s), 1.70-1.85 (6H, m), 1.43-1.52 (6H, m), 1.20-1.37 (108H, br m), 0.88 (9H, t J=6.9 Hz), 0.74 (9H, s), −0.02 (3H, s), −0.26 (3H, s).

Example 14

Synthesis of a Cytosine (C) Type Nucleoside Monomer Compound Having Three Docosyloxy Groups (Compound (E59))

[Formula 106]

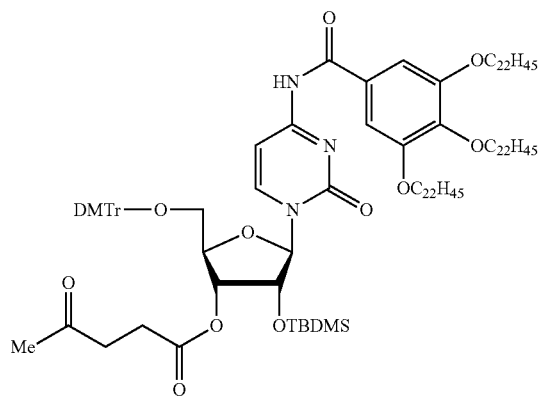

(E59)

(1) Synthesis of a C-Type Nucleoside (Compound (E49))

[Formula 107]

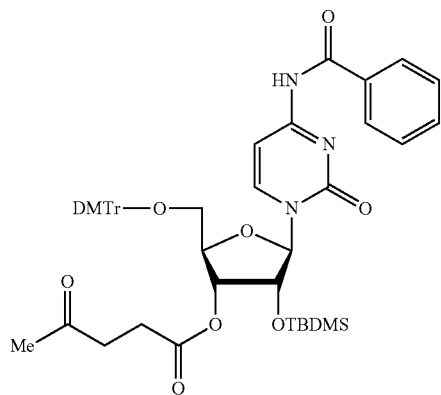

(E49)

5'-O-(1,1-bis(4-Methoxyphenyl)-1-phenylmethyl)-2'-O-tert-butyldimethylsilylcytidine (5.0 g) was dissolved in tetrahydrofuran (20 mL). N,N-Dimethylaminopyridine (80 mg), levulinic acid (997 μL), and 1-ethyl-3-(3-dimethylaminopropyl)carbodiimide hydrochloride (1.9 g) were serially added thereto, the mixture was stirred at room temperature for 1.3 hours, then N,N-dimethylaminopyridine (53 mg), levulinic acid (665 μL), and 1-ethyl-3-(3-dimethylaminopropyl)carbodiimide hydrochloride (1.3 g) were added thereto, and the mixture was further stirred at room temperature for 1.7 hours. To the reaction liquid, ethyl acetate (20 mL), a 10% aqueous solution of potassium hydrogensulfate (75 mL), and water (40 mL) were added for separatory extraction. The obtained organic layer was washed with a 10% aqueous solution of sodium hydrogen carbonate (60 mL) and then dried over anhydrous sodium sulfate, and then the solvent was distilled off. The residue was concentrated under reduced pressure to quantitatively obtain the compound (E49) (6.1 g).

$^1$H NMR (500 MHz, CDCl$_3$) δ 8.86 (1H, br), 8.48 (1H, br), 7.90 (2H, br d J=6.9 Hz), 7.54-7.62 (1H, m), 7.50-7.53 (2H, m), 7.39-7.41 (2H, m), 7.13-7.35 (8H, m), 6.87-6.90 (4H, m), 5.98 (1H, d J=2.5 Hz), 5.23 (1H, dd J=4.4, 7.4 Hz), 4.54-4.55 (1H, m), 4.36-4.39 (1H, m), 3.83 (6H, s), 3.42-3.66 (2H, m), 2.53-2.80 (4H, m), 2.19 (3H, s), 0.89 (9H, s), 0.20 (3H, s), 0.07 (3H, s).

(2) Synthesis of a C-Type Nucleoside Monomer Compound Having Three Docosyloxy Groups (Compound (E59))

[Formula 108]

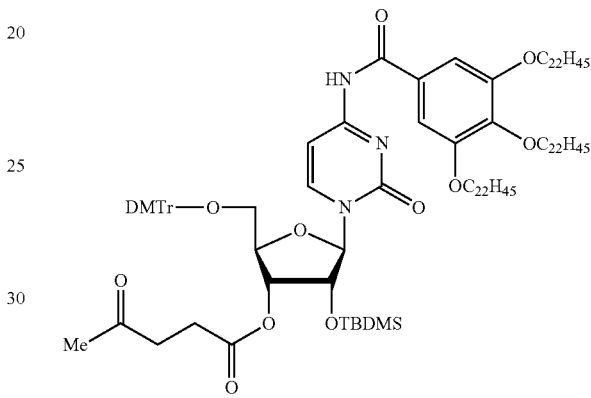

(E59)

The compound (E49) (259 mg) was dissolved in a mixed solution of pyridine (3.0 mL) and toluene (3.0 mL), N,N'-diisopropylethylamine (191 μL) and chlorotrimethylsilane (95 μL) were serially added thereto, and the mixture was stirred at room temperature for 10 minutes. The compound (E46) (167 mg) was added thereto, and the mixture was stirred at 50° C. for 21 hours. The reaction liquid was cooled to room temperature, then morpholine (385 μL) was added thereto, the mixture was stirred at room temperature for 2 hours, then methanol (100 mL) was added, and the precipitated solid was collected by suction filtration and washed with methanol. The obtained residue was dried and then purified by column chromatography by using toluene/pyridine (100/1) as the mobile phase to obtain the compound (E59) (92 mg, percent yield: 34%).

$^1$H NMR (500 MHz, CDCl$_3$) δ 8.70 (1H, br), 8.44 (1H, br s), 7.39-7.41 (2H, m), 7.26-7.35 (8 H, m), 7.08 (2H, br), 6.88 (4H, m), 6.00 (1H, d J=2.6 Hz), 5.24 (1H, dd J=4.4, 6.9 Hz), 4.54 (1H, dd J=2.9, 2.8 Hz), 4.35-4.38 (1H, m), 3.99-4.04 (6H, m), 3.82 (6H, s), 3.42-3.64 (2H, m), 2.73-2.80 (1H, m), 2.61-2.71 (2H, m), 2.53-2.59 (1H, m), 2.19 (3H, s), 1.71-1.86 (6H, m), 1.42-1.51 (6H, m), 1.21-1.36 (108H, br s), 0.86-0.89 (18H, m), 0.19 (3H, s), 0.07 (3H, s).

Example 15

Synthesis of a Guanine (G) Type Nucleoside Monomer Compound Having Three Docosyloxy Groups (Compound (E60))

[Formula 109]

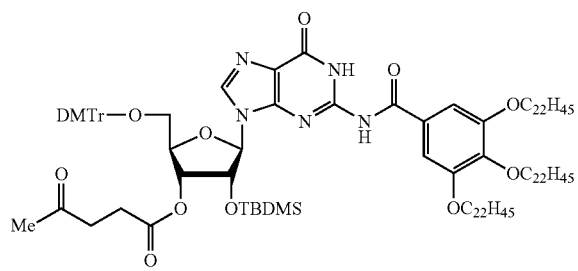

(E60)

(1) Synthesis of a G-Type Nucleoside (Compound (E50))

[Formula 110]

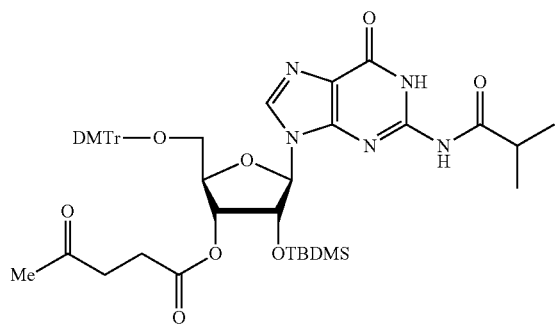

(E50)

5'-O-(1,1-bis(4-Methoxyphenyl)-1-phenylmethyl)-2'-O-tert-butyldimethylsilylguanosine (5.0 g) was dissolved in tetrahydrofuran (21 mL). N,N-Dimethylaminopyridine (159 mg), levulinic acid (1.33 mL), and 1-ethyl-3-(3-dimethylaminopropyl)carbodiimide hydrochloride (2.6 g) were serially added thereto, the mixture was stirred at room temperature for 2 hours, then N,N-dimethylaminopyridine (79 mg), levulinic acid (666 μL), and 1-ethyl-3-(3-dimethylaminopropyl)carbodiimide hydrochloride (1.3 g) were added thereto, and the mixture was further stirred at room temperature for 2.5 hours. To the reaction liquid, ethyl acetate (50 mL) and a 10% aqueous solution of potassium hydrogen sulfate (75 mL) were added for separatory extraction. The obtained organic layer was washed with a 10% aqueous solution of sodium hydrogen carbonate (75 mL) and then dried over anhydrous sodium sulfate, and then the solvent was distilled off. The residue was concentrated under reduced pressure to quantitatively obtain the compound (E50) (5.8 g).

$^1$H NMR (500 MHz, CDCl$_3$) δ 11.90 (1H, br s), 7.78 (1H, s), 7.59-7.62 (2H, m), 7.38-7.43 (4H, m), 7.20-7.28 (4H, m), 6.77-6.83 (4H, m), 5.69 (1H, d J=7.8 Hz), 5.53 (1H, dd J=3.6, 1.8 Hz), 5.39 (1H, dd J=5.8, 8.5 Hz), 4.19-4.21 (1H, br m), 3.77 (6H, d J=9.7 Hz), 3.59 (1H, dd J=10.9, 1.7 Hz), 3.05 (1H, dd J=11.0, 2.5 Hz), 2.55-2.84 (5H, m), 3.06 (3H, s), 0.79 (3H, d J=7.0 Hz), 0.77 (9H, s), 0.53 (3H, d J=6.9 Hz), 0.04 (3H, s), −0.21 (3H, s).

(2) Synthesis of a G-Type Nucleoside Monomer Compound Having Three Docosyloxy Groups (Compound (E60))

[Formula 111]

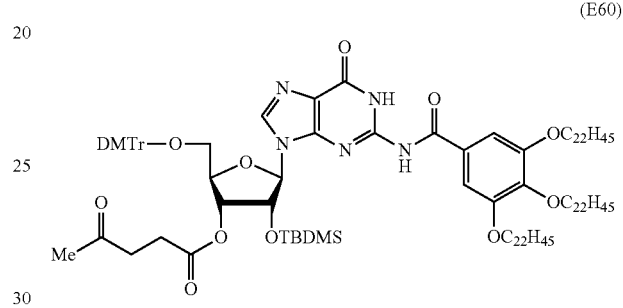

(E60)

The compound (E50) (98 mg) was dissolved in a mixed solution of pyridine (1.7 mL) and toluene (1.7 mL), N,N'-diisopropylethylamine (287 μL) and chlorotrimethylsilane (143 μL) were serially added thereto, and the mixture was stirred at room temperature for 10 minutes. The compound (E46) (84 mg) was added, and the mixture was stirred at 50° C. for 21 hours. The reaction liquid was cooled to room temperature, then morpholine (175 μL) was added thereto, the mixture was stirred at room temperature for 2 hours, then methanol was added, the precipitated solid was collected by suction filtration and washed with methanol. The residue was dried and then purified by column chromatography by using toluene/acetonitrile/pyridine (48/1/1) as the mobile phase to obtain the compound (E60) (57 mg, percent yield: 40%).

$^1$H NMR (500 MHz, CDCl$_3$) δ 12.20 (1H, br s), 8.46 (1H, br s), 7.86 (1H, s), 7.42-7.45 (2H, m), 7.31-7.33 (4H, m), 7.23-7.27 (3H, m), 6.85 (2H, s), 6.78-6.81 (4H, m), 5.84 (1H, d J=6.2 Hz), 5.54 (1H, dd J=3.2, 4.9 Hz), 4.95 (1H, dd J=5.1, 6.1 Hz), 4.25-4.27 (1H, br m), 3.92-4.04 (6H, m), 3.75 (6H, s), 3.49-3.52 (1H, m), 3.27-3.30 (1H, m), 2.58-2.80 (4H, m), 2.18 (3H, s), 1.71-1.81 (6H, m), 1.44-1.50 (6H, m), 1.21-1.37 (108H, br s), 0.88 (9H, t J=6.6 Hz), 0.78 (9H, s), −0.01 (3H, s), −0.15 (3H, s).

Example 16

Synthesis of a Uracil (IT) Type Nucleoside Monomer Compound Having Three Hexadecyloxy Groups (Compound (E61))

[Formula 112]

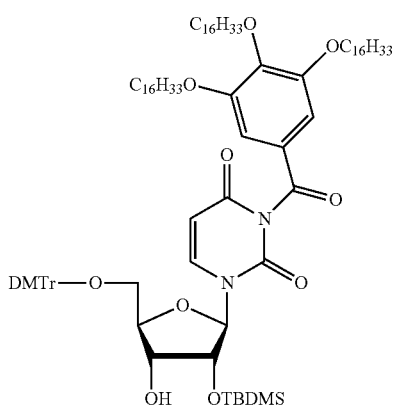

(E61)

The compound (E51) (15.8 mg) was dissolved in chloroform (200 μL), and a 2,4,6-trimethylpyridine/acetic acid solution (4/1) (200 μL) was added thereto. Hydrazine monohydrate (2.0 μL) was added thereto, the mixture was stirred at room temperature for 60 minutes, then acetylacetone (8.4 μL) was added, and the mixture was stirred at room temperature for 5 minutes. Acetonitrile (4 mL) was added at room temperature, and the mixture was stirred and then was cooled to −30° C. The precipitate was subjected to centrifugal sedimentation and then washed with acetonitrile to obtain the compound (E61) (10.0 mg, percent yield: 67%).

$^1$H NMR (500 MHz, CDCl$_3$) δ 8.05 (1H, br d J=8.2 Hz), 7.36-7.40 (2H, m), 7.26-7.33 (7H, m), 7.13 (2H, s), 6.85-6.87 (4H, m), 5.96 (1H, d J=−3.7 Hz), 5.39 (1H, d J=8.2 Hz), 4.36-4.42 (2H, m), 4.12-4.14 (1H, m), 3.94-4.05 (6H, m), 3.81 (6H, d J=1.0 Hz), 3.54 (2H, br), 2.25 (1H, br), 1.70-1.83 (6H, m), 1.42-1.48 (6H, m), 1.22-1.37 (72H, br), 0.91 (9H, s), 0.88 (9H, t J=6.9 Hz), 0.17 (3H, br s), 0.16 (3H, s).

Example 17

Synthesis of a Uracil (U) Type Nucleoside Monomer Compound Having Three Octadecyloxy Groups (Compound (E62))

[Formula 113]

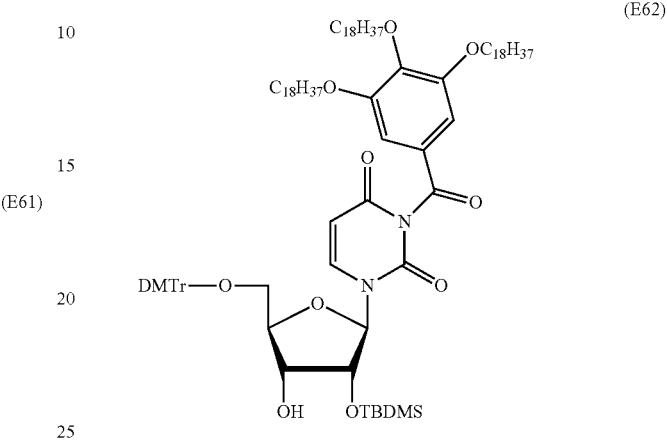

(E62)

The compound (E7) (16.7 mg) was dissolved in chloroform (200 μL), and a 2,4,6-trimethylpyridine/acetic acid solution (4/1) (200 μL) was added thereto. Hydrazine monohydrate (2.0 μL) was added thereto, the mixture was stirred at room temperature for 60 minutes, then acetylacetone (8.4 μL) was added thereto, and the mixture was stirred at room temperature for 5 minutes. Acetonitrile (4 mL) was added at room temperature, and the mixture was stirred and then was cooled to −30° C. The precipitate was subjected to centrifugal sedimentation and then washed with acetonitrile to obtain the compound (E62) (14.9 mg, percent yield: 95%).

$^1$H NMR (500 MHz, CDCl$_3$) δ 8.06 (1H, br d J=7.8 Hz), 7.36-7.40 (2H, m), 7.25-7.34 (7H, m), 7.13 (2H, s), 6.85-6.88 (4H, m), 5.96 (1H, d J=3.5 Hz), 5.39 (1H, d J=8.2 Hz), 4.36-4.42 (2H, m), 4.12-4.14 (1H, m), 3.94-4.05 (6H, m), 3.81 (6H, br), 3.54 (2H, br), 2.25 (1H, br), 1.69-1.82 (6H, m), 1.42-1.48 (6H, m), 1.21-1.36 (84H, br), 0.91 (9H, s), 0.88 (9H, t J=6.9 Hz), 0.17 (3H, br s), 0.16 (3H, s).

Example 18

Synthesis of a Uracil (U) Type Nucleoside Monomer Compound Having Three Docosyloxy Groups (Compound (E63))

[Formula 114]

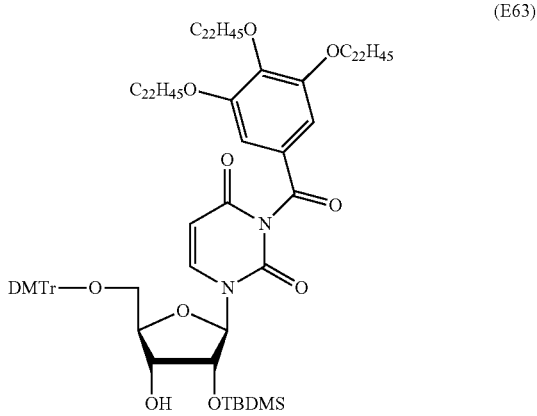

(E63)

The compound (E52) (110 mg) was dissolved in toluene (1 mL), and a 2,4,6-trimethylpyridine/acetic acid solution (4/1) (1 mL) was added thereto. Hydrazine monohydrate (5.8 μL) was added, the mixture was stirred at room temperature for 50 minutes, acetylacetone (37 μL) was added, and the mixture was stirred at room temperature for 5 minutes. Methanol (20 mL) was added at room temperature, the solution was stirred, and then the precipitate was collected by suction filtration and then washed with methanol to obtain the compound (E63) (100 mg, percent yield: 96%).

$^1$H NMR (500 MHz, CDCl$_3$) δ 8.04 (1H, br d J=8.1 Hz), 7.38-7.40 (2H, m), 7.25-7.34 (7H, m), 7.13 (2H, s), 6.84-6.87 (4H, m), 5.96 (1H, d J=3.3 Hz), 5.39 (1H, d J=8.3 Hz), 4.37-4.41 (2H, m), 4.11-4.13 (1H, m), 3.94-4.05 (6H, m), 3.81 (6H, d J=1.0 Hz), 3.54 (2H, br), 2.57 (1H, br), 1.70-1.82 (6H, m), 1.42-1.48 (6H, m), 1.23-1.36 (108H, br), 0.91 (9H, s), 0.88 (9H, t J=6.9 Hz), 0.17 (3H, br s), 0.16 (3H, s).

Example 19

Synthesis of a Deoxythymine (dT) Type Nucleoside Monomer Compound Having Three Octadecyloxy Groups (Compound (E64))

[Formula 115]

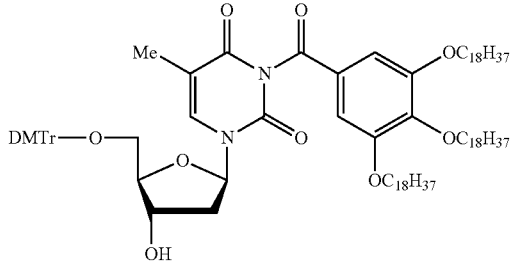

(E64)

The compound (E5) (50 mg) was dissolved in dichloromethane (1 mL), and a 2,4,6-trimethylpyridine/acetic acid solution (4/1) (1 mL) was added thereto. Hydrazine monohydrate (2.3 μL) was added, the mixture was stirred at room temperature for 30 minutes, acetylacetone (10 μL) was added thereto, and the mixture was stirred at room temperature for 5 minutes. Acetonitrile (10 mL) was added at room temperature and the solution was stirred and then concentrated under reduced pressure, and this process was repeated twice. The suspension was cooled to 0° C., and the precipitate was collected by suction filtration and then washed with acetonitrile to obtain the compound (E64) (44.2 mg, percent yield: 95%).

$^1$H NMR (500 MHz, CDCl$_3$) δ 7.69 (1H, br), 7.39-7.42 (2H, m), 7.24-7.33 (7H, m), 7.13 (2H, s), 6.84-6.87 (4H, dd J=9.0, 1.5), 6.39 (1H, t J=7.0), 4.60 (1H, m), 3.96-4.07 (7H, m), 3.80 (6H, s), 3.39-3.53 (2H, m), 2.62 (1H, br), 2.33-2.47 (2H, m), 1.71-1.83 (6H, m), 1.51 (3H, br), 1.42-1.48 (6H, m), 1.21-1.35 (84H, br), 0.88 (9H, J=7.0).

Example 20

Synthesis of a Uracil (U) Type Nucleoside Monomer Compound Having Three Hexadecyloxy Groups (Compound (E65))

[Formula 116]

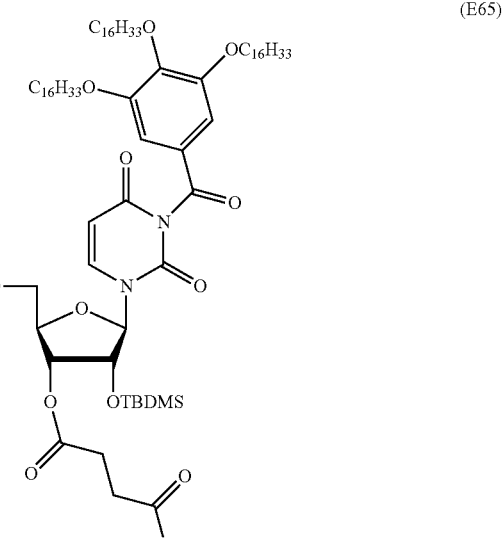

(E65)

To the compound (E51) (158 mg), a 248 mM trichloroacetic acid/toluene solution (5 mL) was added, the mixture was stirred at room temperature for 10 minutes, then methanol (5 mL) was added thereto, and the mixture was stirred. The reaction liquid was concentrated under reduced pressure, then methanol (50 mL) was added, the mixture was cooled to 0° C., and the precipitate was collected by suction filtration and then washed with methanol to obtain the compound (E65) (110 mg, percent yield: 86%).

$^1$H NMR (500 MHz, CDCl$_3$) δ 7.90 (1H, br), 7.13 (2H, s), 5.81-5.87 (1H, m), 5.69 (1H, br), 5.18 (1H, br), 4.57 (1H, br), 4.21-4.25 (1H, m), 3.94-4.09 (7H, m), 3.79 (1H, br d J=12.2 Hz), 2.54-2.87 (5H, m), 2.20 (3H, s), 1.70-1.81 (6H, m), 1.42-1.48 (6H, m), 1.24-1.31 (72H, br), 0.86-0.89 (18H, m), 0.08 (3H, s), 0.06 (3H, s).

Example 21

Synthesis of a Uracil (U) Type Nucleoside Monomer Compound Having Two Docosyloxy Groups (Compound (E66))

[Formula 117]

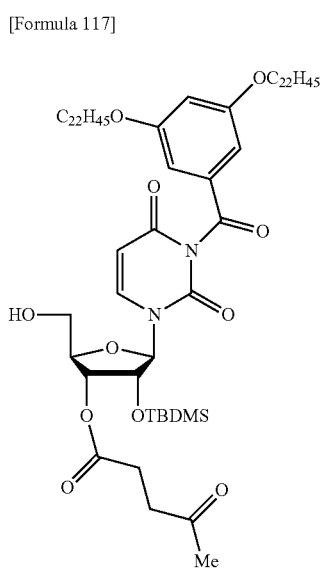

(E66)

To the compound (E53) (151 mg), a 248 mM trichloroacetic acid/toluene solution (5 mL) was added, and the mixture was stirred at room temperature for 10 minutes. The reaction liquid was concentrated under reduced pressure, then a 10% methanol/acetonitrile solution (80 mL) was added thereto, then the mixture was subjected to centrifugal sedimentation, and the sediment was washed with acetonitrile to obtain the compound (E66) (110 mg, percent yield: 91%).

$^1$H NMR (500 MHz, CDCl$_3$) δ 7.85 (1H, br d J=8.2 Hz), 7.02 (2H, d J=2.2 Hz), 6.70 (1H, t J=2.3 Hz), 5.85 (1H, d J=8.3 Hz), 5.66 (1H, d J=4.8 Hz), 5.2 (1H, t J=4.7 Hz), 4.59 (1H, t J=4.8 Hz), 4.21-4.24 (1H, m), 3.91-3.99 (5H, m), 3.77 (1H, br d J=12.6), 2.54-2.87 (5H, m), 2.20 (3H, s), 1.73-1.79 (4H, m), 1.40-1.46 (4H, m), 1.21-1.35 (72H, s), 0.86-0.89 (15H, s), 0.08 (3H, s), 0.06 (3H, s).

Example 22

Synthesis of Uracil (U) Type Nucleoside Monomer Compound Having Three Docosyloxy Groups (Compound (E67))

[Formula 118]

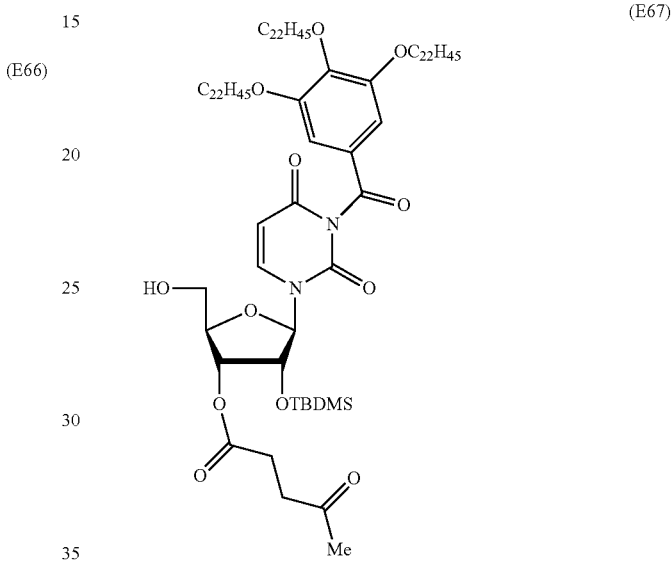

(E67)

To the compound (E52) (11.0 g), a 490 mM trichloroacetic acid/toluene solution (150 mL) was added, the mixture was stirred at room temperature for 10 minutes, then methanol (75 mL) was added thereto, and the mixture was stirred for 5 minutes. The reaction liquid was concentrated under reduced pressure, then acetonitrile (75 mL) was added thereto, and the mixture was concentrated under reduced pressure. Methanol (72 mL) and water (46 mL) were added, the mixture was concentrated under reduced pressure, then methanol (160 mL) was added thereto, the mixture was cooled to 0° C., and the precipitate was collected by suction filtration and then washed with methanol to quantitatively obtain the compound (E67) (9.3 g).

$^1$H NMR (500 MHz, CDCl$_3$) δ 7.91 (1H, br), 7.13 (2H, s), 5.85 (1H, d J=8.2 Hz), 5.68 (1H, br), 5.18 (1H, br), 4.57 (1H, br), 4.22-4.25 (1H, br m), 3.94-4.09 (7H, m), 3.77-3.80 (1H, m), 2.54-2.87 (5H, m), 2.20 (3H, s), 1.69-1.82 (6H, m), 1.42-1.48 (6H, m), 1.22-1.36 (108H, br), 0.86-0.89 (18H, m), 0.08 (3H, s), 0.06 (3H, s).

Example 23

Synthesis of a Deoxythymine (dT) Type Nucleoside Monomer Compound Having Three Hexadecyloxy Groups (Compound (E68))

[Formula 119]

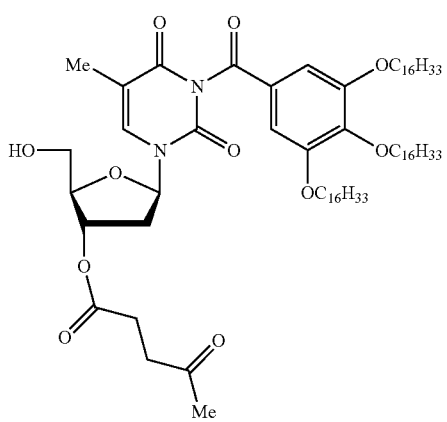

(E68)

To the compound (E56) (2.6 g), a 490 mM trichloroacetic acid/toluene solution (44.3 mL) was added, the mixture was stirred at room temperature for 10 minutes, then methanol (20 mL) was added thereto, and the mixture was stirred. The reaction liquid was concentrated under reduced pressure, then methanol (100 mL) and water (3 mL) were added, the mixture was cooled to 0° C., and then the precipitate was collected by suction filtration and then washed with methanol to obtain the compound (E68) (2.0 g, percent yield: 99%).

$^1$H NMR (500 MHz, CDCl$_3$) δ 7.65 (1H, br), 7.11 (2H, s), 6.26 (1H, br), 5.34-5.37 (1H, m), 4.10-4.12 (1H, m), 3.89-4.05 (9H, m), 2.71-2.82 (2H, m), 2.52-2.62 (2H, m), 2.43 (2H, br), 2.19 (3H, s), 1.97 (3H, d, J=1.3 Hz), 1.69-1.84 (6H, m), 1.42-1.48 (6H, m), 1.22-1.37 (72H, br), 0.86-0.89 (9H, m).

Example 24

Synthesis of a Uracil (U) Type Nucleoside Monomer Compound Having Three Octadecyloxy Groups (Compound (E69))

[Formula 120]

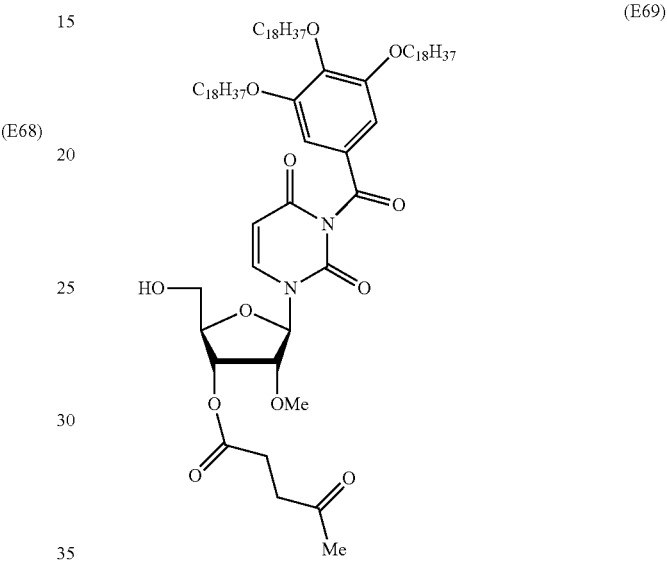

(E69)

The compound (E57) (500 mg) and toluene (5 mL) were measured and dissolved in a 50-mL eggplant type flask. Trichloroacetic acid (0.4 g) was added thereto, and the mixture was stirred at room temperature for 10 minutes. Methanol (2.5 mL) was added thereto, then acetonitrile (10 mL) was added dropwise for 5 minutes, and then the mixture was stirred for 15 minutes under ice cooling. The precipitate was collected by suction filtration, and the obtained residue was washed with acetonitrile containing 5% methanol (5 mL) five times. The obtained powder was dried at 40° C. for 1.5 hours under reduced pressure to obtain the compound (E69) (379 mg, percent yield: 88.2%).

$^1$H NMR (500 MHz, CDCl$_3$) δ 0.88 (9H, t, J=6.80 Hz), 1.22-1.39 (84H, m), 1.42-1.48 (6H, m), 1.67-1.82 (6H, m), 2.20 (3H, s), 2.59-2.86 (5H, m), 3.46 (3H, s), 3.80 (1H, AB brd, J=11.65 Hz), 3.97 (4H, t, J=6.45 Hz), 4.00 (1H, AB dd, J=11.65 Hz), 4.05 (2H, t, J=6.60 Hz), 4.18 (1H, brs), 4.22-4.24 (1H, brm), 5.25 (1H, brm), 5.81 (1H, brm), 5.86 (1H, d, J=8.22 Hz), 7.12 (2H, s), 7.94 (1H, brs).

Example 25

Synthesis of a Uracil (U) Type Nucleoside Monomer Compound Having Two Icosyloxy Groups (Compound (E111))

[Formula 121]

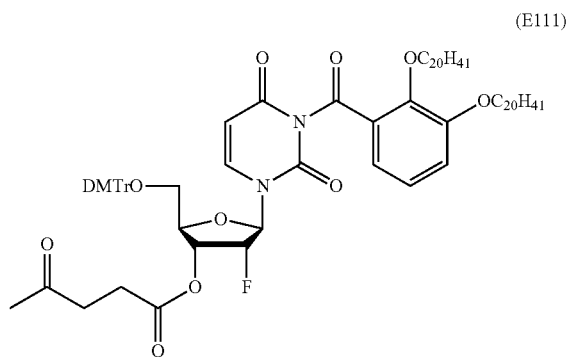

(E111)

(1) Synthesis of Methyl Benzoate Substituted with Two Icosyloxy Groups (Compound (E107))

[Formula 122]

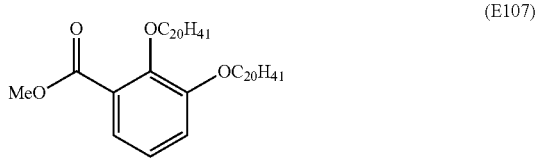

(E107)

Methyl 2,3-dihydroxybenzoate (4.65 g, 27.65 mmol), potassium carbonate (11.47 g, 82.96 mmol), and DMF (250 mL) were measured into a 500-mL eggplant type flask, and the mixture was stirred at 40° C. for 1 hour. Subsequently, n-$C_{20}H_{41}$Br (24.99 g, 69.13 mmol) was added, and the mixture was stirred at 70° C. for 8 hours. The reaction liquid was cooled to room temperature, then city water (250 mL) was added, and the suspension was stirred for 2 hours. The white crystal was collected by suction filtration and washed with city water (100 mL) twice. The residue was dried at 40° C. for 28 hours under reduced pressure to obtain a crude material (25.64 g). MeOH (500 mL) was added thereto, and the suspension was stirred at an outside temperature of 80° C. for 0.5 hours. The reaction liquid was cooled and then was subjected to collection by suction filtration, and then the obtained residue was washed with MeOH (50 mL). This process was repeated. The obtained white crystal was dried at 40° C. under reduced pressure to obtain methyl 2,3-bis(icosyloxy)benzoate (E107, 19.5 g, percent yield: 94.9%).

$^1$H NMR (500 MHz, CDCl$_3$) δ 0.88 (6H, t, J=7.05 Hz), 1.15-1.40 (68H, m), 1.40-1.51 (2H, m), 1.75-1.84 (2H, m), 3.89 (3H, s), 3.97 (2H, t, J=6.40 Hz), 4.02 (2H, t, J=6.70 Hz), 7.02 (1H, d, J=6.30 Hz), 7.03 (1H, d, J=3.15 Hz), 7.28 (1H, dd, J=6.30, 3.15 Hz).

(2) Synthesis of Benzoic Acid Substituted with Two Icosyloxy Groups (Compound (E108))

[Formula 123]

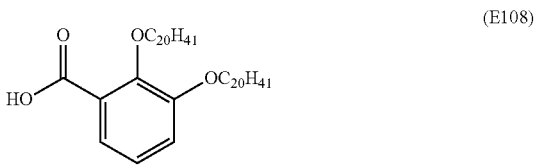

(E108)

Methyl 2,3-bis(icosyloxy)benzoate (E107, 18.0 g, 24.68 mmol), potassium hydroxide (16.62 g, 296.21 mmol), and EtOH (180 mL) were serially measured into a 1-L eggplant type flask, and the mixture was allowed to react at 85° C. for 2 hours. The reaction liquid was cooled, then 2 M HCl (180 mL) was added dropwise under ice cooling. Then city water (200 mL) was added dropwise. The crystal was collected by suction filtration to obtain 2,3-bis(icosyloxy)benzoic acid (E108, 17.9 g, percent yield: 101%).

$^1$H NMR (500 MHz, CDCl$_3$) δ 0.88 (6H, t, J=7.05 Hz), 1.10-1.40 (68H, m), 1.40-1.51 (2H, m), 1.82-1.86 (2H, m), 4.02 (2H, t, J=6.40 Hz), 4.28 (2H, t, J=6.85 Hz), 7.11-7.18 (2H, m), 7.72 (1H, dd, J=8.70, 1.85 Hz), 11.63 (1H, brs).

(3) Synthesis of Benzoyl Chloride Substituted with Two Icosyloxy Groups (Compound (E109))

[Formula 124]

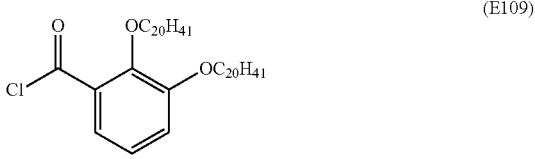

(E109)

2,3-bis(Icosyloxy)benzoic acid (E108, 10.00 g, 13.98 mmol), toluene (70 mL), DMF (2.2 mL), and thionyl chloride (9.18 mL, 125.84 mmol) were serially mixed together in a 500-mL eggplant type flask, and the mixture was allowed to react at 70° C. for 2 hours in an argon atmosphere. The solvent was distilled off under reduced pressure, and the residue was subjected to azeotropic distillation with toluene (200 mL) twice. The residue was finally concentrated and exsiccated under reduced pressure to obtain 2,3-bis(icosyloxy)benzoyl chloride (E109, 10.26 g; percent yield: 100%).

$^1$H NMR (500 MHz, CDCl$_3$) δ 0.88 (6H, t, J=6.85 Hz), 1.10-1.40 (68H, m), 1.40-1.5.1 (2H, m), 1.77-1.84 (2H, m), 3.99 (2H, t, J=6.40 Hz), 4.05 (2H, t, J=6.70 Hz), 7.07-7.11 (2H, m), 7.49 (1H, dd, J=7.30, 2.25 Hz).

(4) Synthesis of a U-Type Nucleoside (Compound (E110))

[Formula 125]

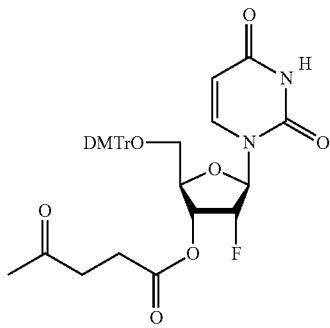

(E110)

1-((2R,3R,4R,5R)-5-((bis(4-Methoxyphenyl)(phenyl)methoxy)methyl)-3-fluoro-4-hydroxytetrahydrofuran-1-yl)pyrimidine-2,4(1H,3H)-dione (3.00 g, 5.47 mmol), DMAP (67 mg, 0.55 mmol), and THF (15 mL) were measured and dissolved in a 100-mL eggplant type flask, and then levrinic acid (0.95 g, 8.20 mmol) was added thereto. WSC.HCl (1.57 g, 8.20 mmol) was added, and the mixture was stirred at the same temperature for 2.0 hours. THF was distilled off under reduced pressure, then EtOAc (40 mL) and a 0.2 M aqueous solution of AcOH.Et$_3$N (pH: 7.0) (15 mL) were added for separation. To the organic layer, a 0.2 M aqueous solution of AcOH.Et$_3$N (pH: 7.0) (15 mL) was added again for separation. The organic layer was dried over anhydrous sodium sulfate, and then the solvent was distilled off. The organic layer was concentrated and exsiccated under reduced pressure to obtain 3'-OLev rU (2'-F) (E110, 3.61 g). The resultant was purified by column chromatography [Silicagel 60 (20 g), 5% Et$_3$N contained EtOAc/n-hexane 0:95-95:0]. The effective fraction was concentrated and exsiccated under reduced pressure to obtain purified 3'-OLev rU (2'-F) (E110, percent yield: 3.57 g, percent yield: 93.5%).

$^1$H NMR (500 MHz, CDCl$_3$) δ 2.19 (3H, s), 2.57-2.66 (2H, m), 2.67-2.84 (2H, m), 3.46 (1H, dd, J=11.35, 2.50 Hz), 3.62 (1H, dd, J=11.35, 2.30 Hz), 3.799 (3H, s), 3.800 (3H, s), 4.30 (1H, brd, J=7.25 Hz), 5.22 (1H, dddd, $^2J_{HF}$=51.61 Hz, J=4.50, 2.25, 2.25 Hz), 5.31-5.37 (1H, m), 5.34 (1H, d, J=8.15 Hz), 6.11 (1H, dd, $^3J_{HF}$=16.10 Hz, J=2.20 Hz), 6.85 (4H, dd, J=8.95, 2.15 Hz), 7.24-7.37 (9H, m), 7.84 (1H, d, J=8.20 Hz), 8.80 (1H, brs).

(5) Synthesis of a U-Type Nucleoside Monomer Compound Having Two Icosyloxy Groups (Compound (E111))

[Formula 126]

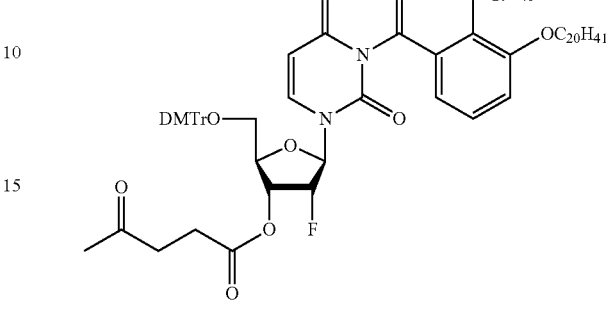

(E111)

The compound (E110) (1.23 g, 1.77 mmol), i-Pr$_2$NEt (1.26 mL), and pyridine (11 mL) were measured and dissolved in a 200-mL eggplant type flask. TMSCl (0.56 mL) and 2,3-bis(icosyloxy)benzoyl chloride (E109, 0.828 g-equivalent) were serially added at room temperature. The mixture was allowed to react at an outside temperature of 60° C. for 3.5 hours. The reaction liquid was cooled to room temperature, and MeOH (72 mL) was added dropwise. The suspension was stirred for 0.5 hours under ice cooling and then was subjected to collection by suction filtration. The powder was washed with MeOH (5 mL×7). The obtained powder was dried at room temperature for 18 hours under reduced pressure to obtain the compound (E111) (1.33 g, percent yield: 81.9%).

$^1$H NMR (500 MHz, CDCl$_3$) δ 0.88 (6H, t, J=7.10 Hz), 1.00-1.40 (64H, m), 1.40-1.52 (2H, m), 1.53-1.75 (4H, m), 1.75-1.88 (2H, m), 2.18 (3H, s), 2.55-2.86 (4H, m), 3.46 (1H, dd, J=11.40, 2.28 Hz), 3.64 (1H, dd, J=11.40, 2.30 Hz), 3.801 (3H, s), 3.803 (3H, s), 3.95 (2H, t, J=6.45 Hz), 3.99 (2H, t, J=7.05 Hz), 4.28 (1H, brd, J=7.40 Hz), 5.22 (1H, dddd, $^2J_{HF}$=51.56 Hz, J=4.40, 2.10, 2.10 Hz), 5.32-5.38 (1H, m), 5.40 (1H, d, J=8.25 Hz), 6.11 (1H, dd, $^3J_{HF}$=15.90 Hz, J=2.05 Hz), 6.85 (4H, dd, J=8.95, 1.95 Hz), 7.05-7.11 (2H, m), 7.23-7.33 (7H, m), 7.37 (2H, dd, J=8.70, 1.50 Hz), 7.47 (1H, dd, J=7.50, 2.05 Hz), 7.91 (1H, d, J=8.25 Hz).

Example 26

Synthesis of a Deoxythymine (dT) Type Nucleoside Monomer Compound Having Two Icosyloxy Groups (Compound (E113))

[Formula 127]

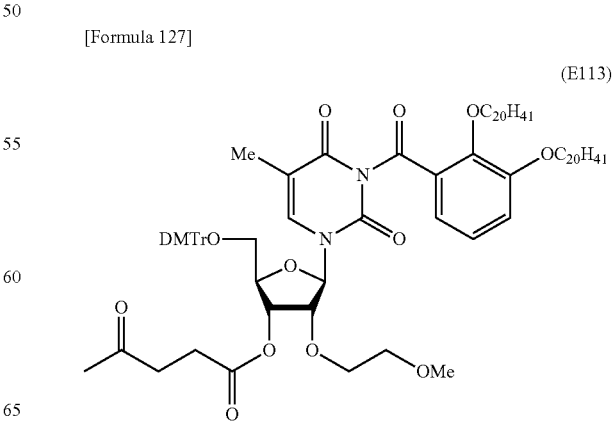

(E113)

(1) Synthesis of a dT-Type Nucleoside (Compound (E112))

[Formula 128]

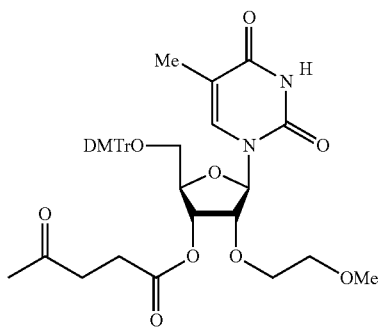
(E112)

1-((2R,3R,4R,5R)-5-((bis(4-Methoxyphenyl)(phenyl)methoxy)methyl)-4-hydroxy-3-(2-methoxyethoxy)tetrahydrofuran-2-yl)-5-methylpyrimidine-2,4(1H,3H)-dione (3.00 g, 4.85 mmol), DMAP (59 mg, 0.48 mmol), and THF (15 mL) were measured and dissolved in a 100 mL-eggplant type flask, and then levrinic acid (0.85 g, 7.27 mmol) was added thereto. WSC.HCl (1.39 g, 7.27 mmol) was added thereto, and the mixture was stirred at the same temperature for 2.0 hours. THF was distilled off under reduced pressure, and then EtOAc (40 mL) and a 0.2 M aqueous solution of AcOH.Et$_3$N (pH: 7.0) (30 mL) were added for separation. To the organic layer, a 0.2 M aqueous solution of AcOH.Et$_3$N (pH: 7.0) (30 mL) was added again for separation. The organic layer was dried over anhydrous sodium sulfate, and then the solvent was distilled off. The organic layer was concentrated and exsiccated under reduced pressure to obtain 3'-OLev rT (2'-OMOE) (E112, 3.13 g, percent yield: 89.8%).

$^1$H NMR (500 MHz, CDCl$_3$) δ 1.36 (3H, d, J=1.15 Hz), 2.19 (3H, s), 2.64-2.82 (4H, m), 3.28 (3H, s), 3.37 (1H, dd, J=10.90, 2.35 Hz), 3.49-3.52 (3H, m), 3.66-3.71 (1H, m), 3.75-3.80 (1H, m), 3.79 (3H×2, s), 4.23-4.25 (1H, m), 4.45 (1H, t, J=5.65 Hz), 5.41 (1H, dd, J=5.25, 3.75 Hz), 6.08 (1H, d, J=6.00 Hz), 6.85 (4H, dd, J=8.65, 3.00 Hz), 7.22-7.31 (7H, m), 7.39 (2H, dd, J=7.10, 1.50 Hz), 7.57 (1H, d, J=1.15 Hz), 8.57 (1H, brs).

(2) Synthesis of a dT-Type Nucleoside Monomer Compound Having Two Icosyloxy Groups (Compound (E113))

[Formula 129]

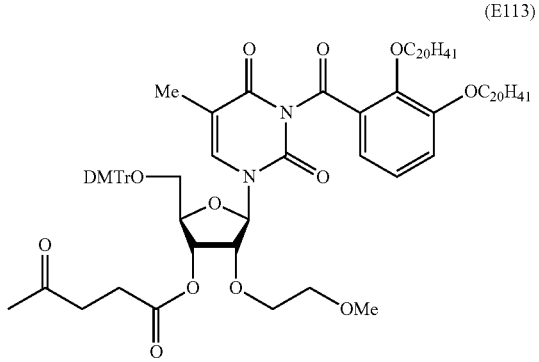
(E113)

The compound (E112) (1.27 g, 1.77 mmol), i-Pr$_2$NEt (1.62 mL), and pyridine (11 mL) were measured and dissolved in a 200-mL eggplant type flask. TMSCl (0.54 mL) and 2,3-bis(icosyloxy)benzoyl chloride (E109, 0.828 g-equivalent) were serially added at room temperature. The mixture was allowed to react at an outside temperature of 60° C. for 1.5 hours. The reaction liquid was cooled to room temperature, and MeOH (55 mL) was added dropwise thereto. The suspension was stirred for 0.5 hours under ice cooling and then was subjected to collection by suction filtration. The powder was washed with MeOH (10 mL×2). The obtained powder was dried at room temperature for 18 hours under reduced pressure to obtain the compound (E113) (1.22 g, percent yield: 74.4%).

$^1$H NMR (500 MHz, CDCl$_3$) δ 0.88 (6H, t, J=6.80 Hz), 1.19-1.37 (64H, m), 1.37 (3H, d, J=0.80 Hz), 1.43-1.48 (2H, m), 1.62-1.68 (4H, m), 1.77-1.83 (2H, m), 2.18 (3H, s), 2.60-2.78 (4H, m), 3.29 (3H, s), 3.37 (1H, dd, J=7.53, 2.35 Hz), 3.49 (2H, t, J=4.30 Hz), 3.52 (1H, dd, J=10.90, 2.35 Hz), 3.64-3.68 (1H, m), 3.76-3.79 (1H, m), 3.80 (3H×2, s), 3.94 (2H, t, J=6.40 Hz), 3.99 (2H, t, J=7.00 Hz), 4.22-4.24 (1H, m), 4.44 (1H, t, J=5.30 Hz), 5.39 (1H, t, J=4.85 Hz), 6.06 (1H, d, J=6.00 Hz), 6.85 (4H, dd, J=8.85, 1.80 Hz), 7.04-7.10 (2H, m), 7.23-7.32 (7H, m), 7.39 (2H, dd, J=7.35, 1.40 Hz), 7.43 (1H, dd, J=7.40, 2.05 Hz), 7.64 (1H, d, J=1.05 Hz).

Example 27

Synthesis of a Deoxythymine (dT) Type Nucleoside Monomer Compound Having Two Icosyloxy Groups (Compound (E114))

[Formula 130]

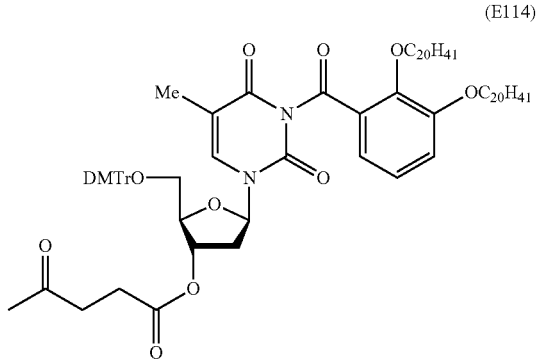
(E114)

The compound (E4) (10.91 g, 15.95 mmol), i-Pr$_2$NEt (10.31 g), and pyridine (98 mL) were measured and dissolved in a 300-mL eggplant type flask. TMSCl (5.07 mL) and 2,3-bis(icosyloxy)benzoyl chloride (E109, 7.46, 10.16 mmol) were serially added at room temperature. The mixture was allowed to react at an outside temperature of 60° C. for 3.5 hours. The reaction liquid was cooled to room temperature, and MeOH (55 mL) was added dropwise thereto. The suspension was stirred for 0.5 hours under ice cooling and then was subjected to collection by suction filtration. The powder was washed with MeOH (50 mL×2). The obtained powder was dried at room temperature for 48 hours under reduced pressure to obtain the compound (E114) (11.09 g, percent yield: 81.5%). The sediment was collected by filtration again from the filtrate and washed with MeOH. The obtained powder was dried at room temperature for 18 hours under reduced pressure to obtain the compound (E114) (1.21 g, percent yield: 8.9%).

$^1$H NMR (500 MHz, CDCl$_3$) δ 0.88 (6H, t, J=6.75 Hz), 1.18-1.39 (64H, m), 1.37 (3H, d, J=0.90 Hz), 1.43-1.49 (2H m), 1.62-1.68 (4H, m), 1.77-1.84 (2H, m), 2.17 (3H, s), 2.40-2.49 (2H, m), 2.49-2.56 (2H, m), 2.68-2.78 (2H, m), 3.45 (1H, dd, J=10.65, 2.30 Hz), 3.50 (1H, dd, J=10.65, 2.45 Hz), 3.80 (3H×2, s), 3.93-4.02 (4H, m), 4.11-4.12 (1H, m), 5.45-5.46 (1H, m), 6.41 (1H, dd, J=5.80, 3.05 Hz), 6.84 (4H, dd, J=9.00, 1.25 Hz), 7.05-7.11 (2H, m), 7.22-7.32 (7H, m), 7.40 (2H, dd, J=8.65, 1.40 Hz) 7.46 (1H, dd, J=7.15, 2.40 Hz), 7.66 (1H, d, J=1.20 Hz).

Example 28

Synthesis of a Uracil (U) Type Nucleoside Monomer Compound Having Two Icosyloxy Groups (Compound (E115))

[Formula 131]

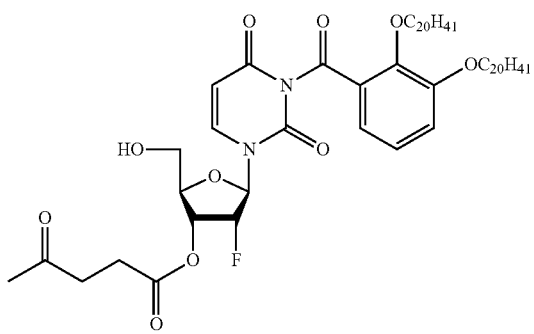

(E115)

The compound (E111) (530 mg) and toluene (2 mL) were measured and dissolved in a 50-mL eggplant type flask. Trichloroacetic acid (0.4 g) was added thereto, and the mixture was stirred at room temperature for 10 minutes. Methanol (2.5 mL) was added, then acetonitrile (10 mL) was added dropwise for 5 minutes, and then the mixture was stirred for 15 minutes under ice cooling. The precipitate was collected by suction filtration, and the obtained residue was washed with acetonitrile containing 5% methanol (5 mL) five times. The obtained powder was dried at 40° C. for 1.5 hours under reduced pressure to obtain the target compound (E115, 440 mg, percent yield: 107%).

$^1$H NMR (500 MHz, CDCl$_3$) δ 0.88 (6H, t, J=7.05 Hz), 1.00-1.40 (64H, m), 1.40-1.52 (2H, m), 1.53-1.75 (2H, m), 1.75-1.88 (2H, m), 2.0-2.35 (2H, brs), 2.19 (3H, s), 2.55-2.90 (4H, m), 3.79 (1H, dd, J=12.70, 2.05 Hz), 3.94-4.01 (6H, m), 4.23-4.30 (1H, brm), 5.27-5.87 (2H, m), 5.83 (1H, d, J=8.25 Hz), 5.90 (1H, dd, $^3J_{HF}$=16.70 Hz, J=2.60 Hz), 7.08-7.11 (2H, m), 7.50 (1H, dd, J=7.50, 2.10 Hz), 7.78 (1H, d, J=8.20 Hz).

Example 29

Synthesis of a Deoxythymine (dT) Type Nucleoside Monomer Compound Having Two Icosyloxy Groups (Compound (E116))

[Formula 132]

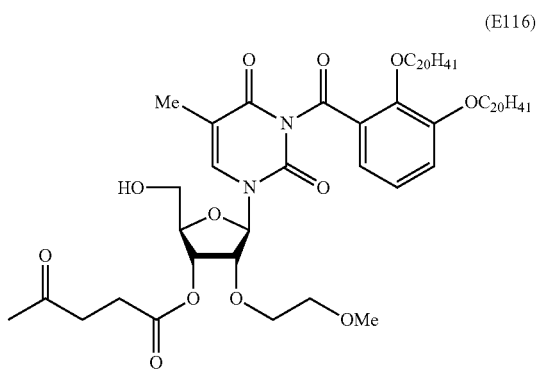

(E116)

The compound (E113) (500 mg) and toluene (5 mL) were measured and dissolved in a 50-mL eggplant type flask. Trichloroacetic acid (0.4 g) was added thereto, and the mixture was stirred at room temperature for 10 minutes. Methanol (2.5 mL) was added thereto, then acetonitrile (10 mL) was added dropwise for 5 minutes, and then the mixture was stirred for 15 minutes under ice cooling. The gel substance was collected by suction filtration, and the obtained residue was washed with methanol (5 mL) and acetonitrile containing 5% methanol (5 mL) five times. The obtained powder was dried at 40° C. for 1.5 hours under reduced pressure to obtain the target compound (E116, 256 mg, percent yield: 65%).

$^1$H NMR (500 MHz, CDCl$_3$) δ 0.88 (6H, t, J=7.05 Hz), 1.19-1.37 (64H, m), 1.43-1.48 (2H, m), 1.62-1.68 (2H, m), 1.77-1.83 (2H, m), 1.94 (3H, d, J=0.95 Hz), 2.05-2.30 (3H, m), 2.20 (3H, s), 2.63-2.84 (4H m), 3.31 (3H, s), 3.45-3.48 (2H, m), 3.67-3.72 (2H, m), 3.74 (1H, dd, J=12.65, 2.15 Hz), 3.90 (1H, dd, J=12.65, 1.95 Hz), 3.93-3.98 (4H, m), 4.20-4.21 (1H, m), 4.48 (1H, t, J=5.25 Hz), 5.29 (1H, t, J=4.70 Hz), 5.64 (1H, d, J=5.10 Hz), 7.05-7.11 (2H, m), 7.47 (1H, dd, J=7.60, 2.00 Hz), 7.50 (1H, d, J=1.00 Hz).

Example 30

Synthesis of a Deoxythymine (dT) Type Nucleoside Monomer Compound Having Two Icosyloxy Groups (Compound (E117))

[Formula 133]

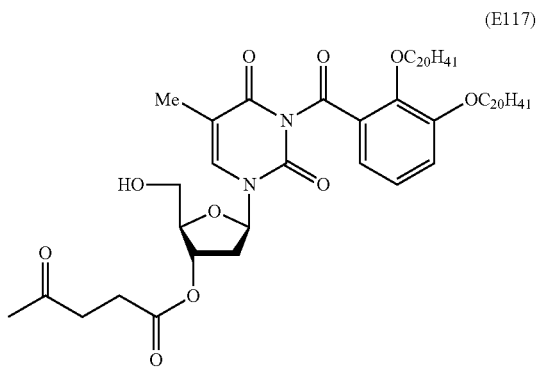

(E117)

103

The compound (E114) (630 mg) and toluene (2 mL) were measured and dissolved in a 50-mL eggplant type flask. Trichloroacetic acid (0.5 g) was added thereto, and the mixture was stirred at room temperature for 10 minutes. Methanol (2.5 mL) was added, then acetonitrile (10 mL) was added dropwise for 5 minutes, and then the mixture was stirred for 15 minutes under ice cooling. The precipitate was collected by suction filtration, and the obtained residue was washed with acetonitrile containing 5% methanol (5 mL) five times. The obtained powder was dried at 40° C. for 1.5 hours under reduced pressure to obtain the target compound (E117, 518 mg, 101%).

$^1$H NMR (500 MHz, CDCl$_3$) δ 0.88 (6H, t, J=6.80 Hz), 1.18-1.39 (64H, m), 1.43-1.49 (2H, m), 1.62-1.68 (2H, m), 1.77-1.84 (2H, m), 1.95 (3H, d, J=1.80 Hz), 2.36 (3H, s), 2.40-2.49 (2H, m), 2.49-2.56 (5H, m), 2.74-2.78 (2H, m), 3.89-3.91 (2H, m), 3.93-3.99 (4H, m), 4.07-4.09 (1H, m), 5.33-5.34 (1H, m), 6.23 (1H, t, J=6.65 Hz), 7.16-7.18 (2H, m), 7.47 (1H, dd, J=7.35, 2.25 Hz), 7.57 (1H, d, J=1.15 Hz).

Example 31

Synthesis of a Nucleic Acid Oligomer (5'-ACGdTdT-3') (Compound (E30)) by Extension Toward the 5'-Terminal End Using a Phosphoramidite Method

[Formula 134]

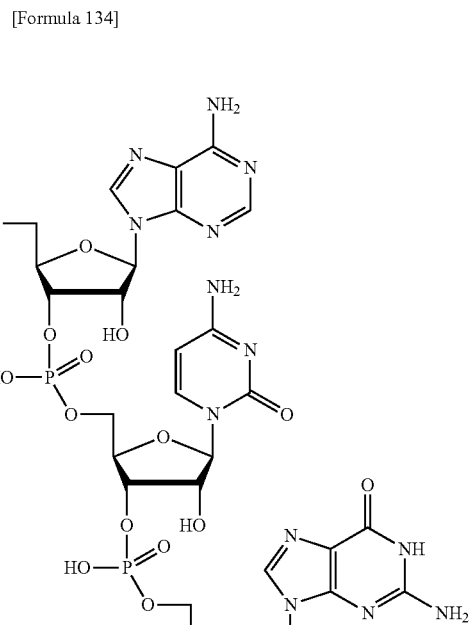
(E30)

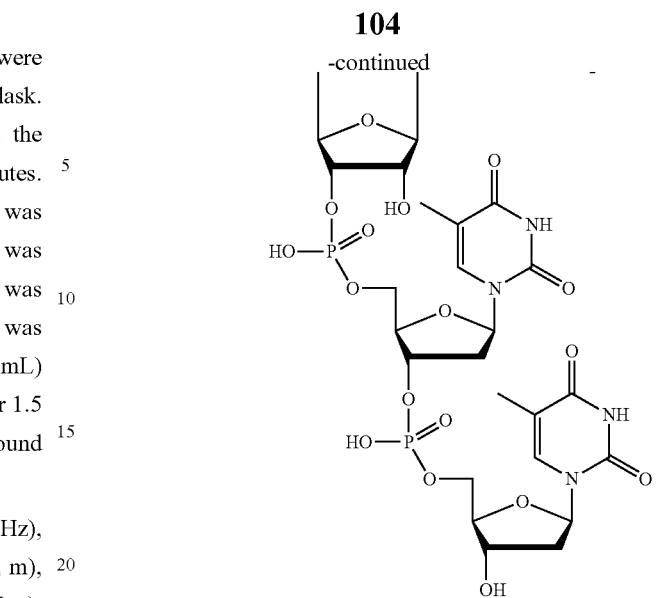

(1) Synthesis of a 5'-OH Form of the Compound (E5) (Compound (E17))

[Formula 135]

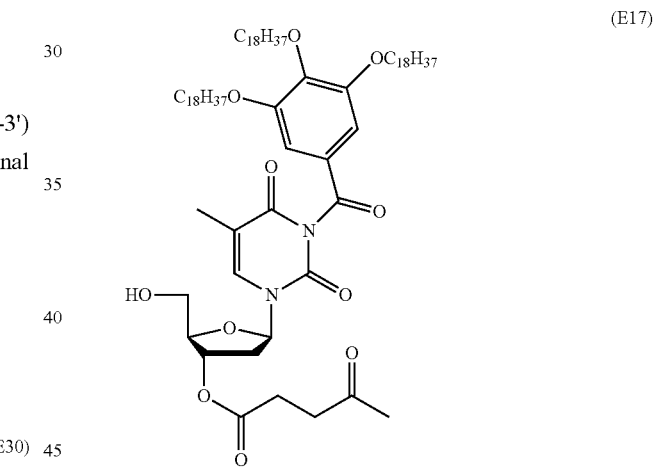
(E17)

To the compound (E5) described in Example 1 (5) (310.4 mg), a 248 mM trichloroacetic acid/toluene solution (10 mL) was added, the mixture was stirred at room temperature for 10 minutes, then methanol (8 mL) was added, and the mixture was stirred. To the reaction liquid, a 10% methanol/acetonitrile solution was added for concentration, and then the residue was cooled to 0° C. and then subjected to collection by suction filtration to obtain the compound (E17) (265.9 mg).

$^1$H NMR (500 MHz, CDCl$_3$) δ 7.62 (1H, br), 7.11 (2H, s), 6.26 (1H, br), 5.36 (1H, m), 4.12 (1H, m), 3.90-4.07 (8H, m), 2.98-3.12 (1H, br), 2.77 (2H, m), 2.58 (2H, m), 2.43 (2H, br), 2.20 (3H, s), 1.97 (3H, d, J=1.0 Hz), 1.69-1.84 (6H, m), 1.41-1.50 (6H, m), 1.19-1.40 (84H, br), 0.88 (9H, t, J=7.0 Hz).

(2) Synthesis of a Nucleic Acid Dimer (Compound (E18)) by a Coupling Reaction Between the Compound (E17) and a Phosphoramidite Compound

[Formula 136]

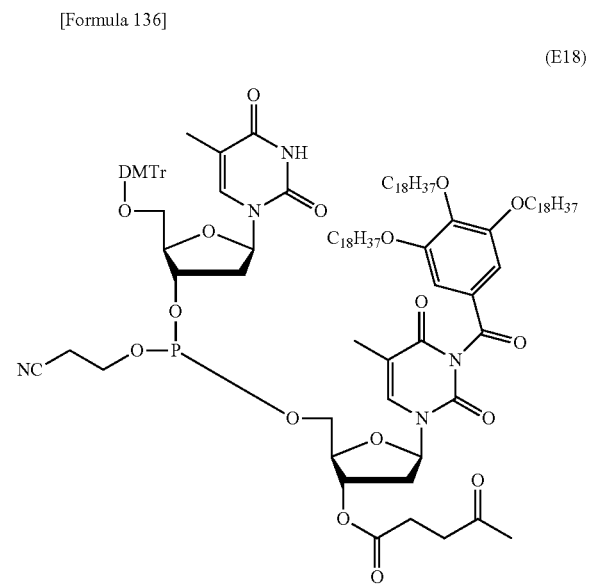

(E18)

To the compound (E17) (257.0 mg) and (2R,3S,5R)-2-((bis(4-methoxyphenyl)(phenyl)methoxy)methyl)-5-(5-methyl-2,4-dioxo-3,4-dihy dropyrimidin-1(2H)-yl)tetrahydro (223.4 mg), toluene (10 mL) was added, and the mixture was stirred at room temperature for 1 hour. 5-Benzylmercapto-1H-tetrazole (144.2 mg) dissolved in acetonitrile (1.5 mL) was added thereto, and the mixture was stirred at room temperature for 2 hours. To the reaction liquid, acetonitrile was added for concentration, and then the residue was collected by suction filtration to obtain the compound (E18) (379.3 mg) as a diastereomer mixture.

$^1$H NMR (500 MHz, CDCl$_3$) δ 7.89, 7.97 (1H, br), 7.44-7.61 (2H, m), 7.39 (2H, m), 7.28 (7H, m), 7.13-7.18 (2H, m), 6.78-6.87 (4H, m), 6.28-6.46 (2H, m), 5.19-5.30 (1H, br m), 4.90-5.02 (1H, br m), 3.91-4.29 (12H, m), 3.76-3.81 (6H, m), 3.33-3.57 (2H, m), 2.21-3.14 (10H, m), 2.17, 2.16 (3H, s), 1.95 (3H, s), 1.69-1.84 (6H, m), 1.40-1.50 (9H, br m), 1.19-1.38 (84H, m), 0.88 (9H, t, J=6.8 Hz).

Note that the (2R,3S,5R)-2-((bis(4-methoxyphenyl)(phenyl)methoxy)methyl)-5-(5-methyl-2,4-dioxo-3,4-dihy dropyrimidin-1(2H)-yl)tetrahydrofuran-3-yl(2-cyanoethyl)diisopropylphosphoramidite described above can be produced from a compound represented by the following Formula or a salt thereof by using a method known per se or a method compliant with a method of producing the compound E33, which will be described below:

[Formula 137]

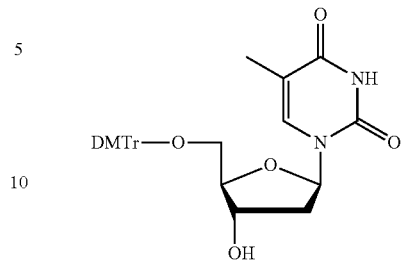

(3) Synthesis of a Compound (E19) by Oxidation of the Compound (E18)

[Formula 138]

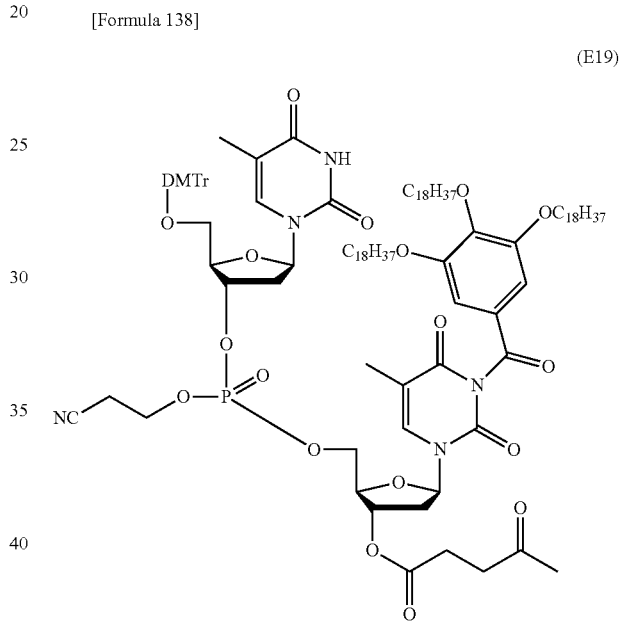

(E19)

To the compound (E18) (344.1 mg), a 0.02 M iodine/pyridine solution (10 mL) and water (500 µL) were added, and the mixture was stirred at room temperature for 45 minutes. Acetonitrile was added thereto for concentration, and then the residue was cooled to 0° C. and collected by suction filtration to obtain the compound (E19) (346.5 mg) as a diastereomer mixture.

$^1$H NMR (500 MHz, CDCl$_3$) δ 8.08 (1H, br s), 7.44-7.57 (2H, m), 7.36 (2H, m), 7.19-7.34 (7H, m), 7.17, 7.14 (2H, s), 6.82-6.87 (4H, m), 6.29-6.45 (2H, m), 5.15-5.32 (2H, m), 4.09-4.41 (6H, m), 3.92-4.07 (6H, m), 3.79-3.80 (6H, m), 3.55 (1H, m), 3.41, (1H, m), 2.18-3.13 (10H, m), 2.16 (3H, m), 2.01 (3H, m), 1.69-1.84 (6H, m), 1.40-1.50 (9H br m), 1.10-1.39 (84H, m), 0.88 (9H, t, J=6.8 Hz).

(4) Synthesis of a 5'-OH Form of the Compound (E19) (Compound (E20))

[Formula 139]

(E20)

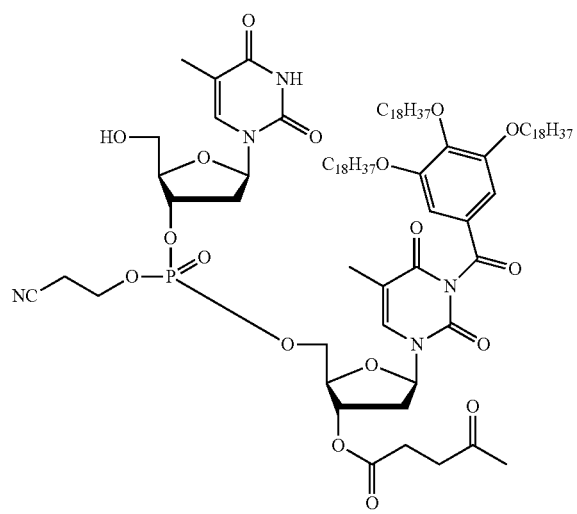

To the compound (E19) (325.2 mg), a 248 mM trichloroacetic acid/toluene solution (10 mL) was added, the mixture was stirred at room temperature for 10 minutes, then methanol (8 mL) was added, and the mixture was stirred. To the reaction liquid, a 10% methanol/acetonitrile solution was added for concentration, and then the residue was cooled to 0° C. and collected by suction filtration to obtain the compound (E20) (288.4 mg) as a diastereomer mixture.

$^1$H NMR (500 MHz, CDCl$_3$) δ 8.03 (1H, br s), 7.39-7.50 (2H, m), 7.15, 7.13 (2H, s), 6.26-6.40 (1H, br), 6.07-6.21 (1H, m), 5.15-5.37 (2H, br m), 4.16-4.45 (6H, m), 3.93-4.08 (6H, m), 3.76-3.93 (2H, m), 3.17-2.27 (11H, br m), 2.19 (3H, s), 2.02 (3H, m), 1.92 (3H, m), 1.69-1.84 (6H, m), 1.40-1.50 (6H, brm), 1.10-1.40 (84H, m), 0.88 (9H, t, J=7.0 Hz).

(4-2) Synthesis of a 5'-OH Form of the Compound (E19) (Compound (E20))

A 0.27 M 5-benzylmercapto-1H-tetrazole/acetonitrile solution (28.8 mL), a (2R,3S,5R)-2-((bis(4-methoxyphenyl)(phenyl)methoxy)methyl)-5-(5-methyl-2,4-dioxo-3,4-dihydropyrimidin-1(2H)-yl(tetrahydrofuran-3-yl(2-cyanoethyl) diisopropylphosphoramidite/toluene solution (0.12 M, 23 mL), and a solution of the compound represented by Formula (E17) (2.3 g) dissolved in toluene (13.8 mL) were serially added in an eggplant type flask, and the mixture was stirred at room temperature for 90 minutes. Acetonitrile was added to the reaction solution, and the mixture was ice-cooled. The reaction mixture was subjected to suction filtration, and the obtained wet crystal was suspended in toluene (4.6 mL), then an iodine/water/pyridine solution (a 0.58 g/0.082 ml/0.73 g mixed solution) was added thereto, and the mixture was stirred at room temperature for 15 minutes. The reaction liquid was concentrated under reduced pressure and then the solvent was substituted with toluene. A 0.67 M trichloroacetic acid/toluene solution (27.5 mL) was added thereto, and the mixture was stirred at room temperature for 10 minutes. Methanol was added to the reaction solution, and the mixture was ice-cooled. The residue was collected by suction filtration to obtain the compound represented by the above-described Formula (E20) (2.5 g).

(5) Synthesis of a Nucleic Acid Trimer (Compound (E21)) by a Coupling Reaction Between the Compound (E20) and a Phosphoramidite Compound

[Formula 140]

(E21)

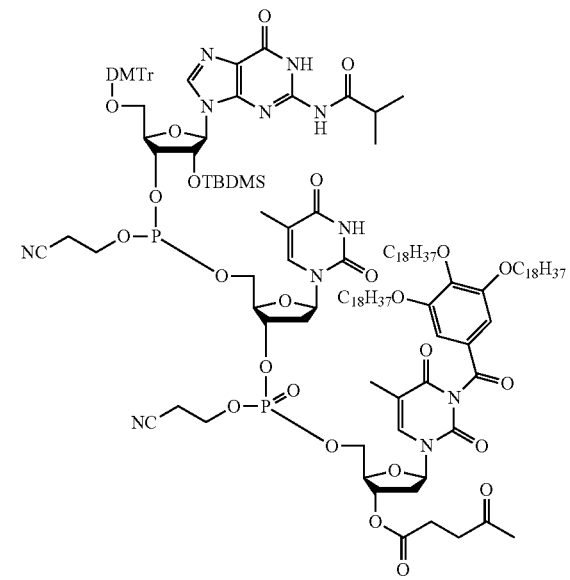

To the compound (E20) (272.1 mg) and (2R,3R,4R,5R)-2-((bis(4-methoxyphenyl)(phenyl)methoxy)methyl)-4-((tert-butyldimethylsilyl)oxy)-5-(2-isobutylamido-6-oxo-1H-purin-9(6H)-yl)tetrahydrofuran-3-yl(2-cyanoethyl) diisopropyl phosphoramidite (291.1 mg), toluene (10 mL) was added, and the mixture was stirred at room temperature for 55 minutes. 5-Benzylmercapto-1H-tetrazole (144.2 mg) dissolved in acetonitrile (1.5 mL) was added thereto, and the mixture was stirred at room temperature for 2 hours. To the reaction liquid, acetonitrile was added for concentration, and then the residue was collected by suction filtration to obtain the compound (E21) (411.9 mg) as a diastereomer mixture.

$^1$H NMR (500 MHz, CDCl$_3$) δ 11.95-12.16 (1H, m), 7.82-7.91 (2H, m), 7.20-7.55 (12H, m), 7.13 (2H, m), 6.79-6.87 (4H, m), 6.30 (2H, br), 5.75-5.89 (1H, m), 4.47-5.33 (3H, m), 4.07-4.44 (8H, m), 3.90-4.06 (6H, m), 3.74-3.81 (6H, m), 1.94-3.55 (25H, m), 1.68-1.83 (6H, m), 1.40-1.51 (6H, br m), 0.92-1.39 (93H, m), 0.88 (9H, m), 0.76-0.83 (9H, m), −0.09-0.02 (3H, m), −0.27--0.20 (3H, m).

Note that the (2R,3R,4R,5R)-2-((bis(4-methoxyphenyl)(phenyl)methoxy)methyl)-4-((tert-butyldimethylsilyl)oxy)-5-(2-isobutylamido-6-oxo-1H-purin-9(6H)-yl)tetrahydrofuran-3-yl(2-cyanoethyl)diisopropyl phosphoramidite described above can be produced from a compound represented by the following Formula or a salt thereof by using a method known per se or a method compliant with the method of producing the compound E33, which will be described below:

[Formula 141]

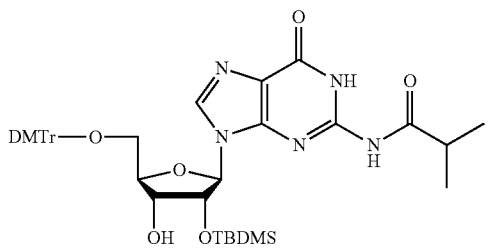

(6) Synthesis of a Compound (E22) by Oxidation of the Compound (E21)

[Formula 142]

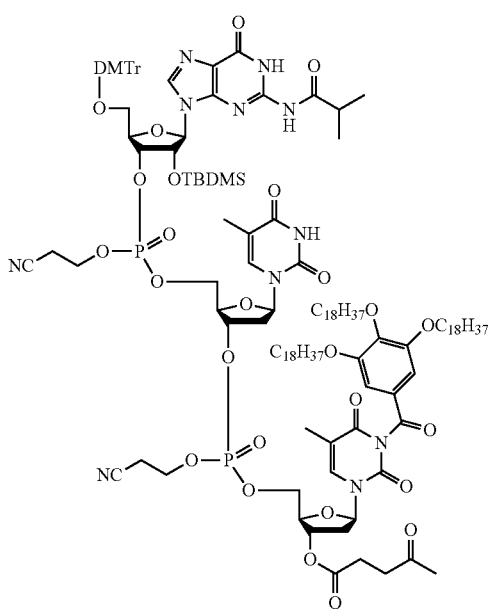

(E22)

The compound (E21) (353.7 mg) was dissolved in toluene (4 mL), then a 0.02 M iodine/pyridine solution (10 mL) and water (500 μL) were added thereto, and the mixture was stirred at room temperature for 15 minutes. Acetonitrile was added thereto for concentration then the residue was cooled to 0° C. and collected by suction filtration to obtain the compound (E22) (362.6 mg) as a diastereomer mixture.

$^1$H NMR (500 MHz, CDCl$_3$) δ 12.11 (1H, m), 7.72-9.54 (2H, m), 7.22-7.56 (12H, m), 7.12-7.14 (2H, m), 6.79-6.85 (4H, m), 6.15-6.38 (2H, br), 5.72-5.80 (1H, m), 4.12-5.34 (14H, m), 3.94-4.08 (6H, m), 3.76-3.80 (6H, m), 1.87-3.60 (22H, m), 1.69-1.84 (6H, m), 1.45 (6H, br), 0.95-1.38 (93H, m), 0.88 (9H, m), 0.77 (9H, m), −0.12-0.04 (3H, m), −0.31-0.14 (3H, m).

(7) Synthesis of a 5'-OH Form of the Compound (E22) (Compound (E23))

[Formula 143]

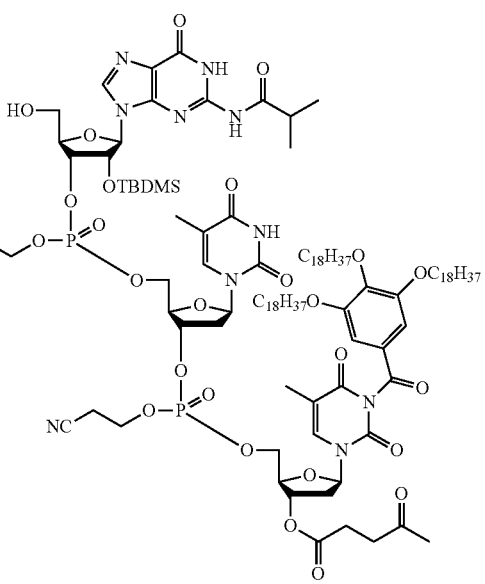

(E23)

To the compound (E22) (360.0 mg), a 248 mM trichloroacetic acid/toluene solution (10 mL) was added, the mixture was stirred at room temperature for 10 minutes, then methanol (8 mL) was added thereto, and the mixture was stirred. To the reaction liquid, a 10% methanol/acetonitrile solution was added for concentration, and then the residue was cooled to 0° C. and collected by suction filtration to obtain the compound (E23) (297.2 mg) as a diastereomer mixture.

$^1$H NMR (500 MHz, CDCl$_3$) δ 12.24-12.37 (1H, m), 9.68-11.28 (2H, m), 7.44-7.70 (3H, m), 7.07-7.13 (2H, m), 5.08-6.34 (6H, m), 4.08-4.69 (11H, m), 3.88-4.05 (9H, m), 1.88-3.31 (23H, m), 1.69-1.83 (6H, m), 1.40-1.50 (6H, br m), 0.99-1.39 (90H, m), 0.86-0.89 (9H, m), 0.68-0.80 (9H, m), −0.24-0.21 (3H, m), −0.47-0.40 (3H, m).

(8) Synthesis of a Nucleic Acid Tetramer (Compound (E24)) by a Coupling Reaction Between the Compound (E23) and a Phosphoramidite Compound
To the compound (E23) (284.5 mg) and (2R,3R,4R,5R)-5-(4-acetamido-2-oxopyrimidin-1(2H)-yl)-2-((bis(4-methoxyphenyl)(phenyl)methoxy)methyl)-4-((tert-bu-
[Formula 144]
(E24)
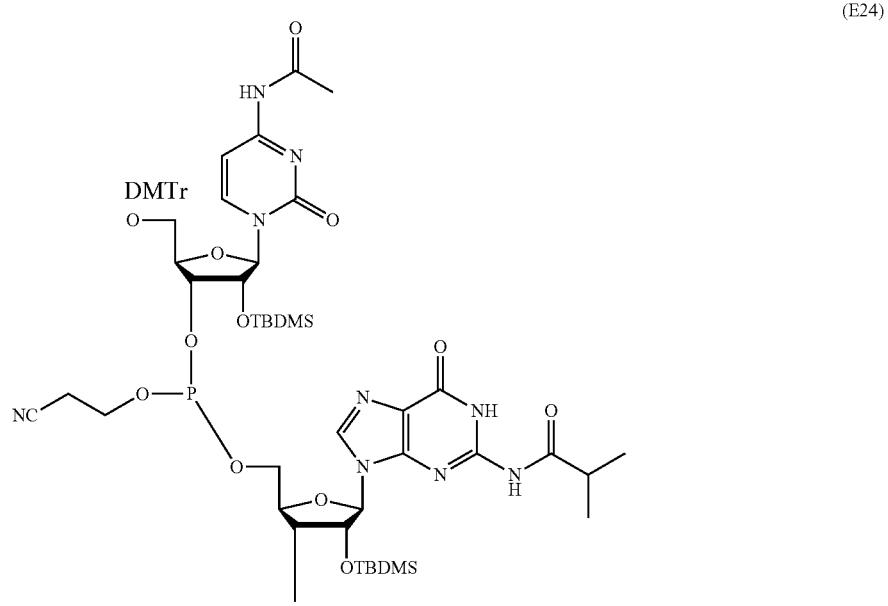
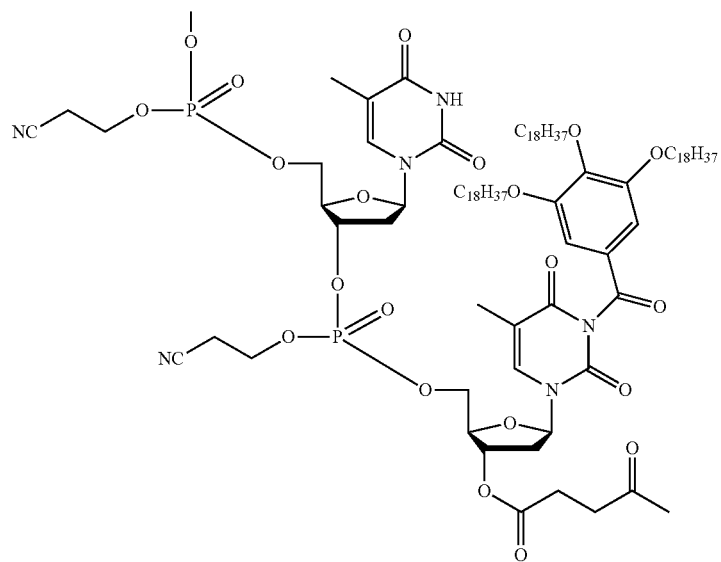

tyldimethylsilyl)oxy)tetrahydrofuran-3-yl(2-cyanoethyl) diisopropylphosphoramidite (270.6 mg), toluene (10 mL) was added, and the mixture was stirred at room temperature for 10 minutes. 5-Benzylmercapto-1H-tetrazole (144.2 mg) dissolved in acetonitrile (1.5 mL) was added thereto, and the mixture was stirred at room temperature for 2 hours. To the reaction liquid, acetonitrile was added for concentration, and then the residue was collected by suction filtration to obtain the compound (E24) (360.8 mg) as a diastereomer mixture.

$^1$H NMR (500 MHz, CDCl$_3$) δ 12.14-12.22 (1H, m), 7.75-9.90 (3H, m), 6.97-7.55 (15H, m), 6.80-6.89 (4H, m), 3.37-6.36 (39H, m), 1.94-3.11 (26H, m), 1.69-1.83 (6H, m), 1.45 (6H, br m), 0.98-1.38 (93H, m), 0.68-0.95 (27H, m), −0.25-0.19 (12H, m).

Note that the (2R,3R,4R,5R)-5-(4-acetamido-2-oxopyrimidin-1(2H)-yl)-2-((bis(4-methoxyphenyl)(phenyl)methoxy)methyl)-4-((tert-butyldimethylsilyl)oxy)tetrahydrofuran-3-yl(2-cyanoethyl)diisopropylphosphoramidite described above can be produced from a compound represented by the following Formula or a salt thereof by using a method known per se or a method compliant with the method of producing the compound E33, which will be described below:

[Formula 145]

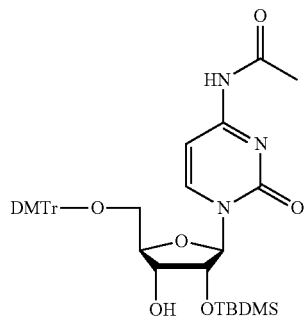

(9) Synthesis of a Compound (E25) by Oxidation of the Compound (E24)

[Formula 146]

(E25)

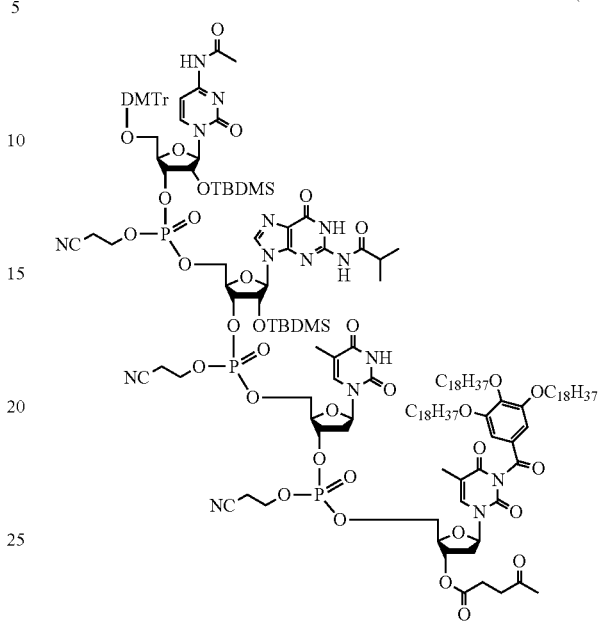
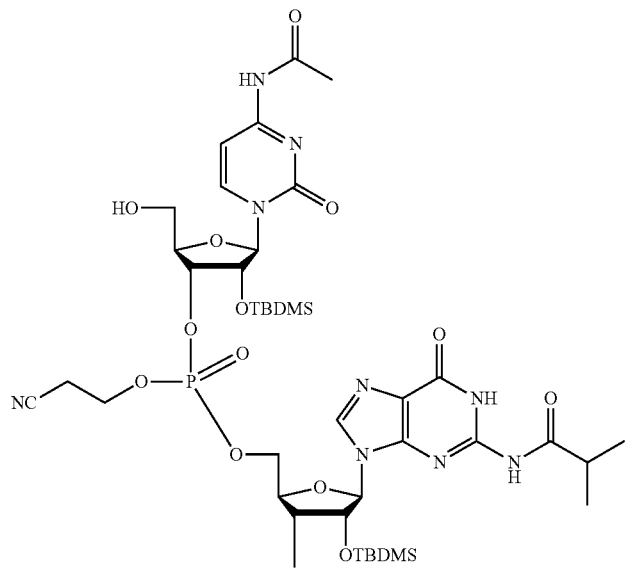

The compound (E24) (258.2 mg) was dissolved in toluene (4 mL), then a 0.02 M iodine/pyridine solution (10 mL) and water (500 μL) were added thereto, and the mixture was stirred at room temperature for 15 minutes. Acetonitrile was added thereto for concentration, and then the residue was cooled to 0° C. and collected by suction filtration to obtain the compound (E25) (336.1 mg) as a diastereomer mixture.

$^1$H NMR (500 MHz, CDCl$_3$) δ 12.15-12.23 (1H, m), 7.47-10.05 (4H, m), 7.02-7.41 (14H, m), 6.81-6.87 (4H, m), 3.40-6.35 (39H, m), 1.91-3.08 (26H, m), 1.70-1.83 (6H, m), 1.45 (6H, br m), 0.96-1.39 (93H, m), 0.68-0.95 (27H, m), −0.30-0.20 (12H, m).

(10) Synthesis of a 5'-OH Form of the Compound (E25) (Compound (E26))

[Formula 147]

(E26)

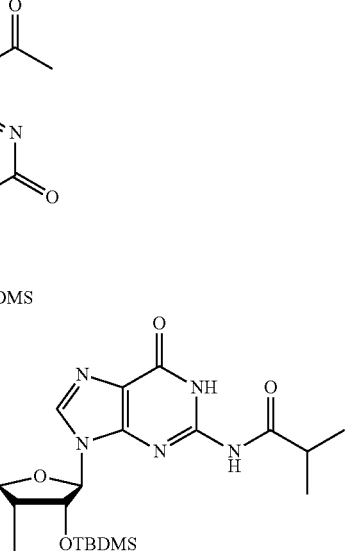

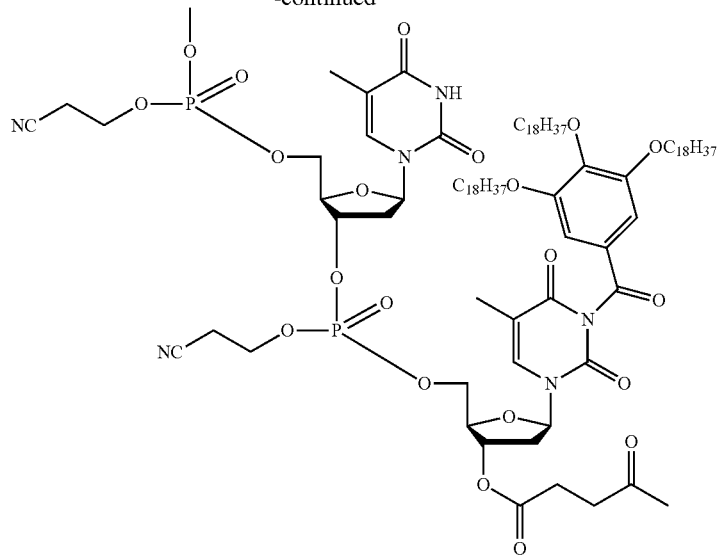

To the compound (E25) (328.7 mg), a 248 mM trichloroacetic acid/toluene solution (10 mL) was added, the mixture was stirred at room temperature for 10 minutes, then methanol (8 mL) was added thereto, and then the mixture was stirred. To the reaction liquid, a 10% methanol/acetonitrile solution was added for concentration, and then the residue was cooled to 0° C. and collected by suction filtration to obtain the compound (E26) (295.3 mg) as a diastereomer mixture.

$^1$H NMR (500 MHz, CDCl$_3$) δ 12.19-12.27 (1H, br m), 7.09-10.49 (9H, br m), 3.67-6.39 (33H, m), 1.88-3.09 (27H, m), 1.70-1.84 (6H, m), 1.45 (6H, br m), 1.00-1.38 (93H, m), 0.67-0.94 (27H, m), −0.30−−0.27 (12H, m).

(11) Synthesis of a Nucleic Acid Pentamer (Compound (E27)) by a Coupling Reaction Between the Compound (E26) and a Phosphoramidite Compound

[Formula 148]

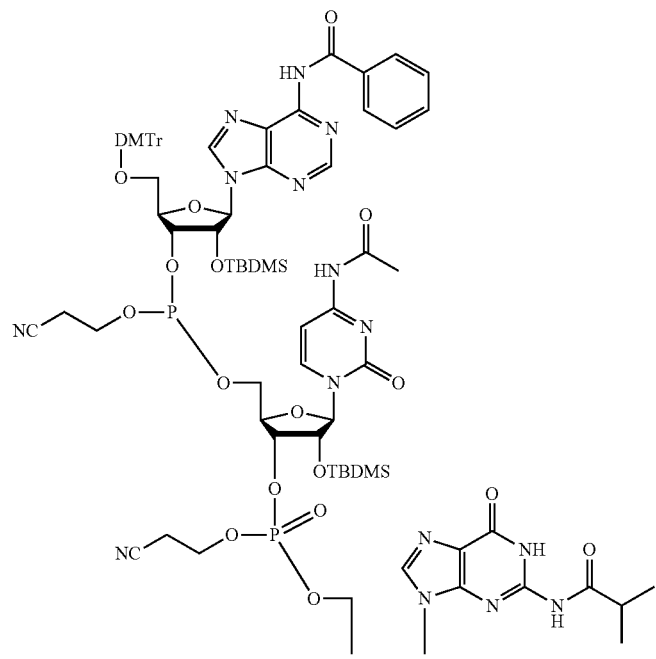

(E27)

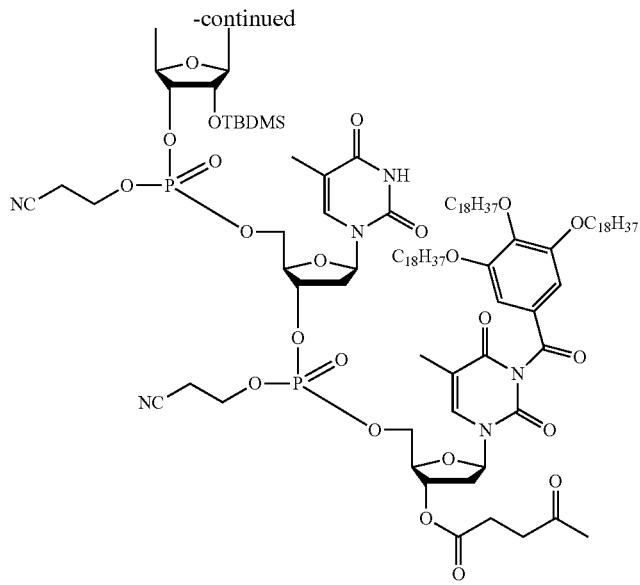

To the compound (E26) (256.4 mg) and (2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl(2-cyanoethyl) diisopropylphosphoramidite (296.5 mg, 300 μmol), toluene (10 mL) was added, and the mixture was stirred at room temperature for 10 minutes. 5-Benzylmercapto-1H-tetrazole (144.2 mg) dissolved in acetonitrile (1.5 mL) was added thereto, and the mixture was stirred at room temperature for 2 hours. To the reaction liquid, acetonitrile was added for concentration, and then the residue was collected by suction filtration to obtain the compound (E27) (337.3 mg) as a diastereomer mixture.

$^1$H NMR (500 MHz, CDCl$_3$) δ 12.03-12.23 (1H, m), 7.60-10.14 (7H, br m), 7.05-7.55 (19H, m), 6.79-6.87 (4H, m), 1.90-6.42 (75H, br m), 1.70-1.82 (6H, m), 1.45 (6H, br m), 1.04-1.36 (93H, m), 0.85-0.93 (18H, m), 0.69-0.78 (18H, m), −0.35-0.23 (18H, m).

(12) Synthesis of a Compound (E28) by Oxidation of the Compound (E27)

[Formula 149]

(E28)

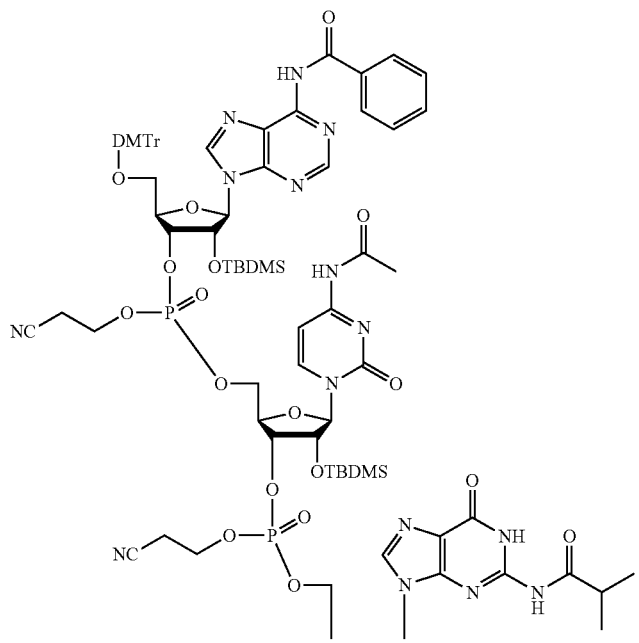

-continued

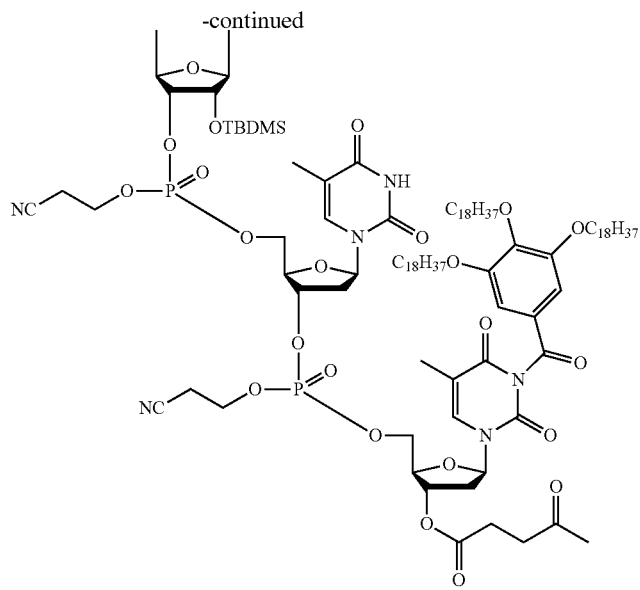

The compound (E27) (322.9 mg) was dissolved in toluene (4 mL), then a 0.02 M iodine/pyridine solution (10 mL) and water (500 μL) were added, and then the mixture was stirred at room temperature for 15 minutes. Acetonitrile was added thereto for concentration, and then the residue was cooled to 0° C. and collected by suction filtration to obtain the compound (E28) (308.4 mg) as a diastereomer mixture.

$^1$H NMR (500 MHz, CDCl$_3$) δ 12.10-12.25 (1H, br m), 7.77-10.07 (7H, br m), 7.05-7.64 (19H, m), 6.78-6.85 (4H, m), 1.90-6.39 (75H, br m), 1.70-1.84 (6H, m), 1.45 (6H, br m), 1.00-1.38 (93H, m), 0.82-0.92 (18H, m), 0.68-0.81 (18H, m), −0.29-0.19 (18H, br m).

(13) Synthesis of a 5'-OH Form of the Compound (E28) (Compound (E29))

[Formula 150]

(E29)

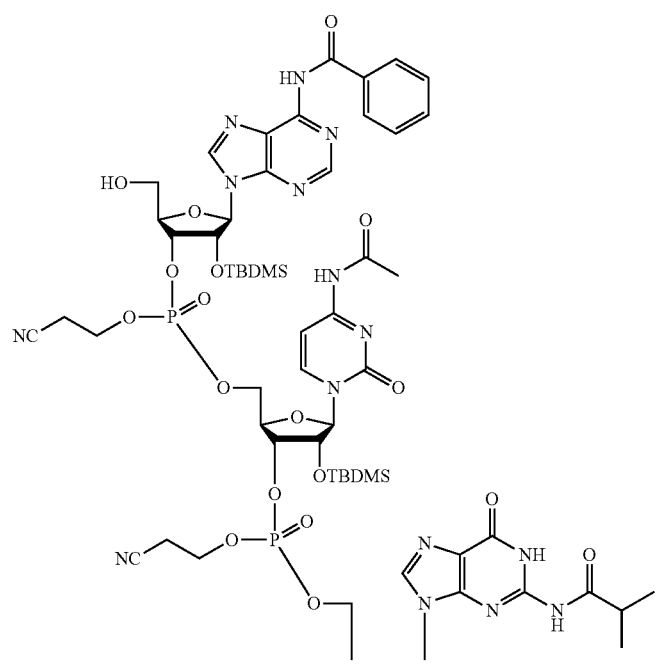

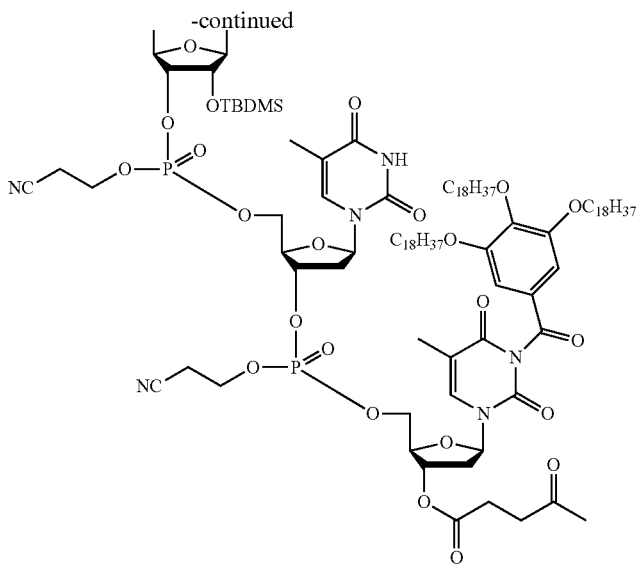

To the compound (E28) (328.7 mg), a 248 mM trichloroacetic acid/toluene solution (10 mL) was added, and the mixture was stirred at room temperature for 10 minutes. To the reaction liquid, a 10% methanol/acetonitrile solution was added for concentration, and then the residue was cooled to 0° C. and subjected to centrifugal separation to obtain the compound (E29) (269.0 mg) as a diastereomer mixture.

$^1$H NMR (500 MHz, CDCl$_3$) δ 12.14-12.27 (1H, br m), 7.23-10.08 (15H, br m), 7.11-7.15 (2H, m), 1.87-6.35 (70H, br m), 1.70-1.83 (6H, m), 1.45 (6H, br m), 1.06-1.39 (93H, m), 0.69-0.93 (36H, m), −0.34-0.19 (18H, m).

(14) Synthesis of a Compound (E30) by Deprotection of the Compound (E29)

[Formula 151]

(E30)

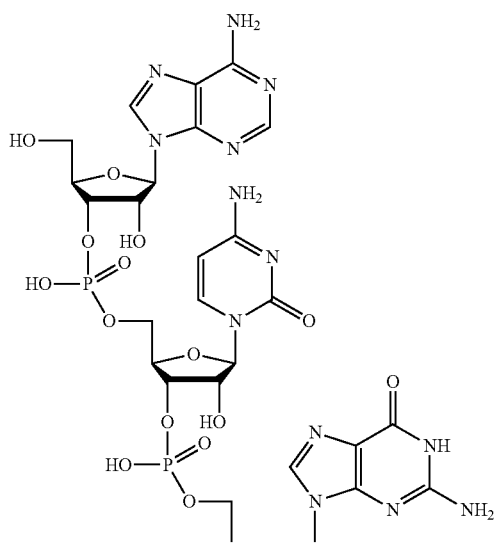

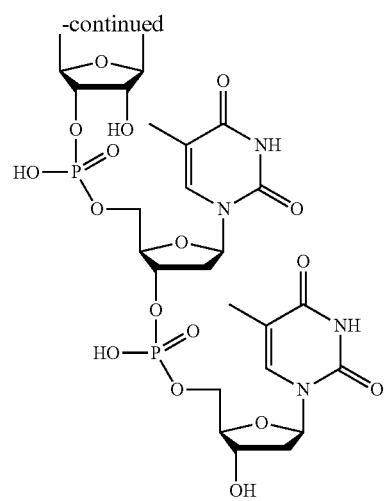

5'-ACGdTdT-3'

The compound (E29) (165.5 mg) was suspended in ethanol (1.5 mL), a 40% aqueous solution of methylamine (5 mL) was added thereto, the mixture was allowed to react at 45° C. for 25 minutes, and then the solid component was filtered off. The residue was washed with dimethylsulfoxide, the wash liquid was combined with the filtrate, and the mixture was cooled with dry ice. Triethylamine trihydrofluoride (7.5 mL) was added, and the mixture was allowed to react at 40° C. for 135 minutes to obtain a reaction solution including the compound (E30) (28.8 g). The obtained reaction solution (4.6 g) was purified by anion exchange chromatography to obtain the compound (E30) (4.1 μmol). The obtained compound (E30) was subjected to identification by HPLC and ESI-MS.

LC-ESI-MS m/z 1524.30 [M-H]$^-$

Example 32

Synthesis of a Nucleic Acid Oligomer (5'-GUdT-3') (Compound (E34)) by Extension Toward the 3'-Terminal End Using a Phosphoramidite Method

[Formula 152]

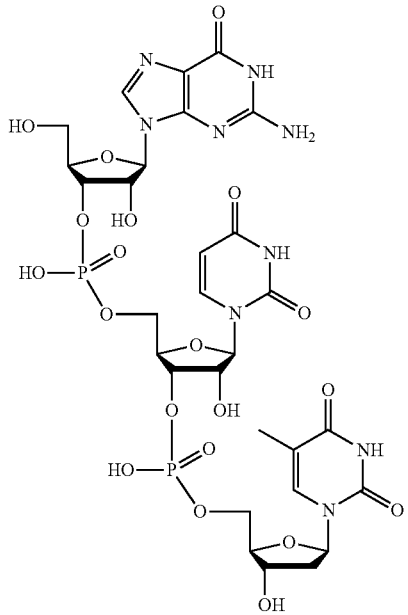

(E34)

(1) Synthesis of a Nucleic Acid Dimer (Compound (E31)) from the dT-Type Nucleoside Monomer Compound Having Three Octadecyloxy Groups (Compound (E5))

[Formula 153]

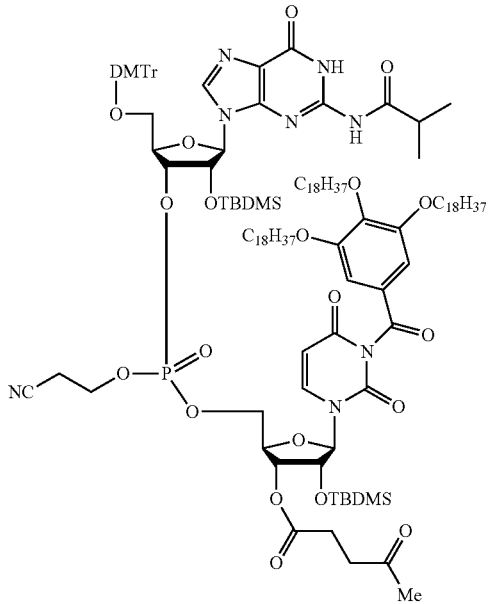

(E31)

Reactions similar to those in the processes (1) to (3) of Example 31 were performed by using the compound (E7) (352.4 mg) instead of the compound (E5) to obtain a dimer block (compound (E31)) as a diastereomer mixture (400.9 mg).

$^1$H NMR (500 MHz, CDCl$_3$) δ 12.18, 12.13 (1H, s), 10.13, 9.55 (1H, br s), 7.83-8.05, (2H, m), 7.20-7.48 (9H, m), 7.13 (2H, m), 6.82-6.86 (4H, m), 6.39, 6.23 (1H, d, J=8.0, 8.5 Hz), 5.87-5.96 (2H, m), 4.72-5.19 (3H, br m), 3.90-4.56 (14H, br m), 3.78-3.80 (6H, m), 3.56-3.68 (1H, br m), 3.17-3.54 (1H, br m), 2.44-2.88 (6H, m), 2.20 (3H, s), 1.70-1.83 (6H, m), 1.45 (6H, br m) 1.19-1.36 (90H, m), 0.74-0.91 (27H, m), −0.04-014 (9H, m), −0.16-0.24 (3H, s).

(2) Synthesis of a 3'-OH Form of the Compound (E31) (Compound (E32))

[Formula 154]

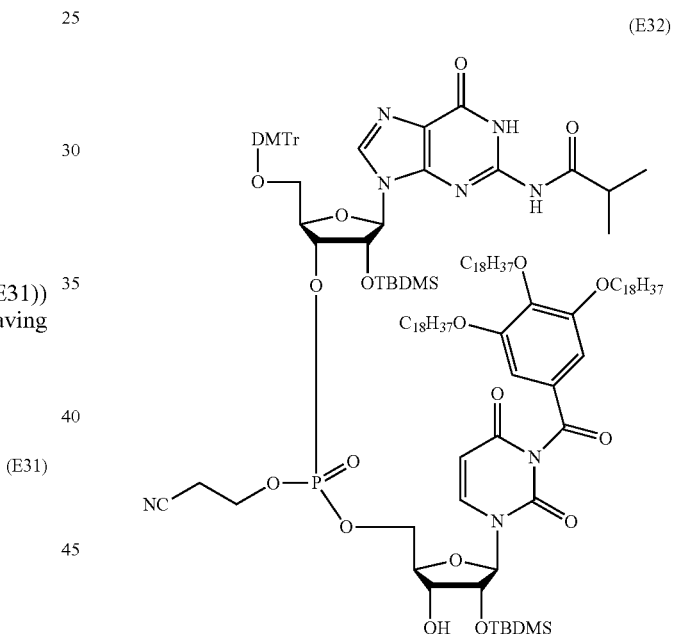

(E32)

The compound (E31) (396.7 mg) was dissolved in dichloromethane (5 mL), a 20% acetic acid/2,4,6-trimethylpyridine solution (5 mL) was added thereto, then hydrazine monohydrate (17 μL) was added thereto, and then the mixture was stirred at room temperature for 1 hour. Acetonitrile was added thereto for concentration, and then the residue was cooled to 0° C. and collected by suction filtration to obtain the compound (E32) (329.2 mg) as a diastereomer mixture.

$^1$H NMR (500 MHz, CDCl$_3$) δ 12.16-12.20 (1H, m), 10.10-9.96 (1H, br m), 7.77-8.01 (2H, m), 7.18-7.47 (9H, m), 7.12 (2H, m), 6.83-6.87 (4H, m), 6.35, 6.23 (1H, d, J=8.0, 8.0 Hz), 5.88-5.98 (2H, m), 4.74-5.12 (2H, m), 3.91-4.57 (14H, br m), 3.79 (6H, m), 3.17-3.65 (2H, m), 2.03-2.77 (4H, m), 1.70-1.82 (6H, m), 1.45 (6H, br), 1.12-1.37 (90H, m), 0.75-0.96 (27H, m), 0.08-0.21 (6H, m), −0.02-0.04 (3H, m), −0.23-0.17 (3H, m).

(3) Synthesis of a 3'-Phosphoramidite Form of the Compound (E32) (Compound (E33))

[Formula 155]

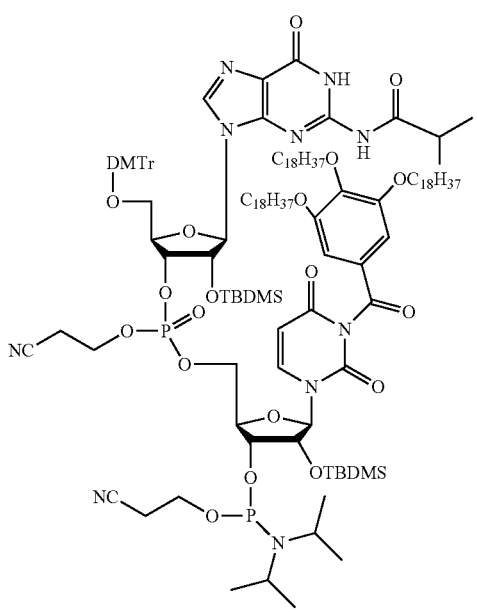

(E33)

The compound (E32) (322.9 mg) was dissolved in dichloromethane (9.8 mL), then 2,4,6-trimethylpyridine (270 µL), 1-methylimidazole (9 µL), and 2-cyanoethyldiisopropylchlorophosphoroamidide (200 µL) were added thereto, and the mixture was stirred at room temperature for 2 hours. Acetonitrile was added thereto for concentration, and then the residue was collected by suction filtration to obtain the compound (E33) (341 mg) as a diastereomer mixture.

$^1$H NMR (500 MHz, CDCl$_3$) δ 12.14-12.23 (1H, m), 9.71-10.45 (1H, br m), 7.59-8.07 (2H, m), 7.21-7.46 (9H, m), 7.09-7.19 (2H, m), 6.79-6.87 (4H, m), 5.84-6.60 (3H, m), 3.16-5.07 (28H, brm), 1.97-2.85 (5H, brm), 1.67-1.83 (6H, br m), 1.40-1.50 (6H, br m) 1.09-1.39 (102H, br m), 0.73-0.97 (27H, m), −0.24-0.17 (12H, m).

(4) Synthesis of a Nucleic Acid Oligomer (5'-GUdT-3') (Compound (E34))

[Formula 156]

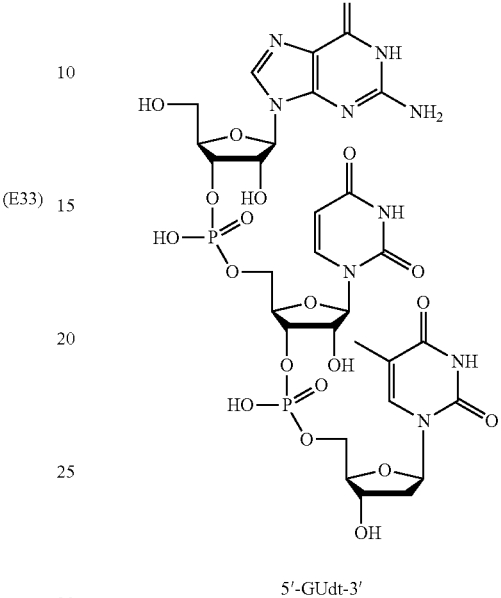

(E34)

5'-GUdt-3'

The compound (E33) (331.0 mg) and the compound (E17) described in Example 31 (58.7 mg) were dissolved in dichloromethane (3.8 mL), then 5-benzylmercapto-1H-tetrazole (33.9 mg) dissolved in acetonitrile (1.5 mL) was added thereto, and the mixture was stirred at room temperature for 5.5 hours. To the reaction liquid, acetonitrile was added for concentration, and then the residue was collected by suction filtration to obtain a precipitate (372 mg). The obtained precipitate (363.9 mg) was dissolved in dichloromethane (5 mL), then a 0.02 M iodine/pyridine solution (10 mL) and water (500 µL) were added thereto, and the mixture was stirred at room temperature for 15 minutes. Acetonitrile was added thereto for concentration; and then the residue was cooled to 0° C. and collected by suction filtration to obtain a precipitate (355.6 mg). To the obtained precipitate (11.0 mg), a 3% trichloroacetic acid/dichloromethane solution (1 mL) was added, and the mixture was stirred at room temperature for 10 minutes. To the reaction liquid, acetonitrile was added for concentration, then a 10% methanol/acetonitrile solution was added, and the mixture was cooled to 0° C. and subjected to centrifugal separation to obtain a precipitate (8.7 mg). The obtained precipitate (7.4 mg) was suspended in ethanol (500 µL), a 40% aqueous solution of methylamine (1.5 mL) was added thereto, the mixture was allowed to react at 45° C. for 25 minutes, and then the solid component was filtered off. The residue was washed with dimethylsulfoxide, the wash liquid was combined with the filtrate, and the mixture was cooled to 0° C. Triethylamine trihydrofluoride (320 µL) was added, and the mixture was allowed to react at 40° C. for 75 minutes to obtain a reaction solution including the compound (E34) (5.9 g). The obtained reaction solution (961 mg) was purified by anion exchange chromatography to obtain the compound (E34) (36 nmol). The compound (E34) was subjected to identification by HPLC and ESI-MS. LC-ESI-MS m/z 892.19 [M-H$^+$]

Example 33

Synthesis of a Nucleic Acid Oligomer (5'-CGUACGU-3') (Compound (E88)) by Extension Toward the 5'-Terminal End Using a Phosphoramidite Method

[Formula 157]

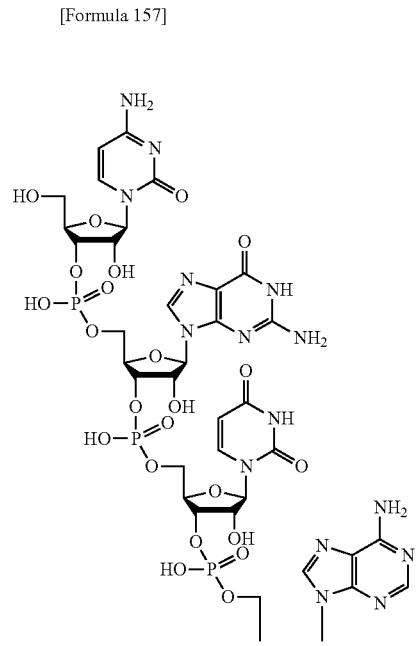

(E88)

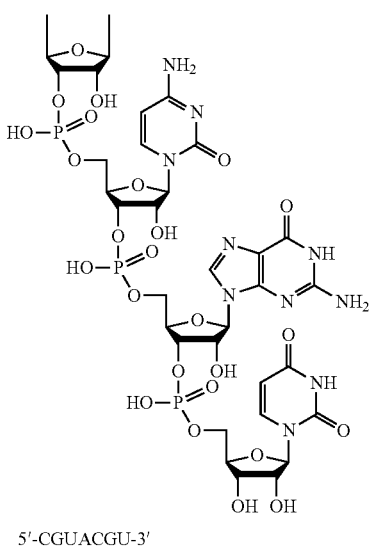

5'-CGUACGU-3'

(1) Synthesis of a Nucleic Acid Dimer (Compound (E76)) by a Coupling Reaction Between the Compound (E67) and a Phosphoramidite Compound

[Formula 158]

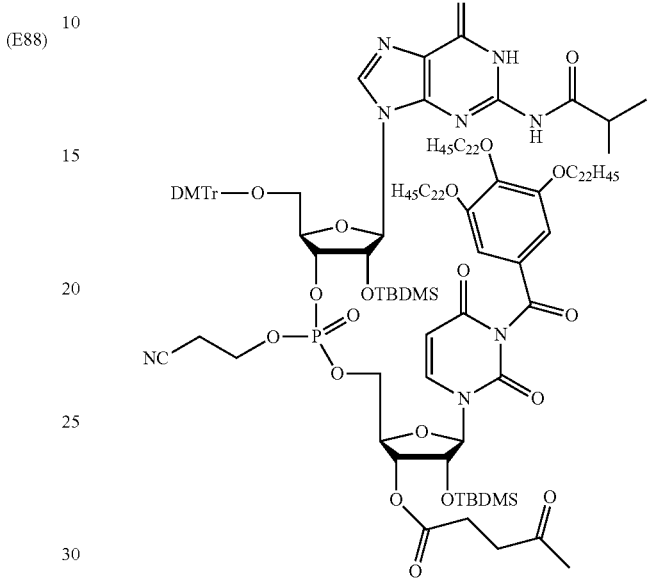

(E76)

To the compound (E67) (613.8 mg) and (2R,3R,4R,5R)-2-((bis(4-methoxyphenyl)(phenyl)methoxy)methyl)-4-((tert-butyldimethylsilyl)oxy)-5-(2-isobutyramido-6-oxo-1H-purin-9(6H)-yl)tetrahydrofuran-3-yl(2-cyanoethyl) diisopropyl phosphoramidite (776.1 mg), toluene (10.0 mL) was added at room temperature, and the mixture was stirred. 5-Benzylmercapto-1H-tetrazole (231.0 mg) dissolved in acetonitrile (2.0 mL) was added thereto, and the mixture was stirred at room temperature for 2 hours. A 0.1 M $I_2$/pyridine solution (8.0 mL) and water (500 μL) were added thereto, the mixture was stirred at room temperature for 15 minutes, then acetonitrile (18 mL) was added for concentration under reduced pressure, then acetonitrile (18 mL) was further added for concentration under reduced pressure, then acetonitrile (36 mL) was added thereto, the mixture was cooled to 0° C., and the precipitated solid was collected by suction filtration and washed with acetonitrile to obtain the compound (E76) (934.4 mg) as a diastereomer mixture.

$^1$H NMR (500 MHz, CDCl$_3$) δ 12.17, 12.12 (1H, s, s), 10.13, 9.54 (1H, br, br), 8.03, 7.85 (1H, br d J=8.5 Hz, br d J=8.5 Hz), 7.93 (1H, s), 7.41-7.47 (2H, m), 7.23-7.36 (7H, m), 7.13 (2H, br), 6.82-6.86 (4H, m), 6.39, 6.22 (1H, d J=8.2 Hz, d J=8.2 Hz), 5.87-5.96 (2H, m), 5.18, (2H, br, br m), 4.92-4.95, 4.86 (1H, m, br t J=5.7 Hz), 4.72-4.75, 4.47-4.56 (2H, m), 4.15-4.41 (5H, m), 3.90-4.06 (7H, m), 3.78-3.80 (6H, m), 3.57-3.64 (1H, m), 3.49-3.53, 3.27-2.29 (1H, m, m), 2.45-2.88 (6H, m), 2.19 (3H, s), 1.70-1.81 (6H, m), 1.41-1.49 (6H, m), 1.20-1.36 (114H, br m), 0.86-0.89 (18H, m), 0.76, 0.78 (9H, s), 0.12, 0.10 (3H, s), 0.04, 0.03 (3H, s), 0.00, −0.03 (3H, s), −0.16, −0.24 (3H, s).

(2) Synthesis of a 5'-OH Form of the Compound (E76) (Compound (E77))

[Formula 159]

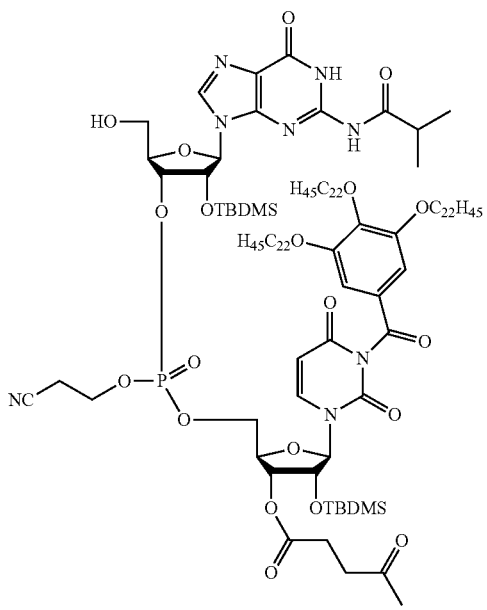

(E77)

To the compound (E76) (918.5 mg), a 490 mM trichloroacetic acid/toluene solution (9.5 mL) was added, the mixture was stirred at room temperature for 10 minutes, then methanol (4.8 mL) was added, and the mixture was stirred for 5 minutes. Acetonitrile (9.5 mL) was added thereto for concentration under reduced pressure, and then acetonitrile (9.5 mL) was added again for concentration under reduced pressure. Methanol (15.0 mL) and water (5.0 mL) were further added for concentration under reduced pressure, then methanol (38.0 mL) was added, the mixture was cooled to 0° C., and the precipitate was collected by suction filtration and washed with methanol to obtain the compound (E77) (767.6 mg) as a diastereomer mixture.

$^1$H NMR (500 MHz, CDCl$_3$) δ 12.20, 12.19 (1H, br s, br s), 10.18, 9.67 (1H, br, br), 8.33, 8.17 (1H, s, br s) 8.00, 7.81 (1H, br d J=8.5 Hz, br d J=7.6 Hz), 7.14, 7.13 (2H, br s, br s), 6.40, (1H, d J=8.2 Hz, d J=8.2 Hz), 5.90-5.99 (2H, m), 5.19-5.21 (2H, m), 4.96-5.06, 4.62-4.85 (2H, m, m), 4.36-4.64, (7H, m), 3.87-4.06 (8H, m), 2.31-2.89 (7H, m), 2.19 (3H, s), 1.70-1.81 (6H, m), 1.40-1.49 (6H, m), 1.20-1.36 (114H, br m), 0.86-0.89 (18H, m), 0.73, 0.76 (9H, s), 0.11, 0.09 (3H, s), 0.05, 0.04 (3H, s), −0.07, −0.08 (3H, s), −0.22, −0.27 (3H, s).

(3) Synthesis of a Nucleic Acid Trimer (Compound (E78)) by a Coupling Reaction Between the Compound (E11) and a Phosphoramidite Compound

[Formula 160]

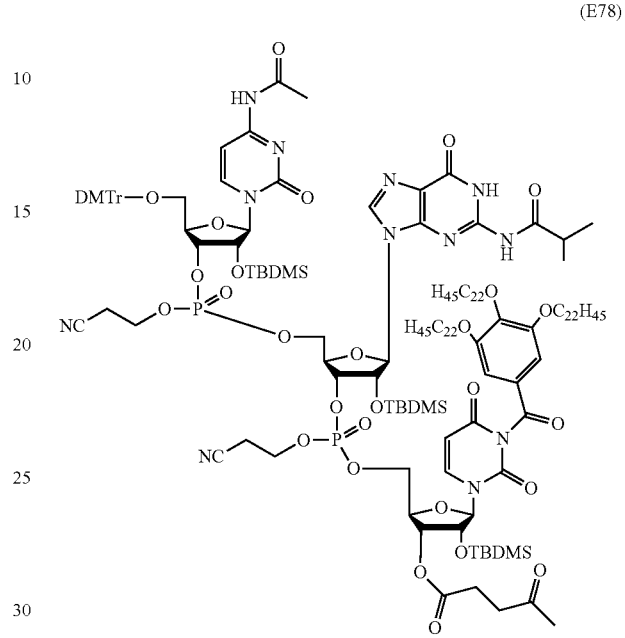

(E78)

To the compound (E77) (755.6 mg) and (2R,3R,4R,5R)-5-(4-acetamido-2-oxopyrimidin-1(2H)-yl)-2-((bis(4-methoxyphenyl)(phenyl)methoxy)methyl)-4-((tert-butyldimethylsilyl)oxy)tetrahydrofuran-3-yl(2-cyanoethyl) diisopropylphosphoramidite (721.7 mg), toluene (10.0 mL) was added at room temperature, and the mixture was stirred. 5-Benzylmercapto-1H-tetrazole (231.0 mg) dissolved in acetonitrile (2.0 mL) was added thereto, and the mixture was stirred at room temperature for 2 hours. A 0.1 M I$_2$/pyridine solution (8.0 mL) and water (500 µL) were added, the mixture was stirred at room temperature for 15 minutes, then acetonitrile (18 mL) was added for concentration under reduced pressure, acetonitrile (18 mL) was further added for concentration under reduced pressure, then acetonitrile (36 mL) was added, the mixture was cooled to 0° C., and the precipitated solid was collected by suction filtration and washed with acetonitrile to obtain the compound (E78) (1.03 g) as a diastereomer mixture.

$^1$H NMR (500 MHz, CDCl$_3$) δ 12.18-12.21 (1H, m), 10.46, 10.37, 10.01, 9.67 (1H, br, br, br, br), 7.67-8.82 (3H, m), 7.25-7.40 (9H, m), 7.13, 7.15 (2H, br s, br s), 6.94-7.12 (1H, m), 6.83-6.88 (4H, m), 5.76-6.24 (4H, m), 3.95-5.37 (23H, m), 3.43-3.82 (9H, m), 2.35-2.89 (9H, m), 2.19-2.25 (6H, s), 1.70-1.82 (6H, m), 1.41-1.49 (6H, m), 1.14-1.36 (114H, br m), 0.83-1.00 (27H, m), 0.79, 0.77, 0.75, 0.74 (9H, s), 0.03-0.29 (12H, s), −0.06, −0.07, −0.08 (3H, s), −0.19, −0.28, −0.29, −0.31 (3H, s).

(4) Synthesis of a 5'-OH Form of the Compound (E78) (Compound (E79))

[Formula 161]

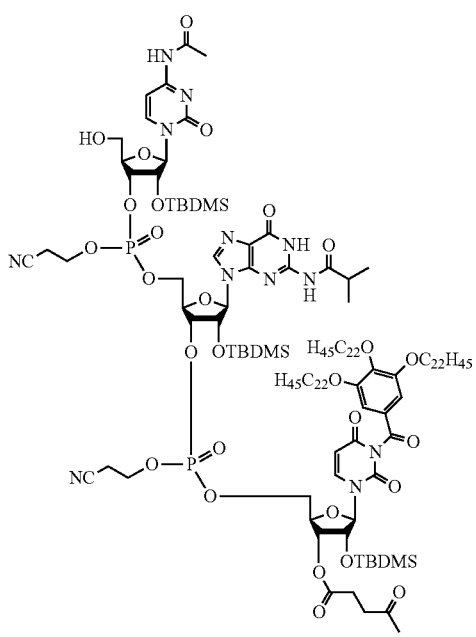

(E79)

To the compound (E78) (1.01 g), a 490 mM trichloroacetic acid/toluene solution (8.7 mL) was added, the mixture was stirred at room temperature for 10 minutes, then methanol (4.4 mL) was added, and the mixture was stirred for 5 minutes. Acetonitrile (8.7 mL) was added thereto for concentration under reduced pressure, and then acetonitrile (8.7 mL) was added again for concentration under reduced pressure. Methanol (15.0 mL) and water (5.0 mL) were further added for concentration under reduced pressure, then methanol (38.0 mL) was added, the mixture was cooled to 0° C., and the precipitate was collected by suction filtration and washed with methanol to obtain the compound (E79) (881.6 mg) as a diastereomer mixture.

$^1$H NMR (500 MHz, CDCl$_3$) δ 12.24, 12.21 (1H, br s, br s), 10.46, 10.43, 10.37, 9.95, 8.81 (1H, br, br, br, br, br), 7.63-8.53 (3H, m), 7.29-7.42 (1H, m), 7.13, (2H, br s), 3.52-6.23 (31H, m), 2.44-2.91 (9H, m), 2.19-2.24 (6H, m), 1.70-1.81 (6H, m), 1.40-1.49 (6H, m), 1.15-1.37 (114H, br m), 0.84-0.93 (27H, m), 0.78, 0.76, 0.74, 0.71 (9H, s), 0.04-0.24 (12H, s), −0.06-0.09 (3H, m), −0.21, −0.28 (3H, s, br s).

(5) Synthesis of a Nucleic Acid Tetramer (Compound (E80)) by a Coupling Reaction Between the Compound (E79) and a Phosphoramidite Compound

[Formula 162]

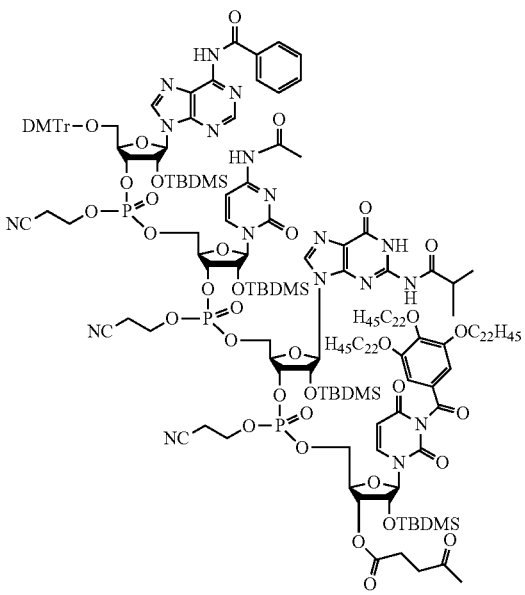

(E80)

To the compound (E79) (876.0 mg) and (2R,3R,4R,5R)-5-(6-benzamido-9H-purin-9-yl)-2-((bis(4-methoxyphenyl)(phenyl)methoxy)methyl)-4-((tert-butyldimethylsilyl)oxy) tetrahydrofuran-3-yl(2-cyanoethyl) diisopropylphosphoramidite (790.6 mg), toluene (10.0 mL) was added at room temperature, and the mixture was stirred. 5-Benzylmercapto-1H-tetrazole (231.0 mg) dissolved in acetonitrile (2.0 mL) was added thereto, and the mixture was stirred at room temperature for 2.5 hours. A 0.1M I$_2$/pyridine solution (8.0 mL) and water (500 μL) were added, the mixture was stirred at room temperature for 15 minutes, then acetonitrile (18 mL) was added for concentration under reduced pressure, acetonitrile (18 mL) was further added for concentration under reduced pressure, then acetonitrile (36 mL) was added, the mixture was cooled to 0° C., and the precipitated solid was collected by suction filtration and washed with acetonitrile to obtain the compound (E80) (1.19 g) as a diastereomer mixture.

$^1$H NMR (500 MHz, CDCl$_3$) δ 12.13-12.22 (1H, m), 8.61-10.48 (3H, m), 7.74-8.36 (5H, m), 7.43-7.63 (5H, m), 7.13-7.36 (11H, m), 6.79-6.85 (4H, m), 3.96-6.32 (34H, br m), 3.62-3.80 (9H, m), 3.37-3.48 (1H, m), 2.38-2.87 (11H, m), 2.16-2.25 (6H, m), 1.70-1.83 (6H, m), 1.41-1.49 (6H, br m), 1.11-1.36 (114H, br m), 0.83-0.93 (27H, m), 0.68-0.78 (18H, m), 0.01-0.22 (12H, m), −0.09-0.02 (6H, m), −0.33-0.17 (6H, m).

(6) Synthesis of a 5'-OH Form of the Compound (E80) (Compound (E81))

[Formula 163]

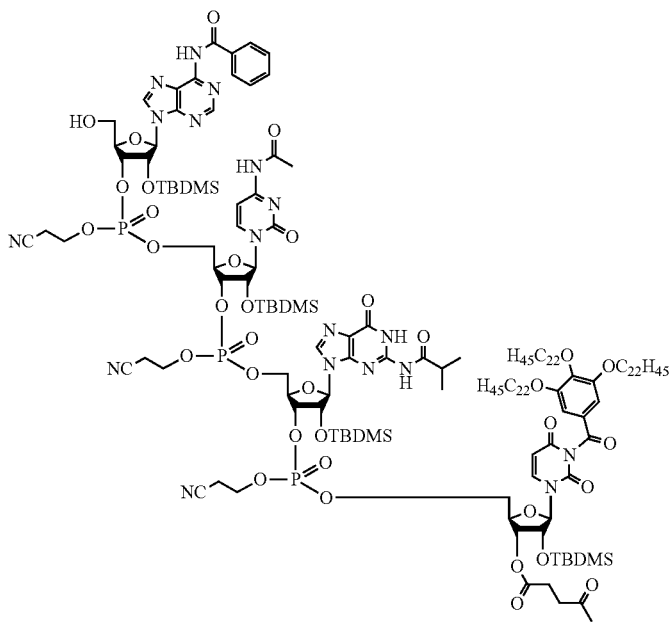

(E81)

To the compound (E80) (590.0 mg), a 490 mM trichloroacetic acid/toluene solution (4.2 mL) was added, the mixture was stirred at room temperature for 10 minutes, then methanol (2.1 mL) was added, and the mixture was stirred for 5 minutes. Acetonitrile (4.2 mL) was added thereto for concentration under reduced pressure, and then acetonitrile (4.2 mL) was added again for concentration under reduced pressure. Methanol (7.5 mL) and water (2.5 mL) were further added for concentration under reduced pressure, then methanol (19.0 mL) was added, the mixture was cooled to 0° C., and the precipitate was collected by suction filtration and washed with methanol to obtain the compound (E81) (499.7 mg) as a diastereomer mixture.

$^1$H NMR (500 MHz, CDCl$_3$) δ 12.12-12.27 (1H, m), 7.37-10.45 (13H, m), 7.12-7.14 (2H, br m), 3.78-6.31 (39H, br m), 2.49-2.96 (11H, m), 2.19-2.26 (6H, m), 1.70-1.81 (6H, m), 1.42-1.49 (6H, br m), 1.10-1.37 (114H, br m), 0.85-0.92 (27H, m), 0.71-0.78 (18H, m), 0.02-0.22 (12H, m), −0.16-0.01 (6H, m), −0.36-0.19 (6H, m).

(7) Synthesis of a Nucleic Acid Pentamer (Compound (E82)) by a Coupling Reaction Between the Compound (E81) and a Phosphoramidite Compound

[Formula 164]

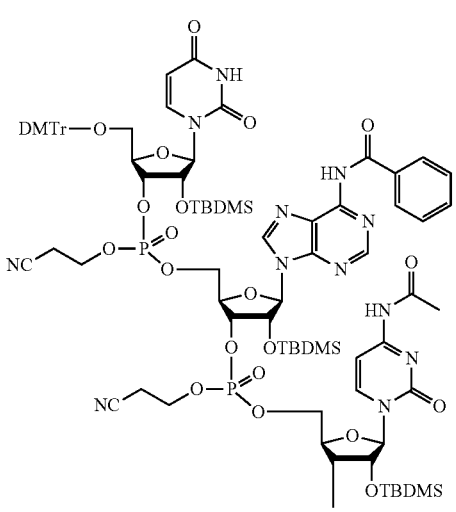

(E82)

-continued

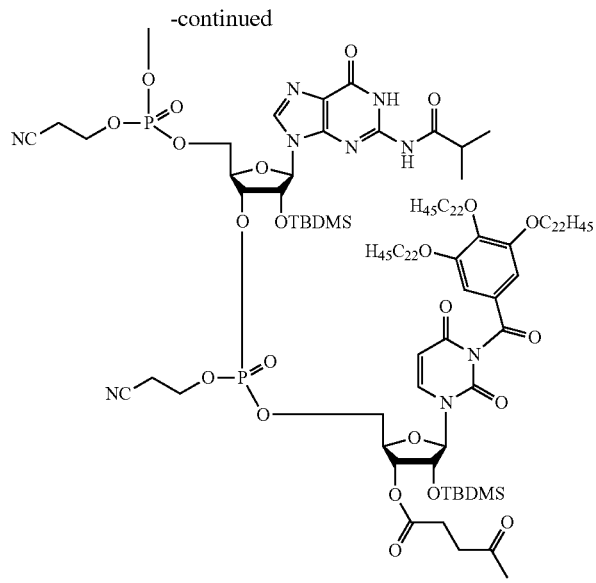

To the compound (E81) (473.2 mg) and (2R,3R,4R,5R)-2-((bis(4-methoxyphenyl)(phenyl)methoxy)methyl)-4-((tert)-butyldimethylsilyl)oxy)-5-(2,4-dioxo-3,4-dihydropyrimidin-1(2H)-yl(tetrahydrofuran-3-yl(2-cyanoethyl) diisopropyl phosphoramidite (344.4 mg), toluene (5 mL) was added at room temperature, and the mixture was stirred. 5-Benzylmercapto-1H-tetrazole (115.3 mg) dissolved in acetonitrile (1 mL) was added thereto, and the mixture was stirred at room temperature for 2.5 hours. A 0.1 M $I_2$/pyridine solution (4.0 mL) and water (250 µL) were added, the mixture was stirred at room temperature for 15 minutes, then acetonitrile (9 mL) was added for concentration under reduced pressure, acetonitrile (9 mL) was further added for concentration under reduced pressure, then acetonitrile (18 mL) was added, the mixture was cooled to 0° C., and the precipitated solid was collected by suction filtration and washed with acetonitrile to obtain the compound (E82) (586.7 mg) as a diastereomer mixture.

$^1$H NMR (500 MHz, CDCl$_3$) δ 12.13-12.22 (1H, m), 7.16-10.51 (24H, m), 7.13-7.14 (2H, br m), 6.81-6.86 (4H, m), 3.41-6.33 (54H, br m), 2.50-2.88 (12H m), 2.14-2.24 (6H, m), 1.70-1.81 (6H, m), 1.41-1.48 (6H, br m), 1.11-1.37 (114H, br m), 0.74-0.93 (54H, m), −0.32-0.21 (30H, m).

(8) Synthesis of a 5'-OH Form of the Compound (E82) (Compound (E83))

[Formula 165]

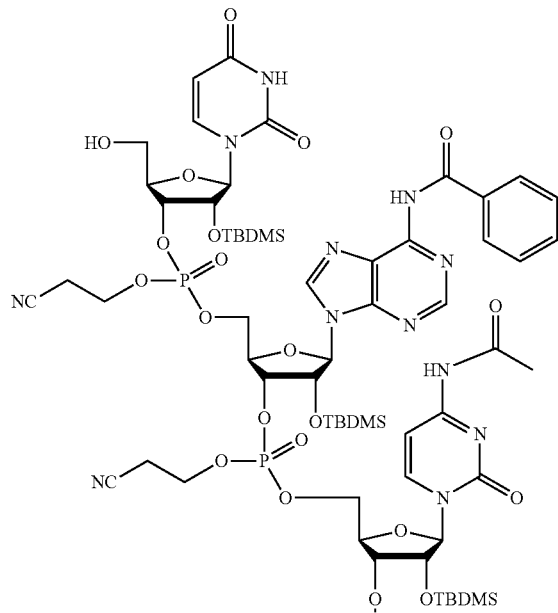

(E83)

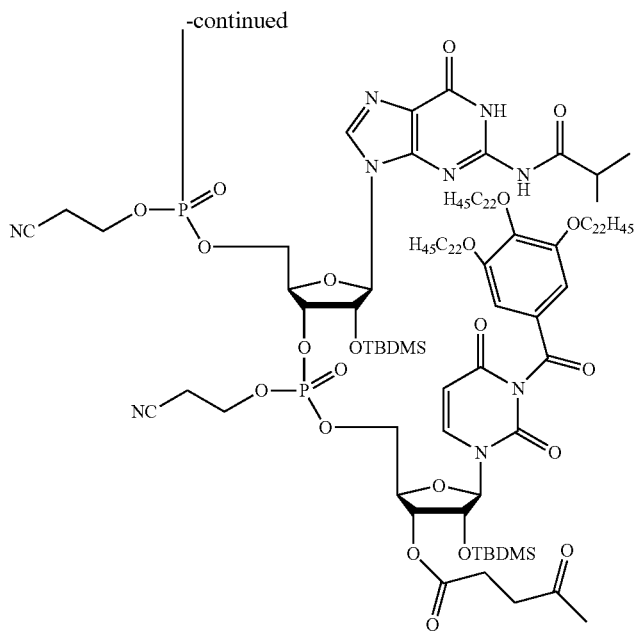

To the compound (E82) (540.9 mg), a 490 mM trichloroacetic acid/toluene solution (3.4 mL) was added, the mixture was stirred at room temperature for 10 minutes, then methanol (1.7 mL) was added, and the mixture was stirred for 5 minutes. Acetonitrile (3.5 mL) was added thereto for concentration under reduced pressure, and then acetonitrile (3.5 mL) was added again for concentration under reduced pressure. Methanol (7.5 mL) and water (1.0 mL) were further added for concentration under reduced pressure, then methanol (40 mL) was added, the mixture was cooled to 0° C., and the precipitate was collected by suction filtration and washed with methanol to obtain the compound (E83) (479.0 mg) as a diastereomer mixture.

$^1$H NMR (500 MHz, CDCl$_3$) δ 12.14-12.24 (1H, m), 7.12-10.51 (17H, m), 3.77-6.36 (49H, br m), 2.49-2.92 (12H, m), 2.15-2.24 (6H, m), 1.70-1.82 (6H, m), 1.41-1.48 (6H, br m), 1.05-1.38 (114H, br m), 0.74-0.93 (54H, m), −0.34-0.17 (30H, m).

(9) Synthesis of a Nucleic Acid Hexamer (Compound (E84)) by a Coupling Reaction Between the Compound (E83) and a Phosphoramidite Compound

[Formula 166]

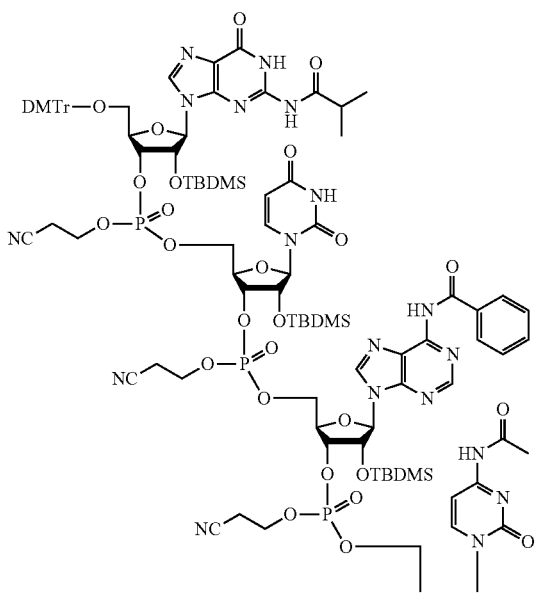

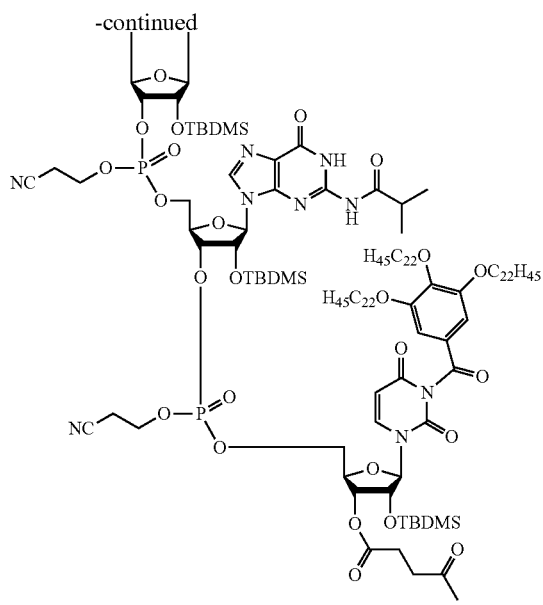

To the compound (E83) (464.1 mg) and (2R,3R,4R,5R)-2-((bis(4-methoxyphenyl)(phenyl)methoxy)methyl)-4-((tert-butyldimethylsilyl)oxy)-5-(2-isobutyramido-6-oxo-1H-purin-9(6H)-yl)tetrahydrofuran-3-yl(2-cyanoethyl) diisopropyl phosphoramidite (388.1 mg), toluene (8.0 mL) was added at room temperature, and the mixture was stirred. 5-Benzylmercapto-1H-tetrazole (115.3 mg) dissolved in acetonitrile (1.0 mL) was added thereto, and the mixture was stirred at room temperature for 2 hours. A 0.1M I$_2$/pyridine solution (4.0 mL) and water (250 μL) were added, the mixture was stirred at room temperature for 15 minutes, and then acetonitrile (9 mL) was added for concentration under reduced pressure. Acetonitrile (18 mL) was further added, the mixture was cooled to 0° C., and the precipitated solid was collected by suction filtration and washed with acetonitrile to obtain the compound (E84) (578.6 mg) as a diastereomer mixture.

$^1$H NMR (500 MHz, CDCl$_3$) δ 12.12-12.30 (2H, m), 7.11-10.56 (28H, m), 6.76-6.87 (4H, m), 3.21-6.32 (63H, br m), 2.41-2.92 (14H, m), 2.14-2.25 (6H, m), 1.70-1.81 (6H, m), 1.41-1.50 (6H, br m), 1.04-1.37 (120H, br m), 0.68-0.93 (63H, m), −0.38-0.24 (36H, m).

(10) Synthesis of a 5'-OH Form of the Compound (E84) (Compound (E85))

[Formula 167]

(E85)

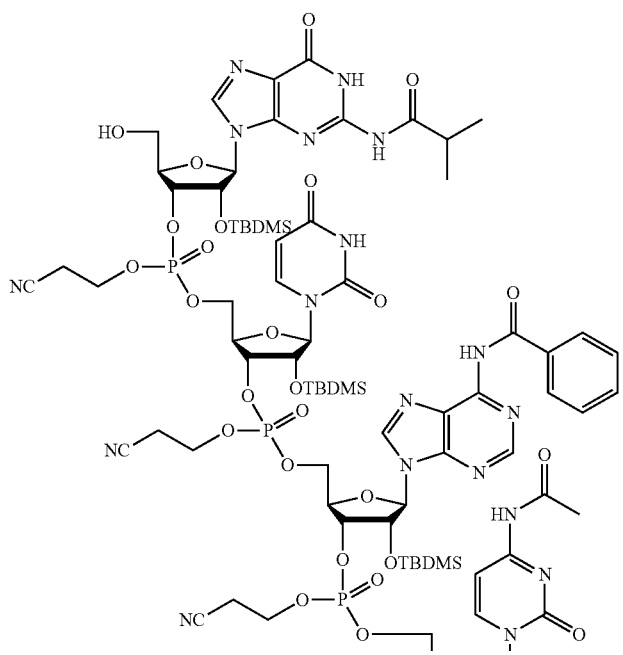

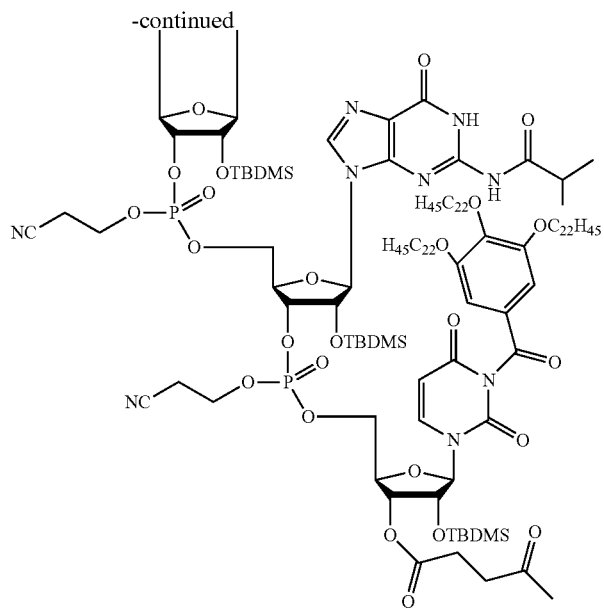

To the compound (E84) (546.2 mg), a 490 mM trichloroacetic acid/toluene solution (3.0 mL) was added, the mixture was stirred at room temperature for 15 minutes, then methanol (3.0 mL) was added, and the mixture was stirred for 5 minutes. Acetonitrile (5.0 mL) was added thereto for concentration under reduced pressure, and then acetonitrile (5.0 mL) was added again for concentration under reduced pressure. Methanol (7.5 mL) and water (1.0 mL) were further added for concentration under reduced pressure, then methanol (40 mL) was added, the mixture was cooled to 0° C., and the precipitate was collected by suction filtration and washed with methanol to obtain the compound (E85) (493.2 mg) as a diastereomer mixture.

$^1$H NMR (500 MHz, CDCl$_3$) δ 12.12-12.30 (2H, m), 7.37-10.52 (17H, m), 7.12-7.15 (2H, br m), 3.76-6.16 (58H, br m), 2.47-2.96 (14H, m), 2.17-2.29 (6H, m), 1.70-1.83 (6H, m), 1.40-1.49 (6H, br m), 0.98-1.39 (120H, br m), 0.61-0.94 (63H, m), −0.43-0.20 (36H, m).

(11) Synthesis of a Nucleic Acid Heptamer (Compound (E86)) by a Coupling Reaction Between the Compound (E85) and a Phosphoramidite Compound

[Formula 168]

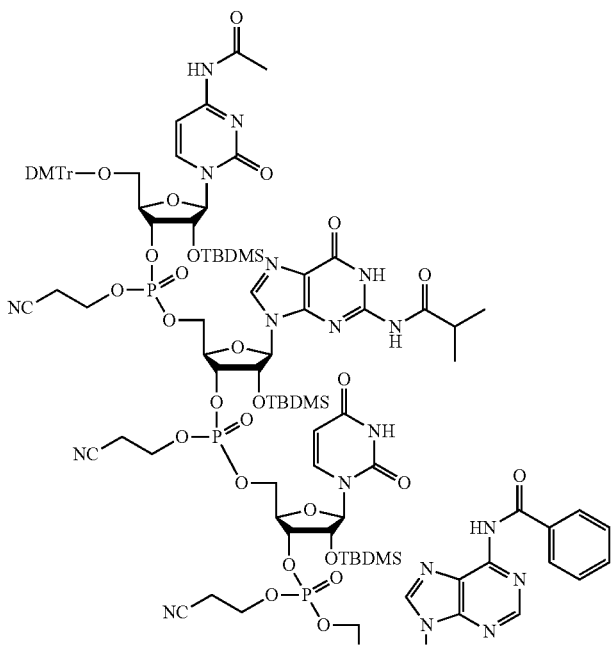

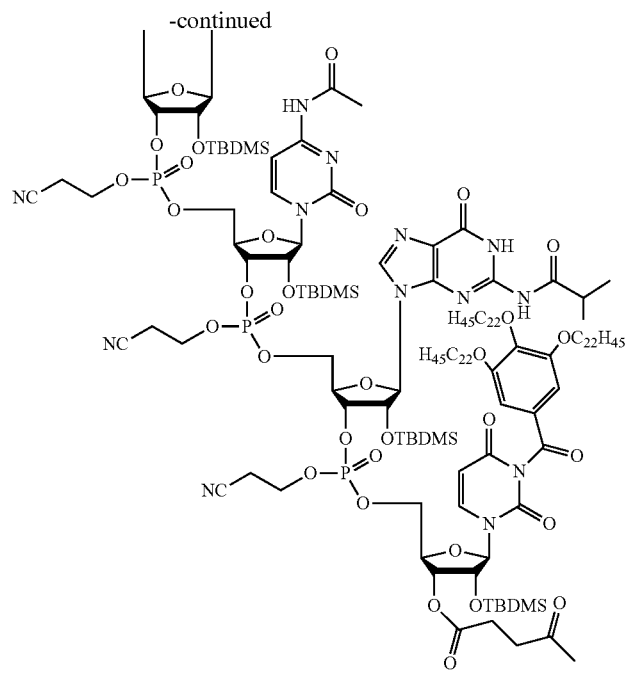

To the compound (E85) (469.6 mg) and (2R,3R,4R,5R)-5-(4-acetamido-2-oxopyrimidin-1(2H)-yl)-2-((bis(4-methoxyphenyl)(phenyl)methoxy) methyl)-4-((tert-butyldimethylsilyl)oxy)tetrahydrofuran-3-yl(2-cyanoethyl) diisopropylphosphoramidite (360.8 mg), toluene (8.0 mL) was added at room temperature, and the mixture was stirred. 5-Benzylmercapto-1H-tetrazole (115.3 mg) dissolved in acetonitrile (1.0 mL) was added thereto, and the mixture was stirred at room temperature for 2 hours. A 0.1 M $I_2$/pyridine solution (4.0 mL) and water (250 μL) were added, the mixture was stirred at room temperature for 15 minutes, and then acetonitrile (9 mL) was added for concentration under reduced pressure. Acetonitrile (18 mL) was added thereto, the mixture was cooled to 0° C., and the precipitated solid was collected by suction filtration and washed with acetonitrile to obtain the compound (E86) (496.0 mg) as a diastereomer mixture.

$^1$H NMR (500 MHz, $CDCl_3$) δ 12.22 (2H, br), 6.93-10.56 (30H, m), 6.77-6.88 (4H, m), 3.38-6.18 (72H, br m), 2.14-2.96 (22H, m), 1.70-1.81 (9H, m), 1.41-1.50 (6H, brm), 1.04-1.37 (120H, br m), 0.79-0.93 (72H, m), −0.34-0.25 (42H, m).

(12) Synthesis of a 5'-OH Form of the Compound (E86) (Compound (E87))

[Formula 169]

(E87)

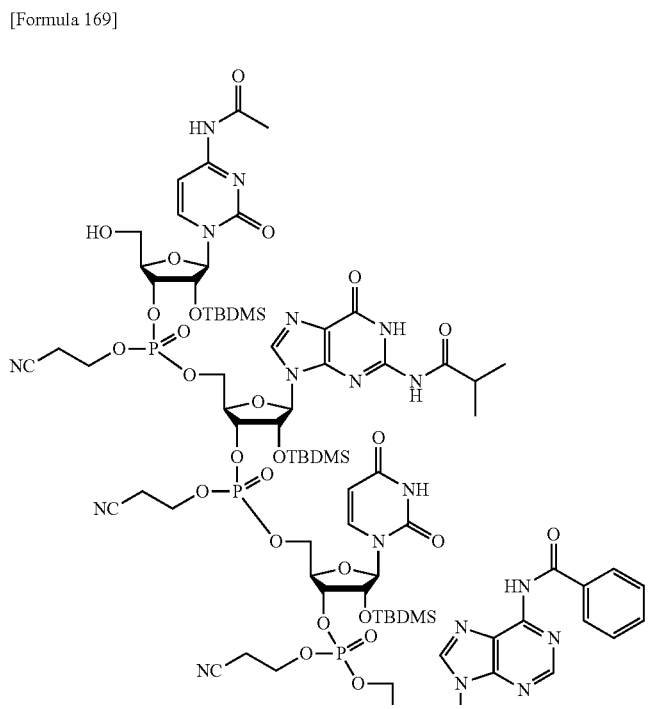

-continued

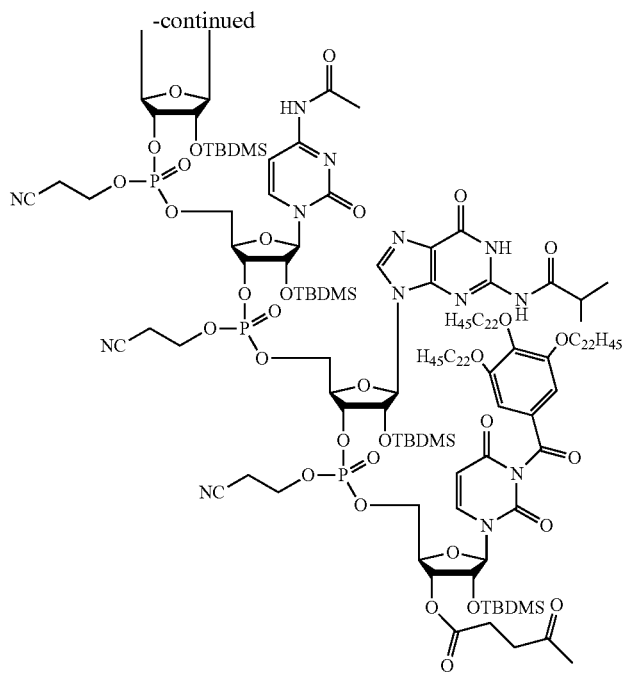

To the compound (E86) (476.0 mg), a 490 mM trichloroacetic acid/toluene solution (3.0 mL) and toluene (2.0 mL) were added, the mixture was stirred at room temperature for 15 minutes, then methanol (5.0 mL) was added, and the mixture was stirred for 5 minutes. Acetonitrile (5 mL) was added thereto for concentration under reduced pressure, and then acetonitrile (5 mL) was added again for concentration under reduced pressure. Methanol (7.5 mL) and water (1.0 mL) were further added for concentration under reduced pressure, then methanol (40 mL) was added, the mixture was cooled to 0° C., and the precipitate was collected by suction filtration and washed with methanol to obtain the compound (E87) (409.4 mg) as a diastereomer mixture.

$^1$H NMR (500 MHz, CDCl$_3$) δ 12.12-12.30 (2H, m), 7.42-10.59 (19H, m), 7.09-7.14 (2H, br m), 3.60-6.38 (67H, br m), 2.47-2.96 (16H, m), 2.13-2.29 (6H, m), 1.70-1.85 (9H, m), 1.40-1.49 (6H, br m), 0.99-1.39 (120H, br m), 0.59-0.99 (72H, m), −0.37-0.28 (42H, m).

(13) Synthesis of the Compound (E88) by Deprotection of the Compound (E87)

[Formula 170]

(E88)

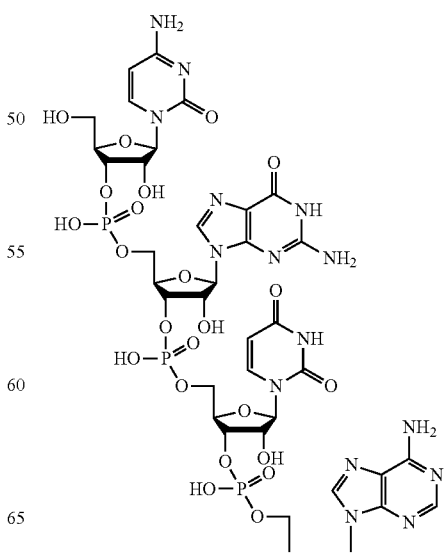

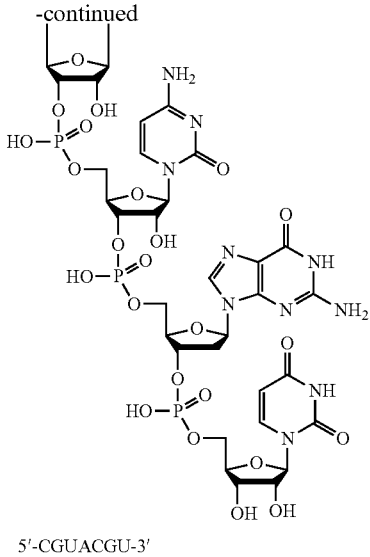

5'-CGUACGU-3'

The compound (E87) (5.5 mg) was suspended in ethanol (500 μL), a 40% aqueous solution of methylamine (1.5 mL) was added, the mixture was stirred at 45° C. for 30 minutes, and then the solid component was filtered off. The residue was washed with dimethylsulfoxide, the wash liquid was combined with the filtrate, and the mixture was cooled in an ice bath. Triethylamine trihydrofluoride (320 μL) was added thereto, and the mixture was stirred at 40° C. for 75 minutes to obtain a reaction solution including the compound (E88) (5.0 g). The obtained reaction solution (4.0 g) was purified by anion exchange chromatography to obtain the compound (E88) (0.23 μmol). The obtained compound (E88) was subjected to identification by HPLC and ESI-MS.

LC-ESI-MS m/z 1088.66 $[M-2H]^{2-}$

Example 34

Synthesis of a Nucleic Acid Oligomer (5'-ACGUACGU-3') (Compound (E91)) by Extension Toward the 5'-terminal end using a phosphoramidite method

[Formula 171]

(E91)

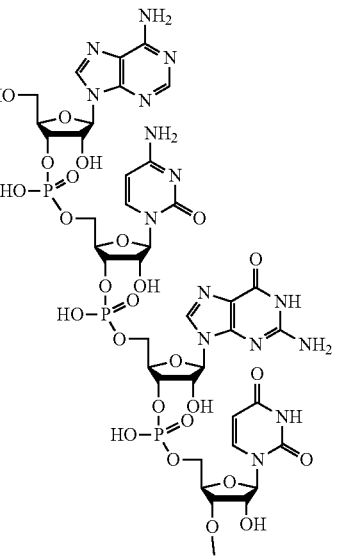

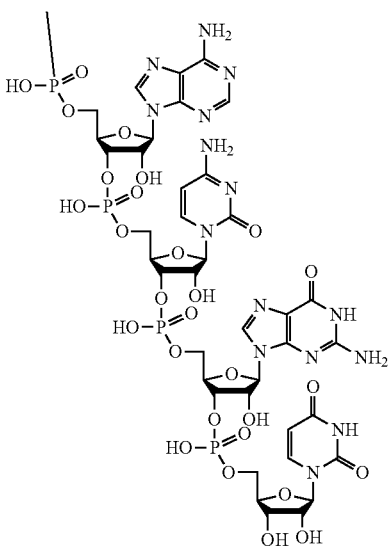

5'-ACGUACGU-3'

(1) Synthesis of a Nucleic Acid Octamer (Compound (E89)) by a Coupling Reaction Between the Compound (E87) and a Phosphoramidite Compound

[Formula 172]

(E89)

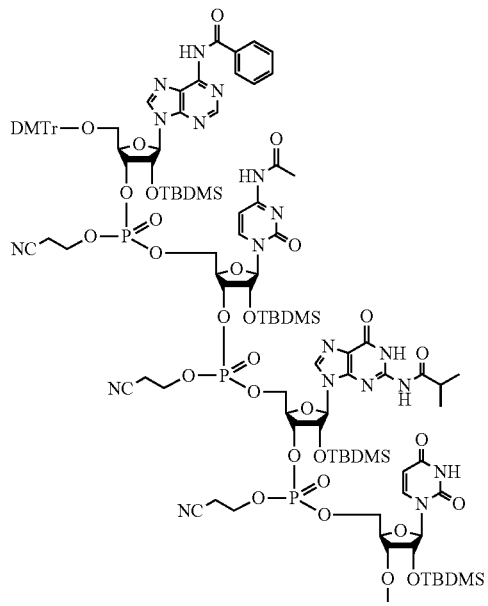
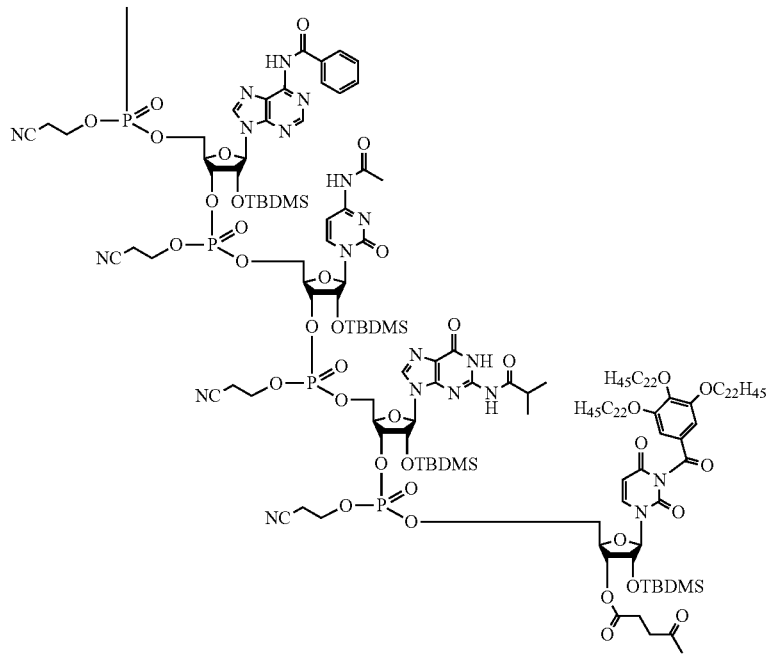

To the compound (E87) (348.1 mg) and (2R,3R,4R,5R)-5-(6-benzamido-9H-purin-9-yl)-2-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (395.3 mg), toluene (8.0 mL) was added at room temperature, and the mixture was stirred. 5-Benzylmercapto-1H-tetrazole (115.3 mg) dissolved in acetonitrile (1.0 mL) was added thereto, and the mixture was stirred at room temperature for 2 hours. A 0.1 M $I_2$/pyridine solution (4.0 mL) and water (250 μL) were added, the mixture was stirred at room temperature for 15 minutes, then acetonitrile (9 mL) was added for concentration under reduced pressure, acetonitrile (18 mL) was further added, the mixture was cooled to 0° C., and the precipitated solid was collected by suction filtration and washed with acetonitrile to obtain the compound (E89) (395.8 mg) as a diastereomer mixture.

$^1$H NMR (500 MHz, CDCl$_3$) δ 12.21 (2H, br), 6.75-10.56 (42H, m), 3.34-6.18 (80H m), 2.14-2.96 (24H, m), 1.70-1.81 (9H, m), 1.40-1.50 (6H, br m), 1.04-1.39 (120H, br m), 0.64-0.96 (81H, m), −0.38-0.22 (48H, m).

(2) Synthesis of a 5'-OH Form of the Compound (E89) (Compound (E90))

[Formula 173]

(E90)

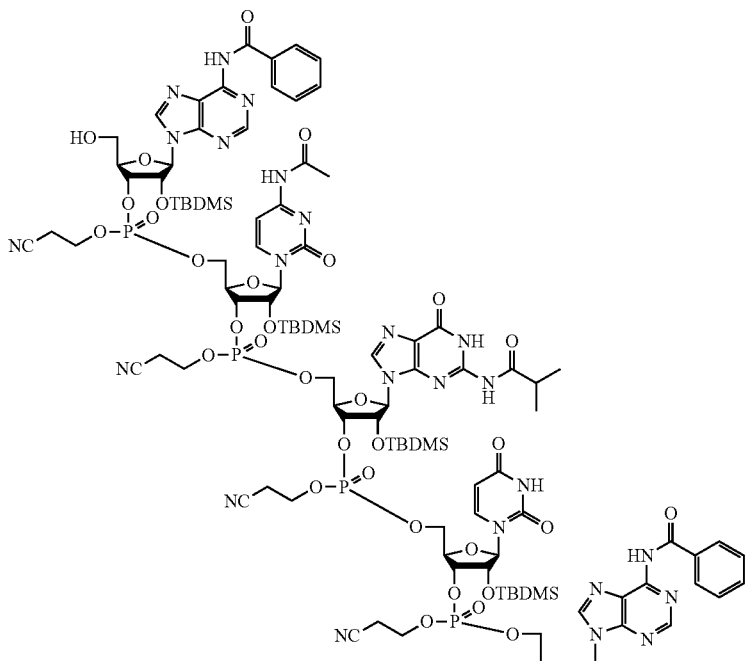

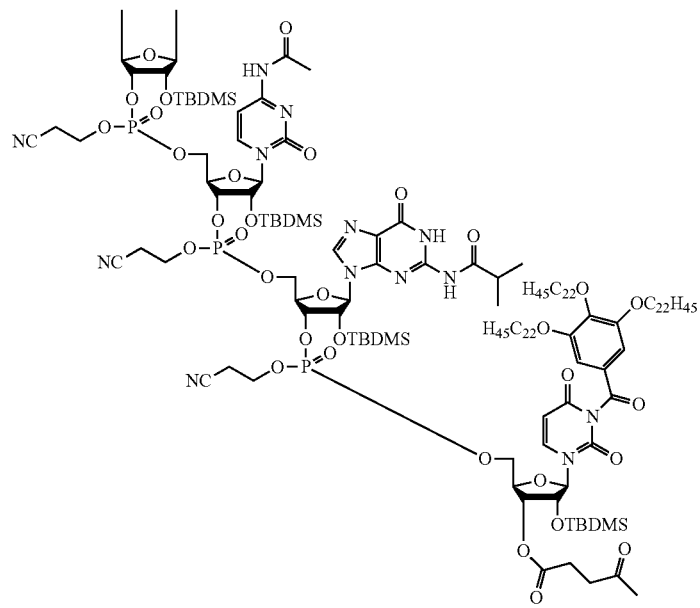

To the compound (E89) (57.1 mg), a 490 mM trichloroacetic acid/toluene solution (250 μL) was added, the mixture was stirred at room temperature for 10 minutes, then methanol (20.0 mL) and water (5.0 mL) were added, the mixture was cooled to 0° C., and the precipitate was collected by suction filtration and washed with methanol to obtain the compound (E90) (49.2 mg) as a diastereomer mixture.

$^1$H NMR (500 MHz, CDCl$_3$) δ 12.21 (2H, br), 7.31-10.52 (27H, br m), 7.13 (2H, br), 3.64-6.16 (75H, br m), 2.46-2.98 (18H, br m), 2.14-2.29 (6H, m), 1.66-1.95 (9H, m), 1.39-1.51 (6H, br m), 1.07-1.39 (120H, br m), 0.68-0.96 (81H, m), −0.35-0.22 (48H, m).

(3) Synthesis of the Compound (E91) by Deprotection of the Compound (E90)

[Formula 174]

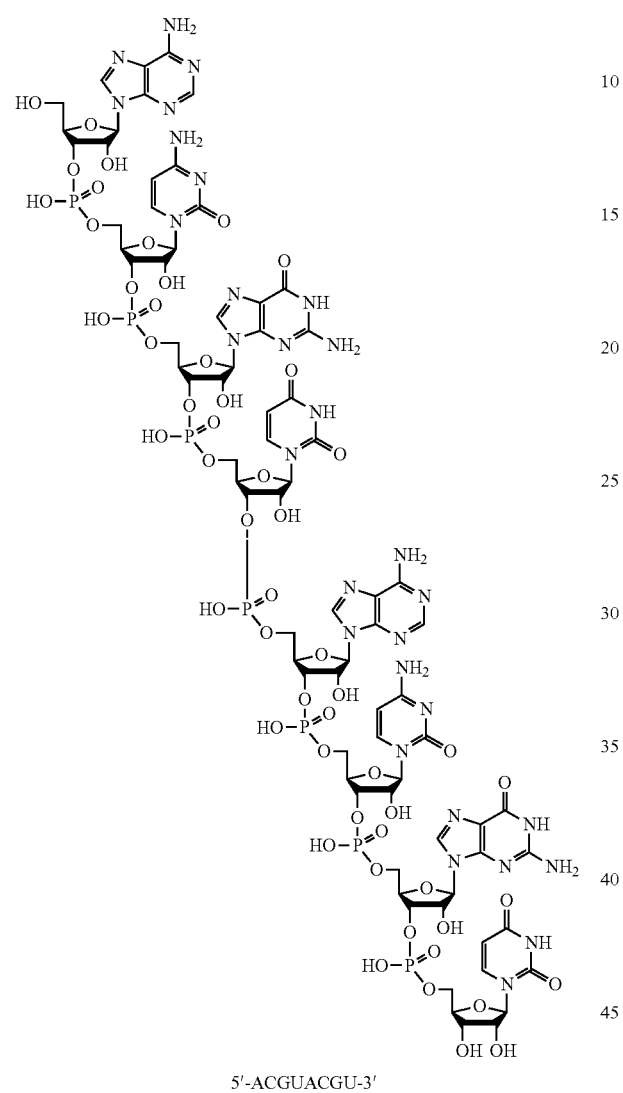

5'-ACGUACGU-3'

The compound (E90) (48.3 mg) was suspended in ethanol (1.0 mL), a 40% aqueous solution of methylamine (3.0 mL) was added, the mixture was stirred at 45° C. for 20 minutes, and then the solid component was filtered off. The residue was washed with dimethylsulfoxide, the wash liquid was combined with the filtrate, and the mixture was cooled in an ice bath. Triethylamine trihydrofluoride (640 μL) was added thereto, and the mixture was stirred at 40° C. for 75 minutes to obtain a reaction solution including the compound (E91) (11.0 g). The obtained reaction solution (5.0 g) was purified by anion exchange chromatography to obtain the compound (E91) (1.18 μmol). The obtained compound (E91) was subjected to identification by HPLC and ESI-MS.

LC-ESI-MS m/z 1253.18 [M-2H]$^{2-}$

Example 35

Synthesis of a Nucleic Acid Oligomer (5'-dTdTdTdTU-3') (Compound (E100)) by Extension Toward the 5'-Terminal End Using an H-Phosphonate Method

[Formula 175]

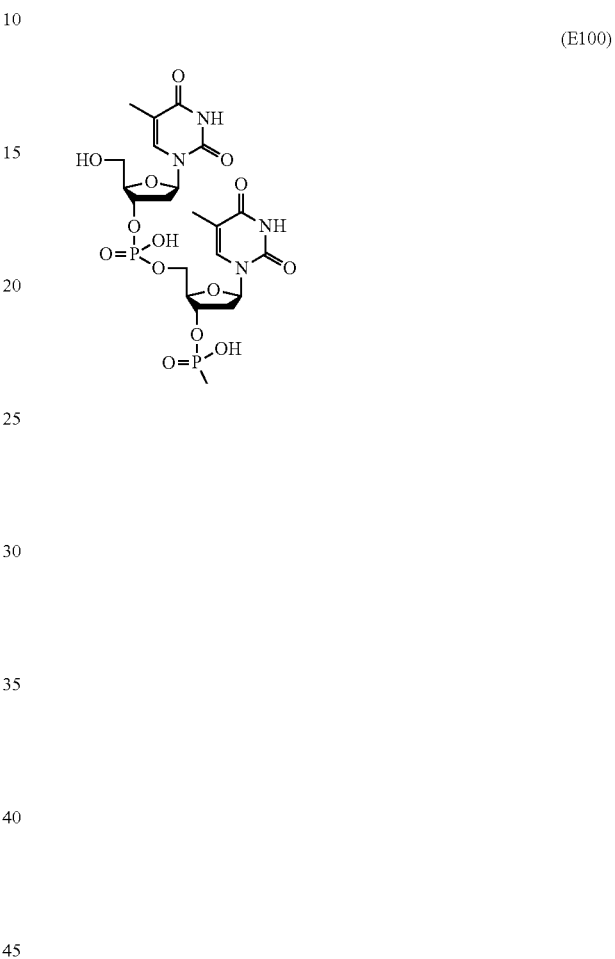

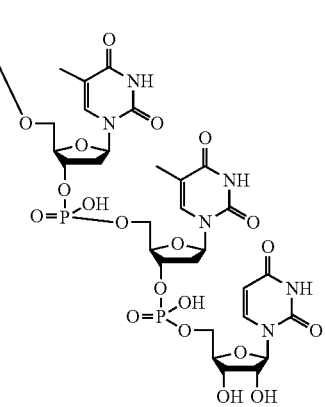

5'-dTdTdTdTU-3'

(1) Synthesis of a Nucleic Acid Dimer (Compound (E92)) by a Coupling Reaction Between the Compound (E67) and a Phosphonate Compound (2) Synthesis of a 5'-OH Form of the Compound (E92) (Compound (E93))

[Formula 176]

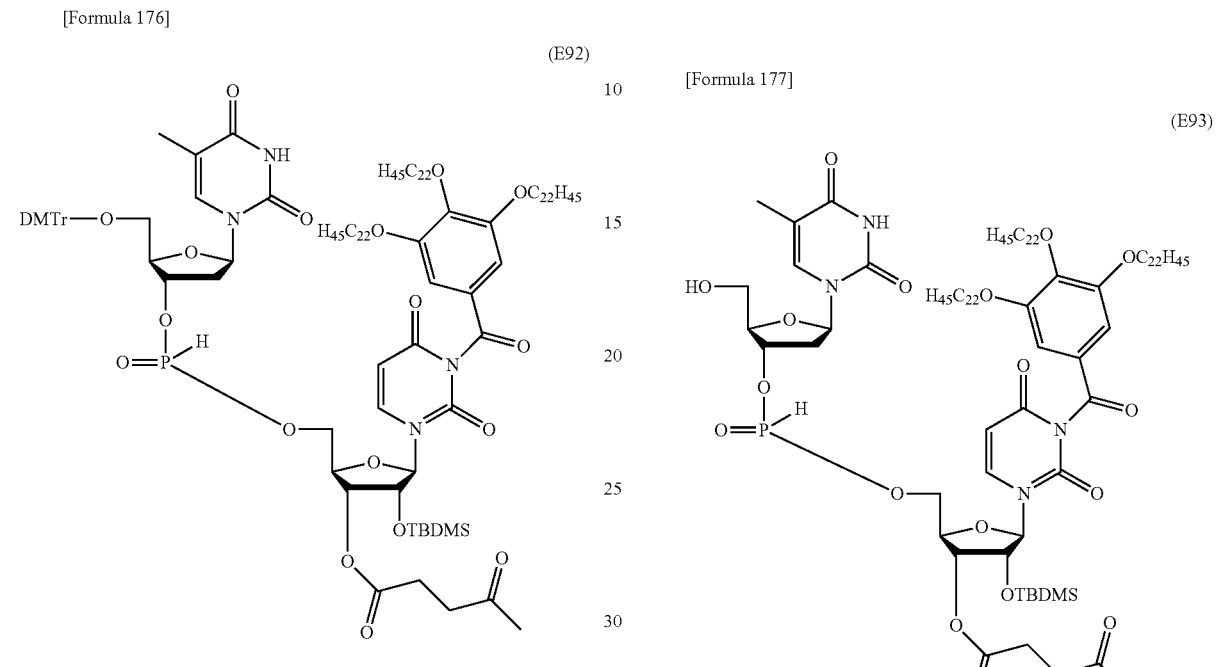

[Formula 177]

To the compound (E67) (153.4 mg) and triethylammonium (2R,3S,5R)-2-((bis(4-methoxyphenyl)(phenyl)methoxy)methyl)-5-(5-methyl-2,4-dioxo-3,4-dihydropyrimidin-1(2H)-yl)tetrahydrofuran-3-yl phosphonate (106.5 mg), toluene (5.0 mL) and pyridine (5.0 mL) were added at room temperature, and the mixture was stirred. Pivaloyl chloride (61.6 µL) was added thereto, the mixture was stirred at room temperature for 75 minutes, and then acetonitrile (20 mL) was added for concentration under reduced pressure. Acetonitrile (20 mL) was added again for concentration under reduced pressure, then acetonitrile (40 mL) was added thereto, the mixture was cooled to 0° C., and the precipitated solid was collected by suction filtration and washed with acetonitrile to obtain the compound (E92) (211.4 mg) as a diastereomer mixture.

$^1$H NMR (500 MHz, CDCl$_3$) δ 7.99, 7.62-7.72 (2H, s, m), 7.55, 7.50 (1H, d J=1.3 Hz, br s), 7.23-7.38 (9H, m), 7.12-7.20 (2H, m), 6.82-6.86 (4H, m), 6.44, 6.35-6.40 (1H, dd J=5.5, 8.6Hz, m), 6.21, 6.22 (1H, s), 5.82-5.86 (2H, m), 5.22-5.27 (1H, m), 5.08, 5.01 (1H, t J=5.8, t J=5.2 Hz), 4.21-4.46 (5H m), 3.93-4.05 (6H, m), 3.79 (6H, br s), 3.51-3.56 (1H, m), 3.37-3.44 (1H, m), 2.40-2.82 (6H, m), 2.13-2.20 (3H, m), 1.70-1.81 (6H, m), 1.40-1.49 (9H, m), 1.21-1.36 (108H, br s), 0.85-0.89 (18H, m), 0.07, 0.07, 0.06 (3H, s), 0.03, 0.03 (3H, s).

To the compound (E92) (209.4 mg), a 245 mM trichloroacetic acid/toluene solution (5.0 mL) was added, the mixture was stirred at room temperature for 10 minutes, then methanol (5.0 mL) was added, and the mixture was stirred for 5 minutes. Acetonitrile (5.0 mL) was added thereto for concentration under reduced pressure. Methanol (4.0 mL) and water (1.0 mL) were added for concentration under reduced pressure, then methanol (10 mL) was further added, the mixture was cooled to 0° C., and the precipitate was collected by suction filtration and washed with methanol to obtain the compound (E93) (136.0 mg) as a diastereomer mixture.

$^1$H NMR (500 MHz, CDCl$_3$) δ 7.40-8.25 (3H, m), 7.12-7.15 (2H, m), 6.11-6.28 (2H, m), 5.80-5.93 (2H, m), 5.25, (1H, br m), 5.13, 5.10 (1H, t J=5.4 Hz, t J=5.4 Hz), 4.46-4.48 (1H, m) 4.14-4.42 (4H, m) 3.78-4.06 (9H, m), 2.42-2.87 (6H, m), 2.20, 2.19 (3H, s, s) 1.93, 1.92 (3H, br d J=1.2 Hz, br d J=1.2 Hz), 1.70-1.81 (6H, m), 1.41-1.48 (6H, m), 1.21-1.37 (108H, br s), 0.85-0.90 (18H, m), 0.07, 0.06 (3H, s), 0.04 (3H, s).

(3) Synthesis of a Nucleic Acid Trimer (Compound (E94)) by a Coupling Reaction Between the Compound (E93) and a Phosphonate Compound

[Formula 178]

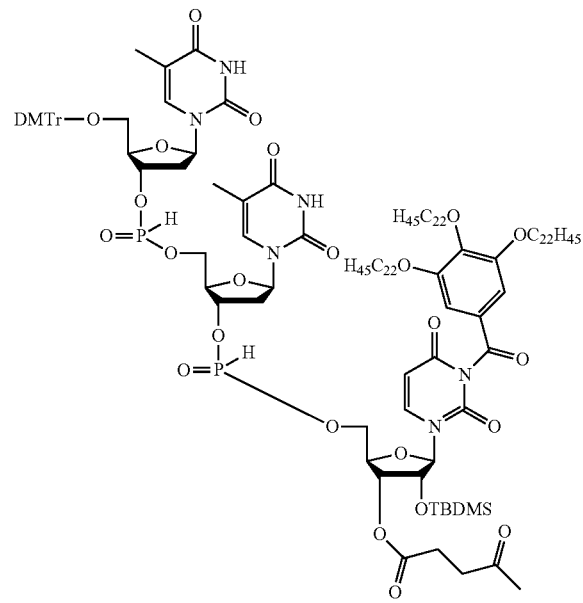

(E94)

To the compound (E93) (132.0 mg) and triethylammonium (2R,3S,5R)-2-((bis(4-methoxyphenyl)(phenyl)methoxy)methyl)-5-(5-methyl-2,4-dioxo-3,4-dihydropyrimidin-1(2H)-yl)tetrahydrofuran-3-yl phosphonate (106.5 mg), toluene (5.0 mL) and pyridine (5.0 mL) were added at room temperature, and the mixture was stirred. Pivaloyl chloride (61.6 µL) was added thereto, the mixture was stirred at room temperature for 75 minutes, and then acetonitrile (20 mL) was added for concentration under reduced pressure. Acetonitrile (20 mL) was added again for concentration under reduced pressure, then acetonitrile (40 mL) was added, the mixture was cooled to 0° C., and the precipitated solid was collected by suction filtration and washed with acetonitrile to obtain the compound (E94) (170.9 mg) as a diastereomer mixture.

$^1$H NMR (500 MHz, CDCl$_3$) δ 7.12-8.53 (16H, m), 6.82-6.86 (4H, m), 5.79-6.45 (6H, m), 5.00-5.33 (3H, m), 3.37-4.49 (22H, m), 2.38-2.88 (8H, m), 2.16-2.20 (3H, m), 1.87-1.91 (3H, br m), 1.70-1.81 (6H, m), 1.38-1.49 (9H, m), 1.22-1.36 (108H, br s), 0.85-0.89 (18H, m), 0.02-0.08, (6H, m).

(4) Synthesis of a 5'-OH Form of the Compound (E94) (Compound (E95))

[Formula 179]

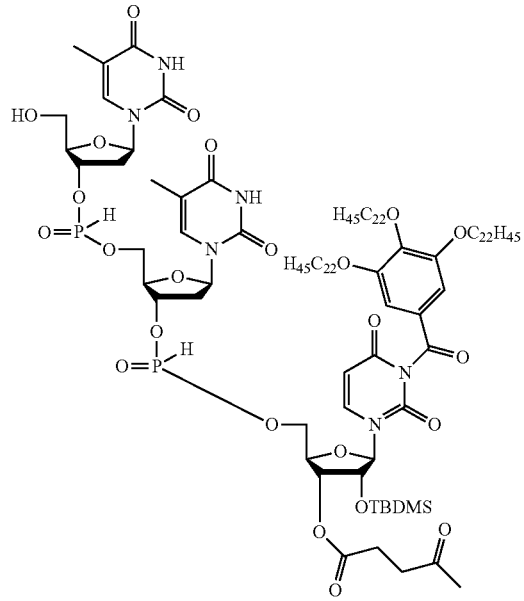

(E95)

To the compound (E94) (161.7 mg), a 245 mM trichloroacetic acid/toluene solution (5.0 mL) was added, the mixture was stirred at room temperature for 10 minutes, then methanol (5.0 mL) was added, and the mixture was stirred for 5 minutes. Acetonitrile (15 mL) was added for concentration under reduced pressure. Methanol (4.0 mL) and water (1.0 mL) were added for concentration under reduced pressure, then methanol (10 mL) was added, the mixture was cooled to 0° C., and the precipitate was collected by suction filtration and washed with methanol to obtain the compound (E95) (129.3 mg) as a diastereomer mixture.

$^1$H NMR (500 MHz, CDCl$_3$) δ 7.12-8.77 (7H, m), 5.77-6.32 (6H, m), 5.23-5.34 (2H, br), 5.08-5.14 (1H, m), 3.38-4.51 (17H, m), 2.36-2.87 (8H, m), 2.18-2.20 (3H, m), 1.88-1.94 (6H, m), 1.69-1.83 (6H, m), 1.42-1.48 (6H, m), 1.19-1.35 (108H, br s), 0.84-0.90 (18H, m), 0.03-0.08, (6H, m).

(5) Synthesis of a Nucleic Acid Tetramer (Compound (E96)) by a Coupling Reaction Between the Compound (E95) and a Phosphonate Compound

[Formula 180]

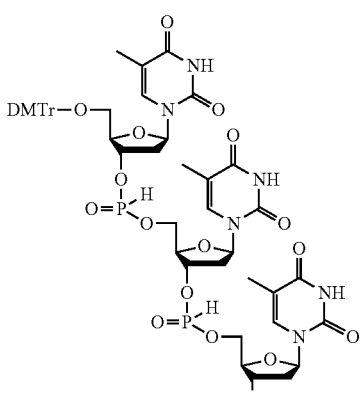

(E96)

159

-continued

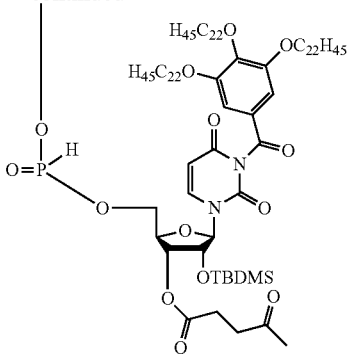

To the compound (E95) (121.5 mg) and triethylammonium (2R,3S,5R)-2-((bis(4-methoxyphenyl)(phenyl)methoxy)methyl)-5-(5-methyl-2,4-dioxo-3,4-dihydropyrimidin-1(2H)-yl)tetrahydrofuran-3-yl phosphonate (106.5 mg), toluene (5.0 mL) and pyridine (5.0 mL) were added at room temperature, and the mixture was stirred. Pivaloyl chloride (61.6 μL) was added thereto, the mixture was stirred at room temperature for 75 minutes, and then acetonitrile (20 mL) was added thereto for concentration under reduced pressure. Acetonitrile (20 mL) was added again for concentration under reduced pressure, then acetonitrile (40 mL) was added, the mixture was cooled to 0° C., and the precipitated solid was collected by suction filtration and washed with acetonitrile to obtain the compound (E96) (146.8 mg) as a diastereomer mixture.

$^1$H NMR (500 MHz, CDCl$_3$) δ 7.12-9.98 (18H, br m), 6.81-6.87 (4H, m), 5.75-6.45 (7H, br m), 5.06-5.43 (4H, br m), 3.32-4.54 (26H, br m), 2.32-2.88 (10H, br m), 2.16-2.21 (3H, m), 1.60-1.94 (12H, br m), 1.06-1.49 (117H, m), 0.80-0.90 (18H, m), 0.03-0.08 (6H, m).

(6) Synthesis of a 5'-OH Form of the Compound (E96) (Compound (E97))

[Formula 181]

(E97)

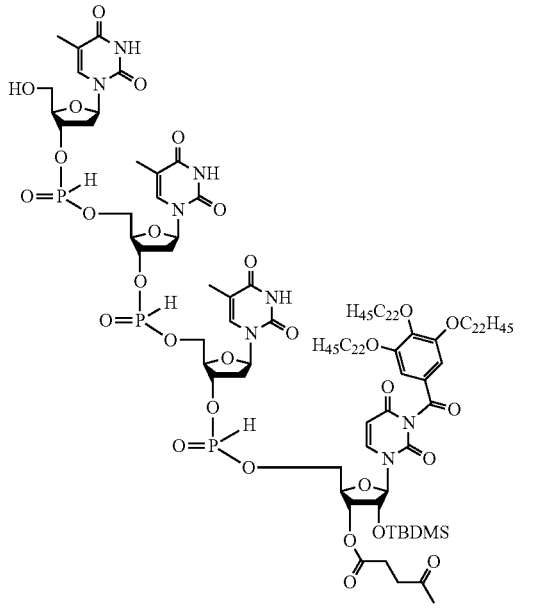

160

To the compound (E96) (128.8 mg), a 245 mM trichloroacetic acid/toluene solution (5.0 mL) was added, the mixture was stirred at room temperate for 10 minutes, then methanol (5.0 mL) was added, and the mixture was stirred for 5 minutes. Acetonitrile (15 mL) was added for concentration under reduced pressure. Methanol (4.0 mL) and water (1.0 mL) were added for concentration under reduced pressure, then methanol (10 mL) was added, the mixture was cooled to 0° C., and the precipitate was collected by suction filtration and washed with methanol to obtain the compound (E97) (95.4 mg) as a diastereomer mixture.

$^1$H NMR (500 MHz, CDCl$_3$) δ 7.11-8.77 (9H, br m), 5.72-6.30 (7H, br m), 5.07-5.39 (4H, br m), 3.70-4.51 (21H, br m), 2.38-2.88 (10H, brm), 2.17-2.21 (3H, m), 1.83-1.94 (9H, m), 1.69-1.82 (6H, m), 1.40-1.49 (6H, m), 1.19-1.38 (108H, br s), 0.83-0.90 (18H, m), 0.03-0.12, >(6H, m).

(7) Synthesis of a Nucleic Acid Pentamer (Compound (E98)) by a Coupling Reaction Between the Compound (E97) and a Phosphonate Compound

[Formula 182]

(E98)

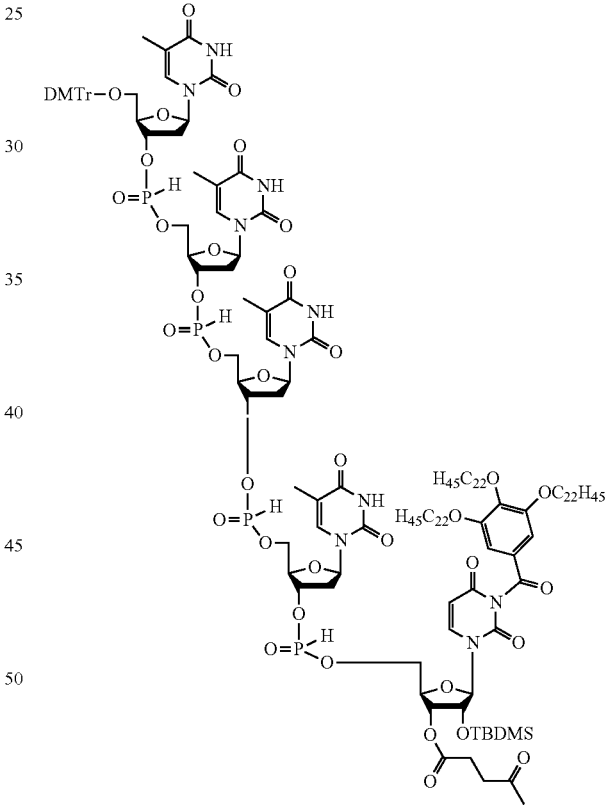

To the compound (E97) (65.9 mg) and triethylammonium (2R,3S,5R)-2-((bis(4-methoxyphenyl)(phenyl)methoxy)methyl)-5-(5-methyl-2,4-dioxo-3,4-dihydropyrimidin-1(2H)-yl)tetrahydrofuran-3-yl phosphonate (106.5 mg), toluene (5.0 mL) and pyridine (5.0 mL) were added at room temperature, and the mixture was stirred. Pivaloyl chloride (61.6 μL) was added thereto, the mixture was stirred at room temperature for 75 minutes, and then acetonitrile (20 mL) was added for concentration under reduced pressure. Acetonitrile (20 mL) was added again for concentration under reduced pressure, then acetonitrile (40 mL) was added, the mixture was cooled to 0° C., and the precipitated solid was collected by suction filtration and washed with acetonitrile to obtain the compound (E98) (81.3 mg) as a diastereomer mixture.

$^1$H NMR (500 MHz, CDCl$_3$) δ 7.12-9.69 (20H, br m), 6.81-6.86 (4H, m), 5.78-6.44 (8H, br m), 5.06-5.42 (5H, br m), 3.34-4.53 (30H, br m), 2.34-2.87 (12H, br m), 2.17-2.20 (3H, m), 1.70-1.94 (15H, br m), 1.07-1.49 (117H, m), 0.81-0.90 (18H, m), 0.02-0.12 (6H, m).

(8) Synthesis of the P—OH Compound (Compound (E99)) by an Oxidation Reaction of the Phosphite Ester Compound (E98)

[Formula 183]

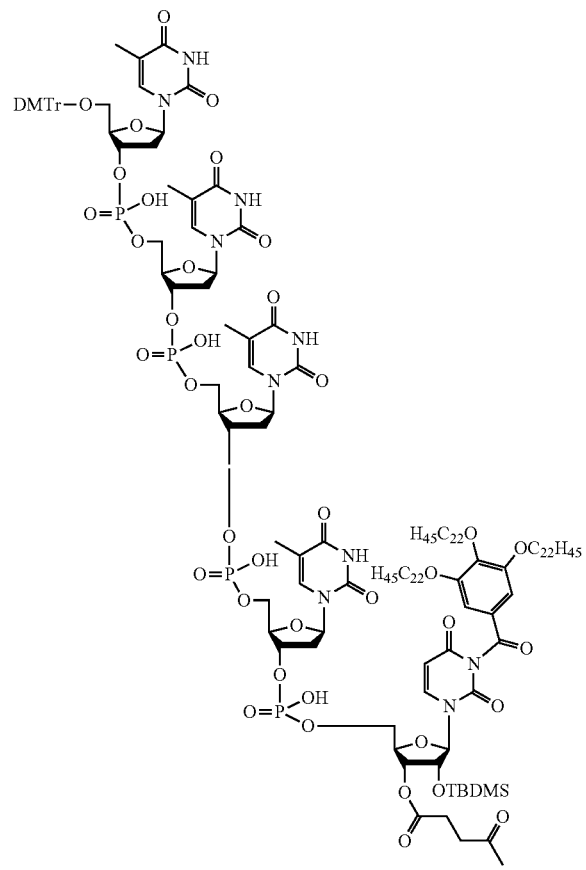

(E99)

To the compound (E98) (44.8 mg), THF (2.0 mL), a 0.1 M I$_2$/pyridine solution (4.0 mL), and water (150 μL) were added, the mixture was stirred at room temperature for 15 minutes, then acetonitrile was added, the mixture was cooled to 0° C., and the precipitated solid was collected by suction filtration and washed with acetonitrile to obtain the compound (E99) (45.6 mg) as a diastereomer mixture.

(9) Synthesis of the Compound (Compound E100) by Deprotection of the Compound (E99)

[Formula 184]

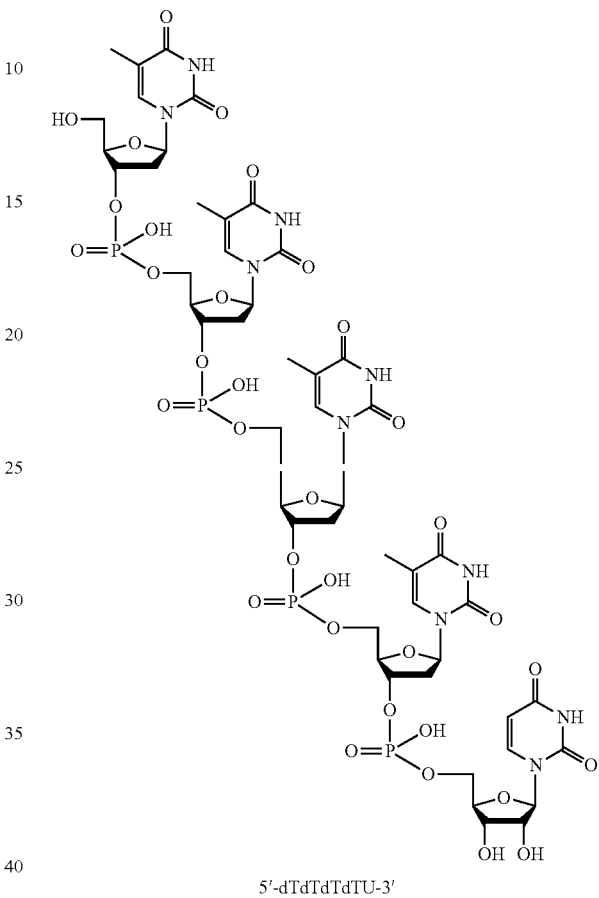

(E100)

5'-dTdTdTdTU-3'

To the compound (E99) (40.5 mg), a 245 mM trichloroacetic acid/toluene solution (2.0 mL), toluene (1.0 mL), and THF (1.0 mL) were added, the mixture was stirred at room temperature for 10 minutes, then methanol (2.0 mL) was added, and then the mixture was stirred at room temperature for 5 minutes. Methanol (10 mL) was added thereto, the mixture was cooled to 0° C., and the precipitate was collected by suction filtration and washed with methanol to obtain a product (34.3 mg) as a diastereomer mixture. The obtained product (27.3 mg) was suspended in ethanol (1.0 mL), a 40% aqueous solution of methylamine (3.0 mL) was added, the mixture was stirred at 45° C. for 20 minutes, and then the solid component was filtered off. The residue was washed with dimethylsulfoxide, the wash liquid was combined with the filtrate, and the mixture was cooled in an ice bath. Triethylamine trihydrofluoride (640 μL) was added thereto, and the mixture was stirred at 40° C. for 75 minutes to obtain a reaction solution including the compound (E100) (12.3 g). The obtained reaction solution (5.7 g) was purified by anion exchange chromatography to obtain the compound (E100) (2.09 μmol). The obtained compound (E100) was subjected to identification by HPLC and ESI-MS.

LC-ESI-MS m/z 1459.25 [M-H]$^-$

Example 36

Synthesis of the Nucleic Acid Oligomer (5'-CGUACGU-3') (Compound (E88)) from a Block Nucleic Acid Oligomer on the 5'-Terminal End Side (5'-CGU-3') and a Block Nucleic Acid Oligomer on the 3'-Terminal End Side (5'-ACGU-3') Using a Block Synthesis Method

[Formula 185]

(E88)

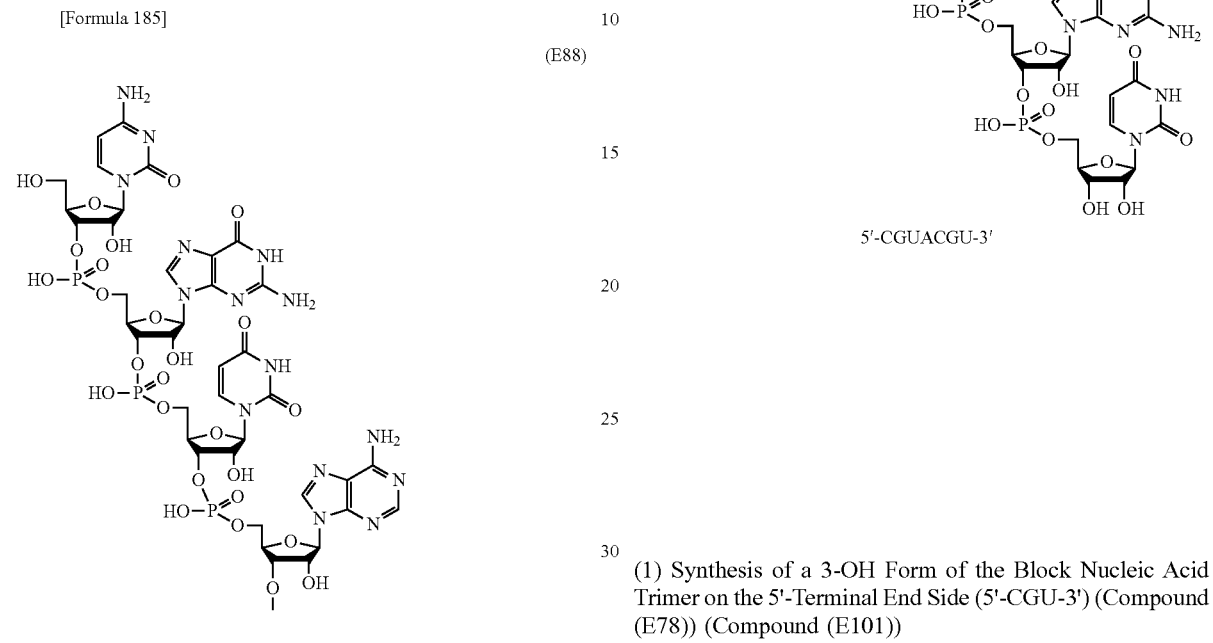

5'-CGUACGU-3'

(1) Synthesis of a 3-OH Form of the Block Nucleic Acid Trimer on the 5'-Terminal End Side (5'-CGU-3') (Compound (E78)) (Compound (E101))

[Formula 186]

(E101)

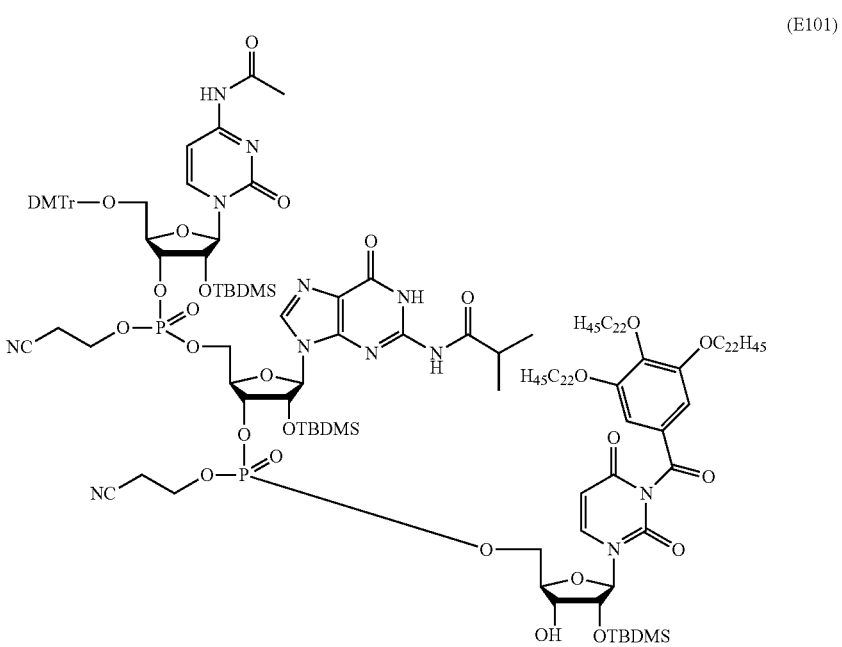

The compound (E78) (880.2 mg) was dissolved in THF (5.0 mL), and a 2,4,6-trimethylpyridine/acetic acid (4/1) solution (5.0 mL) was added. The solution was cooled to 0° C., then hydrazine monohydrate (17.5 μL) was added, the mixture was stirred at 0° C. for 120 minutes, a 2,4,6-trimethylpyridine/acetic acid (4/1) solution (5.0 mL) was added thereto, and the mixture was stirred at room temperature for 60 minutes. To the reaction liquid, acetylacetone (200 μL) was added, and the mixture was stirred at room temperature for 5 minutes. Methanol was added at room temperature, the mixture was stirred, and then the precipitate was collected by suction filtration and washed with methanol to obtain the compound (E101) (768.4 mg).

$^1$H NMR (500 MHz, CDCl$_3$) δ 12.25-12.20 (1H, br), 10.45, 10.36, 10.01, 10.28, 10.26 (1H, br, br, br, br), 8.65 (1H, br), 8.32, 8.26, 8.21, 8.15 (1H, d J=6.9 Hz, d J=6.9 Hz, d J=7.9 Hz, d J=7.6 Hz), 7.61-7.87 (2H m), 7.23-7.39 (9H, m), 7.12-7.15 (2H, m), 6.98-7.05 (1H, m), 6.83-6.88 (4H, m), 5.68-6.23 (4H, m), 3.93-5.14 (23H, m), 3.40-3.83 (8H, m), 2.39-2.91 (6H, m), 2.16-2.25 (3H, s), 1.70-1.84 (6H, m), 1.39-1.51 (6H, m), 1034-1.38 (114H, brm), 0.86-0.93 (27H, m), 0.75-0.79 (9H, s), 0.10-0.21 (12H, s), −0.06-0.03 (3H, s), −0.27-0.18 (3H, s).

(2) Synthesis of the Compound (E88) by a Coupling Reaction Between the Block Nucleic Acid Trimer on the 5'-Terminal End Side (5'-CGU-3') (Compound (E101)) and the Nucleic Acid Oligomer on the 3'-Terminal End Side (5'-ACGU-3') (Compound (E81))

[Formula 187]

(E88)

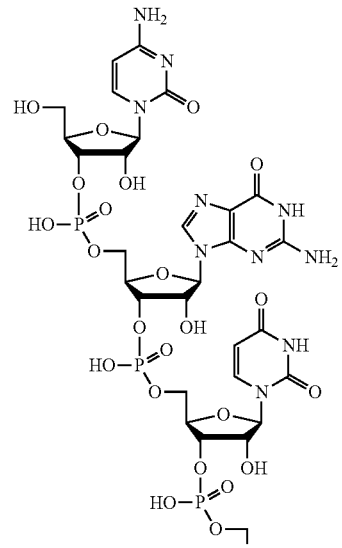

5'-CGUACGU-3'

The compound (E101) (170.2 mg) was dissolved in chloroform (1.8 mL), 2,4,6-trimethylpyridine (40.0 μL), 1-methylimidazole (2.9 μL), and 2-cyanoethyldiisopropylchlorophosphoroamidide (40.2 μL) were added thereto, and the mixture was stirred at room temperature for 1 hour. The compound (E81) (64.6 mg) and 5-benzylmercapto-1H-tetrazole (104.0 mg) dissolved in acetonitrile (900 μL) were added thereto, and the mixture was stirred at room temperature for 2.5 hours. Further, the reaction liquid was heated to 50° C. and stirred for 2 hours, then the reaction liquid was cooled to room temperature, a 0.1 M I$_2$/pyridine solution (1.8 mL) and water (113 μL) were added, and the mixture was stirred at room temperature for 15 minutes. Acetonitrile was added thereto, the mixture was cooled to 0° C., and the precipitated solid was collected by suction filtration and washed with acetonitrile to obtain a product (246.0 mg). To the obtained product (23.1 mg), a 490 mM trichloroacetic acid/toluene solution (300 μL) was added, the mixture was stirred at room temperature for 10 minutes, then methanol (1.7 mL) was added, and the mixture was stirred for 5 minutes. The precipitated product was recovered (26.2 mg) by centrifugal sedimentation. The recovered product (20.1 mg) was suspended in ethanol (1.0 mL), a 40% aqueous solution of methylamine (3.0 mL) was added, the mixture was stirred at 45° C. for 20 minutes, and then the solid component was filtered off. The residue was washed with dimethylsulfoxide, the wash liquid was combined with the filtrate, and the mixture was cooled in an ice bath. Triethylamine trihydrofluoride (640 μL) was added thereto, and the mixture was stirred at 40° C. for 75 minutes to obtain a reaction solution including the compound (E88) (12.0 g). The obtained reaction solution (11.3 g) was purified by anion exchange chromatography to obtain the compound (E88) (0.18 μmol). The obtained compound (E88) was subjected to identification by HPLC and ESI-MS.

LC-ESI-MS m/z 1088.66 [M-2H]$^{2-}$

Example 37

Synthesis of a Nucleic Acid Oligomer (5'-dTdTdTdT-3') (Compound (E106)) from a Block Nucleic Acid Oligomer (5'-dTdT-3') Using a Convergent Synthesis Method by a Block Synthesis Method

[Formula 188]

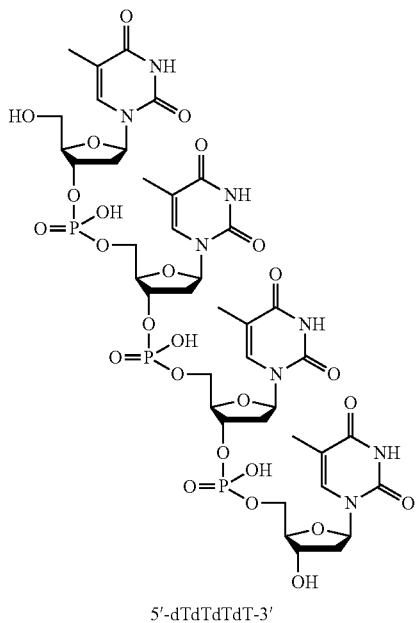

5'-dTdTdTdT-3'

(1) Synthesis of a 3-OH Form of the Block Nucleic Acid Dimer on the 5'-Terminal End Side (5'-dTdT-3') (Compound (E19)) (Compound (E104))

[Formula 189]

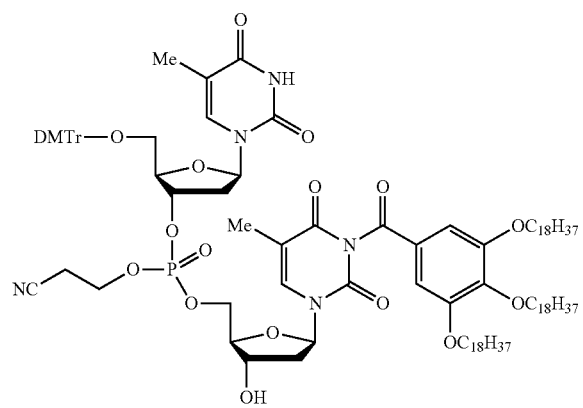

The compound (E19) (477.1 mg) was dissolved in toluene (4.2 mL), a 2,4,6-trimethylpyridine/acetic acid (4/1) solution (4.2 mL) was added thereto, and the mixture was cooled to 0° C. Hydrazine monohydrate (14.6 μL) was added thereto, the mixture was stirred at 0° C. for 120 minutes, a 2,4,6-trimethylpyridine/acetic acid (4/1) solution (4.2 mL) was added, the mixture was further stirred at room temperature for 60 minutes, then acetylacetone (200 μL) was added, and the mixture was stirred at room temperature for 5 minutes. Methanol was added thereto, the mixture was stirred, and then the precipitate was collected by suction filtration and washed with methanol to obtain the compound (E104) (401.2 mg).

$^1$H NMR (500 MHz, CDCl$_3$) δ 8.65, 8.50 (1H, br, br s), 7.57, 7.55 (1H, br d J=1.3 Hz, br d J=1.0 Hz), 7.23-7.38 (10H, m), 7.14, 7.12 (2H, br, br s), 6.83-6.87 (4H, m), 6.35-6.42 (1H, m), 6.20-6.25 (1H, m), 5.12-5.18 (1H, m), 4.51-4.56, 4.43-4.48 (1H, m), 4.15-4.37 (5H, m), 3.93-4.08 (8H, m), 3.77-3.80 (6H, m), 3.53-3.58 (1H, m), 3.38-3.42, (1H, m), 2.23-2.94 (6H, m), 1.92-1.99 (3H, m), 1.69-1.82 (6H, m), 1.40-1.49 (9H, m), 1.10-1.38 (84H, m), 0.85-0.90 (9H, m).

(2) Synthesis of a 3'-Phosphoramidite Form of the Block Nucleic Acid Dimer on the 5'-Terminal End Side (5'-dTdT-3') (Compound (E104)) (Compound (E105))

[Formula 190]

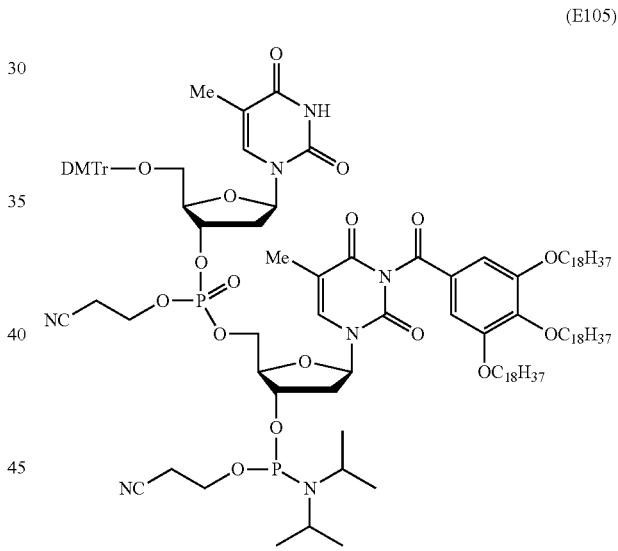

The compound (E104) (23.5 mg) was dissolved in dichloromethane (5.2 mL), then 2,4,6-trimethylpyridine (155 μL), 1-methylimidazole (6.2 μL), and 2-cyanoethyldiisopropylchlorophosphoroamidide (87.0 μL) were added, and the mixture was stirred at room temperature for 1 hour. Acetonitrile was added thereto for concentration, and then the residue was collected by suction filtration to obtain the compound (E105) (250.9 mg) as a diastereomer mixture.

$^1$H NMR (500 MHz, CDCl$_3$) δ 8.06 (1H, br), 7.10-7.70 (11H, m), 7.11-7.18 (2H, m), 6.82-6.86 (4H, m), 6.22-6.46 (2H, m), 5.19 (1H, br), 3.37-4.60 (25H, m), 2.16-2.85 (8H, m), 1.91-1.97 (3H, m), 1.68-1.82 (6H, m), 1.12-1.50 (105H, m), 0.85-0.90 (9H, m).

(3) Synthesis of the Compound (E106) by a Coupling Reaction Between the Block Nucleic Acid Dimer on the 5'-Terminal End Side (5'-dTdT-3') (Compound (E104)) and the Block Nucleic Acid Dimer on the 3'-Terminal End Side (5'-dTdT-3') (Compound (E20))

[Formula 191]

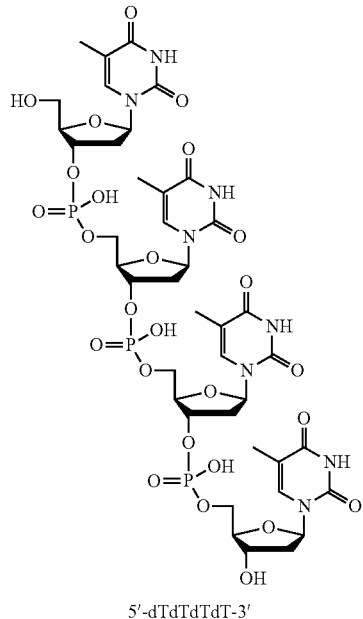

5'-dTdTdTdT-3'

To the compound (E20) (16.1 mg) and the compound (E105) (80.5 mg), toluene (300 μL) was added at room temperature, and the mixture was stirred. 5-Benzylmercapto-1H-tetrazole (11.5 mg) dissolved in acetonitrile (100 μL) was added thereto, and the mixture was stirred at room temperature for 5 hours. A 0.1M $I_2$/pyridine solution (400 μL) and water (25 μL) were added, the mixture was stirred at room temperature for 15 minutes, then acetonitrile (20 mL) was added, the mixture was cooled to 0° C., and the precipitated solid was collected by suction filtration and washed with acetonitrile to obtain a product (90.8 mg). To the obtained product (30.2 mg), a 490 mM trichloroacetic acid/toluene solution (500 μL) was added, the mixture was stirred at room temperature for 10 minutes, then methanol was added, the mixture was cooled to 0° C., and the precipitated product (29.3 mg) was recovered by centrifugal sedimentation. The recovered product (11.0 mg) was suspended in ethanol (500 μL), a 40% aqueous solution of methylamine (1.5 mL) was added, the mixture was stirred at 45° C. for 20 minutes, and then the solid component was filtered off. The residue was washed with dimethylsulfoxide, and the wash liquid was combined with the filtrate to obtain a reaction solution including the compound (E106) (5.8 g). The reaction solution (5.3 g) was purified by anion exchange chromatography to obtain the compound (E106) (32.2 nmol). The obtained compound (E106) was subjected to identification by HPLC and ESI-MS.

LC-ESI-MS m/z 1153.22 [M-H]⁻

Example 38

Synthesis of the Nucleic Acid Oligomer (5'-dTdTdTdT-3') (Compound (E106)) from the Block Nucleic Acid Oligomer (5'-dTdT-3') Using a Convergent Synthesis Method by a Block Synthesis Method

[Formula 192]

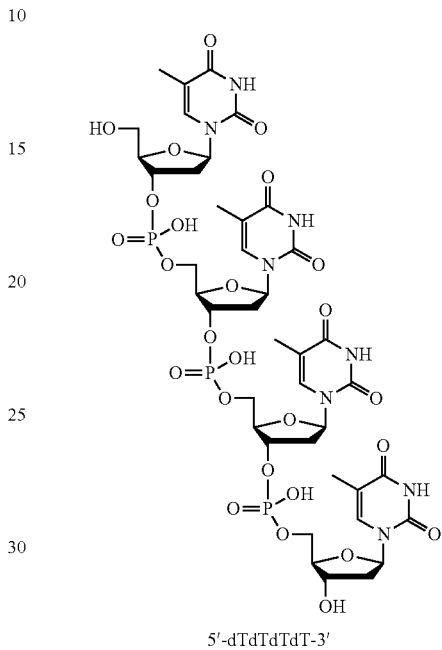

5'-dTdTdTdT-3'

(1) Synthesis of a Nucleic Acid Dimer (5'-dTdT-3') (Compound (E74)) from the dT-Type Nucleoside Monomer Compound (Compound (E56))

[Formula 193]

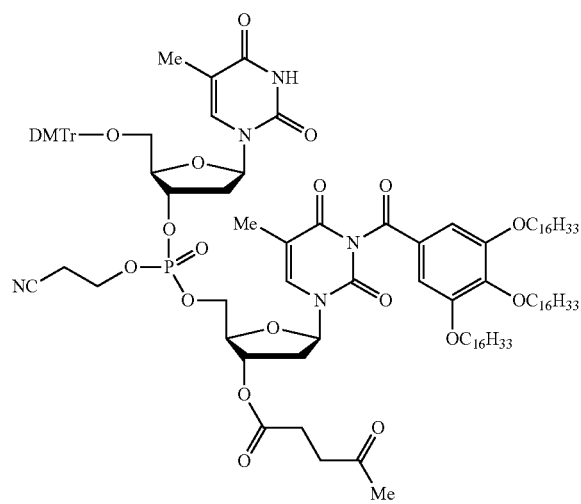

To the compound (E56) (233 mg) and 5'-O-(4,4'-dimethoxytrityl)-2'-deoxythymidine-N,N'-diisopropylaminocyanoethyl phosphoramidite (233 mg), toluene (5 mL) was added at room temperature, and the mixture was stirred.

5-Benzylmercapto-1H-tetrazole (87 mg) dissolved in acetonitrile (750 μL) was added thereto, and the mixture was stirred at room temperature for 2 hours. A 0.1M I$_2$/Pyridine solution (3 mL) and water (188 μL) were added, the mixture was stirred at room temperature for 15 minutes, then acetonitrile was added, the mixture was cooled to 0° C., and the precipitated solid was collected by suction filtration and washed with acetonitrile to obtain the compound (E74) (326 mg, percent yield: 89%) as a diastereomer mixture.

$^1$H NMR (500 MHz, CDCl$_3$) δ 8.30, 8.10 (1H, br, br s), 7.46-7.56 (2H, m), 7.35-7.38 (2H, m), 7.24-7.33 (7H, m), 7.17, 7.14 (2H, br, br s), 6.82-6.86 (4H, m), 6.42, 6.38 (1H, dd J=5.5, 8.7 Hz, dd J=8.7, 8.3 Hz), 6.32 (1H, br), 5.16-5.31 (2H, m), 4.15-4.38 (6H, m), 3.96-4.05 (6H, m), 3.80, 3.79 (6H, s), 3.54-3.57 (1H, m), 3.38-3.42, (1H, m), 2.44-2.81 (9H, m), 2.19-2.31 (1H, m), 2.17 (3H, d J=1.9 Hz), 1.96 (3H, m), 1.70-1.82 (6H, m), 1.41-1.48 (9H, m), 1.23-1.35 (72H, m), 0.88 (9H, t, J=6.9 Hz).

(2) Synthesis of a 3'-OH Form of the Block Nucleic Acid Dimer (5'-dTdT-3') (Compound (E74)) (Compound (E102))

[Formula 194]

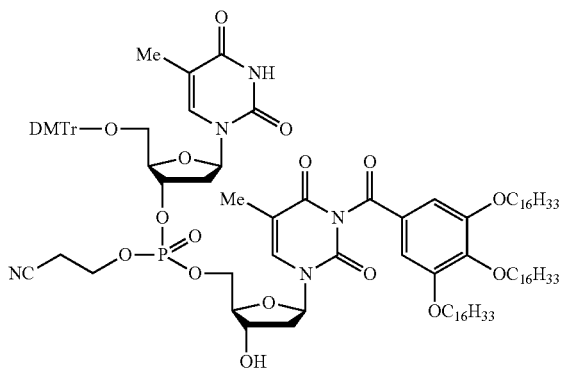

(E102)

The compound (E74) (200.1 mg) was dissolved in toluene (1.9 mL), a 2,4,6-trimethylpyridine/acetic acid (4/1) solution (1.9 mL) was added, and the mixture was cooled to 0° C. Hydrazine monohydrate (6.7 μL) was added, the mixture was stirred at 0° C. for 120 minutes, then toluene (1.9 mL) and a 2,4,16-trimethylpyridine/acetic acid (4/1) solution (1.9 mL) were added, and the mixture was stirred at room temperature for 60 minutes. Acetylacetone (100 μL) was added, and the mixture was stirred at room temperature for 5 minutes. Methanol was added at room temperature, the mixture was stirred, and then the precipitate was collected by suction filtration and washed with methanol to obtain the compound (E102) (180.0 mg).

$^1$H NMR (500 MHz, CDCl$_3$) δ 8.31, 8.16 (1H, br, br s), 7.57, 7.55 (1H, br, br d J=1.0 Hz), 7.23-7.38 (10H, m), 7.14, 7.12 (2H, br, br s), 6.85 (4H, d J=8.5 Hz), 6.35-6.42 (1H, m), 6.19-6.24 (1H, m), 5.13-5.17 (1H, m), 4.53-4.55, 4.44-4.49 (1H, m), 4.16-4.36 (5H, m), 3.94-4.06 (8H, m), 3.80 (6H, s), 3.54-3.57 (1H, m), 3.38-3.42, (1H, m), 2.24-2.79 (6H, m), 1.95 (3H, s), 1.70-1.81 (6H, m), 1.41-1.48 (9H, m), 1.22-1.36 (72H, m), 0.88 (9H, t, J=6.9 Hz).

(3) Synthesis of a 5'-OH Form of the Block Nucleic Acid Dimer (5'-dTdT-3') (Compound (E74)) (Compound (E103))

[Formula 195]

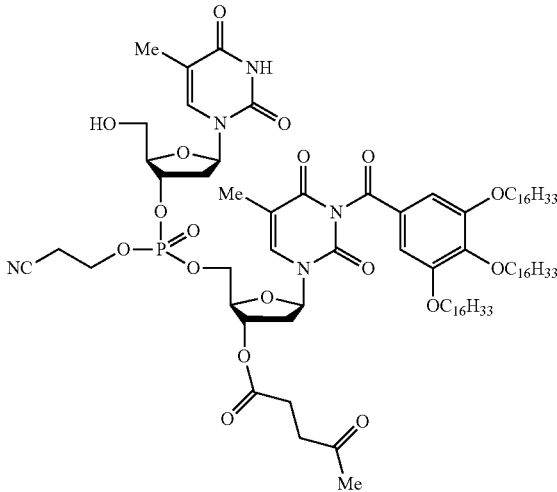

(E103)

To the compound (E74) (127.5 mg), a 490 mM trichloroacetic acid/toluene solution (1.8 mL) was added, the mixture was stirred at room temperature for 10 minutes, then methanol (1.8 mL) was added, and the mixture was stirred for 5 minutes. Methanol (20 mL) was added thereto, the mixture was cooled to 0° C., and the precipitate was collected by suction filtration and washed with methanol to obtain the compound (E103) (97.6 mg) as a diastereomer mixture.

$^1$H NMR (500 MHz, CDCl$_3$) δ 8.30, 8.04 (1H, br, s), 7.50, 7.47 (1H, br, s), 7.41-7.42 (1H, m), 7.15, 7.13 (2H, s, s), 6.32 (1H, m), 6.11-6.20 (1H, m), 5.33-5.34, 5.27-5.30 (1H, m), 5.17-5.21 (1H, m), 4.29-4.41 (4H, m), 4.21-4.25 (2H, m), 3.97-4.05 (6H, m), 3.80-3.94 (2H, m), 2.72-2.86 (5H, m), 2.47-2.62 (5H, m), 2.33 (1H, br), 2.20, 2.19 (3H, d J=2.2 Hz), 2.02, 2.00 (3H, br s, br d J=0.6 Hz), 1.92-1.93 (3H, m), 1.80-1.82 (6H, m), 1.42-1.48 (6H, m), 1.23-1.35 (72H, m), 0.88 (9H, m).

(3) Synthesis of the Compound (E106) by a Coupling Reaction Between the Block Nucleic Acid Dimer (5'-dTdT-3') (Compound (E102)) and the Block Nucleic Acid Dimer (5'-dTdT-3') (Compound (E103))

[Formula 196]

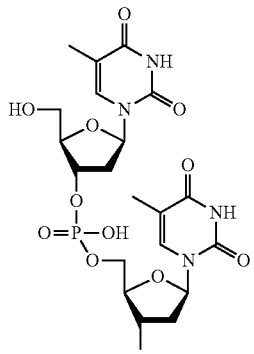

(E106)

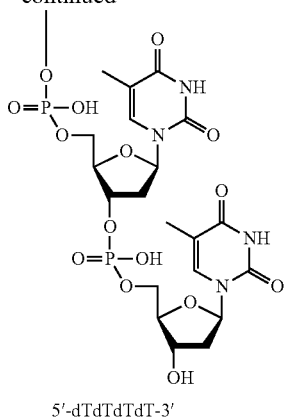

5'-dTdTdTdT-3'

The compound (E102) (34.5 mg) was dissolved in chloroform (600 μL), then 2,4,6-trimethylpyridine (13.3 μL), 1-methylimidazole (1.0 μL), and 2-cyanoethyldiisopropylchlorophosphoroamidide (13.4 μL) were added, and the mixture was stirred at room temperature for 1 hour. The compound (E103) (15.2 mg) and 5-benzylmercapto-1H-tetrazole (34.7 mg) dissolved in acetonitrile (300 μL) were added thereto, the mixture was stirred at room temperature for 4 hours, then a 0.1 M $I_2$/pyridine solution (600 μL) and water 1 (37.5 μL) were added, and the mixture was stirred at room temperature for 15 minutes. Acetonitrile was added thereto, the mixture was cooled to 0° C., and the precipitated solid was collected by suction filtration and washed with acetonitrile to obtain a product (51.9 mg). To the obtained product (26.7 mg), a 490 mM trichloroacetic acid/toluene solution (300 μL) was added, the mixture was stirred at room temperature for 10 minutes, then methanol was added, and the mixture was stirred for 5 minutes. The precipitated product was recovered (24.9 mg) by centrifugal sedimentation. The recovered product (17.3 mg) was suspended in ethanol (1.0 mL), a 40% aqueous solution of methylamine (3.0 mL) was added, the mixture was allowed to react at 45° C. for 20 minutes, and then the solid component was filtered off. The residue was washed with dimethylsulfoxide, and the wash liquid was combined with the filtrate to obtain a reaction solution including the compound (E106) (11.4 g). The obtained reaction solution (10.7 g) was purified by anion exchange chromatography to obtain the compound (E106) (0.79 μmol). The obtained compound (E106) was subjected to identification by HPLC and ESI-MS.

LC-ESI-MS m/z 1153.22 [M-H]$^-$

Example 39

Synthesis of a Dimer Intermediate (E70) in the Synthesis of a Nucleic Acid Oligomer

[Formula 197]

(E70)

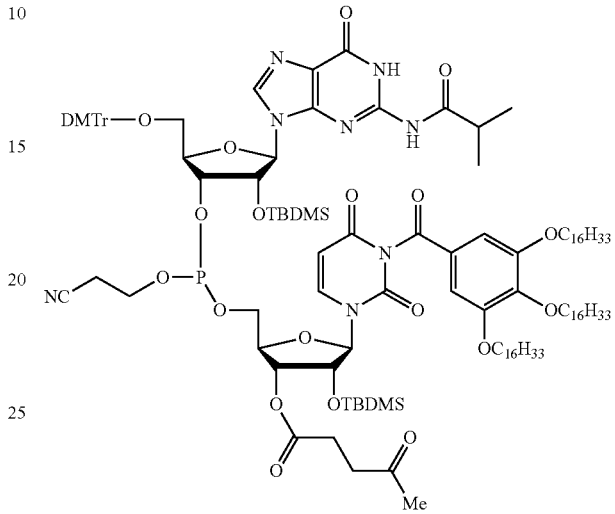

To the compound (E65) (256 mg) and 5'-O-(4,4'-dimethoxytrityl)-2'-O-t-butyldimethylsilyl-guanosine-N2-isobutyryl-N,N'-diisopropylcyanoethyl phosphoramidite (485 mg), dichloromethane (10 mL) was added at room temperature, and the mixture was stirred. 5-Benzylmercapto-1H-tetrazole (135 mg) dissolved in acetonitrile (1.5 mL) was added thereto, and the mixture was stirred at room temperature for 2 hours. The reaction liquid was concentrated under reduced pressure, then acetonitrile (60 mL) was added, the mixture was cooled to 0° C., and the precipitated solid was collected by suction filtration and washed with acetonitrile to obtain the compound (E70) (347 mg, percent yield: 81%) as a diastereomer mixture.

$^1$H NMR (500 MHz, CDCl$_3$) δ 12.21, 12.14 (1H, br s), 10.14, 9.88 (1H, br), 8.30, 8.15 (1H, br, br d J=8.3 Hz), 7.93, 7.87 (1H, s), 7.42-7.47 (2H, m), 7.30-7.36 (6H, m), 7.24-7.27 (1H, m), 7.13, 7.12 (2H, m), 6.84-6.87 (4H, m), 6.42, 6.22 (1H, d J=8.4, d J=7.9 Hz), 5.87-6.01 (1H, d J=3.9 Hz, d, J=2.5 Hz), 5.93, 5.95 (1H, d J=8.9 Hz, d J=7.4 Hz), 5.19, 5.13 (1H, t J=4.9 Hz, dd J=4.5, 7.0 Hz), 4.66-4.72 (1H, m), 4.51-4.60 (1H, m), 3.76-4.42 (19H, br m), 3.50-3.58 (1H, m), 3.37-3.41 (1H, m), 2.65-2.86 (4H, m), 2.50-2.60, (2H, m), 2.12-2.20 (4H, m), 1.70-1.82 (6H, m), 1.39-1.48 (6H, br m), 1.22-1.35 (72H, br m), 0.76-0.89 (33H, m), 0.11, (3H, s), 0.04, 0.02 (3H, m), −0.04, −0.05 (3H, s), −0.27, −0.28 (3H, s).

Example 40

Synthesis of a Dimer Intermediate (E71) in the Synthesis of a Nucleic Acid Oligomer

[Formula 198]

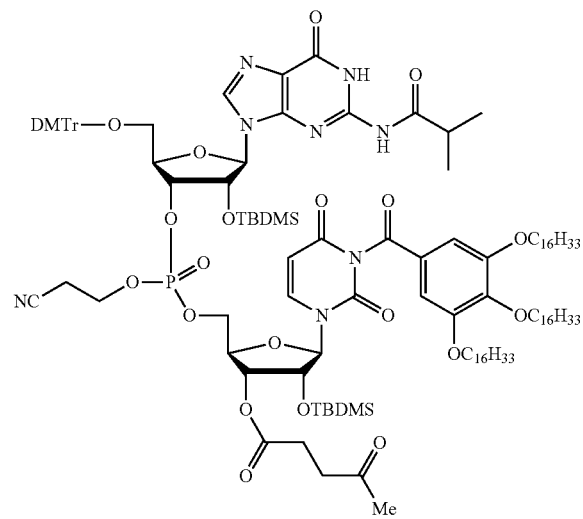

(E71)

To the compound (E70) (344 mg), a 0.02 M iodine/pyridine solution (8 mL) and water (400 μL) were added, and the mixture was stirred at room temperature for 15 minutes. The reaction liquid was concentrated under reduced pressure, then acetonitrile (40 mL) was added, the mixture was cooled to 0° C., and the precipitate was collected by suction filtration to obtain the compound (E71) (218 mg, percent yield: 63%) as a diastereomer mixture.

$^1$H NMR (500 MHz, CDCl$_3$) δ 12.19, 12.14 (1H, s), 10.15, 9.57 (1H, br), 8.03, 7.85 (1H, br d J=8.7 Hz, br d J=7.9 Hz), 7.94, 7.93, (1H, s), 7.40-7.47 (2H, m), 7.23-7.37 (7H, m), 7.13 (2H, br), 6.82-6.87 (4H, m), 6.39, 6.23 (1H, d, J=8.3, 8.3 Hz), 5.87-5.96 (2H, m), 4.72-5.18 (3H, br m), 3.90-4.56 (13H, br m), 3.79-3.80 (6H, m), 3.27-3.64 (2H, m), 2.45-2.90 (6H, m), 1.95-2.20 (4H, br), 1.70-1.82 (6H, m), 1.45 (6H, br m) 1.23-1.34 (72H, br m), 0.75-0.91 (33H, m), 0.12, 0.10 (3H, s), 0.04, 0.02 (3H, s), 0.01, −0.03 (3H, s), −0.16, −0.24 (3H, s).

Example 41

Synthesis of a Dimer Intermediate (E72) in the Synthesis of a Nucleic Acid Oligomer

[Formula 199]

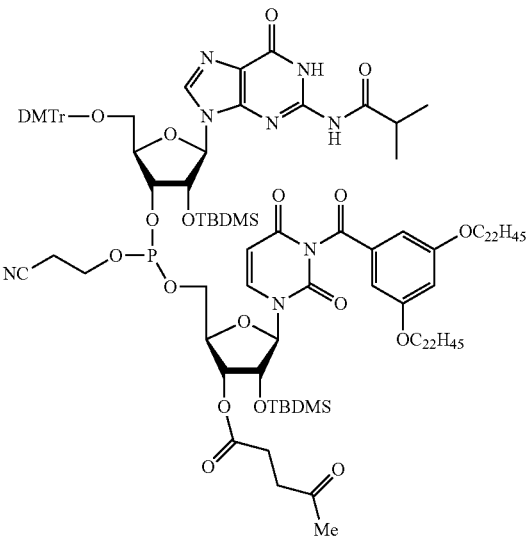

(E72)

To the compound (E66) (133 mg) and 5'-O-(4,4'-dimethoxytrityl)-2'-O-t-butyldimethylsilyl-guanosine-N$^2$-isobutyryl-N,N'-diisopropylcyanoethyl phosphoramidite (267 mg), dichloromethane (10 mL) was added at room temperature, and the mixture was stirred. 5-Benzylmercapto-1H-tetrazole (135 mg) dissolved in acetonitrile (1.5 mL) was added thereto, and the mixture was stirred at room temperature for 2 hours. The reaction liquid was concentrated under reduced pressure, then acetonitrile (60 mL) was added, the mixture was cooled to 0° C., and the precipitated solid was collected by suction filtration and washed with acetonitrile to obtain the compound (E72) (181 mg, percent yield: 79%) as a diastereomer mixture.

$^1$H NMR (500 MHz, CDCl$_3$) δ 12.20, 12.13 (1H, br s), 10.15, 9.84 (1H, br), 8.31, 8.13 (1H, br, br d J=7.7 Hz), 7.93, 7.87 (1H, s), 7.43-7.46 (2H, m), 7.24-7.36 (7H, m), 7.01, 7.00 (2H, br d J=2.3 Hz, br d J=2.1 Hz), 6.84-6.87 (4H, m), 6.69-6.71 (1H, m), 6.43, 6.22 (1H, d J=8.2 Hz, d J=8.4 Hz), 5.83-6.04 (2H, m), 5.31-5.21 (1H, m), 4.64-4.71 (1H, m), 4.52-4.60 (1H, m), 3.76-4.41 (17H, br m), 3.50-3.58 (1H, m), 3.37-3.41 (1H, m), 2.50-2.87 (6H, m), 2.10-2.20, (4H, m), 1.71-1.78 (4H, m), 1.39-1.44 (4H, brm), 1.22-1.35 (72H, br m), 0.76-0.89 (30H, m), 0.12, 0.09 (3H, s), 0.04, 0.03 (3H, br m), −0.03, −0.05 (3H, s), −0.27, (3H, br).

Example 42

Synthesis of a Dimer Intermediate (E73) in the Synthesis of a Nucleic Acid Oligomer

[Formula 200]

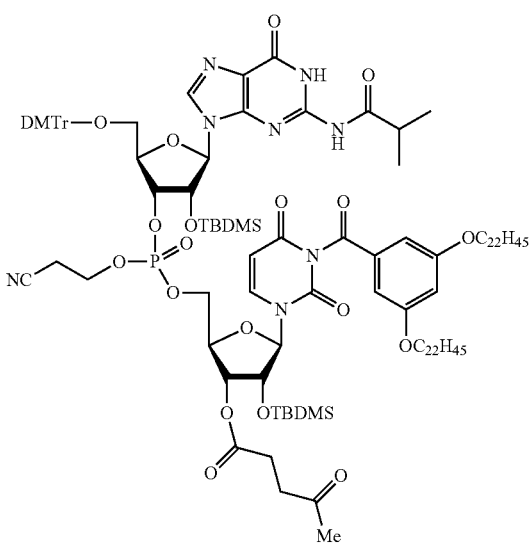

(E73)

To the compound (E72) (159 mg), a 0.02 M iodine/pyridine solution (3.8 mL) and water (192 μL) were added, and the mixture was stirred at room temperature for 15 minutes. The reaction liquid was concentrated under reduced pressure, then acetonitrile (50 mL) was added, the mixture was cooled to 0° C., and the precipitate was collected by suction filtration to obtain the compound (E73) (141 mg, percent yield: 88%) as a diastereomer mixture.

$^1$H NMR (500 MHz, CDCl$_3$) δ 12.17, 12.13 (1H, s), 10.06, 9.56 (1H, br), 8.02, 7.82 (1H, br d J=8.0 Hz, br d J=8.9 Hz), 7.94, 7.93, (1H, s), 7.40-7.47 (2H, m), 7.24-7.37 (7H, m), 7.00-7.02 (2H, m), 6.82-6.86 (4H, m), 6.69-6.71 (1H, m), 6.38, 6.23 (1H, d, J=8.2 Hz, d J=8.1 Hz), 5.87-5.96 (2H, m), 4.71-5.20 (3H, br m), 3.90-4.59 (11H, m), 3.79-3.80 (6H, m), 3.27-3.64 (2H, m), 2.46-2.88 (6H, m), 2.20 (3H, s), 1.95-2.15 (1H, br m), 1.72-1.79 (4H, m), 1.39-1.45 (4H, br m), 1.20-1.35 (72H, br m), 0.76-0.89 (30H, m), 0.12, 0.10 (3H, s), 0.05, 0.03 (3H, s), 0.01, −0.04 (3H, s), −0.15, −0.24 (3H, s).

Example 43

Synthesis of a Dimer Intermediate (E75) in the Synthesis of a Nucleic Acid Oligomer

[Formula 201]

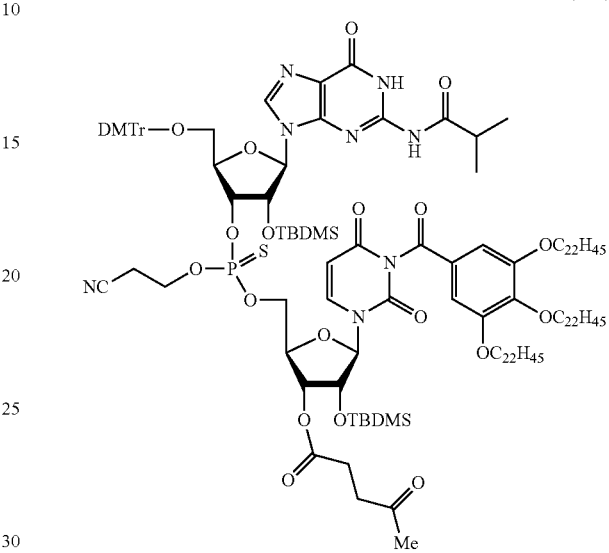

(E75)

To the compound (E67) (174 mg) and 5'-O-(4,4'-dimethoxytrityl)-2'-O-t-butyldimethylsilyl-guanosine-N2-isobutyryl-N,N'-diisopropylcyanoethyl phosphoramidite (194 mg), toluene (2.5 mL) was added at room temperature, and the mixture was stirred. 5-Benzylmercapto-1H-tetrazole (58 mg) dissolved in acetonitrile (500 μL) was added thereto, and the mixture was stirred at room temperature for 2 hours bis(Phenylacetyl)disulfide (67 mg) dissolved in 2,4,6-trimethylpyridine (1 mL) was added thereto, the mixture was stirred at room temperature for 30 minutes, then acetonitrile (50 mL) was added, the mixture was cooled to 0° C., and the precipitated solid was collected by suction filtration and washed with acetonitrile to obtain the compound (E75) (233 mg, percent yield: 96%) as a diastereomer mixture.

$^1$H NMR (500 MHz, CDCl$_3$) δ 12.17, 12.15 (1H, s), 10.13, 9.86 (1H, br), 8.13, 8.01 (1H, d J=8.0 Hz, br), 7.97, 7.94, (1H, s), 7.43-7.49 (2H, m), 7.29-7.39 (6H, m), 7.23-7.28 (1H, m), 7.14, 7.12 (2H, br), 6.84-6.88 (4H, m), 6.42, 6.24 (1H, d, J=8.3, 8.6 Hz), 5.85-5.96 (2H, m), 5.17-5.20 (1H, m), 5.07, 4.95 (1H, dd J=11.1, 5.3 Hz, dd J=4.5, 7.5 Hz), 4.86-4.89, 4.74-4.77 (1H, br m, br m), 3.75-4.52 (19H, br m), 3.30-3.60 (2H, m), 2.49-2.88 (6H, m), 1.99-2.25 (4H, br), 1.70-1.82 (6H, m), 1.43-1.49 (6H, br m) 1.21-1.35 (108H, br m), 0.72-0.89 (33H, m), 0.12 (3H, br), 0.04, 0.02 (3H, br s), −0.03, −0.05 (3H, s), −0.21, −0.26 (3H, s).

Example 44

Synthesis of a Dimer Intermediate (E118) in the Synthesis of a Nucleic Acid Oligomer

[Formula 202]

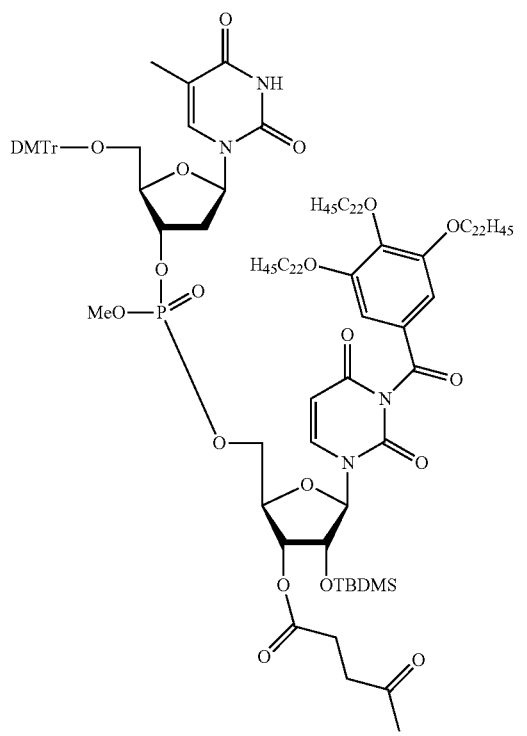

(E118)

Methyl dichlorophosphite (48.2 μL) was added to THF (500 μL) that had been cooled to −78° C., then a solution of 1-((2R,4S,5R)-5-((bis(4-methoxyphenyl)(phenyl)methoxy)methyl)-4-hydroxytetrahydrofuran-2-yl)-5-methylpyrimidine-2,4(1H,3H)-dione (326.8 mg) and 2,4,6-trimethylpyridine (191.6 μL) dissolved in THF (4.4 mL) was added dropwise thereto at −78° C. for 30 minutes, and the mixture was further stirred at the same temperature for 40 minutes. A solution of the compound (E67) (43.5 mg) and 2,4,6-trimethylpyridine (10.6 μL) dissolved in THF (350 μL) was added thereto, the mixture was stirred at −78° C. for 2.5 hours, and then the mixture was further stirred at room temperature for 2 hours. To the reaction liquid, a solution of iodine (126.9 mg) and water (312 μL) dissolved in pyridine (5 mL) was added, the mixture was stirred at room temperature for 15 minutes, then acetonitrile (30 mL) was added, the mixture was cooled to 0° C., and the precipitated solid was collected by suction filtration and washed with acetonitrile to obtain the compound (E118) (45.5 mg) as a diastereomer mixture.

$^1$H NMR (500 MHz, CDCl$_3$) δ 7.62-8.26 (2H, br m), 7.57, 7.52 (1H, br d J=1.18 Hz, br s), 7.23-7.39 (9H, m), 7.14, 7.19 (2H, s, br s), 6.83-6.86 (4H, m), 6.37-6.43 (1H, m), 5.86-5.91 (2H, m), 5.07-5.26 (2H, m), 4.17-4.44 (5H, m), 3.94-4.07 (6H m), 3.79-3.80 (9H, m), 3.50-3.56 (1H, m), 3.37-3.43 (1H, m), 2.40-2.85 (6H, m), 2.16, 2.14 (3H, s), 1.69-1.82 (6H, m), 1.40-1.49 (9H, br m), 1.20-1.36 (108H, br m), 0.86-0.90 (18H, m), 0.02-0.07 (6H, m).

Example 45

Synthesis of a Dimer Intermediate (E119) in the Synthesis of a Nucleic Acid Oligomer

[Formula 203]

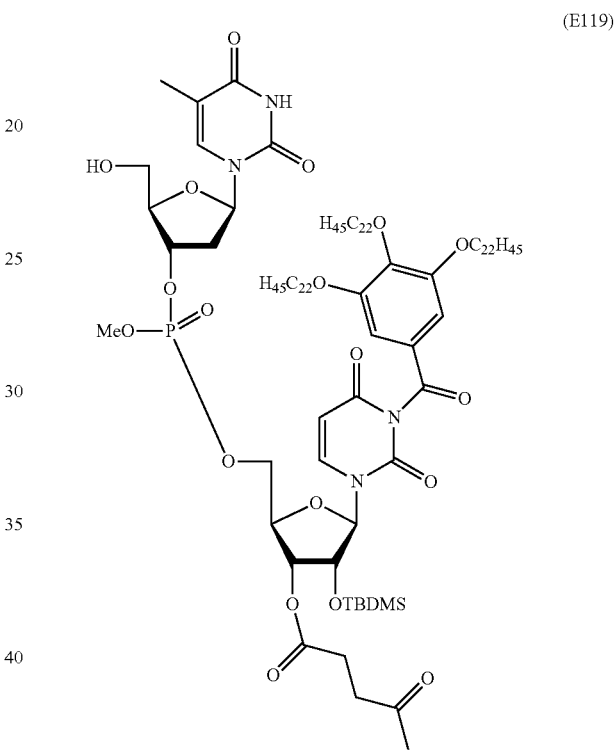

(E119)

To the compound (E118) (10.8 mg), a 490 mM trichloroacetic acid/toluene solution (300 μL) was added, the mixture was stirred at room temperature for 10 minutes, then methanol (20.0 mL) and water (2.0 mL) were added, the mixture was cooled to 0° C., and the precipitate was collected by suction filtration and washed with methanol to obtain the compound (E119) (6.6 mg) as a diastereomer mixture.

$^1$H NMR (500 MHz, CDCl$_3$) δ 8.30, 8.16, 7.80, 7.71, 7.64, 7.42 (3H, br, br, br, d J=8.3 Hz, br d J=8.3 Hz, dd J=7.4, 0.9 Hz), 7.15, 7.13 (2H, s), 6.18, 6.14 (1H, t J=7.3 Hz, br t J=6.6 Hz), 5.84-5.94 (2H, m), 5.10-5.17 (2H, m), 4.43 (1H, t J=4.5 Hz), 4.20-4.41 (4H, m), 3.78-4.06 (12H, m), 2.47-2.86 (6H, m), 2.19, 2.20 (3H, s), 1.92 (3H, dd J=3.5, 1.0 Hz), 1.70-1.83 (6H, m), 1.41-1.48 (6H, m), 1.19-1.37 (108H, br m), 0.86-0.89 (18H, m), 0.07, 0.07 (3H, s, s), 0.04 (3H, s).

Example 46

Synthesis of a Cytosine (C) Type Nucleoside Monomer Compound Having Three Octadecyloxy Groups (Compound (E121))

(1) Synthesis of a C-Type Nucleoside (Compound (E120))

[Formula 204]

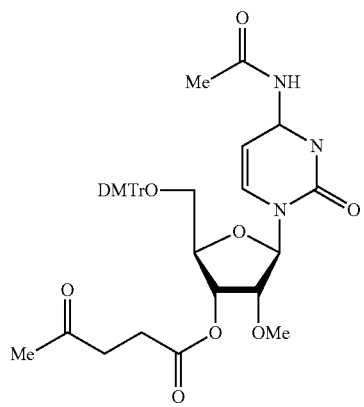

N-(1-((2R,3R,4R,5R)-5-((bis(4-Methoxyphenyl)(phenyl) methoxy)ethyl)-4-hydroxy-3-methoxytetrahydrofuran-2-yl)-2-oxo-1,2-dihydropyrimidin-4-yl)acetamide (3.00 g, 4.99 mmol), DMAP (56 mg, 0.49 mmol), and THF (30 mL) were measured and dissolved in a 100-mL eggplant type flask, then levrinic acid (0.87 g, 7.48 mmol) was added thereto. WSC.HCl (1.43 g, 7.48 mmol) was added thereto, and the mixture was stirred at the same temperature for 2.0 hours. THF was distilled off under reduced pressure, then EtOAc (40 mL) and a 0.2 M aqueous solution of AcOH.Et₃N (pH: 7.0) (30 mL) were added for separation. To the organic layer, a 0.2 M aqueous solution of AcOH.Et₃N (pH: 7.0) (30 mL) was added again for separation. The organic layer was dried over anhydrous sodium sulfate and then filtered. The organic layer was concentrated and exsiccated under reduced pressure to obtain the compound (E120) (yield: 3.41 g, percent yield: 97.7%).

$^1$H NMR (500 MHz, CDCl$_3$) δ 2.19 (3H, s), 2.25 (3H, s), 2.57-2.63 (2H, m), 2.71-2.78 (2H, m), 3.43 (1H, dd, J=11.3, 2.2 Hz), 3.57 (3H, s), 3.67 (1H, dd, J=11.7, 2.5 Hz), 3.82 (6H, s), 4.08 (1H, dd, J=4.7, 1.3 Hz), 4.33 (1H, dt, J=8.6, 2.2 Hz), 5.12 (1H, dd, 8.8, 5.0 Hz), 6.05 (1H, d, J=1.3 Hz), 6.83-6.90 (4H, m), 7.12 (1H, d, J=7.3 Hz), 7.24-7.36 (7H, m), 7.36-7.40 (2H, m), 8.48 (1H, d, J=7.5 Hz), 9.51 (1H, brs).

(2) Synthesis of a Cytosine (C) Type Nucleoside Monomer Compound Having Three Octadecyloxy Groups (Compound (E121))

[Formula 205]

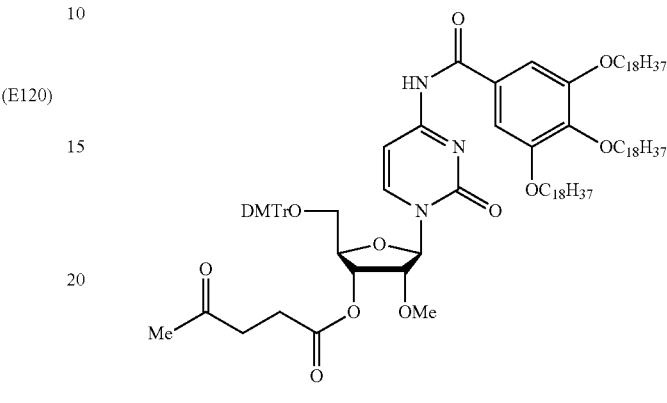

The compound (E120) (0.822 g-equivalent, 1.06 mmol), i-Pr₂NEt (0.682 g, 5.29 mmol), and pyridine (7.5 mL) were measured and dissolved in a 100-mL eggplant type flask. TMSCl (0.23 mL) and 3,4,5-tris(octadecyloxy)benzoyl chloride (0.50 g-equivalent) were serially added at room temperature. The mixture was stirred at an outside temperature of 60° C. for 3 hours. The reaction mixture was cooled to room temperature, then morpholine (1.40 mL) was added, and the mixture was stirred at room temperature for 2 hours. MeOH (50 mL) was added dropwise, and the obtained suspension was stirred at room temperature for 0.5 hours and then was subjected to collection by suction filtration. The powder collected by the filtration was washed with MeOH (50 mL). The obtained powder was dried at room temperature for 18 hours under reduced pressure and then was purified by column chromatography by using toluene/pyridine (50/1) as the mobile phase to obtain the compound (E121) (0.400 g, percent yield: 48%).

$^1$H NMR (500 MHz, CDCl$_3$) δ 0.88 (9H, t, J=7.0 Hz), 1.19-1.41 (84H, m), 1.43-1.53 (6H, m), 1.69-1.78 (2H, m), 1.79-1.88 (4H, m), 2.19 (3H, s), 2.59-2.65 (2H, m), 2.69-2.82 (2H, m), 3.45 (1H, dd, J=11.3, 2.2 Hz), 3.59 (3H, s), 3.67 (1H, dd, J=11.7, 1.3 Hz), 3.83 (6H, s), 3.98-4.06 (6H, m), 4.13 (1H, dd, J=5.0, 1.5 Hz), 4.34 (1H, brd, J=8.2 Hz), 5.17 (1H, dd, J=8.0, 1.5 Hz), 6.09 (1H, d, J=1.3 Hz), 6.88 (4H, dd, J=9.1, 2.2 Hz), 7.06 (1H, brs), 7.24-7.28 (2H, m), 7.30 (4H, dd, 8.8, 3.5 Hz), 7.34 (2H, t, J=7.6 Hz), 7.37-7.42 (3H, m), 8.51 (1H, brs), 8.58 (1H, brs).

Example 47

Synthesis of a Cytosine (C) Type Nucleoside Monomer Compound Having Three Octadecyloxy Groups (Compound (E123))

[Formula 206]

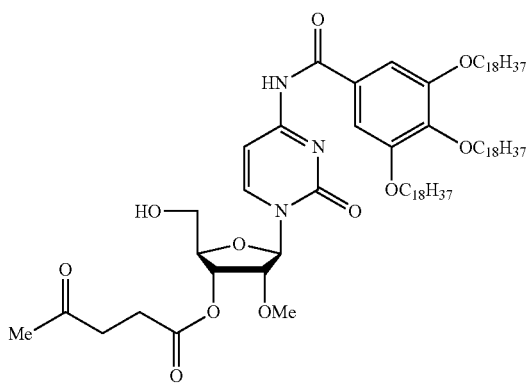

The compound (E121) (0.400 g) was measured into a 50-mL eggplant type flask, and toluene (4 mL) was added thereto for dissolution. Trichloroacetic acid (0.417 g) was added, the mixture was stirred at room temperature for 10 minutes, then methanol (8 mL) was added, and the mixture was stirred. The reaction liquid was concentrated under reduced pressure, then methanol (20 mL) was added, and the mixture was cooled to 0° C. The precipitate was collected by suction filtration and washed with methanol to obtain the compound (E123) (0.32 g, percent yield: 99%).

$^1$H NMR (500 MHz, CDCl$_3$) δ 0.88 (9H, t, J=7.0 Hz), 1.19-1.41 (84H, m), 1.43-1.53 (6H, m), 1.69-1.78 (2H, m), 1.79-1.88 (4H, m), 2.00-3.20 (1H, brs), 2.20 (3H, s), 2.60-2.72 (2H, m), 2.73-2.87 (2H, m), 3.54 (3H, s), 3.80 (1H, dd, J=12.9, 1.9 Hz), 3.95-4.11 (7H, m), 4.30 (1H, brd, J=6.0 Hz), 4.39 (1H, t, J=4.3 Hz), 5.28 (1H, t, J=5.5 Hz), 5.78 (1H, d, J=3.8 Hz), 7.09 (2H, s), 7.57 (1H, brs), 8.25 (1H, d, J=7.6 Hz), 8.85 (1H, brs).

Example 48

Synthesis of a Cytosine (C) Type Nucleoside Monomer Compound Having Two Icosyloxy Groups (Compound (E125))

(1) Synthesis of a C-Type Nucleoside (Compound (E124))

[Formula 207]

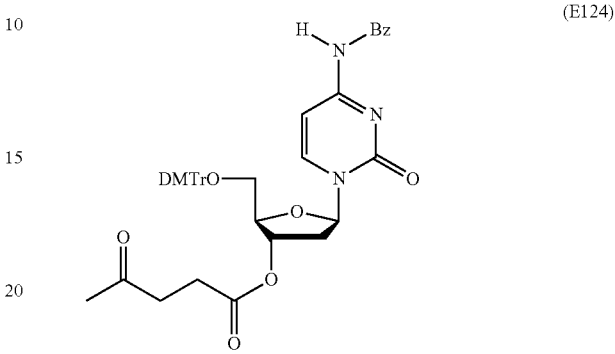

Levrinic acid (1.10 g, 9.47 mmol), DMAP (77 mg, 0.63 mmol), THF (20 mL), and (2R,3S,5R)-5-(4-benzamido-2-oxopyrimidin-1(2H)-yl)-2-((bis(4-methoxyphenyl)(phenyl)methoxy)methyl)tetrahydrofuran-3-yl 4-oxopentanoate (4.00 g, 6.31 mmol) were measured and dissolved in a 100-mL eggplant type flask. WSC.HCl (1.82 g, 9.47 mmol) was added, and the mixture was stirred at the same temperature for 2.0 hours. THF was distilled off under reduced pressure, then EtOAc (50 mL) and a 0.2 M aqueous solution of AcOH.Et$_3$N (pH: 7.0) (40 mL) were added for separation. To the organic layer, a 0.2 M aqueous solution of AcOH.Et$_3$N (pH: 7.0) (40 mL) was added again for separation. The organic layer was dried over anhydrous sodium sulfate, and then the solvent was distilled off. The organic layer was concentrated and exsiccated under reduced pressure to obtain the compound (E124) (4.66 g, percent yield: 101%).

$^1$H NMR (500 MHz, CDCl$_3$) δ 2.20 (3H, s), 2.32-2.37 (1H, m), 2.53-2.64 (2H, m), 2.70-2.84 (4H, m), 3.44-3.50 (1H, m), 3.79 (3H, s), 3.80 (3H, s), 4.27 (1H, br dd, J=5.65, 2.95 Hz), 5.41-5.44 (1H, m), 6.30 (1H, dd, J=7.20, 6.00 Hz), 6.83-6.87 (4H, m), 7.21-7.32 (8H, m), 7.38 (2H, dd, J=7.95, 0.65 Hz), 7.51 (2H, t like, J=7.95 Hz), 7.61 (1H, t, J=7.45 Hz), 7.90 (2H, d, J=7.50 Hz), 8.15 (1H, d, J=7.50 Hz), 8.05 (1H, brs).

(2) Synthesis of a Cytosine (C) Type Nucleoside Monomer Compound Having Two Icosyloxy Groups (Compound (E125))

[Formula 208]

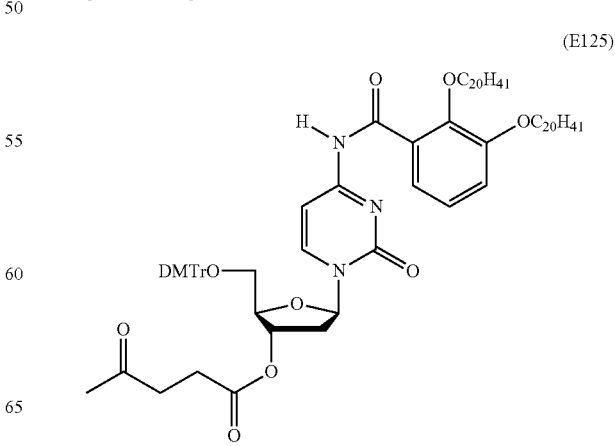

The compound (E124) (0.75 g-equivalent, 1.03 mmol), i-Pr₂NEt (0.93 mL), and pyridine (7 mL) were measured and dissolved in a 200-mL eggplant type flask. TMSCl (0.33 mL) and 2,3-bis(icosyloxy)benzoyl chloride (0.58 g, 0.79 mmol) were serially added at room temperature. The mixture was allowed to react at an outside temperature of 60° C. for 3.5 hours. The reaction mixture was cooled to room temperature, then morpholine (1.45 mL) was added, and the mixture was stirred for 1 hour. Then MeOH (75 mL) was added dropwise, and the obtained suspension was stirred for 1.0 hour. The precipitate was collected by suction filtration and washed with MeOH (10 mLX3). The obtained powder was dried at 40° C. for 1 hour under reduced pressure to obtain the target compound (0.83 g). The obtained compound was purified by column chromatography [Silicagel 60 (9 g), 5% Et₃N contained EtOAc/toluene 0:95 to 20:75]. The effective fraction was concentrated under reduced pressure to obtain an ocherous powder compound (E125) (0.72 g, 69% yield).

¹H NMR (500 MHz, CDCl₃) δ 0.88 (6H, t, J=6.45 Hz), 0.90-1.55 (66H, m), 1.81-1.92 (6H, m), 2.20 (3H, s), 2.19-2.33 (1H, m), 2.57-2.61 (2H, m), 2.73-2.82 (3H, m), 3.46 (2H, d, J=3.15 Hz), 3.79 (3H, s), 3.80 (3H, s), 3.99-4.02 (2H, m), 4.14-4.20 (2H, m), 4.24-4.29 (1H, m), 5.39-5.42 (1H, m), 6.32 (1H, dd, J=7.30, 5.90 Hz), 6.82-6.87 (4H, m), 7.08-7.15 (2H, m), 7.21-7.34 (8H, m), 7.34-7.39 (2H, m), 7.66 (1H, dd, J=7.70, 1.85 Hz), 8.09 (1H, d, J=7.45 Hz), 10.69 (1H, brs).

Example 49

Synthesis of a Cytosine (C) Type Nucleoside Monomer Compound Having Two Icosyloxy Groups (Compound (E126))

[Formula 209]

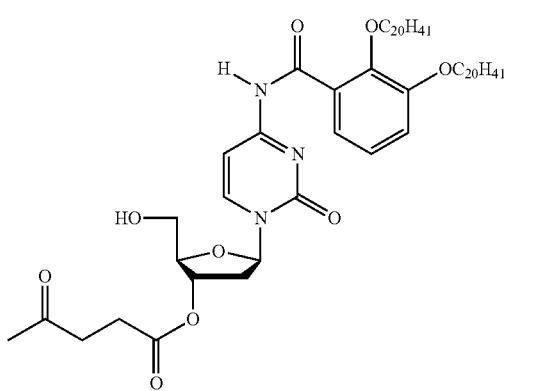

(E126)

The compound (E125) (170 mg) and toluene (2 mL) were measured and dissolved in a 35-mL eggplant type flask. Trichloroacetic acid (110 mg) was added thereto, and the mixture was stirred at room temperature for 10 minutes. Methanol (0.5 mL) was added, then acetonitrile (15 mL) was added dropwise, and then the mixture was stirred at room temperature for 10 minutes. The generated powder was collected by suction filtration and the obtained residue was washed with acetonitrile containing 5% methanol (5 mL) three times. The obtained powder was dried at room temperature for 2.5 hours under reduced pressure to obtain the compound (E126) (103 mg, percent yield: 79%).

¹H NMR (500 MHz, CDCl₃) δ 0.88 (6H, t, J=7.05 Hz), 0.90-1.55 (66H, m), 1.80-1.91 (6H, m), 1.50-2.00 (1H, brs, OH), 2.20 (3H, s), 2.45-2.51 (1H, m), 2.57-2.68 (3H, m), 2.75-2.80 (2H, m), 3.89 (1H, AB dd, J=11.95, 2.75 Hz), 3.97 (1H, AB dd, J=11.95, 2.60 Hz), 3.98-4.01 (2H m), 4.15-4.19 (3H, m), 5.35-5.38 (1H, m), 6.22 (1H dd, J=7.45, 6.05 Hz), 7.08-7.15 (2H, m), 7.63 (1H, d, J=7.45 Hz), 7.66 (1H, dd, J=7.75, 1.85 Hz), 8.16 (1H, d, J=7.50 Hz), 10.72 (1H, brs).

INDUSTRIAL APPLICABILITY

According to the present invention, a novel nucleoside compound in which the base moiety of a nucleoside is substituted by (i) an aromatic hydrocarbon ring carbonyl group having at least one hydrophobic group or (ii) an aromatic hydrocarbon ring thiocarbonyl group having at least one hydrophobic group, etc. can be used as a synthetic unit to produce a nucleic acid oligomer. Use of the present invention can circumvent the need for column chromatography purification after every reaction. Also, use of the present invention can elongate bases both in a direction toward the 3' end and in a direction toward the 5' end and can achieve the efficient large-scale synthesis of a nucleic acid oligomer by a liquid-phase synthesis method. Thus, the present invention is applicable to the production of nucleic acid oligomers such as siRNA, antisense nucleic acids, and vaccine adjuvants and is very useful in the fields of genomic drug discovery, genetic diagnosis or therapy, and the like.

We claim:

1. A compound represented by the following formula (I):

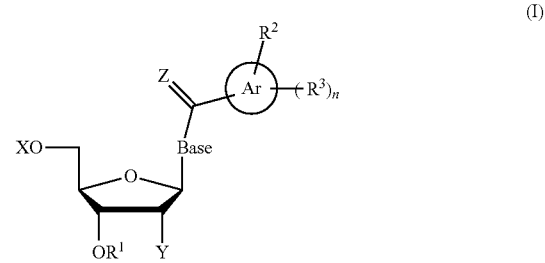

(I)

wherein
X represents a benzyl-type protective group,
R¹ represents an aliphatic acyl-type protective group;
Y represents a hydroxyl protected group with a silyl-type protective group, a hydrogen atom, a halogen atom, cyano group, or a C₁₋₆ alkoxy group;
Base represents

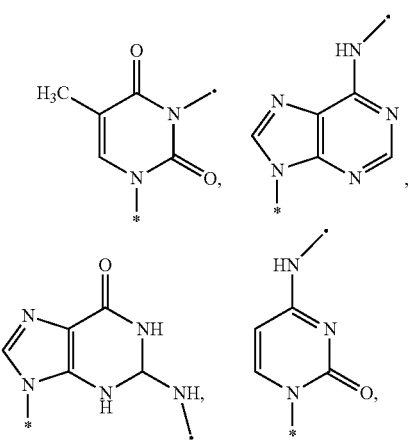

-continued

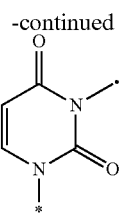

wherein each black circle denotes the site binding to the moiety of the following formula:

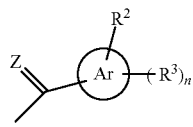

in the compound represented by the formula (I) above, and each asterisk denotes the site binding to another moiety of the compound represented by the formula (I) above to form said compound;

Z represents an oxygen atom;

ring Ar represents a benzene ring;

$R^2$ represents an optionally substituted $C_{10-30}$ alkoxy group;

$R^3$ independently represents a halogen atom, cyano group, or optionally substituted $C_{1-30}$ alkoxy group;

n represents an integer of 1 or 2;

with the proviso that no silyl or silyloxy substitutent moiety can include any Si—H moiety therein, or a salt thereof.

2. The compound according to claim 1, wherein $R^3$ is an optionally substituted $C_{10-30}$ alkoxy group, or a salt thereof.

* * * * *